United States Patent
Liu et al.

(10) Patent No.: US 11,440,952 B2
(45) Date of Patent: Sep. 13, 2022

(54) COMPOSITIONS FOR PREVENTING OR TREATING VIRAL AND OTHER MICROBIAL INFECTIONS

(71) Applicant: InvisiShield Technologies Ltd., Emeryville, CA (US)

(72) Inventors: Cheng Liu, Orinda, CA (US); Hongbing Zhang, Moraga, CA (US); Zhiyuan Yang, Albany, CA (US); Jingyi Xiang, Walnut Creek, CA (US); Ziyou Cui, Moraga, CA (US); Jianying Liu, Albany, CA (US)

(73) Assignee: InvisiShield Technologies Ltd., Emeryville, CA (US)

( * ) Notice: Subject to any disclaimer, the term of this patent is extended or adjusted under 35 U.S.C. 154(b) by 0 days.

(21) Appl. No.: 17/501,955

(22) Filed: Oct. 14, 2021

(65) Prior Publication Data
US 2022/0119501 A1    Apr. 21, 2022

Related U.S. Application Data

(60) Provisional application No. 63/122,432, filed on Dec. 7, 2020, provisional application No. 63/118,570, filed on Nov. 25, 2020, provisional application No. 63/093,076, filed on Oct. 16, 2020.

(51) Int. Cl.

| C07K 16/10 | (2006.01) |
|---|---|
| C07K 14/47 | (2006.01) |
| C07K 7/06 | (2006.01) |
| C07K 7/08 | (2006.01) |
| C07K 19/00 | (2006.01) |
| C12N 15/63 | (2006.01) |
| A61K 39/395 | (2006.01) |
| A61K 38/08 | (2019.01) |
| A61K 38/10 | (2006.01) |
| A61K 38/17 | (2006.01) |
| A61P 31/14 | (2006.01) |
| A61K 9/00 | (2006.01) |
| A61K 47/20 | (2006.01) |
| A61K 39/00 | (2006.01) |

(52) U.S. Cl.
CPC ............ *C07K 16/10* (2013.01); *A61K 9/0043* (2013.01); *A61K 38/08* (2013.01); *A61K 38/10* (2013.01); *A61K 38/17* (2013.01); *A61K 39/3955* (2013.01); *A61K 47/20* (2013.01); *A61P 31/14* (2018.01); *C07K 7/06* (2013.01); *C07K 7/08* (2013.01); *C07K 14/47* (2013.01); *C07K 19/00* (2013.01); *C12N 15/63* (2013.01); *A61K 2039/505* (2013.01); *A61K 2039/543* (2013.01); *C07K 2317/21* (2013.01); *C07K 2317/565* (2013.01); *C07K 2317/622* (2013.01); *C07K 2317/76* (2013.01); *C07K 2319/01* (2013.01); *C07K 2319/035* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| 4,816,567 A | 3/1989 | Cabilly |
|---|---|---|
| 5,591,828 A | 1/1997 | Bosslet |
| 5,821,333 A | 10/1998 | Carter |
| 7,642,228 B2 | 1/2010 | Carter |
| 10,787,501 B1 | 9/2020 | Babb et al. |
| 10,954,289 B1 | 3/2021 | Babb et al. |
| 10,975,139 B1 | 4/2021 | Babb et al. |
| 2011/0287009 A1 | 11/2011 | Scheer |
| 2018/0230447 A1 | 8/2018 | Batlle et al. |
| 2020/0095327 A1 | 3/2020 | Chang et al. |
| 2021/0261650 A1 | 8/2021 | Corti et al. |
| 2021/0277092 A1 | 9/2021 | Crowe, Jr. et al. |
| 2021/0292392 A1 | 9/2021 | Zhang et al. |
| 2021/0292393 A1 | 9/2021 | Westendorf et al. |
| 2021/0300999 A1 | 9/2021 | Crowe, Jr. et al. |

FOREIGN PATENT DOCUMENTS

| CN | 111303280 A | 6/2020 |
|---|---|---|
| EP | 0404097 A2 | 12/1990 |
| WO | 199311161 A1 | 6/1993 |
| WO | 199634103 A1 | 10/1996 |

(Continued)

OTHER PUBLICATIONS

Goldsby, Immunology, 5th edition, 2003, pp. 82-84.*

(Continued)

*Primary Examiner* — Bridget E Bunner
*Assistant Examiner* — Fozia M Hamud
(74) *Attorney, Agent, or Firm* — Morrison & Foerster LLP

(57) ABSTRACT

The present application relates to compositions for preventing or treating viral and other microbial infections. In some embodiments, the present application provides chimeric proteins comprising a target-binding moiety that specifically binds to a pathogen that infects through a mucosa, and a positively charged mucoadhesive peptide fragment. Also provided are antibodies and constructs thereof that specifically binds to an S1 subunit of a spike protein of SARS-CoV-2. Compositions comprising the chimeric proteins, antibodies, or constructs described herein are useful for preventing or treating a microbial infection in an individual, such as a coronavirus infection.

22 Claims, 31 Drawing Sheets
Specification includes a Sequence Listing.

(56) References Cited

FOREIGN PATENT DOCUMENTS

| WO | 2003063772 A2 | 8/2003 |
| WO | 2008016729 A1 | 2/2008 |
| WO | 2013055958 A1 | 4/2013 |
| WO | 2021158521 A1 | 8/2021 |
| WO | 2021168305 A1 | 8/2021 |
| WO | 2021195326 A1 | 9/2021 |
| WO | 2021195485 A1 | 9/2021 |
| WO | 2021216547 A1 | 10/2021 |

OTHER PUBLICATIONS

Huston et al. (Proc. Natl. Acad. Sci., 85(16):5879-5883, 1988).*
Bird et al (Science, 242:243-246, 1988).*
Ward et al. Nature, 341:544-546, 1989.*
Rudikoff, et al. (Proc. Natl. Acad. Sci. USA, 79(6):1979-1983, 1982).*
Abhinandan, K.R. et al. (Aug. 2008, e-pub. Jul. 9, 2008), "Analysis and Improvements To Kabat and Structurally Correct Numbering Of Antibody Variable Domain," Molecular Immunology 45(14):3832-3839.
Adolf-Bryfogle, J. et al. (2015, e-pub. Nov. 11, 2014). "PyIgClassify: A Database of Antibody CDR Structural Classifications," Nucleic Acids Res. 43:D432-D438.
Al-Lazikani, B. et al. (1997). "Standard Conformations for the Canonical Structures of Immunoglobulins," J. Mol. Biol. 273:927-948.
Alves, N.J. (2019, Feb. 15, 2019). "Antibody Conjugation and Formulation," Antibody Therapeutics 2(1):33-39.
BPS Bioscience: ACE-2, His-tag. Available online at https://bpsbioscience.com/ace2-his-tag-11003 [Retrieved online Dec. 21, 2021] https://web.archive.org/web/2020*/https://bpsbioscience.com/ace2-his-tag-11003 published on Jun. 30, 2020 as per Wayback Machine, last visited on Jan. 28, 2022, 3 pages.
Burton, D.R. (1985). "Immunoglobulin G: Functional Sites," Molec. Immunol. 22(3):161-206.
Celerion Applied Translational Medicine. (May 6, 2015). "Intranasal Drug Delivery: Drug Development Considerations," slide presentation by Morimoto, B. H. PhD, Executive Director, Applied Translational Medicine, 28 pages.
Cheadle, C. et al. (Jan. 1992). "Cloning And Expression Of The Variable Regions Of Mouse Myeloma Protein Mopc315 in E. Coli: Recovery Of Active Fv Fragments," Molecular Immunology 29(1):21-30.
Chothia, C. et al. (1987), "Canonical Structures for the Hypervariable Regions of Immunoglobulins," J. Mol. Biol, 196:901-917.
Chowdhury, P.S. (2008). "Engineering Hot Spots for Affinity Enhancement of Antibodies," Methods Mol. Biol. 207:179-196.
Clinical Trials. Eli Lilly and Company (Aug. 4, 2020-). A Study of LY3819253 (LY-CoV555) and LY3832479 (LY-CoV016) in Preventing S AR S-C oV-2 Infection and COVID-19 in Nursing Home Residents and Staff (BLAZE-2). Identifier NCT04497987 Located at https://clinicaltrials.gov/ct2/show/NCT04497987 last visited on Jan. 19, 2022, 27 pages.
Clinical Trials. Regeneron Pharmaceuticals (Jul. 26, 2020-Present). Study Assessing the Safety, Tolerability, Pharmacokinetics, and Immunogenicity of Repeated Subcutaneous Doses of Anti-Spike (S) SARS-CoV-2 Monoclonal Antibodies (REGN10933+REGN10987) in Adult Volunteers as Related to COVID-19. Identifier: NCT04519437, 19 pages.
Clinical Trials. Regeneron Pharmaceuticals (Jun. 11, 2020-Present). Safety, Tolerability, and Efficacy of Anti Spike (S) SARS-CoV-2 Monoclonal Antibodies for Hospitalized Adult Patients With COVID-19. Identifier NCT04426695, 35 pages.
Clinical Trials. Regeneron Pharmaceuticals (Jun. 16, 2020-Present). Safety, Tolerability, and Efficacy of Anti Spike (S) SARS-CoV-2 Monoclonal Antibodies for the Treatment of Ambulatory Adult and Pediatric Patients With COVID-19. Identifier NCT04425629, 32 pages.
Clinical Trials. Regeneron Pharmaceuticals (Jun. 30, 2020-Present). COVID-19 Study Assessing the Efficacy and Safety of Anti-Spike SARS CoV-2 Monoclonal Antibodies for Prevention of SARS CoV-2 Infection Asymptomatic in Healthy Adults and Adolescents Who Are Household Contacts to an Individual With a Positive SARS-CoV-2 RT-PCR Assay. Identifier NCT04452318, 42 pages.
Clinical Trials. Shanghai Junshi Bioscience Co., Ltd. (Jun. 5, 2020-Present). Tolerability, Safety, Pharmacokinetic Profile and Immunogenicity of a Recombinant Humanized Anti-SARS-CoV-2 Monoclonal Antibody (J5016) for Injection in Chinese Health Subjects. Identifier NCT04441918, 20 pages.
Clinical Trials. Vir Biotechnology, Inc. Aug. 27, 2020-). VIR-7831 for the Early Treatment of COVID-19 in Outpatients (COMET-ICE). Identifier NCT04545060, 17 pages.
Cohen, J. (Nov. 10, 2020). "Can A Nose-Full Of Chicken Antibodies Ward Off Coronavirus Infections?," Science Insider, located at https://www.science.org/content/article/can-nose-full-chicken-antibodies-ward-coronavirus-infections#.YfRjAoyfAO4.mailto, last visited on Jan. 30, 2022, 2 pages.
Crowe, J.E. Jr, et al. (Feb. 1994). "Recombinant Human Respiratory Syncytial Virus (RSV) Monoclonal Antibody Fab is Effective Therapeutically When Introduced Directly into the Lungs of RSV-Infected Mice," Proc Natl Acad Sci USA 91(4):1386-1390.
Cui, Y. et al. (2017, e-pub. Jan. 4, 2017). "Monoclonal Antibodies: Formulations Of Marketed Products And Recent Advances In Novel Delivery System," Drug Development and Industrial Pharmacy 11:28, 40 pages.
Cunningham, B.C. et al. (Jun. 2, 1989). "High-Resolution Epitope Mapping of hGH-Receptor Interactions by Alanine-Scanning Mutagenesis," Science 244:1081-1085.
Dall'Acqua, W. et al. (1998). "Contribution of Domain Interface Residues to the Stability of Antibody CH3 Domain Homodimers", Biochemistry37:9266-9273.
Ehrenmann, F. et al. (Jan. 2010, e-pub. Nov. 9, 2009). "IMGT/3Dstructure-DB and IMGT/DomainGapAlign: A Database and a Tool For Immunoglobulins or Antibodies, T Cell Receptors, MHC, IgSF and MhcSF," Nucleic Acids Res. 38:D301-D307.
Ehrick, J.D. et al. (2013, e-pub. Jun. 22, 2013). "Consideration for the Development of Nasal Dosage Forms," Web PDF, Sterile Product Development, pp. 99-144, located at https://link.springer.com/content/pdf/10.1007/978-1-4614-7978-9_5.pdf, last visited on Jan. 31, 2022, 46 pages.
Eroshenko, N et al. (Jul. 2020, e-pub. Jun. 17, 2020). Implications of Antibody-Dependent Enhancement of Infection for SARS-CoV-2 Countermeasures, Nat. Biotechnol. 38:789-791.
Eureka Therapeutics. (Dec. 14, 2020). "Eureka Therapeutics Announces Successful Preclinical Results of InvisiMask™ Human Antibody Nasal Spray Against SARS-CoV-2 Infection," Press Release, located at https://www.eurekatherapeutics.com/media/press-releases/121420/, last visited on Jan. 28, 2022, 3 pages.
Eureka Therapeutics. (Dec. 14, 2020). "InvisiMaskTM Nasal Spray," Web Brochure (FAQ), located at https://www.eurekatherapeutics.com/faqpdf/?utm_source=faq_pdf&utm_medium=hyperlink&utm_campaign=invisimask_faq, last visited on Jan. 28, 2022, 6 pages.
Eureka Therapeutics. (Dec. 14, 2020). "InvisiMaskTM Nasal Spray," Web Brochure, located at https://www.eurekatherapeutics.com/COVID19/, last visited on Jan. 28, 2022, 5 pages.
FDA. CDER. CMC. (Jul. 2002). "Guidance for Industry, Nasal Spray and Inhalation Solution, Suspension, and Spray Drug Products—Chemistry, Manufacturing, and Controls Documentation," Brochure, U.S. Department of Health and Human Services, Food and Drug Administration, Center for Drug Evaluation and Research (CDER), CMC, 49 pages.
Gizurarson, S. (2012). "Anatomical and Historical Factors Affecting Intranasal Drug and Vaccine Delivery," Current Drug Delivery 9(6):566-582.
GLOBALDATA. (Sep. 17, 2020). "A Nasal Spray Vaccine for COVID-19," Analyst Briefing by Scotty Chung-Siu, MPH, Senior Analyst, 3 pages.
Gomez, C.E. et al. (Mar. 11, 2021). "Emerging SARS-CoV-2 Variants and Impact in Global Vaccination Programs against SARS-CoV-2/COVID-19," Vaccines 9(243):1-13.

(56) References Cited

OTHER PUBLICATIONS

Greenberg, A.S. et al. (Mar. 9, 1995). "A New Antigen Receptor Gene Family That Undergoes Rearrangement And Extensive Somatic Diversification In Sharks" Nature 374(6518):168-173.
Halwe, S. et al. (Jul. 29, 2021). "Intranasal Administration of a Monoclonal Neutralizing Antibody Protects Mice against SARS-CoV-2 Infection," Viruses 13(8):1498, 39 pages.
Hamers-Casterman, C. et al. (Jun. 3, 1993). "Naturally Occurring Antibodies Devoid of Light Chains," Nature 363:446-448.
Hassanzadeh-Ghassabeh, G. et al. (2013, e-pub. Jun. 4, 2013). "Nanobodies and their Potential Applications," Nanomedicine (Lond) 8(6):1013-1026.
He, Y. et al. (2006). "Cross-Neutralization of Human and Palm Civet Severe Acute Respiratory Syndrome Coronaviruses by Antibodies Targeting the Receptor-Binding Domain of Spike Protein," The Journal of Immunology 176:6085-6092.
Higgins, T.S. et al. (2020). "Intranasal Antiviral Drug Delivery and Coronavirus Disease (COVID-19): A State-of-the-Art Review," Preprint Manuscript, Intranasal Antiviral Agents and COVID-19, 37 pages.
Hoffmann, M. et al. (Apr. 16, 2020). "SARS-CoV-2 Cell Entry Depends on ACE2 and TMPRSS2 and Is Blocked by a Clinically Proven Protease Inhibitor," Cell 181:271-280.
Holliger, P. et al. (Jul. 1993). "'Diabodies': Small Bivalent and Bispecific Antibody Fragments," Proceedings of the National Academy of Sciences USA 90:6444-6448.
Honegger, A. et al. (Jun. 8, 2001). "Yet Another Numbering Scheme For Immunoglobulin Variable Domains: An Automatic Modeling And Analysis Tool," J. Mol. Biol. 309:657-670.
Hoogenboom, H.R. et al. (2001). "Overview of Antibody Phage-Display Technology and Its Applications," Chapter 1 in Methods in Molecular Biology, O'Brien et al. ed., Humana Press, Totowa, NJ, 178:1-37.
Hulswit, R.J. et al. (Feb. 12, 2019). "Human coronaviruses OC43 and HKU1 bind to 9-O-acetylated sialic acids via a conserved receptor-binding site in spike protein domain A," PNAS 116(7):2681-2690.
Illum, L. (Dec. 2002). "Nasal Drug Delivery: New Developments and Strategies," Drug Discovery Today 7(23):1184-1189.
Illum, L. et al. (1994). "Chitosan as a Novel Nasal Delivery System for Peptide Drugs," Pharmaceutical Research 11(8):1186-1189.
International Search Report and Written Opinion of the International Searching Authority dated Jan. 4, 2022, for International Patent Application No. PCT/US2021/071893, filed Oct. 14, 2021, 19 pages.
Jansen, F.K. et al. (1982). "Immunotoxins: Hybrid Molecules Combining High Specificity and Potent Cytotoxicity," Immunol. Rev. 62:185-216.
Jones, P. et al. (May 29, 1986). "Replacing The Complementarity-Determining Regions in A Human Antibody With Those From A Mouse," Nature 321:522-525.
Kabat, E.A. et al. (1991). Sequences of Proteins of Immunological Interest, 5th Ed. Public Health Service, National Institutes of Health, Bethesda MD., Table of Contents, 21 pages.
Kabat, E.A. et al. (Oct. 10, 1977). "Unusual Distributions Of Amino Acids In Complementarity-Determining (Hypervariable) Segments Of Heavy And Light Chains Of Immunoglobulins And Their Possible Roles In Specificity Of Antibody-Combining Sites," J. Biol. Chem. 252(19):6609-6616.
Kaye, R.S. et al. (2008, e-pub. Nov. 24, 2008). "Development and Testing of Particulate Formulations For The Nasal Delivery Of Antibodies," Journal of Controlled Release 135(2009): 127-135.
Killen, J.A. et al. (Nov. 1, 1984). "Specific Killing Of Lymphocytes That Cause Experimental Autoimmune Myasthenia Gravis By Ricin Toxin-Acetylcholine Receptor Conjugates," J. Immunol. 133(5):2549-2553.
Koussoroplis, S.J. et al. (2014, e-pub. May 17, 2014). "PEGylation of Antibody Fragments Greatly Increases Their Local Residence Time Following Delivery to the Respiratory Tract," J Control Release 187:91-100.

Kulkarni, V. (Jun. 2012). "Formulation and Characterization of Nasal Sprays, An Examination of Nasal Spray Formulation Parameters and Excipients and Their Influence on Key in Vitro Tests," Web PDF, Inhalation, located at https://www.dptiabs.com/wp-content/uploads/2012/08/Formulation_and_Characterization_of_Nasal_Sprays.pdf, last visited on Jan. 31, 2022, 5 pages.
Lefranc, M.-P. et al., (2015, e-pub, Nov. 5, 2014). "IMGT®, The International ImMunoGeneTics Information System® 25 Years On," Nucleic Acids Res. 43:D413-D422.
Lefranc, M.P. et al. (Jan. 2003). "IMGT Unique Numbering For Immunoglobulin And T Cell Receptor Variable Domains And Ig Superfamily V-Like Domains," Dev. Comp. Immunol. 27(1):55-77.
Li, F. (2016, e-pub. Aug. 25, 2016). "Structure, Function, and Evolution of Coronavirus Spike Proteins," Annu Rev Virol. 3(1):237-261.
Li, W. et al. (2005). "Receptor and viral determinants of SARS-coronavirus adaptation to human ACE2," The EMBO Journal 24(8): 1634-1643.
Lu, G. et al. (Aug. 8, 2013). "Molecular Basis of Binding Between Novel Human Coronavirus MERS-CoV and its Receptor CD26," Nature 500:227-232.
MacCallum, R.M. et al. (1996). "Antibody-Antigen Interactions: Contact Analysis and Binding Site Topography," J. Mol. Biol. 262:732-745.
Marple, B, et al. (2004). "Review Article, Safety Review of Benzalkonium Chloride Used As A Preservative In Intranasal Solutions: An Overview Of Conflicting Data And Opinions," Otolaryngol Head Neck Surg 130:131-41.
Millet, J.K. et al. (2015, e-pub. Nov. 22, 2014). "Host Cell Proteases: Critical determinants of Coronavirus Tropism and Pathogenesis," Virus Research 202:120-134.
Morimoto, B. H. (PhD) (May 6, 2015). "Intranasal Drug Delivery: Drug Development Considerations," slide presentation for CELERION Applied Translational Medicine, 28 pages.
Morrison, S.C. et al. (Nov. 1984). "Chimeric Human Antibody Molecules: Mouse Antigen-Binding Domains With Human Constant Region Domains," Proc. Natl. Acad. Sci. USA 81:6851-6855.
Plückthun, A. (1994). "Antibodies from *Escherichia coli*," in Chapter 11 The Pharmacology of Monoclonal Antibodies, vol. 113, Rosenburg and Moore eds., Springer-Verlag, New York, pp. 269-315, 48 pages.
Presta, L.G. (1992). "Antibody Engineering," Current Opinion in Structural Biology 2:593-596.
Raag, R. et al. (Jan. 1995). "Single-chain Fvs," The FASEB Journal 9:73-80.
Ramakrishnan, S. et al. (Jan. 1984). "Comparison of the Selective Cytotoxic Effects of Immunotoxins Containing Ricin A Chain or Pokeweed Antiviral Protein and Anti-Thy 1.1 Monoclonal Antibodies," Cancer Res. 44:201-208.
Riechmann, L. et al. (Mar. 24, 1988). "Reshaping Human Antibodies for Therapy," Nature 332:323-329.
Riediker, M. et al. (Jul. 27, 2020). "Estimation of Viral Aerosol Emissions From Simulated Individuals With Asymptomatic to Moderate Coronavirus Disease 2019," JAMA Netw Open. 3(7):e2013807, 10 pages.
Scheraga, H.A. (1992). "Predicting Three-Dimensional Structures of Oligopeptides," Rev. Computational Chem. 3:73-142.
Suh, W. et al. (2001). "Anti-JL1 Antibody-Conjugated Poly (L-lysine) for Targeted Gene Delivery to Leukemia T Cells," Journal of Controlled Release 72(2001):171-178.
Sui, J. et al. (Feb. 24, 2004). "Potent Neutralization Of Severe Acute Respiratory Syndrome (SARS) Coronavirus By A Human mAb To S1 Protein That Blocks Receptor Association," 101(8):2536-2541.
Tang, J.W. et al. (Apr. 2021). "Emergence of a New SARS-CoV-2 variant in the UK,"Journal of Infection 82(4):e27-e28.
Taylor, P.C. et al. (Jun. 2021). "Neutralizing Monoclonal Antibodies For Treatment Of COVID-19," Nat Rev Immunol 21:382-393.
Thorat, S. (2016). "Formulation and Product Development of Nasal Spray: An Overview," Scholars Journal of Applied Medical Sciences (SJAMS) 4(8D):2976-2985.
Van Den Brink, E.N. et al. (Feb. 2005). "Molecular and Biological Characterization of Human Monoclonal Antibodies Binding to the

(56) References Cited

OTHER PUBLICATIONS

Spike and Nucleocapsid Proteins of Severe Acute Respiratory Syndrome Coronavirus," Journal of Virology 79(3):1635-1644.
Vitetta, E.S. et al. (Nov. 20, 1987). "Redesigning Nature's Poisons to Create Anti-Tumor Reagents," Science 238:1098-1104.
Walls, A.C. et al. (Apr. 16, 2020). "Structure, Function, and Antigenicity of the SARS-Cov-2 Spike Glycoprotein," Cell 180:281-292.
Walsh, S. et al. (Oct. 2004). "Extended Nasal Residence Time of Lysostaphin and an Anti-Staphylococcal Monoclonal Antibody by Delivery in Semisolid or Polymeric Carriers," Pharm Res. 21 (10): 1770-1775.
Wang, Q. et al., (May 14, 2020). "Structural and Functional Basis of SARS-CoV-2 Entry by Using Human ACE2," Cell 181:894-904.
Wang, W. et al. "Antibody Structure, Instability, and Formulation," J. of Pharmaceutical Sciences 96(1):1-26 (Jan. 2007).
Weltzin, R. et al. (Jul. 1999). "Intranasal Antibody Prophylaxis for Protection Against Viral Disease," Clinical Microbiology Review 12(3):383-393.
Widjaja I. et al. (2019, e-pub. Apr. 2, 2019). "Towards A Solution To MERS: Protective Human Monoclonal Antibodies Targeting Different Domains And Functions Of The MERS-Coronavirus Spike Glycoprotein," Emerging Microbes & Infections 8(1):516-530.
Ye, J. et al. (Jul. 2013). "IgBLAST: An Immunoglobulin Variable Domain Sequence Analysis Tool," Nucleic acids research 41(W1):W34-W40.
Zhang, H. et al., (Dec. 9, 2020). "Intranasal administration of SARS-CoV-2 neutralizing human antibody prevents infection in mice." bioRxiv located at https://doi.org/10.1101/2020.12.08.416677, last visited on Jan. 30, 2022, 14 pages.
Zhou, P. et al. (Mar. 12, 2020, e-pub. Feb. 3, 2020). "A Pneumonia Outbreak Associated With A New Coronavirus Of Probable Bat Origin," Nature 579:270-273.
Zhu, Z. et al. (Jul. 17, 2007). "Potent Cross-Reactive Neutralization Of SARS Coronavirus Isolates By Human Monoclonal Antibodies," PNAS 104(29):12123-12128.
ZOLA In: Monoclonal Antibodies: A Manual of Techniques, © CRC Press Inc., Boca Raton, FL (1987) pp. 147-158.

\* cited by examiner

No Ab     #26

COMPOSITIONS FOR PREVENTING OR TREATING VIRAL AND OTHER MICROBIAL INFECTIONS

CROSS REFERENCE TO RELATED APPLICATIONS

This application claims priority benefits of U.S. Provisional Application No. 63/093,076, filed Oct. 16, 2020, U.S. Provisional Application No. 63/118,570, filed Nov. 25, 2020, and U.S. Provisional Application No. 63/122,432, filed Dec. 7, 2020, the contents of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: SEQLIST.TXT, date recorded: Oct. 13, 2021, size: 138,775 bytes).

FIELD

The invention relates to compositions and methods for preventing or treating viral and other microbial infections, such as coronavirus infections.

BACKGROUND

Respiratory microbial infections, including viral and bacterial infections, are a leading cause of adult and pediatric illness and mortality worldwide. There is a large unmet need for novel treatment and prevention methods that more effectively target these infections. The rapid spread and high morbidity and mortality of SARS-CoV-2 infection, the virus that causes COVID-19, has resulted in severe human health and economic impacts in 2020. The number of SARS-CoV-2 infection cases and hospitalizations have surged as increases in social activity and mobility have led to increased incidences of viral transmission. SARS-CoV-2 infection is transmitted primarily from person-to-person through respiratory droplets when an infected person talks, sneezes, or coughs. Infectious droplets can land in the mouths or noses of people who are nearby or possibly be inhaled into the lungs, with the upper respiratory mucosal surfaces being the initial and predominant sites for the viral infection. In addition, airborne transmission of the virus can occur through aerosol particles that linger in the air for longer periods of time and can travel further from their origin than droplets. Facemasks are being used as the first line of defense, but they are passive barriers to infection and their efficacy is imperfect. Therapeutic discovery and prevention efforts are necessary to halt the pandemic spread of SARS-CoV-2.

Therapeutic drug development for COVID-19 treatment includes small-molecule and large-molecule (e.g., antibodies) drug candidates. Although there are currently no approved therapeutic antibodies, a number of neutralizing antibodies that target the Receptor Binding Domain (RBD) of SARS-CoV-2 spike (S) protein are in clinical trials. Paradoxically, such antibodies may enable viral entry via antibody-dependent enhancement (ADE) of infection, a significant concern when using therapeutic antibodies. ADE occurs when antibodies facilitate viral entry into host cells and enhance viral infection in these cells. ADE has been observed for many viruses. Antibodies that target one serotype of viruses, but only subneutralize another, often lead to ADE of the latter viruses. ADE has significant impact on viral epidemiology, especially for secondary infections by closely related viral subtypes, as well as development of vaccines and antibody-based therapies against viral infections. See, Eroshenko, N et al., 2020 Nat. Biotechnol. 38:789-791.

The current pharmaceutical prevention strategy for COVID-19 is focused on the development of SARS-CoV-2 vaccines; however, such vaccine approaches may be burdened by viral gene mutations and ADE probabilities. Therefore, safe and flexible methods to prevent SARS-CoV-2 infection are of urgent demand. Such methods are also needed to prevent other respiratory microbial infections.

BRIEF SUMMARY

The present application provides compositions and methods for preventing or treating an infection caused by a pathogen that infects through a mucosa in an individual, such as a coronavirus (e.g., SARS-CoV-2) infection. Thus, one aspect of the present application provides a chimeric protein comprising: (a) a target-binding moiety that specifically binds to a component of a pathogen (e.g., SARS-CoV, SARS-CoV-2, including variants thereof, that infects through a mucosa (e.g., the nasal passage); and (b) a mucoadhesive peptide fragment comprising about 5 to about 50 positively charged amino acid residues, wherein the mucoadhesive peptide fragment facilitates attachment of the chimeric protein to the mucosa.

In some embodiments according to any one of the chimeric proteins described above, the chimeric protein comprises a single polypeptide chain. In some embodiments, the chimeric protein comprises two or more polypeptide chains. In some embodiments, the chimeric protein comprises two or more mucoadhesive peptide fragments. In some embodiments, each of the two or more mucoadhesive peptide fragments comprises about 5 to about 50 positively charged amino acid residues. In some embodiments, the mucoadhesive peptide fragment or each of the two or more mucoadhesive peptide fragments comprises about 6 to about 30 comprises about 5 to about 50 positively (e.g., about 6-30 such as 12) charged amino acid residues. In some embodiments, the chimeric protein comprises two or more mucoadhesive peptide fragments, wherein each of the two or more mucoadhesive peptide fragments comprises about 11 to about 15 positively charged amino acid residues.

In some embodiments according to any one of the chimeric proteins described above, the mucoadhesive peptide fragment comprises about 6 to about 30 positively charged amino acid residues, wherein the positively charged amino acid residues are selected from the group consisting of lysine, arginine, histidine, ornithine, and combinations thereof. In some embodiments, the positively charged amino acid residues are lysine residues. In some embodiments, the mucoadhesive peptide fragment comprises about 6 to about 30 (e.g., 6, 12, 24, or 30) lysine residues. In some embodiments, the positively charged amino acid residues are arginine residues. In some embodiments, the mucoadhesive peptide fragment comprises about 6 to about 30 (e.g., 6, 12, 24, or 30) arginine residues. In some embodiments, the positively charged amino acid residues are histidine residues. In some embodiments, the mucoadhesive peptide fragment comprises about 6 to about 30 (e.g., 6, 12, 24, or 30) histidine residues. In some embodiments, the positively charged amino acid residues are ornithine residues. In some embodiments, the mucoadhesive peptide fragment comprises about 6 to about 30 (e.g., 6, 12, 24, or 30) ornithine residues.

In some embodiments according to any one of the chimeric proteins described above, the positively charged amino residues are contiguous with each other. In some embodiments, the positively charged amino acid residues are interspersed with non-positively charged amino acid residues. In some embodiments, at least 50% of the amino acid residues in the mucoadhesive peptide fragment are positively charged amino acid residues. In some embodiments, the mucoadhesive peptide fragment is no more than about 15 kD.

In some embodiments according to any one of the chimeric proteins described above, the mucoadhesive peptide fragment has an isoelectric point (pI) higher than the pH of the mucosa.

In some embodiments according to any one of the chimeric proteins described above, the half-life of the chimeric protein on the mucosa is at least 12 hours. In some embodiments, the half-life of the chimeric protein on the mucosa is at least 24 hours.

In some embodiments according to any one of the chimeric proteins described above, the mucoadhesive peptide fragment does not facilitate penetration of the chimeric protein into a cell of the mucosa.

In some embodiments according to any one of the chimeric proteins described above, the mucoadhesive peptide fragment does not disrupt folding of the chimeric protein within a host cell expressing the chimeric protein.

In some embodiments according to any one of the chimeric proteins described above, the mucoadhesive peptide fragment does not interfere the specific binding between the target-binding moiety and the component of the pathogen.

In some embodiments according to any one of the chimeric proteins described above, the mucoadhesive peptide fragment is covalently fused to the target-binding moiety. In some embodiments, mucoadhesive peptide fragment is fused to the target-binding moiety via a bond or a peptide linker (e.g., a flexible linker). In some embodiments, the mucoadhesive peptide fragment is chemically conjugated to the target-binding moiety.

In some embodiments according to any one of the chimeric proteins described above, the component of the pathogen is a surface molecule. In some embodiments, the component of the pathogen is a secreted molecule.

In some embodiments according to any one of the chimeric proteins described above, the target-binding moiety comprises an inhibitory polypeptide that inhibits binding of the component of the pathogen to a receptor on a cell of the mucosa. In some embodiments, the target-binding moiety comprises a natural receptor of the component of the pathogen or a fragment derived from the natural receptor. In some embodiments, the target-binding moiety comprises an extracellular binding domain (EBD) of the natural receptor. In some embodiments, the target-binding moiety comprises an extracellular binding domain (EBD) of angiotensin-converting enzyme 2 (ACE2).

In some embodiments according to any one of the chimeric proteins described above, the target-binding moiety comprises an antibody moiety. In some embodiments, the antibody moiety is a full-length antibody. In some embodiments, the antibody moiety is selected from the group consisting of an IgG, an IgA, an IgM, and an IgD. In some embodiments, the antibody moiety is an antigen-binding fragment selected from the group consisting of a Fab, a Fab', a (Fab')$_2$, an Fv, a single chain Fv (scFv), an scFv-Fc, a disulfide stabilized Fv fragment (dsFv), a (dsFv)$_2$, an scFv dimer, a domain antibody, a camelized single domain antibody, a bivalent domain antibody, a minibody, and a VHH. In some embodiments, the antibody moiety is a human, humanized, camelid, or chimeric antibody or an antigen-binding fragment thereof. In some embodiments, the mucoadhesive peptide fragment is fused to the C-terminus of a heavy chain of the antibody moiety. In some embodiments, the chimeric protein comprises (1) two polypeptide chains each comprising from the N-terminus to the C-terminus: an antibody heavy chain of the antibody moiety, optionally a peptide linker, and the mucoadhesive peptide fragment; and (2) two polypeptide chains each comprising an antibody light chain of the antibody moiety. In some embodiments, the mucoadhesive peptide fragment is fused to the C-terminus of a light chain of the antibody moiety.

In some embodiments according to any one of the chimeric proteins described above, the pathogen is a bacterium that causes a respiratory infection. In some embodiments, the bacterium is selected from the group consisting of *Streptococcus pyogenes, Haemophilus influenzae, Streptococcus pneumoniae, Mycoplasma pneumoniae, Moraxella catarrhalis, Pseudomonas aeruginosa*, and *Mycobacterium tuberculosis*.

In some embodiments according to any one of the chimeric proteins described above, the pathogen is a virus that causes a respiratory infection. In some embodiments, the virus is selected from the group consisting of coronaviruses, respiratory syncytial viruses, influenza viruses, and adenoviruses. In some embodiments, the virus is a coronavirus. In some embodiments, the virus is selected from the group consisting of SARS-CoV, SARS-CoV-2, and MERS-CoV. In some embodiments, the virus is SARS-CoV-2. In some embodiments, the SARS-CoV-2 is WIV4 (also known as "hCoV-19/WIV04/2019" or "BetaCoV/WIV04/2019"). In some embodiments, the SARS-CoV-2 is a variant selected from the group consisting of a B.1.1.7 variant, a B.1.351 variant, a B.1.526 variant, a B1.526.1 variant, a B1.617 variant, a B.1.617.1 variant, a B.1.617.2 variant, a B1.617.3 variant, a P.2 variant, a P.1 (B.1.1.28.1) variant, an A.23.1 variant, a CAL.20C variant, a B.1.427 variant, a B.1.429 variant, a B.1.525 variant, and a P.1.351 variant. In some embodiments, the SARS-CoV-2 is a B.1.1.7 variant. In some embodiments, the SARS-CoV-2 is a B.1.351 variant. In some embodiments, the SARS-CoV-2 is a B.1.617.2 variant. In some embodiments, the component of the pathogen is a spike (S) protein.

In some embodiments according to any one of the chimeric proteins described above, the target-binding moiety comprises: (1) a VH comprising an HC-CDR1 comprising the amino acid sequence of SEQ ID NO: 1, an HC-CDR2 comprising the amino acid sequence of SEQ ID NO: 2, and an HC-CDR3 comprising the amino acid sequence of SEQ ID NO: 3; a VL comprising an LC-CDR1 comprises the amino acid sequence of SEQ ID NO: 4, an LC-CDR2 comprising the amino acid sequence of SEQ ID NO: 5, and an LC-CDR3 comprising the amino acid sequence of SEQ ID NO: 6; (2) a VH comprising an HC-CDR1 comprising the amino acid sequence of SEQ ID NO: 7, an HC-CDR2 comprising the amino acid sequence of SEQ ID NO: 8, and an HC-CDR3 comprising the amino acid sequence of SEQ ID NO: 9; a VL comprising an LC-CDR1 comprises the amino acid sequence of SEQ ID NO: 10, an LC-CDR2 comprising the amino acid sequence of SEQ ID NO: 11, and an LC-CDR3 comprising the amino acid sequence of SEQ ID NO: 12; (3) a VH comprising an HC-CDR1 comprising the amino acid sequence of SEQ ID NO: 13, an HC-CDR2 comprising the amino acid sequence of SEQ ID NO: 14, and an HC-CDR3 comprising the amino acid sequence of SEQ ID NO: 15; a VL comprising an LC-CDR1 comprises the amino acid sequence of SEQ ID NO: 16, the HC-LDR2 comprises the amino acid sequence of SEQ ID NO: 17, and an LC-CDR3 comprising the amino acid sequence of SEQ ID NO: 18; (4) a VH comprising an HC-CDR1 comprising the amino acid sequence of SEQ ID NO: 19, an HC-CDR2 comprising the amino acid sequence of SEQ ID NO: 20, and an HC-CDR3 comprising the amino acid sequence of SEQ ID NO: 21; a VL comprising an LC-CDR1 comprises the amino acid sequence of SEQ ID NO: 22, an LC-CDR2 comprising the amino acid sequence of SEQ ID NO: 23, and an LC-CDR3 comprising the amino acid sequence of SEQ ID NO: 24; (5) a VH comprising an HC-CDR1 comprising the amino acid sequence of SEQ ID NO: 25, an HC-CDR2 comprising the amino acid sequence of SEQ ID NO: 26, and an HC-CDR3 comprising the amino acid sequence of SEQ ID NO: 27; a VL comprising LC-CDR1 comprises the amino acid sequence of SEQ ID NO: 28, an LC-CDR2 comprising the amino acid sequence of SEQ ID NO: 29, and an LC-CDR3 comprising the amino acid sequence of SEQ ID NO: 30; (6) a VH comprising an HC-CDR1 comprising the amino acid sequence of SEQ ID NO: 31, an HC-CDR2 comprising the amino acid sequence of SEQ ID NO: 32, and an HC-CDR3 comprising the amino acid sequence of SEQ ID NO: 33; a VL comprising LC-CDR1 comprises the amino acid sequence of SEQ ID NO: 34, an LC-CDR2 comprising the amino acid sequence of SEQ ID NO: 35, and an LC-CDR3 comprising the amino acid sequence of SEQ ID NO: 36; (7) a VH comprising an HC-CDR1 comprising the amino acid sequence of SEQ ID NO: 37, an HC-CDR2 comprising the amino acid sequence of SEQ ID NO: 38, and an HC-CDR3 comprising the amino acid sequence of SEQ ID NO: 39; a VL comprising LC-CDR1 comprises the amino acid sequence of SEQ ID NO: 40, an LC-CDR2 comprising the amino acid sequence of SEQ ID NO: 41, and an LC-CDR3 comprising the amino acid sequence of SEQ ID NO: 42; (8) a VH comprising an HC-CDR1 comprising the amino acid sequence of SEQ ID NO: 43, an HC-CDR2 comprising the amino acid sequence of SEQ ID NO: 44, and an HC-CDR3 comprising the amino acid sequence of SEQ ID NO: 45; a VL comprising LC-CDR1 comprises the amino acid sequence of SEQ ID NO: 46, an LC-CDR2 comprising the amino acid sequence of SEQ ID NO: 47, and an LC-CDR3 comprising the amino acid sequence of SEQ ID NO: 48; (9) VH comprising an HC-CDR1 comprising the amino acid sequence of SEQ ID NO: 49, an HC-CDR2 comprising the amino acid sequence of SEQ ID NO: 50, and an HC-CDR3 comprising the amino acid sequence of SEQ ID NO: 51; a VL comprising LC-CDR1 comprises the amino acid sequence of SEQ ID NO: 52, an LC-CDR2 comprising the amino acid sequence of SEQ ID NO: 53, and an LC-CDR3 comprising the amino acid sequence of SEQ ID NO: 54; or (10) a VH comprising an HC-CDR1 comprising the amino acid sequence of SEQ ID NO: 55, an HC-CDR2 comprising the amino acid sequence of SEQ ID NO: 56, and an HC-CDR3 comprising the amino acid sequence of SEQ ID NO: 57; a VL comprising LC-CDR1 comprises the amino acid sequence of SEQ ID NO: 58, an LC-CDR2 comprising the amino acid sequence of SEQ ID NO: 59, and an LC-CDR3 comprising the amino acid sequence of SEQ ID NO: 60. In some embodiments, the target-binding moiety comprises: a VH comprising a HC-CDR1 comprising the amino acid sequence of SEQ ID NO: 37, an HC-CDR2 comprising the amino acid sequence of SEQ ID NO: 38, and an HC-CDR3 comprising the amino acid sequence of SEQ ID NO: 39; and a VL comprising a LC-CDR1 comprising the amino acid sequence of SEQ ID NO: 40, an HC-CDR2 comprising the amino acid sequence of SEQ ID NO: 41, and an HC-CDR3 comprising the amino acid sequence of SEQ ID NO: 42

In some embodiments according to any one of the chimeric proteins described above, the target-binding moiety comprises: (1) a VH comprising an amino acid sequence having at least about 90% (e.g., at least 91%, 92%, 93%, 94%, 95%, 96%, 97%, 98%, or 99%, or 100%) sequence identity to the amino acid sequence of SEQ ID NO: 61, and a VL comprising an amino acid sequence having at least about 90% (e.g., at least 91%, 92%, 93%, 94%, 95%, 96%, 97%, 98%, or 99%, or 100%) sequence identity to the amino acid sequence of SEQ ID NO: 62; (2) a VH comprising an amino acid sequence having at least about 90% (e.g., at least 91%, 92%, 93%, 94%, 95%, 96%, 97%, 98%, or 99%, or 100%) sequence identity to the amino acid sequence of SEQ ID NO: 63, and a VL comprising an amino acid sequence having at least about 90% (e.g., at least 91%, 92%, 93%, 94%, 95%, 96%, 97%, 98%, or 99%, or 100%) sequence identity to the amino acid sequence of SEQ ID NO: 64; (3) a VH comprising an amino acid sequence having at least about 90% (e.g., at least 91%, 92%, 93%, 94%, 95%, 96%, 97%, 98%, or 99%, or 100%) sequence identity to the amino acid sequence of SEQ ID NO: 65, and a VL comprising an amino acid sequence having at least about 90% sequence identity to the amino acid sequence of SEQ ID NO: 66; (4) a VH comprising an amino acid sequence having at least about 90% (e.g., at least 91%, 92%, 93%, 94%, 95%, 96%, 97%, 98%, or 99%, or 100%) sequence identity to the amino acid sequence of SEQ ID NO: 67, and a VL comprising an amino acid sequence having at least about 90% (e.g., at least 91%, 92%, 93%, 94%, 95%, 96%, 97%, 98%, or 99%, or 100%) sequence identity to the amino acid sequence of SEQ ID NO: 68; (5) a VH comprising an amino acid sequence having at least about 90% (e.g., at least 91%, 92%, 93%, 94%, 95%, 96%, 97%, 98%, or 99%, or 100%) sequence identity to the amino acid sequence of SEQ ID NO: 69 and a VL comprising an amino acid sequence having at least about 90% (e.g., at least 91%, 92%, 93%, 94%, 95%, 96%, 97%, 98%, or 99%, or 100%) sequence identity to the amino acid sequence of SEQ ID NO: 70; (6) a VH comprising an amino acid sequence having at least about 90% (e.g., at least 91%, 92%, 93%, 94%, 95%, 96%, 97%, 98%, or 99%, or 100%) sequence identity to the amino acid sequence of SEQ ID NO: 71, and a VL comprising an amino acid sequence having at least about 90% (e.g., at least 91%, 92%, 93%, 94%, 95%, 96%, 97%, 98%, or 99%, or 100%) sequence identity to the amino acid sequence of SEQ ID NO: 72; (7) a VH comprising an amino acid sequence having at least about 90% (e.g., at least 91%, 92%, 93%, 94%, 95%, 96%, 97%, 98%, or 99%, or 100%) sequence identity to the amino acid sequence of SEQ ID NO: 73, and a VL comprising an amino acid sequence having at least about 90% (e.g., at least 91%, 92%, 93%, 94%, 95%, 96%, 97%, 98%, or 99%, or 100%) sequence identity to the amino acid sequence of SEQ ID NO: 74; (8) a VH comprising an amino acid sequence having at least about 90% sequence identity to the amino acid sequence of SEQ ID NO: 75, and a VL comprising an amino acid sequence having at least about 90% (e.g., at least 91%, 92%, 93%, 94%, 95%, 96%, 97%, 98%, or 99%, or 100%) sequence identity to the amino acid sequence of SEQ ID NO: 76; (9) a VH comprising an amino acid sequence having at least about 90% (e.g., at least 91%, 92%, 93%, 94%, 95%, 96%, 97%, 98%, or 99%, or 100%) sequence identity to the amino acid sequence of SEQ ID NO: 77, and a VL comprising an amino acid sequence having at least about 90% (e.g., at least 91%, 92%, 93%, 94%, 95%, 96%, 97%, 98%, or 99%, or 100%) sequence identity to the amino acid sequence of SEQ ID NO: 78; or (10) a VH comprising an amino acid sequence having at least about 90% (e.g., at least 91%, 92%, 93%, 94%, 95%, 96%, 97%, 98%, or 99%, or 100%) sequence identity to the amino acid sequence of SEQ ID NO: 79, and a VL comprising an amino acid sequence having at least about 90% (e.g., at least 91%, 92%, 93%, 94%, 95%, 96%, 97%, 98%, or 99%, or 100%) sequence identity to the amino acid sequence of SEQ ID NO: 80. In some embodiments, the target-binding moiety comprises a VH comprising an amino acid sequence having at least about 90% (e.g., at least 91%, 92%, 93%, 94%, 95%, 96%, 97%, 98%, or 99%, or 100%) sequence identity to the amino acid sequence of SEQ ID NO: 75, and a VL comprising an amino acid sequence having at least about 90% (e.g., at least 91%, 92%, 93%, 94%, 95%, 96%, 97%, 98%, or 99%, or 100%) sequence identity to the amino acid sequence of SEQ ID NO: 76.

In some embodiments, according to any one of the chimeric proteins described above, the target-binding moiety comprises a scFv comprising an amino acid sequence having at least about 90% (e.g., at least 91%, 92%, 93%, 94%, 95%, 96%, 97%, 98%, or 99%, or 100%) sequence identity to the amino acid sequence of any one of SEQ ID NOs: 81-90. In some embodiments, the target-binding moiety comprises a scFv comprising an amino acid sequence having at least about 90% (e.g., at least 91%, 92%, 93%, 94%, 95%, 96%, 97%, 98%, or 99%, or 100%) sequence identity to the amino acid sequence of SEQ ID NO: 87.

In some embodiments according to any one of the chimeric proteins described above, the mucosa is selected from the group consisting of nasal mucosa, larynx mucosa, trachea mucosa, bronchi mucosa, lung mucosa, eye mucosa, and combinations thereof.

Another aspect of the present application provides a pharmaceutical composition comprising any one of the chimeric proteins described above, and a pharmaceutically acceptable carrier. In some embodiments, the pharmaceutical composition comprises a plurality of chimeric proteins, wherein the target-binding moieties of the chimeric proteins are different from each other. In some embodiments, there is provided a pharmaceutical composition comprising at least two chimeric proteins according to any one of the chimeric proteins described above, wherein the two chimeric proteins have different target-binding moieties.

In some embodiments according to any one of the pharmaceutical compositions described above, the chimeric protein is present at a concentration of about 0.6 mg/mL to about 6 mg/mL (e.g., about 1 mg/mL to about 3 mg/mL).

In some embodiments according to any one of the pharmaceutical compositions described above, the pharmaceutically acceptable carrier comprises a stabilizing agent that maintains the weak reducing environment in nasal area. In some embodiments, the stabilizing agent is methionine. In some embodiments, the methionine is present at a concentration of about 0.05% to about 0.2% (e.g., about 0.075% to about 0.125%, such as about 0.1%) (w/w).

In some embodiments according to any one of the pharmaceutical compositions described above, the pharmaceutical composition has a pH of about 4.5 to about 7.5, e.g., about 6.0 to about 7.0, such as about 6.5. In some embodiments, the pharmaceutically acceptable carrier comprises a buffering agent, such as a citrate buffer or a phosphate buffer. In some embodiments, the pharmaceutically acceptable carrier comprises a citrate buffer. In some embodiments, the pharmaceutically acceptable carrier comprises about 20 mM to about 50 mM (e.g., about 20 mM to about 30 mM, such as about 25 mM) citrate.

In some embodiments according to any one of the pharmaceutical compositions described above, the pharmaceutical composition has an osmolality of about 230 to about 330 Osm/kg (e.g., about 250 to about 300 Osm/kg, such as about 280 Osm/kg). In some embodiments, the pharmaceutically acceptable carrier comprises an osmolality adjusting agent. In some embodiments, the osmolality adjusting agent is NaCl. In some embodiments, the pharmaceutically acceptable carrier comprises about 100 mM to about 150 mM (e.g., about 110 mM to about 130 mM, such as about 125 mM) NaCl.

In some embodiments according to any one of the pharmaceutical compositions described above, the pharmaceutically acceptable carrier further comprises a surfactant. In some embodiments, the surfactant is polysorbate 80. In some embodiments, the pharmaceutically acceptable carrier comprises about 0.01% to about 0.1% (e.g., about 0.01% to about 0.05%, such as about 0.02%) (w/w) polysorbate 80.

In some embodiments according to any one of the pharmaceutical compositions described above, the pharmaceutically acceptable carrier further comprises a viscosity-enhancing agent. In some embodiments, the viscosity-enhancing agent is selected from the group consisting of glycerin, dextran and hydroxyethylcellulose. In some embodiments, the viscosity-enhancing agent is glycerin. In some embodiments, the pharmaceutically acceptable carrier comprises about 1% to about 10% (e.g., about 2.5% to about 7.5%, such as about 5%) (w/w) glycerin.

In some embodiments according to any one of the pharmaceutical compositions described above, the pharmaceutically acceptable carrier further comprises a preservative. In some embodiments, the preservative is potassium sorbate. In some embodiments, the pharmaceutically acceptable carrier comprises about 0.05% to about 0.2% (e.g., about 0.075% to about 0.125%, such as about 0.1%) (w/w) potassium sorbate.

In some embodiments according to any one of the pharmaceutical compositions described above, the pharmaceutically acceptable carrier comprises about 25 mM citrate at pH 6.5, about 125 mM NaCl, about 5% glycerin, about 0.1% methionine, about 0.02% polysorbate 80, and about 0.1% potassium sorbate.

In some embodiments according to any one of the pharmaceutical compositions described above, the SARS-CoV-2 is WIV4 (i.e., hCoV-19/WIV04/2019 or BetaCoV/WIV04/2019). In some embodiments, the SARS-CoV-2 is a variant selected from the group consisting of a B.1.1.7 variant, a B.1.351 variant, a B.1.526 variant, a B1.526.1 variant, a B1.617 variant, a B.1.617.1 variant, a B.1.617.2 variant, a B1.617.3 variant, a P.2 variant, a P.1 (B.1.1.28.1) variant, an A.23.1 variant, a CAL.20C variant, a B.1.427 variant, a B.1.429 variant, a B.1.525 variant, and a P.1.351 variant. In some embodiments, the SARS-CoV-2 is a B.1.1.7 variant. In some embodiments, the SARS-CoV-2 is a B.1.351 variant. In some embodiments, the SARS-CoV-2 is a B.1.617.2 variant. In some embodiments, the pharmaceutical composition is for preventing or treating infection by a plurality of SARS-CoV-2 variants.

In some embodiments according to any one of the pharmaceutical compositions described above, the pharmaceutical composition is for nasal administration, e.g., via a nasal spray or a nebulizer.

Another aspect of the present application provides an isolated nucleic acid or a set of isolated nucleic acids encoding a chimeric protein according to any one of the chimeric proteins described above. In some embodiments, the present application provides a vector comprising any one of the nucleic acids described above, or a set of vectors comprising any set of nucleic acids described above.

In some embodiments, the present application provides a host cell comprising any one of the chimeric proteins described above, the nucleic acid or set of nucleic acids described above, or the vector or the set of vectors described above. In some embodiments, the present application provides a method of preparing a chimeric protein, comprising: (a) culturing any one of the host cells described above under conditions effective to express the chimeric protein; and (b) obtaining the expressed chimeric protein from the host cell.

Another aspect of the present application provides a method of preventing or treating an infection caused by a pathogen that infects through a mucosa in an individual, comprising administering to the individual an effective amount of any one of the chimeric proteins described above, or any one of the pharmaceutical compositions described above. In some embodiments, the chimeric protein or the pharmaceutical composition is administered to the individual before the individual is exposed to the pathogen. In some embodiments, the chimeric protein or the pharmaceutical composition is administered to the individual within about 72 hours after the individual is exposed to the pathogen. In some embodiments, the chimeric protein or the pharmaceutical composition is administered topically onto the mucosa. In some embodiments, the chimeric protein or the pharmaceutical composition is administered via a nasal spray, an inhaler, a nebulizer, or an eye drop. In some embodiments, the chimeric protein or the pharmaceutical composition is administered once or twice daily. In some embodiments, the chimeric protein is administered at a dose of about 0.1 mg-1 mg (e.g., per nostril or per eye).

One aspect of the present application provides an isolated antibody or antigen binding fragment thereof, comprising: (1) a VH comprising a HC-CDR1 sequence, a HC-CDR2 sequence, and a HC-CDR3 sequence of the VH sequence of SEQ ID NO: 61 and a VL comprising a LC-CDR1 sequence, a LC-CDR2 sequence, and a LC-CDR3 sequence of the VL sequence SEQ ID NO: 62; (2) a VH comprising a HC-CDR1 sequence, a HC-CDR2 sequence, and a HC-CDR3 sequence of the VH sequence of SEQ ID NO: 63 and a VL comprising a LC-CDR1 sequence, a LC-CDR2 sequence, and a LC-CDR3 sequence of the VL sequence SEQ ID NO: 64; (3) a VH comprising a HC-CDR1 sequence, a HC-CDR2 sequence, and a HC-CDR3 sequence of the VH sequence of SEQ ID NO: 65 and a VL comprising a LC-CDR1 sequence, a LC-CDR2 sequence, and a LC-CDR3 sequence of the VL sequence SEQ ID NO: 66; (4) a VH comprising a HC-CDR1 sequence, a HC-CDR2 sequence, and a HC-CDR3 sequence of the VH sequence of SEQ ID NO: 67 and a VL comprising a LC-CDR1 sequence, a LC-CDR2 sequence, and a LC-CDR3 sequence of the VL sequence SEQ ID NO: 68; (5) a VH comprising a HC-CDR1 sequence, a HC-CDR2 sequence, and a HC-CDR3 sequence of the VH sequence of SEQ ID NO: 69 and a VL comprising a LC-CDR1 sequence, a LC-CDR2 sequence, and a LC-CDR3 sequence of the VL sequence SEQ ID NO: 70; (6) a VH comprising a HC-CDR1 sequence, a HC-CDR2 sequence, and a HC-CDR3 sequence of the VH sequence of SEQ ID NO: 71 and a VL comprising a LC-CDR1 sequence, a LC-CDR2 sequence, and a LC-CDR3 sequence of the VL sequence SEQ ID NO: 72; (7) a VH comprising a HC-CDR1 sequence, a HC-CDR2 sequence, and a HC-CDR3 sequence of the VH sequence of SEQ ID NO: 73 and a VL comprising a LC-CDR1 sequence, a LC-CDR2 sequence, and a LC-CDR3 sequence of the VL sequence SEQ ID NO: 74; (8) a VH comprising a HC-CDR1 sequence, a HC-CDR2 sequence, and a HC-CDR3 sequence of the VH sequence of SEQ ID NO: 75 and a VL comprising a LC-CDR1 sequence, a LC-CDR2 sequence, and a LC-CDR3 sequence of the VL sequence SEQ ID NO: 76; (9) a VH comprising a HC-CDR1 sequence, a HC-CDR2 sequence, and a HC-CDR3 sequence of the VH sequence of SEQ ID NO: 77 and a VL comprising a LC-CDR1 sequence, a LC-CDR2 sequence, and a LC-CDR3 sequence of the VL sequence SEQ ID NO: 78; or (10) a VH comprising a HC-CDR1 sequence, a HC-CDR2 sequence, and a HC-CDR3 sequence of the VH sequence of SEQ ID NO: 79 and a VL comprising a LC-CDR1 sequence, a LC-CDR2 sequence, and a LC-CDR3 sequence of the VL sequence SEQ ID NO: 80.

In some embodiments according to any one of the isolated antibodies or antigen binding fragments thereof described above, the isolated antibody or antigen binding fragment thereof comprises: (1) a VH comprising an HC-CDR1 comprising the amino acid sequence of SEQ ID NO: 1, an HC-CDR2 comprising the amino acid sequence of SEQ ID NO: 2, and an HC-CDR3 comprising the amino acid sequence of SEQ ID NO: 3; a VL comprising an LC-CDR1 comprises the amino acid sequence of SEQ ID NO: 4, an LC-CDR2 comprising the amino acid sequence of SEQ ID NO: 5, and an LC-CDR3 comprising the amino acid sequence of SEQ ID NO: 6; (2) a VH comprising an HC-CDR1 comprising the amino acid sequence of SEQ ID NO: 7, an HC-CDR2 comprising the amino acid sequence of SEQ ID NO: 8, and an HC-CDR3 comprising the amino acid sequence of SEQ ID NO: 9; a VL comprising an LC-CDR1 comprises the amino acid sequence of SEQ ID NO: 10, an LC-CDR2 comprising the amino acid sequence of SEQ ID NO: 11, and an LC-CDR3 comprising the amino acid sequence of SEQ ID NO: 12; (3) a VH comprising an HC-CDR1 comprising the amino acid sequence of SEQ ID NO: 13, an HC-CDR2 comprising the amino acid sequence of SEQ ID NO: 14, and an HC-CDR3 comprising the amino acid sequence of SEQ ID NO: 15; a VL comprising an LC-CDR1 comprises the amino acid sequence of SEQ ID NO: 16, the HC-LDR2 comprises the amino acid sequence of SEQ ID NO: 17, and an LC-CDR3 comprising the amino acid sequence of SEQ ID NO: 18; (4) a VH comprising an HC-CDR1 comprising the amino acid sequence of SEQ ID NO: 19, an HC-CDR2 comprising the amino acid sequence of SEQ ID NO: 20, and an HC-CDR3 comprising the amino acid sequence of SEQ ID NO: 21; a VL comprising an LC-CDR1 comprises the amino acid sequence of SEQ ID NO: 22, an LC-CDR2 comprising the amino acid sequence of SEQ ID NO: 23, and an LC-CDR3 comprising the amino acid sequence of SEQ ID NO: 24; (5) a VH comprising an HC-CDR1 comprising the amino acid sequence of SEQ ID NO: 25, an HC-CDR2 comprising the amino acid sequence of SEQ ID NO: 26, and an HC-CDR3 comprising the amino acid sequence of SEQ ID NO: 27; a VL comprising LC-CDR1 comprises the amino acid sequence of SEQ ID NO: 28, an LC-CDR2 comprising the amino acid sequence of SEQ ID NO: 29, and an LC-CDR3 comprising the amino acid sequence of SEQ ID NO: 30; (6) a VH comprising an HC-CDR1 comprising the amino acid sequence of SEQ ID NO: 31, an HC-CDR2 comprising the amino acid sequence of SEQ ID NO: 32, and an HC-CDR3 comprising the amino acid sequence of SEQ ID NO: 33; a VL comprising LC-CDR1 comprises the amino acid sequence of SEQ ID NO: 34, an LC-CDR2 comprising the amino acid sequence of SEQ ID NO: 35, and an LC-CDR3 comprising the amino acid sequence of SEQ ID NO: 36; (7) a VH comprising an HC-CDR1 comprising the amino acid sequence of SEQ ID NO: 37, an HC-CDR2 comprising the amino acid sequence of SEQ ID NO: 38, and an HC-CDR3 comprising the amino acid sequence of SEQ ID NO: 39; a VL comprising LC-CDR1 comprises the amino acid sequence of SEQ ID NO: 40, an LC-CDR2 comprising the amino acid sequence of SEQ ID NO: 41, and an LC-CDR3 comprising the amino acid sequence of SEQ ID NO: 42; (8) a VH comprising an HC-CDR1 comprising the amino acid sequence of SEQ ID NO: 43, an HC-CDR2 comprising the amino acid sequence of SEQ ID NO: 44, and an HC-CDR3 comprising the amino acid sequence of SEQ ID NO: 45; a VL comprising LC-CDR1 comprises the amino acid sequence of SEQ ID NO: 46, an LC-CDR2 comprising the amino acid sequence of SEQ ID NO: 47, and an LC-CDR3 comprising the amino acid sequence of SEQ ID NO: 48; (9) VH comprising an HC-CDR1 comprising the amino acid sequence of SEQ ID NO: 49, an HC-CDR2 comprising the amino acid sequence of SEQ ID NO: 50, and an HC-CDR3 comprising the amino acid sequence of SEQ ID NO: 51; a VL comprising LC-CDR1 comprises the amino acid sequence of SEQ ID NO: 52, an LC-CDR2 comprising the amino acid sequence of SEQ ID NO: 53, and an LC-CDR3 comprising the amino acid sequence of SEQ ID NO: 54; or (10) a VH comprising an HC-CDR1 comprising the amino acid sequence of SEQ ID NO: 55, an HC-CDR2 comprising the amino acid sequence of SEQ ID NO: 56, and an HC-CDR3 comprising the amino acid sequence of SEQ ID NO: 57; a VL comprising LC-CDR1 comprises the amino acid sequence of SEQ ID NO: 58, an LC-CDR2 comprising the amino acid sequence of SEQ ID NO: 59, and an LC-CDR3 comprising the amino acid sequence of SEQ ID NO: 60.

In some embodiments according to any one of the isolated antibodies or antigen binding fragments thereof described above, the antibody or antigen binding fragment thereof comprises: (1) a VH comprising an amino acid sequence having at least about 90% sequence identity to the amino acid sequence of SEQ ID NO: 61, and a VL comprising an amino acid sequence having at least about 90% sequence identity to the amino acid sequence of SEQ ID NO: 62; (2) a VH comprising an amino acid sequence having at least about 90% sequence identity to the amino acid sequence of SEQ ID NO: 63, and a VL comprising an amino acid sequence having at least about 90% sequence identity to the amino acid sequence of SEQ ID NO: 64; (3) a VH comprising an amino acid sequence having at least about 90% sequence identity to the amino acid sequence of SEQ ID NO: 65, and a VL comprising an amino acid sequence having at least about 90% sequence identity to the amino acid sequence of SEQ ID NO: 66; (4) a VH comprising an amino acid sequence having at least about 90% sequence identity to the amino acid sequence of SEQ ID NO: 67, and a VL comprising an amino acid sequence having at least about 90% sequence identity to the amino acid sequence of SEQ ID NO: 68; (5) a VH comprising an amino acid sequence having at least about 90% sequence identity to the amino acid sequence of SEQ ID NO: 69 and a VL comprising an amino acid sequence having at least about 90% sequence identity to the amino acid sequence of SEQ ID NO: 70; (6) a VH comprising an amino acid sequence having at least about 90% sequence identity to the amino acid sequence of SEQ ID NO: 71, and a VL comprising an amino acid sequence having at least about 90% sequence identity to the amino acid sequence of SEQ ID NO: 72; (7) a VH comprising an amino acid sequence having at least about 90% sequence identity to the amino acid sequence of SEQ ID NO: 73, and a VL comprising an amino acid sequence having at least about 90% sequence identity to the amino acid sequence of SEQ ID NO: 74; (8) a VH comprising an amino acid sequence having at least about 90% sequence identity to the amino acid sequence of SEQ ID NO: 75, and a VL comprising an amino acid sequence having at least about 90% sequence identity to the amino acid sequence of SEQ ID NO: 76; (9) a VH comprising an amino acid sequence having at least about 90% sequence identity to the amino acid sequence of SEQ ID NO: 77, and a VL comprising an amino acid sequence having at least about 90% sequence identity to the amino acid sequence of SEQ ID NO: 78; or (10) a VH comprising an amino acid sequence having at least about 90% sequence identity to the amino acid sequence of SEQ ID NO: 79, and a VL comprising an amino acid sequence having at least about 90% sequence identity to the amino acid sequence of SEQ ID NO: 80.

In some embodiments according to any one of the isolated antibodies or antigen binding fragments thereof described above, the antibody or antigen binding fragment thereof specifically binds an S1 subunit of a spike (S) protein of SARS-CoV-2.

In some embodiments according to any one of the isolated antibodies or antigen binding fragments thereof described above, the antibody or antigen binding fragment thereof is selected from the group consisting of a full-length antibody, a Fab, a Fab', a $(Fab')_2$, an Fv, a single chain Fv (scFv), an scFv-Fc, a disulfide stabilized Fv fragment (dsFv), a $(dsFv)_2$, an scFv dimer, a domain antibody, a bivalent domain antibody, and a minibody.

Also provided is an isolated antibody or antigen binding fragment thereof that specifically binds to the same or substantially the same epitope competitively with any one of the isolated antibodies or antigen binding fragments thereof described above.

One aspect of the present application provides an isolated antibody construct comprising an antibody moiety comprising any one of the isolated antibodies or antigen binding fragments thereof described above. In some embodiments, the isolated antibody construct is a chimeric protein further comprising a mucoadhesive peptide fragment comprising about 5 to about 50 (e.g., 5, 6, 12, 24, 30, 40, or 50) positively charged amino acid residues (e.g., lysines, arginines, histidines, and/or ornithines), wherein the mucoadhesive peptide fragment facilitates attachment of the chimeric protein to a mucosa. In some embodiments, the isolated antibody construct is a multispecific antibody. In some embodiments, the isolated antibody construct is an immunoconjugate comprising the antibody moiety and an effector molecule. In some embodiments, the isolated antibody construct comprises an effector molecule that is a therapeutic agent selected from the group consisting of a drug, a toxin, a radioisotope, a protein, a peptide, and a nucleic acid. In some embodiments, the isolated antibody construct comprises a label.

In some embodiments, the present application provides an isolated nucleic acid or a set of isolated nucleic acids encoding any one of the antibodies or antigen binding fragments thereof described above, or any one or more polypeptides of the antibody construct described above. In some embodiments, the present application provides a vector comprising any one of the isolated nucleic acids or sets of isolated nucleic acids described above. In some embodiments, the present application provides a vector comprising any one of the nucleic acids described above, or a set of vectors comprising any set of nucleic acids described above.

In some embodiments, the present application provides a host cell comprising any one of the antibodies or antigen binding fragments thereof described above, the nucleic acid or set of nucleic acids described above, or the vector or the sets of vectors described above.

In some embodiments, the present application provides a pharmaceutical composition comprising any one of the antibodies or antigen binding fragments thereof of described above, or any one of the antibody constructs described above, and a pharmaceutically acceptable carrier.

One aspect of the present application provides a formulation for nasal administration comprising: (a) an antibody that specifically binds to a component of SARS-CoV-2, (b) a methionine, (c) a buffering agent, and (d) an osmolality adjusting agent, wherein the formulation has a pH of about 4.5 to about 7.5 (e.g., about 6.0 to about 7.0, such as about 6.5), and wherein the formulation has an osmolality of about 230 to about 330 Osm/kg (e.g., about 250 to about 300 Osm/kg, such as about 280 Osm/kg). In some embodiments, the antibody specifically recognizes the S1 protein of SARS-CoV-2. In some embodiments, the antibody is any one of the isolated antibodies (anti-S1 antibodies) or antigen-binding fragments thereof described above. In some embodiments, the antibody is any one of the chimeric proteins described above comprising an antibody moiety that specifically binds to a component of SARS-CoV-2.

In some embodiments according to any one of the formulations described above, the antibody is present at a concentration of about 0.6 mg/mL to about 6 mg/mL (e.g., about 1 mg/mL to about 3 mg/mL).

In some embodiments according to any one of the formulations described above, the methionine is present at a concentration of about 0.05% to about 0.2% (e.g., about 0.075% to about 0.125%, such as about 0.1%) (w/w).

In some embodiments according to any one of the formulations described above, the formulation has a pH of about 6.5. In some embodiments, the buffering agent is a citrate or a phosphate. In some embodiments, the buffering agent is a citrate. In some embodiments, the formulation comprises a citrate at a concentration of about 20 mM to about 50 mM (e.g., about 20 mM to about 30 mM, such as about 25 mM).

In some embodiments according to any one of the formulations described above, the osmolality adjusting agent is NaCl. In some embodiments, the formulation comprises NaCl at a concentration of about 100 mM to about 150 mM (e.g., about 110 mM to about 130 mM, such as about 125 mM).

In some embodiments according to any one of the formulations described above, the formulation further comprises a surfactant. In some embodiments, the surfactant is polysorbate 80. In some embodiments, the formulation comprises polysorbate 80 at a concentration of about 0.01% to about 0.1% (e.g., about 0.01% to about 0.05%, such as about 0.02%) (w/w).

In some embodiments according to any one of the formulations described above, the formulation further comprises a viscosity-enhancing agent. In some embodiments, the viscosity-enhancing agent is selected from the group consisting of glycerin, dextran and hydroxyethylcellulose. In some embodiments, the viscosity-enhancing agent is glycerin. In some embodiments, the formulation comprises glycerin at a concentration of about 1% to about 10% (e.g., about 2.5% to about 7.5%, such as about 5%) (w/w).

In some embodiments according to any one of the formulations described above, the formulation further comprises a preservative. In some embodiments, the preservative is potassium sorbate. In some embodiments, the formulation comprises potassium sorbate at a concentration of about 0.05% to about 0.2% (e.g., about 0.075% to about 0.125%, such about 0.1%) (w/w).

In some embodiments according to any one of the formulations described above, the formulation comprises about 25 mM citrate at pH 6.5, about 125 mM NaCl, about 5% glycerin, about 0.1% methionine, about 0.02% polysorbate 80, and about 0.1% potassium sorbate.

One aspect of the present application provides a method of preventing or treating a SARS-CoV-2 infection in an individual, comprising administering to the individual an effective amount of any one of the antibodies or antigen binding fragments thereof described above, any one of the antibody constructs described above, or any one of the formulations described above. In some embodiments, the SARS-CoV-2 is WIV4 (i.e., hCoV-19/WIV04/2019 or Beta-CoV/WIV04/2019). In some embodiments, the SARS-CoV-2 is a variant selected from the group consisting of a B.1.1.7 variant, a B.1.351 variant, a B.1.526 variant, a B1.526.1 variant, a B1.617 variant, a B.1.617.1 variant, a B.1.617.2 variant, a B1.617.3 variant, a P.2 variant, a P.1 (B.1.1.28.1) variant, an A.23.1 variant, a CAL.20C variant, a B.1.427 variant, a B.1.429 variant, a B.1.525 variant, and a P.1.351 variant. In some embodiments, the SARS-CoV-2 is a B.1.1.7 variant. In some embodiments, the SARS-CoV-2 is a B.1.1.7 variant. In some embodiments, the SARS-CoV-2 is a B.1.351 variant. In some embodiments, the SARS-CoV-2 is a B.1.617.2 variant.

Another aspect of the present application provides a method of detecting SARS-CoV-2 in a sample, comprising contacting the sample with any one of the antibodies or antigen binding fragments thereof described above, or any one of the antibody constructs described above. In some embodiments, the antibody construct is an immunoconjugate comprising a label.

In some embodiments, there is provided a method of diagnosing whether an individual has a SARS-CoV-2 infection, comprising: a) administering an effective amount of any one of the antibody constructs described above the individual; and b) determining the level of the label in the individual. In some embodiments, the method further comprises a method of diagnosis described above wherein a level of the label above a threshold level indicates that the individual has SARS-CoV-2 infection. In some embodiments, the antibody construct is an immunoconjugate comprising a label.

In some embodiments, there is provided a method of diagnosing whether an individual has a SARS-CoV-2 infection, comprising: a) contacting a sample derived from the individual with any one of the antibodies or antigen binding fragments thereof of described above, or any one of the antibody constructs described above; and b) determining the amount of SARS-CoV-2 S1 in the sample bound with the antibody, antigen binding fragment thereof, or the antibody construct. In some embodiments, a value for the amount of SARS-CoV-2 S1 bound above a threshold level indicates that the individual has SARS-CoV-2 infection. In some embodiments, the antibody construct is an immunoconjugate comprising a label.

In some embodiments, there is provided a method of diagnosing whether an individual has a SARS-CoV-2 infection, comprising: a) contacting a sample derived from the individual with any one of the antibodies or antigen binding fragments thereof of described above, or any one of the antibody constructs described above; and b) determining the amount of the antibody, antigen binding fragment thereof, or the antibody construct bound with materials in the sample. In some embodiments, a value for the amount of the antibody, antigen binding fragment thereof, or the antibody construct bound above a threshold level indicates that the individual has SARS-CoV-2 infection. In some embodiments, the antibody construct is an immunoconjugate comprising a label.

Also provided are kits and articles of manufacture (e.g., a nasal spray medicament) comprising any one of the compositions described above and instructions for any one of the methods described above.

BRIEF DESCRIPTION OF THE DRAWINGS

The drawings illustrate certain embodiments of the features and advantages of this disclosure. These embodiments are not intended to limit the scope of the appended claims in any manner.

DETAILED DESCRIPTION

Figure 1:
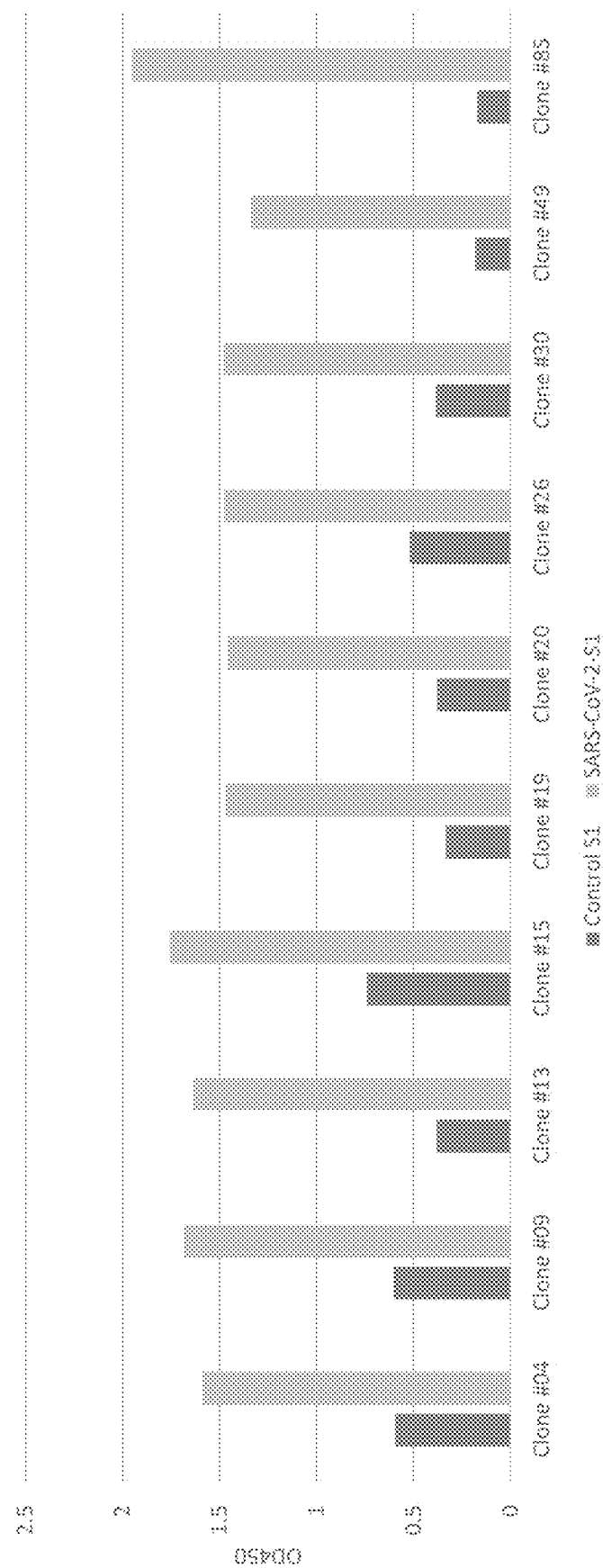
FIG. 1 shows binding of exemplary phage clones to SARS-CoV-2 spike protein in comparison to a coronavirus spike protein mixture (Control S1) as confirmed by ELISA.

The present application provides compositions and methods for preventing or treating an infection caused by a microbial pathogen that infects through a mucosa in an individual by targeting the microbial pathogen using a chimeric protein that has a positively charged mucoadhesive peptide fragment. For example, the compositions described herein may comprise a chimeric protein or cocktails of different chimeric proteins, comprising an antibody or non-antibody polypeptide that targets SARS-CoV-2 spike protein, and is modified with a positively charged peptide that prevents the SARS-CoV-2 virus from reaching its primary target cell population in the respiratory tract (e.g., nasal) mucosa for human infection. The compositions can be administered via the nasal passages using a respiratory spray.

Inventors of the present application developed human antibodies that recognize the SARS-CoV-2 S1 spike protein ("anti-S1 antibodies") and chimeric proteins comprising an anti-S1 antibody fused to a positively charged mucoadhesive peptide fragment. The chimeric proteins have significantly enhanced affinity to mucin molecules compared to unmodified anti-S1 antibodies, which leads to improved stability in respiratory mucosa. The chimeric proteins showed improved potency as compared to unmodified anti-S1 antibodies in blocking SARS-CoV-2 infection in a cell-based assay. Administration of an exemplary chimeric protein into mouse nostrils blocked the infection of mice that were exposed to high titer SARS-CoV-2 pseudovirus at least 10 hours after the initial treatment, even at the lowest concentrations of the chimeric protein tested. The protection against SARS-CoV-2 was effective in both nasal and lung areas seven days after viral exposure. The exemplary chimeric protein was highly stable and maintained its SARS-CoV-2 neutralizing activity in a nasal spray formulation. Additionally, chimeric proteins having Fc portions of IgG are easy to manufacture compared to IgA molecules. Nasal spray of the chimeric proteins can be developed as an affordable and effective prophylactic product to protect people from infection by exposure to SARS-CoV-2 virus in the air (e.g., via the nasal passages).

Compared to other methods that block microbial infection, which involve systemic administration of antibodies that do not have a positively charged mucoadhesive peptide fragment, the methods described herein require administration of much less protein, leading to a large cost reduction that is critical for any pandemic situation. The compositions may also be self-administered, which greatly relieves the burden on an overwhelmed health care system. Importantly, the methods described herein can avoid the potential problem of ADE resulting from conventional antibody therapy or vaccination.

Accordingly, one aspect of the present application provides a chimeric protein comprising: (a) a target-binding moiety that specifically binds to a component of a pathogen that infects through a mucosa; and (b) a mucoadhesive peptide fragment comprising about 5 to about 50 positively charged amino acid residues (e.g., lysines or histidines), wherein the mucoadhesive peptide fragment facilitates attachment of the chimeric protein to the mucosa. In some embodiments, the pathogen is SARS-CoV-2.

Also provided are novel antibodies and constructs thereof that specifically bind to an S1 subunit of a spike protein of SARS-CoV-2. The antibodies and constructs are useful for treating, preventing, or diagnosing an infection by SARS-CoV-2 in an individual.

I. Definitions

The term "target-binding moiety" is used herein to refer to a molecule or a fragment thereof that is capable of specifically binding to a target. In some embodiments, a target-binding moiety is a polypeptide, which may comprise any number of polypeptide chains. In some embodiments, a target-binding moiety is an antibody or antigen-binding fragment. In some embodiments, a target-binding moiety is not derived from an antibody. A target-binding moiety may have one or more target-binding site. In some embodiments, the target-binding moiety is monospecific. In some embodiments, the target-binding moiety is multispecific, e.g., bispecific.

As used herein, a "mucoadhesive peptide fragment" refers to a peptide that carries one or more positive charges and is capable of interacting with a mucosa, e.g., via electrostatic interactions.

As used herein, a "receptor" refers to a receptor on a host cell that facilitates or mediates microbial entry into the host cell. A receptor may be membrane-bound or a soluble receptor.

As used herein, "treatment" or "treating" is an approach for obtaining beneficial or desired results including clinical results. For purposes of this application, beneficial or desired clinical results include, but are not limited to, one or more of the following: decreasing one more symptoms resulting from the disease, diminishing the extent of the disease, stabilizing the disease (e.g., preventing or delaying the worsening of the disease), preventing or delaying the spread of the disease, preventing or delaying the occurrence or recurrence of the disease, delay or slowing the progression of the disease, ameliorating the disease state, providing a remission (whether partial or total) of the disease, decreasing the dose of one or more other medications required to treat the disease, delaying the progression of the disease, increasing the quality of life, and/or prolonging survival. Also encompassed by "treatment" is a reduction of pathological consequence of the disease. The methods of the present application contemplate any one or more of these aspects of treatment.

"Preventing," as used herein, includes providing prophylaxis with respect to the occurrence or recurrence of a disease in a subject that may be predisposed to the disease but has not yet been diagnosed with the disease.

An "effective amount" of an agent refers to an amount effective, at dosages and for periods of time necessary, to achieve the desired therapeutic or prophylactic result. An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. For purposes of this application, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved. The effective amount can be ascertained by measuring relevant physiological effects, and it can be adjusted in connection with the dosing regimen and diagnostic analysis of the subject's condition, and the like.

The terms "individual," "subject" and "patient" are used interchangeably herein to describe a mammal, including humans. In some embodiments, the individual is human. In some embodiments, an individual suffers from a respiratory infection. In some embodiments, the individual is in need of treatment.

The terms "polypeptide" and "protein" are used interchangeably to refer to a polymer of amino acid residues and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present application, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts, which produce the proteins or errors due to PCR amplification.

As used herein, the term "antibody" or "antibody moiety" includes full-length antibodies (including full-length 4-chain antibodies or full-length heavy chain antibodies, which have an immunoglobulin Fc region), and antigen-binding fragments thereof.

As used herein, a "neutralizing antibody" refers to an antibody that defends a host cell from an infectious agent by neutralizing any effect (e.g., cytotoxicity) it has biologically. A "non-neutralizing antibody" refers to an antibody that specifically binds to an infectious agent but is incapable of ameliorating the biological effects of the infectious agent on the host cell. A "sub-neutralizing antibody" refers to an antibody that is capable of partially neutralizing the biological effects of the infectious agent on the host cell. A subneutralizing antibody may ameliorate one or more biological effects of an infectious agent on the host cell by no more than about any one of 90%, 80%, 70%, 60%, 50%, 40%, 30%, 20%, 10% or less compared to a neutralizing antibody.

A full-length four-chain antibody comprises two heavy chains and two light chains. The variable regions of the light and heavy chains are responsible for antigen-binding. The variables region in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen-binding but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), 1gA1 (al heavy chain), or 1gA2 (α2 heavy chain).

The term "heavy chain-only antibody" or "HCAb" refers to a functional antibody, which comprises heavy chains, but lacks the light chains usually found in 4-chain antibodies. Camelid animals (such as camels, llamas, or alpacas) are known to produce HCAbs. The variable region of a heavy chain-only antibody is referred herein as "VHH." A VHH is one type of single-domain antibody. A "single-domain antibody" or "sdAb" refers to a single antigen-binding polypeptide having three complementary determining regions (CDRs). The sdAb alone is capable of binding to the antigen without pairing with a corresponding CDR-containing polypeptide. Some VHHs may also be known as Nanobodies. Camelid VHH is one of the smallest known antigen-binding antibody fragments (see, e.g., Hamers-Casterman et al., Nature 363:446-8 (1993); Greenberg et al., Nature 374:168-73 (1995); Hassanzadeh-Ghassabeh et al., Nanomedicine (Lond), 8:1013-26 (2013)). A basic VHH has the following structure from the N-terminus to the C-terminus: FR1-CDR1-FR2-CDR2-FR3-CDR3-FR4, in which FR1 to FR4 refer to framework regions 1 to 4, respectively, and in which CDR1 to CDR3 refer to the complementarity determining regions 1 to 3.

The term "antigen-binding fragment" as used herein refers to an antibody fragment including, for example, a diabody, a Fab, a Fab', a F(ab')2, an Fv fragment, a disulfide stabilized Fv fragment (dsFv), a $(dsFv)_2$, a bispecific dsFv (dsFv-dsFv'), a disulfide stabilized diabody (ds diabody), a single-chain antibody molecule (scFv), an scFv dimer (bivalent diabody), an scFv-Fc fusion protein, a minibody (i.e., scFv-CH3 fusion protein), a multispecific antibody formed from a portion of an antibody comprising one or more CDRs, a VHH, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies.

The term "epitope" as used herein refers to the specific group of atoms or amino acids on an antigen to which an antibody or antibody moiety binds. Two antibodies or antibody moieties may bind the same epitope within an antigen if they exhibit competitive binding for the antigen.

As used herein, a first antibody moiety "competes" for binding to a target (e.g., S1 of spike protein) with a second antibody moiety when the first antibody moiety inhibits target binding of the second antibody moiety by at least about 50% (such as at least about any of 55%, 60%, 65%, 70%, 75%, 80%, 85%, 90%, 95%, 98% or 99%) in the presence of an equimolar concentration of the first antibody moiety, or vice versa. A high throughput process for "binning" antibodies based upon their cross-competition is described in PCT Publication No. WO 03/48731.

As use herein, the term "specifically binds," "specifically recognizing," or "is specific for" refers to measurable and reproducible interactions, such as binding between a target and an antibody or antibody moiety that is determinative of the presence of the target in the presence of a heterogeneous population of molecules, including biological molecules. For example, an antibody or antibody moiety that specifically recognizes a target (which can be an epitope) is an antibody or antibody moiety that binds this target with greater affinity, avidity, more readily, and/or with greater duration than its bindings to other targets. In some embodiments, an antibody or antibody moiety that specifically recognizes an antigen reacts with one or more antigenic determinants of the antigen (such as SARS-CoV-2 spike protein) with a binding affinity that is at least about 10 times its binding affinity for other targets (such as MERS-CoV spike protein or a non-respiratory-pathogen protein).

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); Chothia et al., J. Mol. Biol. 196: 901-917 (1987); Al-Lazikani B. et al., J. Mol. Biol., 273: 927-948 (1997); MacCallum et al., J. Mol. Biol. 262:732-745 (1996); Abhinandan and Martin, Mol. Immunol., 45: 3832-3839 (2008); Lefranc M. P. et al., Dev. Comp. Immunol., 27: 55-77 (2003); and Honegger and Plückthun, J. Mol. Biol., 309:657-670 (2001), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table A as a comparison. CDR prediction algorithms and interfaces are known in the art, including, for example, Abhinandan and Martin, Mol. Immunol., 45: 3832-3839 (2008); Ehrenmann F. et al., Nucleic Acids Res., 38: D301-D307 (2010); and Adolf-Bryfogle J. et al., Nucleic Acids Res., 43: D432-D438 (2015). The contents of the references cited in this paragraph are incorporated herein by reference in their entireties for use in the present invention and for possible inclusion in one or more claims herein.

TABLE A

CDR DEFINITIONS

|  | Kabat[1] | Chothia[2] | MacCallum[3] | IMGT[4] | AHo[5] |
|---|---|---|---|---|---|
| VH CDR1 | 31-35 | 26-32 | 30-35 | 27-38 | 25-40 |
| VH CDR2 | 50-65 | 53-55 | 47-58 | 56-65 | 58-77 |
| VH CDR3 | 95-102 | 96-101 | 93-101 | 105-117 | 109-137 |
| VL CDR1 | 24-34 | 26-32 | 30-36 | 27-38 | 25-40 |
| VL CDR2 | 50-56 | 50-52 | 46-55 | 56-65 | 58-77 |
| VL CDR3 | 89-97 | 91-96 | 89-96 | 105-117 | 109-137 |

[1]Residue numbering follows the nomenclature of Kabat et al., supra
[2]Residue numbering follows the nomenclature of Chothia et al., supra
[3]Residue numbering follows the nomenclature of MacCallum et al., supra
[4]Residue numbering follows the nomenclature of Lefranc et al., supra
[5]Residue numbering follows the nomenclature of Honegger and Plückthun, supra The term "chimeric antibodies" refer to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this invention (see U.S. Pat. No. 4,816,567; and Morrison et al., Proc. Natl. Acad. Sci. USA, 81:6851-6855 (1984)).

The term "semi-synthetic" in reference to an antibody or antibody moiety means that the antibody or antibody moiety has one or more naturally occurring sequences and one or more non-naturally occurring (i.e., synthetic) sequences.

"Fv" is the minimum antibody fragment, which contains a complete antigen-recognition and -binding site. This fragment consists of a dimer of one heavy- and one light-chain variable region domain in tight, non-covalent association. From the folding of these two domains emanate six hypervariable loops (3 loops each from the heavy and light chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv," also abbreviated as "sFv" or "scFv," are antibody fragments that comprise the VH and VL antibody domains connected into a single polypeptide chain.

In some embodiments, the scFv polypeptide further comprises a polypeptide linker between the VH and VL domains, which enables the scFv to form the desired structure for antigen binding. For a review of scFv, see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments prepared by constructing scFv fragments (see preceding paragraph) typically with short linkers (such as about 5 to about 10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" scFv fragments in which the VH and VL domains of the two antibodies are present on different polypeptide chains. Diabodies are described more fully in, for example, EP 404,097; WO 93/11161; and Hollinger et al., *Proc. Natl. Acad. Sci. USA*, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region (HVR) of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

The "CH1 domain" of a human IgG Fc region (also referred to as "C1" of "H1" domain) usually extends from about amino acid 118 to about amino acid 215 (EU numbering system).

"Hinge region" is generally defined as stretching from Glu216 to Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions.

The "CH2 domain" of a human IgG Fc region (also referred to as "C2" of "H2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec Immunol.* 22:161-206 (1985).

The "CH3 domain" (also referred to as "C2" or "H3" domain) comprises the stretch of residues C-terminal to a CH2 domain in an Fc region (i.e. from about amino acid residue 341 to the C-terminal end of an antibody sequence, typically at amino acid residue 446 or 447 of an IgG).

The term "substantially similar" or "substantially the same," as used herein, denotes a sufficiently high degree of similarity between two or more numeric values such that one of skill in the art would consider the difference between the two or more values to be of little or no biological and/or statistical significance within the context of the biological characteristic measured by said value. In some embodiments the two or more substantially similar values differ by no more than about any one of 5%, 10%, 15%, 20%, 25%, or 50%.

A polypeptide "variant" means a biologically active polypeptide having at least about 80% amino acid sequence identity and no more than 100% identity with the native sequence polypeptide after aligning the sequences and introducing gaps, if necessary, to achieve the maximum percent sequence identity. Such variants include, for instance, polypeptides wherein one or more amino acid residues are added, or deleted, at the N- or C-terminus of the polypeptide. In some embodiments, a variant has at least about 80% amino acid sequence identity. In some embodiments, a variant has at least about 90% amino acid sequence identity. In some embodiments, a variant has at least about 95% amino acid sequence identity with the native sequence polypeptide.

As used herein, "Percent (%) amino acid sequence identity" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN' (DNASTAR) software. Those skilled in the art can determine appropriate parameters for measuring alignment, including any algorithms needed to achieve maximal alignment over the full length of the sequences being compared.

The term "label" when used herein refers to a detectable compound or composition, which can be conjugated directly or indirectly to an antibody moiety (e.g., anti-S1 antibody). The label may be detectable by itself (e.g., radioisotope labels or fluorescent labels) or, in the case of an enzymatic label, may catalyze chemical alteration of a substrate compound or composition, which is detectable.

An "isolated" antibody or construct as used herein refers to a construct that (1) is not associated with proteins found in nature, (2) is free of other proteins from the same source, (3) is expressed by a cell from a different species, or (4) does not occur in nature.

The term "isolated nucleic acid" as used herein is intended to mean a nucleic acid of genomic, cDNA, or synthetic origin or some combination thereof, which by virtue of its origin the "isolated nucleic acid" (1) is not associated with all or a portion of a polynucleotide in which the "isolated nucleic acid" is found in nature, (2) is operably linked to a polynucleotide which it is not linked to in nature, or (3) does not occur in nature as part of a larger sequence.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "vector" is used to describe a polynucleotide that may be engineered to contain a cloned polynucleotide or polynucleotides that may be propagated in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that may be used in colorimetric assays, e.g., (3-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), and 293 and CHO cells, and their derivatives, such as 293-6E and DG44 cells, respectively.

As used herein, a "variant" virus refers to an isolate of a virus whose genome sequence differs from that of a reference virus and the difference in the genome sequence confers new phenotypic properties such as increased fitness compared to the reference virus. When referring to a viral species in the present application, such as SARS-CoV-2, it is understood that the species encompass variants as well as the reference virus that was first isolated and identified. In some embodiments, the variant virus described herein is a "variant of interest", i.e., a variant with specific genetic markers that have been associated with changes to receptor binding, reduced neutralization by antibodies generated against previous infection or vaccination, reduced efficacy of treatments, potential diagnostic impact, and/or predicted increase in transmissibility and/or disease severity. In some embodiments, the variant virus described herein is a "variant of concern", i.e., a variant for which there is evidence of an increase in transmissibility, more severe disease (e.g., increased hospitalizations and/or deaths), significant reduction in neutralization by antibodies generated during previous infection or vaccination, reduced effectiveness of treatments or vaccines, and/or diagnostic detection failures. In some embodiments, the variant virus described herein is a "variant of high consequence", i.e., a variant of high consequence has clear evidence that prevention measures or medical countermeasures (MCMs) have significantly reduced effectiveness relative to previously circulating variants.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

As used herein, "a pharmaceutically acceptable carrier" refers to a pharmaceutically acceptable substrate, composition or vehicle used in the process of drug delivery, which may have one or more ingredients including, but not limited to, excipient(s), binder(s), diluent(s), solvent(s), filler(s), and/or stabilizer(s).

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter.

As used herein and in the appended claims, the singular forms "a," "an," and "the" include plural referents unless the context clearly dictates otherwise.

II. Chimeric Proteins

The present application provides chimeric proteins (such as fusion proteins) comprising: (a) a target-binding moiety that specifically binds a component of a pathogen that infects through a mucosa; and (b) a mucoadhesive peptide fragment comprising about 5 to about 50 (e.g., about 6-30 such as 12) positively charged amino acid residues, wherein the mucoadhesive peptide fragment facilitates attachment of the chimeric protein to the mucosa. In some embodiments, the positively charged amino acid residues are selected from the group consisting of lysine, arginine, histidine, ornithine, and combinations thereof. In some embodiments, the positively charged amino acid residues are lysines. In some embodiments, the mucoadhesive peptide fragment is a polylysine peptide having about 5 to about 50 (e.g., about 6-30 such as 12) contiguous lysines. In some embodiments, the positively charged amino acid residues are histidines. In some embodiments, the mucoadhesive peptide fragment is a polyhistidine peptide having about 5 to about 50 (e.g., about 6-30 such as 12) contiguous histidines. In some embodiments, the positively charged amino acid residues are contiguous with each other. In some embodiments, the positively charged amino acid residues are interspersed with non-positively charged amino acid residues. In some embodiments, the mucoadhesive peptide fragment is covalently fused to the target-binding moiety. In some embodiments, the mucoadhesive peptide fragment is non-covalently associated with the target-binding moiety, e.g., via a dimerization domain. In some embodiments, the component of the pathogen is a surface molecule. In some embodiments, the component of the pathogen is a secreted molecule. In some embodiments, the pathogen is a bacterium, e.g., *Streptococcus pyogenes, Haemophilus influenzae, Streptococcus pneumoniae, Mycoplasma pneumoniae,*

*Moraxella catarrhalis, Pseudomonas aeruginosa*, or *Mycobacterium tuberculosis*. In some embodiments, the pathogen is a virus, e.g., a coronavirus, a respiratory syncytial virus, an influenza virus, or an adenovirus. In some embodiments, the pathogen causes a respiratory infection. In some embodiments, the mucosa is selected from the group consisting of nasal mucosa, larynx mucosa, trachea mucosa, bronchi mucosa, lung mucosa, eye mucosa, and combinations thereof.

In some embodiments, there is provided a chimeric protein (e.g., fusion protein) comprising: (a) a target-binding moiety that specifically binds a component of a coronavirus (e.g., SARS-CoV-2); and (b) a mucoadhesive peptide fragment comprising about 5 to about 50 (e.g., about 6-30 such as 12) positively charged amino acid residues, wherein the mucoadhesive peptide fragment facilitates attachment of the chimeric protein to a mucosa. In some embodiments, the positively charged amino acid residues are selected from the group consisting of lysine, arginine, histidine, ornithine, and combinations thereof. In some embodiments, the positively charged amino acid residues are lysines. In some embodiments, the mucoadhesive peptide fragment is a polylysine peptide having about 5 to about 50 (e.g., about 6-30 such as 12) contiguous lysines. In some embodiments, the positively charged amino acid residues are histidines. In some embodiments, the mucoadhesive peptide fragment is a polyhistidine peptide having about 5 to about 50 (e.g., about 6-30 such as 12) contiguous histidines. In some embodiments, the positively charged amino acid residues are contiguous with each other. In some embodiments, the positively charged amino acid residues are interspersed with non-positively charged amino acid residues. In some embodiments, the mucoadhesive peptide fragment is covalently fused to the target-binding moiety. In some embodiments, the mucoadhesive peptide fragment is non-covalently associated with the target-binding moiety, e.g., via a dimerization domain. In some embodiments, the component of the pathogen is a surface molecule, e.g., spike protein such as S1 subunit of spike protein. In some embodiments, the component of the pathogen is a secreted molecule. In some embodiments, the mucosa is selected from the group consisting of nasal mucosa, larynx mucosa, trachea mucosa, bronchi mucosa, lung mucosa, eye mucosa, and combinations thereof.

In some embodiments, there is provided a chimeric protein (e.g., fusion protein) comprising: (a) an antibody moiety that specifically binds a component of a pathogen that infects through a mucosa; and (b) a mucoadhesive peptide fragment comprising about 5 to about 50 (e.g., about 6-30 such as 12) positively charged amino acid residues, wherein the mucoadhesive peptide fragment facilitates attachment of the chimeric protein to the mucosa. In some embodiments, the positively charged amino acid residues are selected from the group consisting of lysine, arginine, histidine, ornithine, and combinations thereof. In some embodiments, the positively charged amino acid residues are lysines. In some embodiments, the mucoadhesive peptide fragment is a polylysine peptide having about 5 to about 50 (e.g., about 6-30 such as 12) contiguous lysines. In some embodiments, the positively charged amino acid residues are histidines. In some embodiments, the mucoadhesive peptide fragment is a polyhistidine peptide having about 5 to about 50 (e.g., about 6-30 such as 12) contiguous histidines. In some embodiments, the positively charged amino acid residues are contiguous with each other. In some embodiments, the positively charged amino acid residues are interspersed with non-positively charged amino acid residues. In some embodiments, the mucoadhesive peptide fragment is covalently fused to the antibody moiety. In some embodiments, the mucoadhesive peptide fragment is non-covalently associated with the antibody moiety, e.g., via a dimerization domain. In some embodiments, the component of the pathogen is a surface molecule. In some embodiments, the component of the pathogen is a secreted molecule. In some embodiments, the pathogen is a bacterium, e.g., *Streptococcus pyogenes, Haemophilus influenzae, Streptococcus pneumoniae, Mycoplasma pneumoniae, Moraxella catarrhalis, Pseudomonas aeruginosa*, or *Mycobacterium tuberculosis*. In some embodiments, the pathogen is a virus, e.g., a coronavirus, a respiratory syncytial virus, an influenza virus, or an adenovirus. In some embodiments, the pathogen causes a respiratory infection. In some embodiments, the pathogen is SARS-CoV-2. In some embodiments, the mucosa is selected from the group consisting of nasal mucosa, larynx mucosa, trachea mucosa, bronchi mucosa, lung mucosa, eye mucosa, and combinations thereof. In some embodiments, the antibody moiety is a full-length antibody (e.g., IgG, IgA, IgM or IgD). In some embodiments, the antibody moiety is an antigen-binding fragment selected from the group consisting of a Fab, a Fab', a $(Fab')_2$, an Fv, a single chain Fv (scFv), an scFv-Fc, a disulfide stabilized Fv fragment (dsFv), a (dsFv) 2, an scFv dimer, a domain antibody, a camelized single domain antibody, a bivalent domain antibody, a minibody, and a VHH.

In some embodiments, there is provided a chimeric protein (e.g., fusion protein) comprising: (a) an antibody moiety that specifically binds a spike protein of SARS-CoV-2; and (b) a mucoadhesive peptide fragment comprising about 5 to about 50 (e.g., about 6-30 such as 12) positively charged amino acid residues, wherein the mucoadhesive peptide fragment facilitates attachment of the chimeric protein to a mucosa. In some embodiments, the antibody moiety specifically binds to an S1 subunit of the spike protein. In some embodiments, the antibody moiety comprises any one of the antibodies or antigen binding fragments thereof as described in Tables 2-4 and 6-8.

In some embodiments, the antibody moiety comprises an antibody heavy chain variable region (VH) comprising a heavy chain complementarity determining region (HC-CDR)1 comprising the amino acid sequence of SEQ ID NO: 37, an HC-CDR2 comprising the amino acid sequence of SEQ ID NO: 38, and an HC-CDR3 comprising the amino acid sequence of SEQ ID NO: 39; and a light chain variable region comprising a light chain complementarity determining region (LC-CDR)1 comprising the amino acid sequence of SEQ ID NO: 40, an HC-CDR2 comprising the amino acid sequence of SEQ ID NO: 41, and an HC-CDR3 comprising the amino acid sequence of SEQ ID NO: 42. In some embodiments, the antibody moiety comprises a VH comprising an amino acid sequence having at least about 90% sequence identity to the amino acid sequence of SEQ ID NO: 75, and a VL comprising an amino acid sequence having at least about 90% sequence identity to the amino acid sequence of SEQ ID NO: 76. In some embodiments, the antibody moiety comprises a scFv comprising an amino acid sequence having at least about 90% sequence identity to the amino acid sequence of SEQ ID NO: 87. In some embodiments, the positively charged amino acid residues are selected from the group consisting of lysine, arginine, histidine, ornithine, and combinations thereof. In some embodiments, the positively charged amino acid residues are lysines. In some embodiments, the mucoadhesive peptide fragment is a polylysine peptide having about 5 to about 50 (e.g., about 6-30 such as 12) contiguous lysines. In some embodiments, the positively charged amino acid residues are histidines. In some embodiments, the mucoadhesive peptide fragment is a polyhistidine peptide having about 5 to about 50 (e.g., about 6-30 such as 12) contiguous histidines. In some embodiments, the positively charged amino acid residues are contiguous with each other. In some embodiments, the positively charged amino acid residues are interspersed with non-positively charged amino acid residues. In some embodiments, the mucoadhesive peptide fragment is covalently fused to the antibody moiety. In some embodiments, the mucoadhesive peptide fragment is non-covalently associated with the antibody moiety, e.g., via a dimerization domain. In some embodiments, the mucosa is selected from the group consisting of nasal mucosa, larynx mucosa, trachea mucosa, bronchi mucosa, lung mucosa, eye mucosa, and combinations thereof. In some embodiments, the antibody moiety is a full-length antibody (e.g., IgG, IgA, IgM or IgD). In some embodiments, the antibody moiety is an antigen-binding fragment selected from the group consisting of a Fab, a Fab', a (Fab')$_2$, an Fv, a single chain Fv (scFv), an scFv-Fc, a disulfide stabilized Fv fragment (dsFv), a (dsFv) 2, an scFv dimer, a domain antibody, a camelized single domain antibody, a bivalent domain antibody, a minibody, and a VHH.

In some embodiments, there is provided a chimeric protein (e.g., fusion protein) comprising a full-length antibody comprising: a first antibody heavy chain, a second antibody heavy chain, a first antibody light chain, and a second antibody light chain, wherein the antibody specifically binds to a component of a pathogen that infects through a mucosa, wherein the chimeric protein comprises: (a) a first polypeptide comprising the first antibody heavy chain fused to a first mucoadhesive peptide fragment; (b) a second polypeptide comprising the second antibody heavy chain fused to a second mucoadhesive peptide fragment; (c) a third polypeptide comprising the first antibody light chain; and (d) the fourth polypeptide comprising a second antibody light chain, wherein the first and second mucoadhesive peptide fragments each comprise about 5 to about 50 positively charged amino acid residues, wherein the first and second mucoadhesive peptide fragments facilitate attachment of the chimeric protein to the mucosa. In some embodiments, the first polypeptide comprises from the N-terminus to the C-terminus: the first antibody heavy chain, an optional peptide linker, and the first mucoadhesive peptide fragment. In some embodiments, the second polypeptide comprises from the N-terminus to the C-terminus: the second antibody heavy chain, an optional peptide linker, and the second mucoadhesive peptide fragment. In some embodiments, the first mucoadhesive peptide fragment is identical is to the second mucoadhesive peptide fragment. In some embodiments, the first mucoadhesive peptide fragment is different from the second mucoadhesive peptide fragment. In some embodiments, the full-length antibody is a monospecific antibody. In some embodiments, the full-length antibody is a bispecific antibody. In some embodiments, the positively charged amino acid residues are selected from the group consisting of lysine, arginine, histidine, ornithine, and combinations thereof. In some embodiments, the positively charged amino acid residues are lysines. In some embodiments, the mucoadhesive peptide fragment is a polylysine peptide having about 5 to about 50 (e.g., about 6-30 such as 12) contiguous lysines. In some embodiments, the positively charged amino acid residues are histidines. In some embodiments, the mucoadhesive peptide fragment is a polyhistidine peptide having about 5 to about 50 (e.g., about 6-30 such as 12) contiguous histidines. In some embodiments, the positively charged amino acid residues are contiguous with each other. In some embodiments, the positively charged amino acid residues are interspersed with non-positively charged amino acid residues. In some embodiments, the component of the pathogen is a surface molecule. In some embodiments, the component of the pathogen is a secreted molecule. In some embodiments, the pathogen is a bacterium, e.g., *Streptococcus pyogenes, Haemophilus influenzae, Streptococcus pneumoniae, Mycoplasma pneumoniae, Moraxella catarrhalis, Pseudomonas aeruginosa*, or *Mycobacterium tuberculosis*. In some embodiments, the pathogen is a virus, e.g., a coronavirus, a respiratory syncytial virus, an influenza virus, or an adenovirus. In some embodiments, the pathogen causes a respiratory infection. In some embodiments, the pathogen is SARS-CoV-2. In some embodiments, the component is spike protein (e.g., S1) of SARS-CoV-2. In some embodiments, the mucosa is selected from the group consisting of nasal mucosa, larynx mucosa, trachea mucosa, bronchi mucosa, lung mucosa, eye mucosa, and combinations thereof. In some embodiments, the full-length antibody is IgG, IgA, IgM or IgD.

In some embodiments, there is provided a chimeric protein (e.g., fusion protein) comprising: (a) an scFv that specifically binds to a component of a pathogen that infects through a mucosa; and (b) a mucoadhesive peptide fragment, wherein the mucoadhesive peptide fragment comprises about 5 to about 50 positively charged amino acid residues, wherein the mucoadhesive peptide fragment facilitates attachment of the chimeric protein to the mucosa. In some embodiments, the chimeric protein comprises a polypeptide comprising: from the N-terminus to the C-terminus: the scFv, an optional peptide linker, and the mucoadhesive peptide fragment. In some embodiments, the scFv comprises from the N-terminus to the C-terminus: VH, an optional linker, and VL. In some embodiments, the scFv comprises from the N-terminus to the C-terminus: VL, an optional linker, and VH. In some embodiments, the chimeric protein further comprises one or more constant domains of an antibody, e.g., CH1, CL, CH2 and/or CH3. In some embodiments, the chimeric protein further comprises an Fc. In some embodiments, the positively charged amino acid residues are selected from the group consisting of lysine, arginine, histidine, ornithine, and combinations thereof. In some embodiments, the positively charged amino acid residues are lysines. In some embodiments, the mucoadhesive peptide fragment is a polylysine peptide having about 5 to about 50 (e.g., about 6-30 such as 12) contiguous lysines. In some embodiments, the positively charged amino acid residues are histidines. In some embodiments, the mucoadhesive peptide fragment is a polyhistidine peptide having about 5 to about 50 (e.g., about 6-30 such as 12) contiguous histidines. In some embodiments, the positively charged amino acid residues are contiguous with each other. In some embodiments, the positively charged amino acid residues are interspersed with non-positively charged amino acid residues. In some embodiments, the component of the pathogen is a surface molecule. In some embodiments, the component of the pathogen is a secreted molecule. In some embodiments, the pathogen is a bacterium, e.g., *Streptococcus pyogenes, Haemophilus influenzae, Streptococcus pneumoniae, Mycoplasma pneumoniae, Moraxella catarrhalis, Pseudomonas aeruginosa*, or *Mycobacterium tuberculosis*. In some embodiments, the pathogen is a virus, e.g., a coronavirus, a respiratory syncytial virus, an influenza virus, or an adenovirus. In some embodiments, the pathogen causes a respiratory infection. In some embodiments, the pathogen is SARS-CoV-2. In some embodiments, the component is spike protein (e.g., S1) of SARS-CoV-2. In some embodiments, the mucosa is selected from the group consisting of nasal mucosa, larynx mucosa, trachea mucosa, bronchi mucosa, lung mucosa, eye mucosa, and combinations thereof.

In some embodiments, there is provided a chimeric protein (e.g., fusion protein) comprising: (a) a first scFv and a second scFv that each specifically binds to a component of a pathogen that infects through a mucosa; and (b) a first and a second mucoadhesive peptide fragments, wherein the mucoadhesive peptide fragments each comprise about 5 to about 50 positively charged amino acid residues, wherein the mucoadhesive peptide fragments facilitate attachment of the chimeric protein to the mucosa; wherein the chimeric protein comprises: (1) a first polypeptide comprising from the N-terminus to the C-terminus: the first scFv, an optional linker, CH2 domain, CH3 domain, an optional linker, and the first mucoadhesive peptide fragment; and (2) a second polypeptide comprising from the N-terminus to the C-terminus: the second scFv, an optional linker, CH2 domain, CH3 domain, an optional linker, and the second mucoadhesive peptide fragment. In some embodiments, the first mucoadhesive peptide fragment is identical is to the second mucoadhesive peptide fragment. In some embodiments, the first mucoadhesive peptide fragment is different from the second mucoadhesive peptide fragment. In some embodiments, the first scFv and the second scFv specifically binds to the same component of the pathogen. In some embodiments, the first scFv and the second scFv specifically binds to different variants of the same component, different components of the same pathogen, or components of different pathogens. In some embodiments, the positively charged amino acid residues are selected from the group consisting of lysine, arginine, histidine, ornithine, and combinations thereof. In some embodiments, the positively charged amino acid residues are lysines. In some embodiments, the mucoadhesive peptide fragment is a polylysine peptide having about 5 to about 50 (e.g., about 6-30 such as 12) contiguous lysines. In some embodiments, the positively charged amino acid residues are histidines. In some embodiments, the mucoadhesive peptide fragment is a polyhistidine peptide having about 5 to about 50 (e.g., about 6-30 such as 12) contiguous histidines. In some embodiments, the positively charged amino acid residues are contiguous with each other. In some embodiments, the positively charged amino acid residues are interspersed with non-positively charged amino acid residues. In some embodiments, the component of the pathogen is a surface molecule. In some embodiments, the component of the pathogen is a secreted molecule. In some embodiments, the pathogen is a bacterium, e.g., *Streptococcus pyogenes, Haemophilus influenzae, Streptococcus pneumoniae, Mycoplasma pneumoniae, Moraxella catarrhalis, Pseudomonas aeruginosa*, or *Mycobacterium tuberculosis*. In some embodiments, the pathogen is a virus, e.g., a coronavirus, a respiratory syncytial virus, an influenza virus, or an adenovirus. In some embodiments, the pathogen causes a respiratory infection. In some embodiments, the pathogen is SARS-CoV-2. In some embodiments, the component is spike protein (e.g., S1) of SARS-CoV-2. In some embodiments, the mucosa is selected from the group consisting of nasal mucosa, larynx mucosa, trachea mucosa, bronchi mucosa, lung mucosa, eye mucosa, and combinations thereof.

In some embodiments, there is provided a chimeric protein (e.g., fusion protein) comprising: (a) an inhibitory polypeptide that specifically binds a component of a pathogen that infects through a mucosa, wherein the inhibitory polypeptide inhibits binding of the component of the pathogen to a receptor on a cell of the mucosa; and (b) a mucoadhesive peptide fragment comprising about 5 to about 50 (e.g., about 6-30 such as 12) positively charged amino acid residues, wherein the mucoadhesive peptide fragment facilitates attachment of the chimeric protein to the mucosa. In some embodiments, the positively charged amino acid residues are selected from the group consisting of lysine, arginine, histidine, ornithine, and combinations thereof. In some embodiments, the positively charged amino acid residues are lysines. In some embodiments, the mucoadhesive peptide fragment is a polylysine peptide having about 5 to about 50 (e.g., about 6-30 such as 12) contiguous lysines. In some embodiments, the positively charged amino acid residues are histidines. In some embodiments, the mucoadhesive peptide fragment is a polyhistidine peptide having about 5 to about 50 (e.g., about 6-30 such as 12) contiguous histidines. In some embodiments, the positively charged amino acid residues are contiguous with each other. In some embodiments, the positively charged amino acid residues are interspersed with non-positively charged amino acid residues. In some embodiments, the mucoadhesive peptide fragment is covalently fused to the inhibitory polypeptide. In some embodiments, the mucoadhesive peptide fragment is non-covalently associated with inhibitory polypeptide, e.g., via a dimerization domain. In some embodiments, the component of the pathogen is a surface molecule. In some embodiments, the component of the pathogen is a secreted molecule. In some embodiments, the pathogen is a bacterium, e.g., *Streptococcus pyogenes, Haemophilus influenzae, Streptococcus pneumoniae, Mycoplasma pneumoniae, Moraxella catarrhalis, Pseudomonas aeruginosa*, or *Mycobacterium tuberculosis*. In some embodiments, the pathogen is a virus, e.g., a coronavirus, a respiratory syncytial virus, an influenza virus, or an adenovirus. In some embodiments, the pathogen causes a respiratory infection. In some embodiments, the pathogen is SARS-CoV-2. In some embodiments, the mucosa is selected from the group consisting of nasal mucosa, larynx mucosa, trachea mucosa, bronchi mucosa, lung mucosa, eye mucosa, and combinations thereof. In some embodiments, the inhibitory polypeptide comprises a natural receptor of the component of the pathogen or a fragment derived from the natural receptor. In some embodiments, the inhibitory polypeptide comprises an extracellular binding domain (EBD) of the natural receptor, e.g., ACE2.

In some embodiments, the half-life of the chimeric protein on the mucosa is at least about any one of 6 hours, 8 hours, 10 hours, 12 hours, 14 hours, 16 hours, 18 hours, 20 hours 22 hours, 24 hours, 30 hours, 36 hours, 48 hours or more. In some embodiments, the half-life of the chimeric protein on the mucosa is at least 12 hours. In some embodiments, the half-life of the chimeric protein on the mucosa is at least 24 hours.

The half-life of the chimeric protein on the mucosa may be determined using known in vitro assays in the art. In view of the size and polar properties of the chimeric protein, mucosal (e.g., nasal) absorption of the chimeric protein is minimal because of low membrane permeability of the chimeric protein. However, mucociliary clearance of the chimeric protein may play a role in the half-life of the chimeric proteins. The mucoadhesive peptide fragment can improve the retention time of the chimeric protein on the mucosa. For example, an in vitro model cell system, such as mucosal epithelial cells, may be used to determine the amount of the chimeric protein remaining on cell/mucin surface by FACS or immunofluorescence. As another example, mucosa related components, such as mucin, could be used to incubate with a chimeric protein and determine the amount of the chimeric protein associated with mucin by ELISA. In both methods, for chimeric proteins comprising an IgG, anti-IgG secondary antibodies can be used as a detection probe.

In some embodiments, the chimeric protein comprises the amino acid sequence of SEQ ID NO: 98. In some embodiments, the chimeric protein comprises a first polypeptide comprising the amino acid sequence of SEQ ID NO: 96, and a second polypeptide comprising the amino acid sequence of SEQ ID NO: 97.

In some embodiments, the chimeric protein comprises a first polypeptide comprising the amino acid sequence of SEQ ID NO: 131, and a second polypeptide comprising the amino acid sequence of SEQ ID NO: 97.

In some embodiments, the chimeric protein comprises a first polypeptide comprising the amino acid sequence of SEQ ID NO: 132, and a second polypeptide comprising the amino acid sequence of SEQ ID NO: 97.

Without being bound by any theory or hypothesis, SARS-CoV-2 infection occurs mainly through respiratory droplets and possible airborne transmission. Upper respiratory surfaces are the dominant and initial sites for SARS-CoV-2 virus infection. The nasal epithelium produces a physical glycoprotein barrier to inhaled particles including allergens and pathogens, preventing penetration to the epithelial surface of mucosal tissues. One major component of the mucosal layer of nasal and respiratory tract are mucins, a family of large glycoproteins that coat the surface of the respiratory epithelium. Mucins, the primary non-aqueous component of mucus, are a complex and heterogeneous structure, which carry a highly negative charge. The inventors of the present application, in some embodiments, engineered a polymeric lysine tail which, when covalently linked to an antibody, confers to the conjugate (i.e., chimeric protein) positive charges. The antibody with its positively charged poly-lysine tail can form a layer of SARS-CoV-2-binding antibody that can line the nasal/respiratory tract and prevent the virus from binding to the viral receptor-expressing epithelial cells. A positively charged antibody could also bind the phospholipid bilayer of cell membranes, also negatively charged. This 'sticky" property of polymeric lysine imparts to the antibody a longer half-life in the respiratory mucosal epithelium, providing a lengthened period of protection. Therefore, the engineered antibody-polylysine conjugate can function as a neutralizing antibody, which can block SARS-CoV-2 viral entry into the cells of the respiratory cavity, even if the virus might penetrate the mucosal barrier and reach viral receptor-positive epithelial cells. In other embodiments, other positively charged mucoadhesive polymers, such as those comprising arginine, histidine, and/or ornithine residues can be used in place of polylysines. In some embodiments, inhibitory polypeptides, such as soluble fragments of receptors on the host cell, e.g., ACE2 fragment, can be used in place of the antibody to construct the chimeric protein. Furthermore, the chimeric protein may be expressed as a fusion protein, or the mucoadhesive peptide fragment may be chemically conjugated to antibodies or non-antibody-based target-binding moieties.

The different aspects and embodiments are discussed in various sections below in further detail.

A. Target-Binding Moieties

The chimeric proteins described herein comprise a target-binding moiety that specifically binds to a component of a pathogen that infects through a mucosa. Exemplary mucosa includes, but are not limited to, nasal mucosa, larynx mucosa, trachea mucosa, bronchi mucosa, lung mucosa, eye mucosa, and combinations thereof.

In some embodiments, the target-binding moiety comprises a polypeptide. For example, the target-binding moiety may comprise one or more (e.g., 2, 3, 4 or more) polypeptide chains. These one or more polypeptide chains may be bound together, for example, via an S—S bonds or multimerization domains.

In some embodiments, the target-binding moiety is an antibody moiety, including full-length antibodies, and any suitable antigen binding fragments. In some embodiments, the antibody moiety is a full-length antibody. In some embodiments, the antibody moiety is selected from the group consisting of an IgG, an IgA, an IgM, and an IgD. In some embodiments, the antibody moiety is an antigen-binding fragment selected from the group consisting of a Fab, a Fab', a (Fab')$_2$, an Fv, a single chain Fv (scFv), an scFv-Fc, a disulfide stabilized Fv fragment (dsFv), a (dsFv)$_2$, an scFv dimer, a domain antibody, a camelized single domain antibody, a bivalent domain antibody, a minibody, and a VHH. In some embodiments, the antibody moiety is a human, humanized, camelid, or chimeric antibody or an antigen-binding fragment thereof.

In some embodiments, the target-binding moiety comprises a scFv. In some embodiments, the target-binding moiety is a scFv. In some embodiments, the target-binding moiety is a scFv-Fc fusion protein. In some embodiments, the target-binding moiety is a scFv-CH3 fusion protein. In some embodiments, the scFv comprises a VH fused to a VL via a peptide linker. In some embodiments, the scFv comprises a VL fused to a VH via a peptide linker. In some embodiments, the peptide linker has the sequence SRGGGGSGGGGSGGGGSLEMA (SEQ ID NO: 91).

In humans, IgA is the major antibody isotype secreted in the upper airways; its presence there correlates with resistance to infection by some respiratory viruses. Antibody delivery to the upper airway mucosal surface, mimicking naturally secreted antibody, can prevent virus from reaching its target or directly neutralize infectious virus, and may prove a very useful strategy for prophylaxis. Indeed, antibodies have been shown to provide protection of the respiratory tract from viral infection when given prophylactically. IgA antibodies have a unique structure and glycosylation pattern that enables binding to mucin molecules in the airway epithelium, resulting in extension of their half-lives in the mucosa. While secretory IgA antibodies are more efficient than IgG antibodies in providing effective viral protection, IgG antibodies have a well-established modality for large-scale manufacturing and characterization, both of which are essential for providing an affordable and scalable source of antibodies for a prophylactic approach.

In some embodiments, the target-binding moiety comprises an inhibitory polypeptide that inhibits binding of the component of the pathogen to a receptor on a cell of the mucosa. In some embodiments, the target-binding moiety comprises a natural receptor of the component of the pathogen or a fragment derived from the natural receptor. In some embodiments, the target-binding moiety comprises an extracellular binding domain (EBD) of the natural receptor, e.g., ACE2.

In some embodiments, the target-binding moiety comprises a purification tag, e.g., a His tag, such as HHHHHH-GAYPYDVPDYAS (SEQ ID NO: 92).

In some embodiments, the pathogen is a virus, such as a coronavirus, a respiratory syncytial virus, an influenza virus, or an adenovirus. In some embodiments, the pathogen is a bacterium, such as *Streptococcus pyogenes, Haemophilus influenzae, Streptococcus pneumoniae, Mycoplasma pneumoniae, Moraxella catarrhalis, Pseudomonas aeruginosa,* or *Mycobacterium tuberculosis*. In some embodiments, the pathogen causes respiratory infections.

In humans, coronaviruses cause mild to severe respiratory tract illnesses ranging from the common cold to more serious diseases such as coronavirus disease 2019 (COVID-19), severe acute respiratory syndrome (SARS) and Middle East respiratory syndrome (MERS). Other viruses that can cause respiratory illness including Respiratory Syncytial virus (RSV), Influenza Virus, and some Adenoviruses. Yet other respiratory infections are caused by bacteria, such as *Streptococcus pyogenes* and *Haemophilus influenzae*. The method mentioned above will apply to all the infections mentioned above. The target-binding moieties described herein may target any one of these pathogens.

The component of the pathogen can be a protein-based molecule, or a non-protein-based molecule (e.g., oligosaccharide). In some embodiments, the component is a glycoprotein.

The component of the pathogen may be a surface molecule on the pathogen, or a secreted molecule by the pathogen. For example, the component may be a glycoprotein on the surface of a bacterium or a virus. In some embodiments, the component is a capsid protein, an envelope protein, or a viral membrane fusion protein. In some embodiments, the component is a spike protein. In some embodiments, the component is an endotoxin of a bacterium. In some embodiments, the component is a lipopolysaccharide (LPS). In some embodiments, the component is a virulence factor or a toxin secreted by the pathogen.

Exemplary pathogens, targets, and target-binding moieties are further described below, and in Section III.

Coronaviruses

In some embodiments, the pathogen is a coronavirus. In some embodiments, the pathogen is selected from the group consisting of SARS-CoV, SARS-CoV-2, and MERS-CoV, including variants thereof. In some embodiments, the pathogen is SARS-CoV-2. In some embodiments, the pathogen is a reference coronavirus or a coronavirus having substantially the same genomic sequence (e.g., fewer than any one of 200, 100, 50, 20, 10, 5, 4, 3, 2, or 1 mutations) and phenotypes as the reference coronavirus. In some embodiments, the pathogen is a variant coronavirus that has one or more mutations in the genomic sequence compared to the reference coronavirus, wherein the one or more mutations contribute to phenotypic differences, such as increased viral fitness, including for example, infectivity, virulence, and/or drug resistance.

In some embodiments, the pathogen is SARS-CoV-2. In some embodiments, the pathogen is a reference SARS-CoV-2 (e.g., WIV4, i.e., hCoV-19/WIV04/2019 or BetaCoV/WIV04/2019) or a SARS-CoV-2 virus having substantially the same genomic sequence (e.g., fewer than any one of 200, 100, 50, 20, 10, 5, 4, 3, 2, or 1 mutations) and phenotypes as the reference SARS-CoV-2. The genome sequence of the reference SARS-CoV-2 WIV4 can be found on Genbank (NCBI Reference Sequence: NC 045512.2), which is also known as 2019-nCoV. In some embodiments, the SARS-CoV-2 is a variant, such as a variant of interest, a variant of concern, or a variant of high consequence. In some embodiments, the SARS-CoV-2 is a variant selected from the group consisting of a B.1.1.7 variant, a B.1.351 variant, a B.1.526 variant, a B1.526.1 variant, a B1.617 variant, a B.1.617.1 variant, a B.1.617.2 variant, a B1.617.3 variant, a P.2 variant, a P.1 (also known as B.1.1.28.1) variant, an A.23.1 variant, a CAL.20C variant, a B.1.427 variant, a B.1.429 variant, a B.1.525 variant, and a P.1.351 variant. In some embodiments, the SARS-CoV-2 variant is a B.1.1.7 variant. In some embodiments, the SARS-CoV-2 variant is a B.1.351 variant. In some embodiments, the SARS-CoV-2 variant is a B.1.617.2 variant. Other variants of SARS-CoV-2 are known in the art. For example, See, Gomez et al., *Vaccines* 9(3): 243, 2021 and Tang et al., *Journal of Infection* 82: e27-e28, 2021, which are incorporated herein by reference in their entirety. In some embodiments, the SARS-CoV-2 variant has one or more mutations (e.g., insertion, deletion, and/or substitution) in the spike protein. In some embodiments, the one or more mutations in the spike protein may affect viral fitness, such as infectivity, virulence, and/or drug resistance (e.g., resistance to neutralizing antibodies and/or resistance to a vaccine). For example, the SARS-CoV-2 variant may have L452R and/or E484K substitutions in the spike protein. In some embodiments, the one or more mutations in the spike protein do not substantially alter viral fitness. In some embodiments, the SARS-CoV-2 variant does not have a mutation in the spike protein.

In some embodiments, the component of the pathogen is a spike protein of a coronavirus. In some embodiments, the component is S1 subunit of the spike protein. In some embodiments, the component is S2 subunit of the spike protein. In some embodiments, the component is not a spike protein.

In some embodiments, the target-binding moiety is an antibody that specifically binds to the component, e.g., spike protein. In some embodiment, the target-binding moiety is derived from a subneutralizing or non-neutralizing antibody for a virulent coronavirus.

In some embodiments, the target-binding moiety is an inhibitory polypeptide that inhibits binding of the component to a receptor on a cell of the mucosa. In some embodiments, the target-binding moiety comprises a natural receptor of the component of the pathogen or a fragment derived from the natural receptor of a coronavirus. In some embodiments, the target-binding moiety comprises an extracellular binding domain (EBD) of the natural receptor of a coronavirus. In some embodiments, the target-binding moiety comprises an EBD of ACE2. In some embodiments, the target-binding moiety comprises a truncated version of ACE2.

For example, an exemplary sequence of the EBD of human ACE2 is shown as the italicized portion below (SEQ ID NO: 115). In some embodiments, the chimeric protein comprises an EBD of human ACE2 fused to a mucoadhesive peptide fragment, e.g., a polylysine fragment. An exemplary chimeric protein is shown below as SEQ ID NO: 116.

```
EBD of human ACE2 fused to a mucoadhesive peptide
fragment having six lysine residues
                                        SEQ ID NO: 116
QSTIEEQAKTFLDKFNHEAEDLFYQSSLASWNYNTNITEENVQNMNNAGD

KWSAFLKEQSTLAQMYPLQEIQNLTVKLQLQALQQNGSSVLSEDKSKRLN

TILNTMSTIYSTGKVCNPDNPQECLLLEPGLNEIMANSLDYNERLWAWES

WRSEVGKQLRPLYEEYVVLKNEMARANHYEDYGDYWRGDYEVNGVDGYDY

SRGQLIEDVEHTFEEIKPLYEHLHAYVRAKLMNAYPSYISPIGCLPAHLL

GDMWGRFWTNLYSLTVPFGQKPNIDVTDAMVDQAWDAQRIFKEAEKFFVS

VGLPNMTQGFWENSMLTDPGNVQKAVCHPTAWDLGKGDFRILMCTKVTMD

DFLTAHHEMGHIQYDMAYAAQPFLLRNGANEGFHEAVGEIMSLSAATPKH

LKSIGLLSPDFQEDNETEINFLLKQALTIVGTLPFTYMLEKWRWMVFKGE
```

-continued

IPKDQWMKKWWEMKREIVGVVEPVPHDETYCDPASLFHVSNDYSFIRYYT

RTLYQFQFQEALCQAAKHEGPLHKCDISNSTEAGQKLFNMLRLGKSEPWT

LALENVVGAKNMNVRPLLNYFEPLFTWLKDQNKNSFVGWSTDWSPYADQS

IKVRISLKSALGDKAYEWNDNEMYLFRSSVAYAMRQYFLKVKNQMILFGE

EDVRVANLKPRISFNFFVTAPKNVSDIIPRTEVEKAIRMSRSRINDAFRL

NDNSLEFLGIQPTLGPPNQPPVSGGGGSKKKKKK

In nature, the spike protein (also referred to as spike glycoprotein, or S protein) of coronaviruses mediates viral entry into the host cells. Table 1 below shows identified viral receptors for various coronaviruses. See, also, Raj V S et al. Chapter 15 of Helena Jane Maier et al. (eds.), Coronaviruses: Methods and Protocols, Methods in Molecular Biology, vol. 1282, Springer Science+Business Media New York 2015; Li F. Annu Rev Virol. 2016; 3(1): 237-261; Hulswit 2019 and Zhou et al., Nature 579: 270, 2020, which are incorporated herein by reference in their entirety. Chimeric proteins based on these host receptors are contemplated herein.

TABLE 1

Host viral receptors for coronaviruses.

| Viral receptor on host cells | Coronavirus (underlined are human coronaviruses) |
|---|---|
| aminopeptidase N (APN) | HCoV-229E, TGEV, PEDV, PRCV, FIPV, CCoV |
| angiotensin-converting enzyme 2 (ACE2) | SARS-CoV-2, SARS-CoV, HCoV-NL63 |
| dipeptidyl peptidase 4 (DPP4, also known as CD26) | MERS-CoV, HKU4 |
| N-acetyl-9- O -acetylneuraminic acid (9-O-Ac-Neu5Ac) | HCoV-OC43, HCoV-HKU1, BCoV |
| murine carcinoembryonic antigen related adhesion molecule 1 (mCEACAM) | MHV |

Coronaviruses are a group of related viruses that cause diseases in mammals and birds. In humans, coronaviruses cause respiratory tract infections that can range from mild to lethal. Mild illnesses include some cases of the common cold (e.g., with symptoms such as fever, sore throat), while more lethal varieties can cause SARS, MERS, and COVID-19. Coronaviruses can cause pneumonia (either direct viral pneumonia or secondary bacterial pneumonia) and bronchitis (either direct viral bronchitis or secondary bacterial bronchitis).

Coronaviruses are large pleomorphic spherical particles with bulbous surface projections. The average diameter of the virus particles is around 120 nm (0.12 μm). The diameter of the envelope is ~80 nm (0.08 μm) and the spikes are ~20 nm (0.02 μm) long. The viral envelope consists of a lipid bilayer where the membrane (M), envelope (E) and spike (S) structural proteins are anchored. A subset of coronaviruses (specifically the members of betacoronavirus subgroup A) also have a shorter spike-like surface protein called hemagglutinin esterase (HE). Inside the envelope, there is the nucleocapsid, which is formed from multiple copies of the nucleocapsid (N) protein, which are bound to the positive-sense single-stranded RNA genome in a continuous beads-on-a-string type conformation. The lipid bilayer envelope, membrane proteins, and nucleocapsid protect the virus when it is outside the host cell.

Infection begins when the viral spike (S) glycoprotein attaches to its complementary host cell receptor. After attachment, a protease of the host cell cleaves and activates the receptor-attached spike protein. Depending on the host cell protease available, cleavage and activation allows the virus to enter the host cell by endocytosis or direct fusion of the viral envelope with the host membrane. On entry into the host cell, the virus particle is uncoated, and its genome enters the cell cytoplasm. The coronavirus RNA genome has a 5' methylated cap and a 3' polyadenylated tail, which allows the RNA to attach to the host cell's ribosome for translation. The host ribosome translates the initial overlapping open reading frame of the virus genome and forms a long polyprotein. The polyprotein has its own proteases, which cleave the polyprotein into multiple nonstructural proteins.

The coronaviruses can be classified into four genera: alpha, beta, gamma, and delta CoVs (Woo et al., 2009). Previously identified human CoVs that cause human disease include the alphaCoVs hCoV-NL63 and hCoV-229E and the betaCoVs HCoV-OC43, HKU1, severe acute respiratory syndrome CoV (SARS-CoV), Middle East respiratory syndrome CoV (MERS-CoV) and Severe acute respiratory syndrome coronavirus 2 (SARS-CoV-19; previously known as 2019-nCoV (Lu et al., 2015; Wevers and van der Hoek, 2009; Zhu et al., 2020). HCoV-OC43, HCoV-HKU1, HCoV-229E and HCoV-NL63 continually circulate in the human population and produce generally mild symptoms of the common cold in adults and children worldwide.

SARS-CoV and MERS-CoV are zoonotic pathogens originating from animals. Detailed investigations indicate that SARS-CoV is transmitted from civet cats to humans and MERS-CoV from dromedary camels to humans (Azhar et al., 2014; Ge et al., 2013; Guan et al., 2003). Bats and birds, as warm-blooded flying vertebrates, are an ideal natural reservoir for the coronavirus gene pool (bats the reservoir for alphacoronavirus and betacoronavirus—and birds the reservoir for gammacoronavirus and deltacoronavirus). The large number of host bat and avian species, and their global range, has enabled extensive evolution and dissemination of coronaviruses.

SARS-CoV-2 is a betacoronavirus from group 2B with approximately 70% genetic similarity to the SARS-CoV. The virus has a 96% similarity to a bat coronavirus (SARSr-CoV_RaTG13), so it is widely suspected to originate from bats as well.

Coronaviruses have been recognized as causing pathological conditions in veterinary medicine since the 1930s. Coronaviruses primarily infect the upper respiratory and gastrointestinal tract of mammals and birds. They also cause a range of diseases in farm animals and domesticated pets, some of which can be serious and are a threat to the farming industry. Exemplary coronaviruses that infect animals include the infectious bronchitis virus (IBV) for chickens, porcine coronavirus (transmissible gastroenteritis coronavirus, TGEV), porcine respiratory coronavirus (PEDV), bovine coronavirus (BCoV), feline enteric coronavirus, feline infectious peritonitis virus (FIPV), ferret enteric coronavirus, ferret systemic coronavirus, canine coronavirus (CCoV), mouse hepatitis virus (MEW), sialodacryoadenitis virus (SDAV), and swine acute diarrhea syndrome coronavirus (SADS-CoV).

A naturally occurring spike protein of a coronavirus forms homotrimers protruding from the viral surface. The S protein comprises two functional subunits responsible for binding to the host cell receptor (S1 subunit) and fusion of the viral and cellular membranes (S2 subunit). For many CoVs, S is cleaved at the boundary between the S1 and S2 subunits, which remain non-covalently bound in the prefusion conformation. The distal S1 subunit comprises the receptor-binding domain(s) and contributes to stabilization of the prefusion state of the membrane-anchored S2 subunit that contains the fusion machinery. For all CoVs, S is further cleaved by host proteases at the so-called S$_2$' site located immediately upstream of the fusion peptide. This cleavage has been proposed to activate the protein for membrane fusion via extensive irreversible conformational changes. As a result, coronavirus entry into susceptible cells is a complex process that requires the concerted action of receptor-binding and proteolytic processing of the S protein to promote virus-cell fusion. See, Walls et al., *Cell* 180, 281-292, 2020.

For example, the S protein of SARS-CoV could be cleaved by trypsin at two distinct sites, one located at the boundary of S1 and S2, the "classical" S1/S2 site (R667 P1 residue), and the S2' site (R797 P1 residue). Protease cleavage of SARS-CoV S is thought to be sequential, with the S1/S2 cleavage occurring first and enhancing subsequent cleavage at S2'. It is the second cleavage event, at S2', that is believed to be crucial for fusion activation of S. The S1/S2 cleavage appears dispensable for syncytia formation and virus—cell fusion. See, Millet 2015, Virus Research 202: 120-134.

The spike protein of SARS-CoV-2 can be cleaved by both furin at the S1/S2 site and the transmembrane protease/serine (TMPRSS) protease 2, TMPRSS2, at the S2' site. See, Hoffman et al., Cell 181, 271-280, 2020. The furin cleavage site of SARS-CoV-2 is located between amino acids 685 and 686 of the S protein. SARS-CoV-2 and SARS-CoV both use ACE2 as the receptor to enter human cells. See, Zhou et al., Nature 579: 270, 2020.

S1 of the spike protein can be further divided into an N-terminal domain (NTD) and a C-terminal domain (CTD), both of which can function as a receptor-binding entity (e.g., SARS-CoV and MERS-CoV utilize the S1 CTD to recognize the receptor (also called receptor binding domain [RBD]) (Li et al., 2005; Lu et al., 2013).

SARS-CoV-2

In some embodiments, the target-binding moiety specifically binds a component of SARS-CoV-2. In some embodiments, the component is a surface molecule of SARS-CoV-2. In some embodiments, the surface molecule is a spike (S) protein. In some embodiments, the surface molecule is an S1 subunit of the S protein. An exemplary S1 sequence of SARS-CoV-2 is shown below as SEQ ID NO: 93. Exemplary antibodies that specifically binds to S1 are disclosed herein in Section III.

```
Spike protein S1 subunit of SARS-CoV-2.
                                       SEQ ID NO: 93
VNLTTRTQLPPAYTNSFTRGVYYPDKVFRSSVLHSTQDLFLPFFSNVTWF

HAIHVSGTNGTKRFDNPVLPFNDGVYFASTEKSNIIRGWIFGTTLDSKTQ

SLLIVNNATNVVIKVCEFQFCNDPFLGVYYHKNNKSWMESEFRVYSSANN

CTFEYVSQPFLMDLEGKQGNFKNLREFVFKNIDGYFKIYSKHTPINLVRD

LPQGFSALEPLVDLPIGINITRFQTLLALHRSYLTPGDSSSGWTAGAAAY

YVGYLQPRTFLLKYNENGTITDAVDCALDPLSETKCTLKSFTVEKGIYQT

SNFRVQPTESIVRFPNITNLCPFGEVFNATRFASVYAWNRKRISNCVADY

SVLYNSASFSTFKCYGVSPTKLNDLCFTNVYADSFVIRGDEVRQIAPGQT

-continued
GKIADYNYKLPDDFTGCVIAWNSNNLDSKVGGNYNYLYRLFRKSNLKPFE

RDISTEIYQAGSTPCNGVEGFNCYFPLQSYGFQPTNGVGYQPYRVVVLSF

ELLHAPATVCGPKKSTNLVKNKCVNFNFNGLTGTGVLTESNKKFLPFQQF

GRDIADTTDAVRDPQTLEILDITPCSFGGVSVITPGTNTSNQVAVLYQDV

NCTEVPVAIHADQLTPTWRVYSTGSNVFQTRAGCLIGAEHVNNSYECDIP

IGAGICASYQTQTNSPRRAR
```

SARS-CoV-2 S protein includes a signaling peptide (amino acid residues 1-19), S1 region containing a NTD (amino acid residues 20-286) and a CTD (amino acid residues 319-541), a S2 region (amino acid residues 686-1213), a transmembrane region (amino acid residues 1214-1236), and a short cytoplasmic domain (amino acid residues 1237-1273). The CTD, in particular amino acid residues 333-527, play key roles in binding to ACE2. In particular, amino acid residues A475, K417, G446, Y449, G496, Q498, T500, G502, Y489, F486, and N487 contribute to binding of the SARS-CoV-2 CTD with huACE2. See, Wang et al., 2020, Cell 181, 1-11, which is incorporated herein by reference in its entirety.

In some embodiments, the target-binding moiety can recognize two or more isolates or clusters of SARS-CoV-2 (e.g., cluster A, B or C; or any one of the isolates as disclosed in Forster et al. "Phylogenetic network analysis of SARS-CoV-2 genomes" in PNAS, 2020). In some embodiments, the target-binding moiety specifically blocks binding of one or more variants of the S1 protein of SARS-CoV-2 to human ACE2, including the SARS-CoV-2 S1 spike protein variants of Table 10, such as an S1 protein comprising one or more mutations selected from the group consisting of D614G, V367F, N439K, A435S, V483A, K458R, G4765, R408I, V503F, A522V, Y508H, L452R, A520S, I472V, T478I, F490S, and/or P384L.

In some embodiments, the target-binding moiety can recognize two or more variants of SARS-CoV-2. In some embodiments, the component is derived from a reference SARS-CoV-2. In some embodiments, the component is derived from a SARS-CoV-2 variant. In some embodiments, there is provided a composition comprising a plurality of chimeric proteins that are capable of recognizing a plurality of SARS-CoV-2 variant and reference viruses. In some embodiments, the plurality of chimeric proteins each contain the same target-binding moiety. In some embodiments, at least two of the plurality of chimeric proteins contain different target-binding moieties, which recognize different SARS-CoV-2 variants.

Exemplary SARS-CoV-2 variants and their properties are shown in the Table B below. The chimeric proteins and compositions described herein may be used for treating any one of the SARS-CoV-2 variants described herein. The SARS-COV-2 variants described herein are named according to the Phylogenetic Assignment of Named Global Outbreak (PANGO) Lineages software. It is understood that the same variants may be referred to using different naming systems and algorithms in the art. SARS-CoV-2 variant classifications and definitions, as well as a list of known SARS-CoV-2 variants can be found at worldwide web.cdc.gov/coronavirus/2019-ncov/variants/variant-info.html.

TABLE B

SARS-CoV-2 variants and properties.

| Name | Spike Protein Substitutions | Phenotypes |
| --- | --- | --- |
| B.1.525 | Spike: A67V, 69del, 70del, 144del, E484K, D614G, Q677H, F888L | Potential reduction in neutralization by some Emergency Use Authorization (EUA) monoclonal antibody treatments<br>Potential reduction in neutralization by convalescent and post-vaccination sera |
| B.1.526 | Spike: (L5F*), T95I, D253G, (S477N*), (E484K*), D614G, (A701V*) | Reduced susceptibility to the combination of bamlanivimab and etesevimab monoclonal antibody treatment; however, the clinical implications of this are not known. Alternative monoclonal antibody treatments are available.<br>Reduced neutralization by convalescent and post-vaccination sera |
| B.1.526.1 | Spike: D80G, 144del, F157S, L452R, D614G, (T791I*), (T859N*), D950H | Potential reduction in neutralization by some EUA monoclonal antibody treatments<br>Potential reduction in neutralization by convalescent and post-vaccination sera |
| B.1.617 | Spike: L452R, E484Q, D614G | Potential reduction in neutralization by some EUA monoclonal antibody treatments<br>Slightly reduced neutralization by post-vaccination sera |
| B.1.617.1 | Spike: (T95I), G142D, E154K, L452R, E484Q, D614G, P681R, Q1071H | Potential reduction in neutralization by some EUA monoclonal antibody treatments<br>Potential reduction in neutralization by post-vaccination sera |
| B.1.617.2 | Spike: T19R, (G142D), 156del, 157del, R158G, L452R, T478K, D614G, P681R, D950N | Potential reduction in neutralization by some EUA monoclonal antibody treatments<br>Potential reduction in neutralization by post-vaccination sera |
| B.1.617.3 | Spike: T19R, G142D, L452R, E484Q, D614G, P681R, D950N | Potential reduction in neutralization by some EUA monoclonal antibody treatments<br>Potential reduction in neutralization by post-vaccination sera |
| P.2 | Spike: E484K, (F565L*), D614G, V1176F | Potential reduction in neutralization by some EUA monoclonal antibody treatments<br>Reduced neutralization by post-vaccination sera |
| B.1.1.7 | 69del, 70del, 144del, (E484K*), (S494P*), N501Y, A570D, D614G, P681H, T716I, S982A, D1118H (K1191N*) | ~50% increased transmission<br>Potential increased severity based on hospitalizations and case fatality rates<br>No impact on susceptibility to EUA monoclonal antibody treatments<br>Minimal impact on neutralization by convalescent and post-vaccination sera |
| B.1.351 | D80A, D215G, 241del, 242del, 243del, K417N, E484K, N501Y, D614G, A701V | ~50% increased transmission<br>Significant decrease in susceptibility to the combination of bamlanivimab and etesevimab monoclonal antibody treatment, but other EUA monoclonal antibody treatments are available<br>Reduced neutralization by convalescent and post-vaccination sera |
| B.1.427 | L452R, D614G | ~20% increased transmissibility<br>Modest decrease in susceptibility to the combination of bamlanivimab and etesevimab; however, the clinical implications of this decrease are not known. Alternative monoclonal antibody treatments are available.<br>Reduced neutralization by convalescent and post-vaccination sera |
| B.1.429 | S13I, W152C, L452R, D614G | ~20% increased transmissibility<br>Modest decrease in susceptibility to the combination of bamlanivimab and etesevimab; however, the clinical implications of this decrease are not known. Alternative monoclonal antibody treatments are available.<br>Reduced neutralization by convalescent and post-vaccination sera |
| P.1 | L18F, T20N, P26S, D138Y, R190S, K417T, E484K, N501Y, D614G, H655Y, T1027I | Significant decrease in susceptibility to the combination of bamlanivimab and etesevimab monoclonal antibody treatment, but other EUA monoclonal antibody treatments are available<br>Reduced neutralization by convalescent and post-vaccination sera |

Exemplary antibodies against SARS-CoV-2 (e.g., SARS-CoV-2 monoclonal antibodies that specifically bind to spike protein) are known in the art, including, for example, casirivimab, imdevimab, sotrovimab, bamlanivimab, etesevimab, TY027, BRII-196, BRII-198, ABBV-47D11, COVI-GUARD (STI-1499), MW33, HFB30132A, ADM03820, HLX70 DZIF-10c, COVI-AMG (STI-2020), BGB DXP593, SCTA01, AZD7442 (AZD8895 and AZD1061), CT-P59, ADG20, C144-LS and C-135-LS, MAD0004J08, DXP593, LY-CoV1404, LY3853113, VIR-7832, COR-101, ZRC- 3308, DXP604, LY-CovMab, JMB2002, XVR011, and biosimilars thereof. Exemplary SARS-CoV-2 antibodies are described in, for example, Taylor, P. C. et al. Neutralizing monoclonal antibodies for treatment of COVID-19. *Nat Rev Immunol* 21, 382-393 (2021), US2021/0292392A1, US2021/0277092A1, US2021/0300999A1, US2021/0292393A1, US2021/0261650A1, U.S. Ser. No. 10/975, 139B1, U.S. Ser. No. 10/954,289B1, U.S. Ser. No. 10/787, 501B1, WO2021/195326A1, WO2021/195485A1, WO2021/158521A1, and WO2021/168305A1, the contents of which are herein incorporated by reference in their entirety. Sequences of exemplary SARS-CoV-2 antibodies are provided in Table 2. A list of known SARS-CoV-2 antibodies can be found at world wide web. antibodysociety.org/covid-19-biologics-tracker/.

The chimeric proteins described herein may comprise the heavy chain and light chain CDRs, VH and VL, and/or heavy chain and light chain of any one of the SARS-CoV-2 antibodies described herein, including antibody sequences in Tables 2 and 6-8.

TABLE 2

Exemplary SARS-CoV-2 antibodies

| Antibody | References | VH/VL Sequences (CDRs are in bold) |
|---|---|---|
| Casirivimab | US10787501B1; US10954289B1; US10975139B1 Regeneron Pharmaceuticals (2020, Jun. 16-Present). Safety, Tolerability, and Efficacy of Anti-Spike (S) SARS-CoV-2 Monoclonal Antibodies for the Treatment of Ambulatory Adult and Pediatric Patients With COVID-19. Identifier NCT04425629. Regeneron Pharmaceuticals (2020, Jul. 26-Present). Study Assessing the Safety, Tolerability, Pharmacokinetics, and Immunogenicity of Repeated Subcutaneous Doses of Anti-Spike (S) SARS-CoV-2 Monoclonal Antibodies (REGN10933 + REGN10987) in Adult Volunteers as Related to COVID-19. Identifier: NCT04519437. Regeneron Pharmaceuticals (2020, Jun. 30-Present). COVID-19 Study Assessing the Efficacy and Safety of Anti-Spike SARS CoV-2 Monoclonal Antibodies for Prevention of SARS CoV-2 Infection Asymptomatic in Healthy Adults and Adolescents Who Are Household Contacts to an Individual With a Positive SARS-CoV-2 RT-PCR Assay. Identifier NCT04452318. | VH (SEQ ID NO: 121): QVQLVESGGGLVKPGGSLRLSCAASGF TFSDYYMSWIRQAPGKGLEWVSYITYS GSTIVYADSVKGRFTISRDNAKSSLY LQMNSLRAEDTAVYYCARDRGTTMVP FDYWGQGTLVTVSSASTKGPSVFPLAP SSKSTSGGTAALGCLVKDYFPEPVTVS WNSGALTSGVHTFPAVLQSSGLYSLSS VVTVPSSSLGTQTYICNVNHKPSNTKVD KKVEPKSCDKTHTCPPCPAPELLGGPSV FLFPPKPKDTLMISRTPEVTCVVVDVSH EDPEVKFNWYVDGVEVHNAKTKPREE QYNSTYRVVSVLTVLHQDWLNGKEYK CKVSNKALPAPIEKTISKAKGQPREPQV YTLPPSRDELTKNQVSLTCLVKGFYPSD IAVEWESNGQPENNYKTTPPVLDSDGSF FLYSKLTVDKSRWQQGNVFSCSVMHE ALHNHYTQKSLSLSPGK VL (SEQ ID NO: 122): DIQMTQSPSSLSASVGDRVTITCQASQD ITNYLNWYQQKPGKAPKLLIYAASNLE TGVPSRFSGSGSGTDFTFTISGLQPEDIA TYYCQQYDNLPLTFGGGTKVEIKRTVA APSVFIFPPSDEQLKSGTASVVCLLNNF YPREAKVQWKVDNALQSGNSQESVTE QDSKDSTYSLSSTLTLSKADYEKHKVY ACEVTHQG LSSPVTKSFNRGEC |
| Imdevimab | Regeneron Pharmaceuticals (2020, Jun. 11-Present). Safety, Tolerability, and Efficacy of Anti-Spike (S) SARS-CoV-2 Monoclonal Antibodies for Hospitalized Adult Patients With COVID-19. Identifier NCT04426695 | VH (SEQ ID NO: 123): QVQLVESGGGVVQPGRSLRLSCAASGF TFSNYAMYWVRQAPGKGLEWVAVISY DGSNKYYADSVKGRFTISRDNSKNTLY LQMNSLRTEDTAVYYCASGSDYGDYL LVYWGQGTLVTVSSASTKGPSVFPLAP SSKSTSGGTAALGCLVKDYFPEPVTVS WNSGALTSGVHTFPAVLQSSGLYSLSS VVTVPSSSLGTQTYICNVNHKPSNTKVD KKVEPKSCDKTHTCPPCPAPELLGGPSV FLFPPKPKDTLMISRTPEVTCVVVDVSH EDPEVKFNWYVDGVEVHNAKTKPREE QYNSTYRVVSVLTVLHQDWLNGKEYK CKVSNKALPAPIEKTISKAKGQPREPQV YTLPPSRDELTKNQVSLTCLVKGFYPSD IAVEWESNGQPENNYKTTPPVLDSDGSF FLYSKLTVDKSRWQQGNVFSCSVMHE ALHNHYTQKSLSLSPGK VL (SEQ ID NO: 124): QSALTQPASVSGSPGQSITISCTGTSSDV GGYNYVSWYQQHPGKAPKLMIYDVSK RPSGVSNRFSGSKSGNTASLTISGLQSE DEADYYCNSLTSISTWVFGGGTKLTVL GQPKAAPSVTLFPPSSEELQANKATLVC LISDFYPGAVTVAWKADSSPVKAGVET TTPSKQSNNKYAASSYLSLTPEQWKSH RSYSCQVTHEGSTVEKTVAPTECS |

TABLE 2-continued

Exemplary SARS-CoV-2 antibodies

| Antibody | References | VH/VL Sequences (CDRs are in bold) |
|---|---|---|
| Sotrovimab (VIR-7831/GSK4182136) | Vir Biotechnology, Inc. (2020, Aug. 27-). VIR-7831 for the Early Treatment of COVID-19 in Outpatients (COMET-ICE). Identifier NCT04545060. | VH (SEQ ID NO: 125): QVQLVQSGAEVKKPGASVKVSCKASG YPFTSYGISWVRQAPGQGLEWMGWIS TYQGNTNYAQKFQGRVTMTTDTSTTT GYMELRRLRSDDTAVYYCARDYTRGA WFGESLIGGFDNWGQGTLVTVSSAST KGPSVFPLAPSSKSTSGGTAALGCLVKD YFPEPVTVSWNSGALTSGVHTFPAVLQ SSGLYSLSSVVTVPSSSLGTQTYICNVN HKPSNTKVDKKVEPKSCDKTHTCPPCP APELLGGPSVFLFPPKPKDTLMISRTPEV TCVVVDVSHEDPEVKFNWYVDGVEVH NAKTKPREEQYNSTYRVVSVLTVLHQD WLNGKEYKCKVSNKALPAPIEKTISKA KGQPREPQVYTLPPSRDELTKNQVSLTC LVKGFYPSDIAVEWESNGQPENNYKTT PPVLDSDGSFFLYSKLTVDKSRWQQGN VFSCSVLHEALHSHYTQKSLSLSPGK<br>VL (SEQ ID NO: 126): EIVLTQSPGTLSLSPGERATLSCRASQT VSSTSLAWYQQKPGQAPRLLIYGASSR ATGIPDRFSGSGSGTDFTLTISRLEPEDF AVYYCQQHDTSLTFGGGTKVEIKRTV AAPSVFIFPPSDEQLKSGTASVVCLLNN FYPREAKVQWKVDNALQSGNSQESVT EQDSKDSTYSLSSTLTLSKADYEKHKV YACEVTHQGLSSPVTKSFNRGEC |
| Bamlanivimab (Also known as LY-CoV555) | US2020/0095327A1 Eli Lilly and Company (2020, Aug. 4-). A Study of LY3819253 (LY-CoV555) and LY3832479 (LY-CoV016) in Preventing SARS-CoV-2 Infection and COVID-19 in Nursing Home Residents and Staff (BLAZE-2). Identifier NCT04497987 | VH (SEQ ID NO: 127): QVQLVQSGAEVKKPGSSVKVSCKASGG TFSNYAISWVRQAPGQGLEWMGRIIPI LGIANYAQKFQGRVTITADKSTSTAY MELSSLRSEDTAVYYCARGYYEARHY YYYYAMDVWGQGTAVTVSSASTKGPS VFPLAPSSKSTSGGTAALGCLVKDYFPE PVTVSWNSGALTSGVHTFPAVLQSSGL YSLSSVVTVPSSSLGTQTYICNVNHKPS NTKVDKRVEPKSCDKTHTCPPCPAPELL GGPSVFLFPPKPKDTLMISRTPEVTCVV VDVSHEDPEVKFNWYVDGVEVHNAKT KPREEQYNSTYRVVSVLTVLHQDWLN GKEYKCKVSNKALPAPIEKTISKAKGQP REPQVYTLPPSREEMTKNQVSLTCLVK GFYPSDIAVEWESNGQPENNYKTTPVL DSDGSFFLYSKLTVDKSRWQQGNVFSC SVMHEALHNHYTQKSLSLSPGK<br>VL (SEQ ID NO: 128): DIQMTQSPSSLSASVGDRVTITCRASQSI SSYLSWYQQKPGKAPKLLIYAASSLQS GVPSRFSGSGSGTDFTLTITSLQPEDFAT YYCQQSYSTPRTFGQGTKVEIKRTVAA PSVFIFPPSDEQLKSGTASVVCLLNNFY PREAKVQWKVDNALQSGNSQESVTEQ DSKDSTYSLSSTLTLSKADYEKHKVYA CEVTHQGLSSPVTKSFNRGEC |

TABLE 2-continued

| Exemplary SARS-CoV-2 antibodies | | |
|---|---|---|
| Antibody | References | VH/VL Sequences (CDRs are in bold) |
| Etesevimab (Also known as LY-CoV016, JS016) | Shanghai Junshi Bioscience Co., Ltd. (2020, Jun. 5-). Tolerability, Safety, Pharmacokinetic Profile and Immunogenicity of a Recombinant Humanized Anti-SARS-CoV-2 Monoclonal Antibody (JS016) for Injection in Chinese Health Subjects. Identifier NCT04441918. Eli Lilly and Company (2020, Aug. 4-). A Study of LY3819253 (LY-CoV555) and LY3832479 (LY-CoV016) in Preventing SARS-CoV-2 Infection and COVID-19 in Nursing Home Residents and Staff (BLAZE-2). Identifier NCT04497987 | VH (SEQ ID NO: 129):<br>EVQLVESGGGLVQPGGSLRLSCAASGF<br>TVSSNYMSWVRQAPGKGLEWVSVIYS<br>GGSTFYADSVKGRFTISRDNSMNTLFL<br>QMNSLRAEDTAVYYCARVLPMYGDY<br>LDYWGQGTLVTVSSASTKGPSVFPLAP<br>SSKSTSGGTAALGCLVKDYFPEPVTVS<br>WNSGALTSGVHTFPAVLQSSGLYSLSS<br>VVTVPSSSLGTQTYICNVNHKPSNTKVD<br>KRVEPKSCDKTHTCPPCPAPEAAGGPSV<br>FLFPPKPKDTLMISRTPEVTCVVVDVSH<br>EDPEVKFNWYVDGVEVHNAKTKPREE<br>QYNSTYRVVSVLTVLHQDWLNGKEYK<br>CKVSNKALPAPIEKTISKAKGQPREPQV<br>YTLPPSREEMTKNQVSLTCLVKGFYPSD<br>IAVEWESNGQPENNYKTTPPVLDSDGSF<br>FLYSKLTVDKSRWQQGNVFSCSVMHE<br>ALHNHYTQKSLSLSPGK<br>VL (SEQ ID NO: 130):<br>DIVMTQSPSSLSASVGDRVTITCRASQSI<br>SRYLNWYQQKPGKAPKLLIYAASSLQS<br>GVPSRFSGSGSGTDFTLTISSLQPEDFAT<br>YYCQQSYSTPPEYTFGQGTKLEIKRTV<br>AAPSVFIFPPSDEQLKSGTASVVCLLNN<br>FYPREAKVQWKVDNALQSGNSQESVT<br>EQDSKDSTYSLSSTLTLSKADYEKHKV<br>YACEVTHQGLSSPVTKSFNRGEC |

SARS-CoV

In some embodiments, the target-binding moiety specifically binds a component of SARS-CoV. In some embodiments, the component is derived from a reference SARS-CoV-2. In some embodiments, the component is derived from a SARS-CoV-2 variant. In some embodiments, the component is a surface molecule of SARS-CoV. In some embodiments, the surface molecule is a spike (S) protein. In some embodiments, the surface molecule is an S1 subunit of the S protein. Sequences of SARS-CoV S1 proteins are known in the art, including, for example, UniProtKB ID: P59594, UniProt KB ID: P0DTC2, NCBI RefSeq ID: YP_009724390.1, GeneBank ID: AAP41037.1. In some embodiments, SARS-CoV S1 protein comprises the amino acid sequence of SEQ ID NO: 94.

spike glycoprotein subunit of SARS-CoV

SEQ ID NO: 94

```
MFIFLLFLTLTSGSDLDRCTTFDDVQAPNYTQHTSSMRGVYYPDEIFRSD

TLYLTQDLFLPFYSNVTGFHTINHTFGNPVIPFKDGIYFAATEKSNVVRG

WVFGSTMNNKSQSVIIINNSTNVVIRACNFELCDNPFFAVSKPMGTQTHT

MIFDNAFNCTFEYISDAFSLDVSEKSGNFKHLREFVFKNKDGFLYVYKGY

QPIDVVRDLPSGFNTLKPIFKLPLGINITNFRAILTAFSPAQDIWGTSAA

AYFVGYLKPTTFMLKYDENGTITDAVDCSQNPLAELKCSVKSFEIDKGIY

QTSNFRVVPSGDVVRFPNITNLCPFGEVFNATKFPSVYAWERKKISNCVA

DYSVLYNSTFFSTFKCYGVSATKLNDLCFSNVYADSFVVKGDDVRQIAPG

QTGVIADYNYKLPDDFMGCVLAWNTRNIDATSTGNYNYKYRYLRHGKLRP

FERDISNVPFSPDGKPCTPPALNCYWPLNDYGFYTTTGIGYQPYRVVVLS

FELLNAPATVCGPKLSTDLIKNQCVNFNFNGLTGTGVLTPSSKRFQPFQQ
```

-continued

```
FGRDVSDFTDSVRDPKTSEILDISPCSFGGVSVITPGTNASSEVAVLYQD

VNCTDVSTAIHADQLTPAWRIYSTGNNVFQTQAGCLIGAEHVDTSYECDI

PIGAGICASYHTVSLLRSTSQKSIVAYTMSLGADSSIAYSNNTIAIPTNF

SISITTEVMPVSMAKTSVDCNMYICGDSTECANLLLQYGSFCTQLNRALS

GIAAEQDRNTREVFAQVKQMYKTPTLKYFGGFNFSQILPDPLKPTKRSFI

EDLLFNKVTLADAGFMKQYGECLGDINARDLICAQKFNGLTVLPPLLTDD

MIAAYTAALVSGTATAGWTFAGAALQIPFAMQMAYRFNGIGVTQNVLYEN

QKQIANQFNKAISQIQESLTTTSTALGKLQDVVNQNAQALNTLVKQLSSN

FGAISSVLNDILSRLDKVEAEVQIDRLITGRLQSLQTYVTQQLIRAAEIR

ASANLAATKMSECVLGQSKRVDFCGKGYHLMSFPQAAPHGVVFLHVTYVP

SQERNFTTAPAICHEGKAYFPREGVFVFNGTSWFITQRNFFSPQIITTDN

TFVSGNCDVVIGIINNTVYDPLQPELDSFKEELDKYFKNHTSPDVDLGDI

SGINASVVNIQKEIDRLNEVAKNLNESLIDLQELGKYEQYIKWPWYVWLG

FIAGLIAIVMVTILLCCMTSCCSCLKGACSCGSCCKFDEDDSEPVLKGVK

LHYT
```

In some embodiments, the target-binding moiety is an antibody that specifically binds to the S1 protein of SARS-CoV, or an antigen-binding fragment thereof. In some embodiments, the antibody inhibits the binding of SARS-CoV spike protein S1 to the cell surface. In some embodiments, the target-binding moiety is an antibody that binds within the receptor-binding domain of the S protein of SARS-CoV, or an antigen-binding fragment thereof. In some embodiments, the antibody specifically binds to amino acid residues 318-510 of the S1 protein, wherein the numbering is based on SEQ ID NO: 94. In some embodiments, the antibody is a neutralizing human monoclonal antibody that blocks the binding of S1 protein to its receptor angiotensin-converting enzyme 2 (ACE2) on host cells. In some embodiments, the antibody specifically binds to amino acid residues 261-672 of the S1 protein, wherein the numbering is based on SEQ ID NO: 94. In some embodiments, the antibody is able to cross-neutralize several SARS-CoV isolates. In some embodiments, the antibody is raised to the different conformational epitopes of the receptor-binding domain of the S1 protein. In some embodiments, SARS-CoV human isolates (e.g., Tor2, GD03T0013) or palm civet (*Paguma larvata*) isolate fusion proteins (e.g., Sz3 S1-Fc) may be used as immunogens to induce high titers of cross-neutralizing antibodies.

Exemplary antibodies against the S1 protein of SARS-CoV are known in the art, including, for example, CR3041, CR3001, CR3002, CR3009, CR3013, and CR3018, reported in van den Brink, et al. "Molecular and Biological Characterization of Human Monoclonal Antibodies Binding to the Spike and Nucleocapsid Proteins of Severe Acute Respiratory Syndrome Coronavirus." Journal of Virology 79.3 (2005): 1635-1644; 80R, as reported in Sui, et al. "Potent neutralization of severe acute respiratory syndrome (SARS) coronavirus by a human mAb to S1 protein that blocks receptor association." 101.8 (2004): 2536-2541; m396 and 5230.15 reported in Zhu, et al. "Potent cross-reactive neutralization of SARS coronavirus isolates by human monoclonal antibodies." PNAS 104.29 (2007): 12123-12129; Conf I-VI monoclonal antibodies reported in He, et al. "Cross-Neutralization of Human and Palm Civet Severe Acute Respiratory Syndrome Coronaviruses by Antibodies Targeting the Receptor-Binding Domain of Spike Protein." The Journal of Immunology 176 (2006): 6085-6092, which are incorporated by reference in their entirety. Exemplary antibody sequences against S1 of SARS-CoV are shown in Tables 3-4. In some embodiments, the target-binding moiety is a derivative of any one of the antibodies against the S1 protein of SARS-CoV described herein. In some embodiments, the antibodies that compete with any of these art-recognized antibodies for binding to the S1 protein of SARS-CoV can be used.

In some embodiments, the target-binding moiety is an antibody or antigen-binding fragment derived from CR3041, including biosimilars thereof. In some embodiments, the anti-S1 antibody comprises a VH and a VL, wherein the VH comprises an HC-CDR1 comprising the amino acid sequence of SEQ ID NO: 99, a HC-CDR2 comprising the amino acid sequence of SEQ ID NO: 100, and an HC-CDR3 comprising the amino acid sequence of SEQ ID NO: 101; and wherein the VL comprises an LC-CDR1 comprising the amino acid sequence of SEQ ID NO: 102, an LC-CDR2 comprising the amino acid sequence of SEQ ID NO: 103, and an LC-CDR3 comprising the amino acid sequence of SEQ ID NO: 104. In some embodiments, the anti-S1 antibody comprises a VH comprising the amino acid sequence of SEQ ID NO: 105, and/or a VL comprising the amino acid sequence of SEQ ID NO: 106.

In some embodiments, the target-binding moiety is an antibody or antigen-binding fragment derived from 80R, including biosimilars thereof. In some embodiments, the anti-S1 antibody comprises a VH and a VL, wherein the VH comprises an HC-CDR1 comprising the amino acid sequence of SEQ ID NO: 107, a HC-CDR2 comprising the amino acid sequence of SEQ ID NO: 108, and a HC-CDR3 comprising the amino acid sequence of SEQ ID NO: 109; and wherein the VL comprises a LC-CDR1 comprising the amino acid sequence of SEQ ID NO: 110, a LC-CDR2 comprising the amino acid sequence of SEQ ID NO: 111, and a LC-CDR3 comprising the amino acid sequence of SEQ ID NO: 112. In some embodiments, the anti-S1 antibody comprises a VH comprising the amino acid sequence of SEQ ID NO: 113, and/or a VL comprising the amino acid sequence of SEQ ID NO: 114.

TABLE 3

Exemplary SARS-CoV antibody CDR sequences

| Antibody | SEQ ID NO: | HCDR1/ LCDR1 | SEQ ID NO: | HCDR2/ LCDR2 | SEQ ID NO: | HCDR3/ LCDR3 |
|---|---|---|---|---|---|---|
| CR3041 | 99 | DHYMD | 100 | RTRNKANSYTTEYAASVKG | 101 | GISPFYFDY |
|  | 102 | RASQSISSYLN | 103 | AASSLQS | 104 | QQSYSTPPT |
| 80R | 107 | SYAMH | 108 | VISYDGSNKYYADSVKG | 109 | DRSYYLDY |
|  | 110 | RASQSVRSNLA | 111 | DASTRAT | 112 | QQRSNWPPT |

TABLE 4

Exemplary SARS-CoV antibody VH/VL sequences

| Antibody | SEQ ID NO: | VH | SEQ ID NO: | VL |
|---|---|---|---|---|
| CR3041 | 105 | EVQLVESGGGLVQPGGSLRLSCAASGFTFSDHYMDWVRQAPGKGLEWVGRTRNKANSYTTEYAASVKGRFTISRDDSKNSLYLQMNSLKTEDTAVYYCARGISPFYFDYWGQGTLVTV | 106 | ELTQSPSSLSASVGDRVTITCRASQSISSYLNWYQQKPGKAPKLLIYAASSLQSGVPSRFSGSGSGTDFTLTISSLQPEDFATYYCQQSYSTPPTFGQGTKVEIK |

TABLE 4-continued

Exemplary SARS-CoV antibody VH/VL sequences

| Antibody | SEQ ID NO: | VH | SEQ ID NO: | VL |
|---|---|---|---|---|
| 80R | 113 | EVQLVQSGGGVVQPGKSLRLSC AASGFAFSSYAMHWVRQAPGKG LEWVAVISYDGSNKYYADSVKG RFTISRDNSKNTLYLQMNSLRA EDTAVYYCARDRSYYLDYWGQG TLVTVSS | 114 | TTLTQSPATLSLSPGERATLSCRASQ SVRSNLAWYQQKPGQAPRPLIYDAST RATGIPDRFSGSGSGTDFTLTISRLE PEDFAVYYCQQRSNWPPTFGQGTKVE VK |

The spike (S) protein of SARS-CoV mediates receptor binding and viral entry (i.e., viral infection) of host cells, and is therefore an attractive target for vaccine design. The S protein is a type I transmembrane glycoprotein possessing an S1 domain, comprising amino acid residues 1 to 672 of the S protein. A fragment located in the central region of the S1 domain, amino acid residues 318-510, is defined as the receptor-binding domain. The receptor-binding domain of the S1 protein is a major determinant of SARS-CoV neutralization. Antibodies targeting the S1 protein, and in particular the receptor binding domain, represent a large class of useful therapeutics for prevention and treatment of SARS-CoV infection.

MERS-CoV

In some embodiments, the target-binding moiety specifically binds a component of MERS-CoV. In some embodiments, the component is a surface molecule of MERS-CoV. In some embodiments, the surface molecule is a spike (S) protein. In some embodiments, the surface molecule is an S1 protein. In some embodiments, the surface molecule is an S2 protein. Sequences of MERS-CoV S proteins are known in the art, including, for example, UniProtKB ID: A0A023SFE5.

In some embodiments, the target-binding moiety is an antibody that binds within the receptor-binding domain of the S protein of MERS-CoV, or an antigen-binding fragment thereof. In some embodiments, the target-binding moiety is an antibody that specifically binds to the S1 protein of MERS-CoV, or an antigen-binding fragment thereof. In some embodiments, the target-binding moiety is an antibody that specifically binds to the S2 protein of MERS-CoV, or an antigen-binding fragment thereof. In some embodiments, the antibody inhibits the binding of MERS-CoV spike protein to the host cell surface. In some embodiments, the antibodies bind non-overlapping epitopes on MERS-CoV S protein with high affinity and hinders the three functions of the virus: sialic acid binding, receptor binding and membrane fusion. Exemplary antibodies against the S1 and S2 proteins of MERS-CoV are known in the art, including, for example, 1.10f3, 7.7g6, 1.6f9, 1.2g5, 1.8e5, 4.6e10, 1.6c7 and 3.5g6, reported in Widjaja, et al. "Towards a solution to MERS: protective human monoclonal antibodies targeting different domains and functions of the MERS-coronavirus spike glycoprotein." Emerging Microbes & Infections 8 (2019): 516-530, which is incorporated by reference in its entirety.

The MERS-CoV spike protein (S) mediates viral entry into host cells and is comprised of three S proteins: the S1 subunits, comprising the receptor-binding domain, and the S2 subunit, responsible for facilitating membrane-anchored fusion. The S1 domains mediate viral binding to the host cell surface via sialoglycoconjugates and receptor binding, while the S2 domain conducts fusion of viral membranes to host cell membranes. The design of effective neutralizing antibodies against MERS-CoV should therefore target each functionally distinct MERS-CoV S protein domain, to successfully interfere with viral function.

B. Mucoadhesive Peptide Fragments

The chimeric proteins described herein comprise one or more (e.g., 1, 2, 3, 4 or more) mucoadhesive peptide fragments.

In some embodiments, the target-binding moiety comprises the same number of polypeptide chains as the number of mucoadhesive peptide fragment(s) in the chimeric protein. In some embodiments, the target-binding moiety comprises more polypeptide chains than the number of mucoadhesive peptide fragment(s) in the chimeric protein. In some embodiments, each polypeptide chain of the target-binding moiety is coupled to (e.g., fused to) a mucoadhesive peptide fragment. In some embodiments, the target-binding moiety comprises polypeptide chains that are not coupled (e.g., fused to) a mucoadhesive peptide fragment.

In some embodiments, the mucoadhesive peptide fragment is fused to any position in the target-binding moiety that does not interference with binding of the target-binding moiety to the component of the pathogen. In some embodiments, the mucoadhesive peptide fragment is fused to a site that is distal from the target-binding site. In some embodiments, the mucoadhesive peptide fragment is fused to the C-terminus of an antibody heavy chain in the target-binding moiety. In some embodiments, the mucoadhesive peptide fragment is fused to the C-terminus of an antibody light chain in the target-binding moiety.

In some embodiments, the chimeric protein comprises a single polypeptide chain comprising the target-binding moiety and a mucoadhesive peptide fragment.

In some embodiments, the chimeric protein comprises: (a) a first polypeptide comprising a first polypeptide chain of the target-binding moiety and a first mucoadhesive peptide fragment; and (b) a second polypeptide comprising a second polypeptide of the target-binding moiety and a second mucoadhesive peptide fragment. In some embodiments, the target-binding moiety further comprises polypeptide chains that are not coupled to (e.g., fused to) a mucoadhesive peptide fragment.

In some embodiments, the mucoadhesive peptide fragment comprises about 5 to about 300 positively charged amino acid residues. In some embodiments, the mucoadhesive peptide fragment comprises about 5 to about 10 positively charged amino acid residues. In some embodiments, the mucoadhesive peptide fragment comprises about 11 to about 15 positively charged amino acid residues. In some embodiments, the mucoadhesive peptide fragment comprises about 16 to about 20 positively charged amino acid residues. In some embodiments, the mucoadhesive peptide fragment comprises about 21 to about 25 positively charged amino acid residues. In some embodiments, the mucoadhesive peptide fragment comprises about 26 to about 30 positively charged amino acid residues. In some embodiments, the mucoadhesive peptide fragment comprises about 8 to about 25 positively charged amino acid residues. In some embodiments, the mucoadhesive peptide fragment comprises about 10 to about 22 positively charged amino acid residues. In some embodiments, the mucoadhesive peptide fragment comprises about 12 to about 20 positively charged amino acid residues. In some embodiments, the mucoadhesive peptide fragment comprises about 14 to about 18 positively charged amino acid residues. In some embodiments, the mucoadhesive peptide fragment comprises any one of about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, 300, or more positively charged amino acid residues. In some embodiments, the mucoadhesive peptide fragment comprises about any one of about 5-10, 11-15, 16-20, 21-25, 26-30, 31-35, 36-40, 41-45, 46-50, 51-55, 56-60, 61-65, 66-70, 71-75, 76-80, 81-85, 86-90, 91-95, 96-100, 101-110, 111-120, 121-130, 131-140, 141-150, 151-160, 161-170, 171-180, 181-190, 191-200, 201-210, 211-220, 221-230, 231-140, 241-150, 251-160, 261-270, 271-180, 281-290, 291-300, 5-15, 5-20, 5-25, 8-15, 8-20, 8-25, 10-20, 10-25, 12-20, 12-25, 15-25, 15-30, 5-30, 6-30, or 5-50, positively charged amino acid residues. In some embodiments, the mucoadhesive peptide fragment comprises at least about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, or more, positively charged amino acid residues. In some embodiments, the mucoadhesive peptide fragment comprises no more than about 300, 290, 280, 270, 260, 250, 240, 230, 220, 210, 200, 190, 180, 170, 160, 150, 140, 130, 120, 110, 100, 95, 90, 85, 80, 75, 70, 65, 60, 55, 50, 45, 40, 35, 30, 29, 28, 27, 26, 25, 24, 23, 22, 21, 20, 19, 18, 17, 16, 15, 14, 13, 12, 10, 9, 8, 7, 6, or 5 positively charged amino acid residues.

In some embodiments, the mucoadhesive peptide fragment comprises about 5 to about 50 positively charged amino acid residues (e.g., lysines or histidines). In some embodiments, the mucoadhesive peptide fragment comprises about 6 to about 30 positively charged amino acid residues (e.g., lysines or histidines). In some embodiments, the mucoadhesive peptide fragment comprises about 6, 12, 18, 24 or 30 positively charged amino acid residues (e.g., lysines or histidines).

In some embodiments, the chimeric protein comprises two or more mucoadhesive peptide fragments. In some embodiments, each of the two or more mucoadhesive peptide fragments comprises about 5 to about 300 positively charged amino acid residues. In some embodiments, each of the two or more mucoadhesive peptide fragments comprises about 5 to about 10 positively charged amino acid residues. In some embodiments, each of the two or more mucoadhesive peptide fragments comprises about 11 to about 15 positively charged amino acid residues. In some embodiments, each of the two or more mucoadhesive peptide fragments comprises about 16 to about 20 positively charged amino acid residues. In some embodiments, each of the two or more mucoadhesive peptide fragments comprises about 21 to about 25 positively charged amino acid residues. In some embodiments, each of the two or more mucoadhesive peptide fragments comprises about 26 to about 30 positively charged amino acid residues. In some embodiments, each of the two or more mucoadhesive peptide fragments comprises about 8 to about 25 positively charged amino acid residues. In some embodiments, each of the two or more mucoadhesive peptide fragments comprises about 10 to about 22 positively charged amino acid residues. In some embodiments, each of the two or more mucoadhesive peptide fragments comprises about 12 to about 20 positively charged amino acid residues. In some embodiments, each of the two or more mucoadhesive peptide fragments comprises about 14 to about 18 positively charged amino acid residues. In some embodiments, each of the two or more mucoadhesive peptide fragments comprises any one of about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, 300, or more, positively charged amino acid residues. In some embodiments, each of the two or more mucoadhesive peptide fragments comprises any one of about 5-10, 11-15, 16-20, 21-25, 26-30, 31-35, 36-40, 41-45, 46-50, 51-55, 56-60, 61-65, 66-70, 71-75, 76-80, 81-85, 86-90, 91-95, 96-100, 101-110, 111-120, 121-130, 131-140, 141-150, 151-160, 161-170, 171-180, 181-190, 191-200, 201-210, 211-220, 221-230, 231-240, 241-250, 251-260, 261-270, 271-280, 281-290, 291-300, 5-15, 5-20, 5-25, 8-15, 8-20, 8-25, 10-20, 10-25, 12-20, 12-25, 15-25, 15-30, 5-30, 6-30, or 5-50, positively charged amino acid residues. In some embodiments, each of the two or more mucoadhesive peptide fragments comprises at least about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, or more, positively charged amino acid residues. In some embodiments, each of the two or more mucoadhesive peptide fragments comprises no more than about 300, 290, 280, 270, 260, 250, 240, 230, 220, 210, 200, 190, 180, 170, 160, 150, 140, 130, 120, 110, 100, 95, 90, 85, 80, 75, 70, 65, 60, 55, 50, 45, 40, 35, 30, 29, 28, 27, 26, 25, 24, 23, 22, 21, 20, 19, 18, 17, 16, 15, 14, 13, 12, 10, 9, 8, 7, 6, or 5 positively charged amino acid residues.

In some embodiments, the total number of positively charged amino acid residues in the mucoadhesive peptide fragment(s) in the chimeric protein is about 5 to about 600. In some embodiments, the total number of positively charged amino acid residues in the mucoadhesive peptide fragment(s) in the chimeric protein is about 5 to about 20. In some embodiments, the total number of positively charged amino acid residues in the mucoadhesive peptide fragment(s) in the chimeric protein is about 11 to about 30. In some embodiments, the total number of positively charged amino acid residues in the mucoadhesive peptide fragment(s) in the chimeric protein is about 16 to about 40. In some embodiments, the total number of positively charged amino acid residues in the mucoadhesive peptide fragment(s) in the chimeric protein is about 21 to about 50. In some embodiments, the total number of positively charged amino acid residues in the mucoadhesive peptide fragment(s) in the chimeric protein is about 26 to about 60. In some embodiments, the total number of positively charged amino acid residues in the mucoadhesive peptide fragment(s) in the chimeric protein is about 8 to about 50. In some embodiments, the total number of positively charged amino acid residues in the mucoadhesive peptide fragment(s) in the chimeric protein is about 10 to about 44. In some embodiments, the total number of positively charged amino acid residues in the mucoadhesive peptide fragment(s) in the chimeric protein is about 12 to about 40. In some embodiments, the total number of positively charged amino acid residues in the mucoadhesive peptide fragment(s) in the chimeric protein is about 14 to about 36.

In some embodiments, the total number of positively charged amino acid residues in the mucoadhesive peptide fragment(s) in the chimeric protein comprises any one of about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, 300, 350, 400, 450, 550, 600, or more. In some embodiments, the total number of positively charged amino acid residues in the mucoadhesive peptide fragment(s) in the chimeric protein comprises any one of about 5-10, 11-15, 16-20, 21-25, 26-30, 31-35, 36-40, 41-45, 46-50, 51-55, 56-60, 61-65, 66-70, 71-75, 76-80, 81-85, 86-90, 91-95, 96-100, 101-110, 111-120, 121-130, 131-140, 141-150, 151-160, 161-170, 171-180, 181-190, 191-200, 201-210, 211-220, 221-230, 231-240, 241-250, 251-160, 261-270, 271-280, 281-290, 291-300, 301-310, 311-320, 321-330, 331-340, 341-350, 351-360, 361-370, 371-380, 381-390, 391-400, 401-410, 411-420, 421-430, 431-440, 441-450, 451-460, 461-470, 471-480, 481-490, 491-500, 501-510, 511-520, 521-530, 531-540, 541-550, 551-560, 561-570, 571-580, 581-590, 591-600, 5-15, 5-20, 5-25, 8-15, 8-20, 8-25, 10-20, 10-25, 12-20, 12-25, 15-25, 15-30, 5-30, 6-30, or 5-50. In some embodiments, the total number of positively charged amino acid residues in the mucoadhesive peptide fragment(s) in the chimeric protein comprises at least about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, or more. In some embodiments, the total number of positively charged amino acid residues in the mucoadhesive peptide fragment(s) in the chimeric protein comprises no more than about 600, 590, 580, 570, 560, 550, 540, 530, 520, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 95, 90, 85, 80, 75, 70, 65, 60, 55, 50, 45, 40, 35, 30, 29, 28, 27, 26, 25, 24, 23, 22, 21, 20, 19, 18, 17, 16, 15, 14, 13, 12, 10, 9, 8, 7, 6, or 5.

In some embodiments, the number of positively charged amino acid residues in the mucoadhesive peptide fragment(s) per target-binding site in the target-binding moiety is about 5 to about 30. In some embodiments, the number of positively charged amino acid residues in the mucoadhesive peptide fragment(s) per target-binding site in the target-binding moiety is about 8 to about 25. In some embodiments, the number of positively charged amino acid residues in the mucoadhesive peptide fragment(s) per target-binding site in the target-binding moiety is about 10 to about 22. In some embodiments, the number of positively charged amino acid residues in the mucoadhesive peptide fragment(s) per target-binding site in the target-binding moiety is about 12 to about 20. In some embodiments, the number of positively charged amino acid residues in the mucoadhesive peptide fragment(s) per target-binding site in the target-binding moiety is about 14 to about 18. In some embodiments, the number of positively charged amino acid residues in the mucoadhesive peptide fragment(s) per target-binding site in the target-binding moiety comprises any of about 5, 6, 7, 8, 9, 10, 11, 12, 13, 14, 15, 16, 17, 18, 19, 20, 21, 22, 23, 24, 25, 26, 27, 28, 29, 30, or more. In some embodiments, the number of positively charged amino acid residues in the mucoadhesive peptide fragment(s) per target-binding site in the target-binding moiety is any one of about 5-10, 11-15, 16-20, 21-25, 26-30, 5-15, 5-20, 5-25, 8-15, 8-20, 8-25, 10-20, 10-25, 12-20, 12-25, 15-25, 15-30, 5-30, or 6-30. In some embodiments, the number of positively charged amino acid residues in the mucoadhesive peptide fragment(s) per target-binding site in the target-binding moiety is at least about 5, 6, 7, 8, 9, 10, 11, 12, 13, 14, 15, 16, 17, 18, 19, 20, 21, 22, 23, 24, 25, 30, or more. In some embodiments, the number of positively charged amino acid residues in the mucoadhesive peptide fragment(s) per target-binding site in the target-binding moiety is no more than about 30, 29, 28, 27, 26, 25, 24, 23, 22, 21, 20, 19, 18, 17, 16, 15, 14, 13, 12, 10, 9, 8, 7, 6, or 5.

The mucoadhesive peptide fragment(s) may comprise any suitable positively charged amino acid residues at physiological pH of the mucosa, including naturally occurring and synthetic amino acid residues such as lysine, arginine, and ornithine. In some embodiments, the mucoadhesive peptide fragment comprises lysines only. In some embodiments, the mucoadhesive peptide fragment comprises arginines only. In some embodiments, the mucoadhesive peptide fragment comprises ornithines only. In some embodiments, the mucoadhesive peptide fragment comprises both lysines and arginines. In some embodiments, the mucoadhesive peptide fragment comprises an equal number of lysines and arginines. In some embodiments, the mucoadhesive peptide fragment comprises unequal numbers of lysines and arginines. In some embodiments, the mucoadhesive peptide fragment comprises both lysines and ornithines. In some embodiments, the mucoadhesive peptide fragment comprises an equal number of lysines and ornithines. In some embodiments, the mucoadhesive peptide fragment comprises unequal numbers of lysines and ornithines. In some embodiments, the mucoadhesive peptide fragment comprises both arginines and ornithines. In some embodiments, the mucoadhesive peptide fragment comprises an equal number of arginines and ornithines. In some embodiments, the mucoadhesive peptide fragment comprises lysines, arginines, and ornithines. In some embodiments, the mucoadhesive peptide fragment comprises an equal number of lysines, arginines, and ornithines. In some embodiments, the mucoadhesive peptide fragment comprises unequal numbers of lysines, arginines, and ornithines. In some embodiments, the mucoadhesive peptide fragment(s) comprises one or more non-naturally occurring amino acid residues that are positively charged at physiological pH of the mucosa.

In some embodiments, the mucoadhesive peptide fragment has an isoelectric point (pI) higher than the pH of the mucosa. The pH values of various mucosa in human are known. For example, the human nasal mucosa may have a pH range of about 5.5 to about 6.5, about 5.5 to about 6.6, about 6.44 to about 6.91, about 6.4 to about 7.9, or about 6.4 to about 6.5. In some examples, the human nasal mucosa may have a pH of about 6.6. In other examples, the human tracheal mucosa may have a pH range of about 6.1 to about 7.9, or a pH of about 6.71. In further examples, the human bronchial mucosa may have a pH range of about 5.7 to about 6.6 or about 7 to about 7.5. In some examples, the human bronchial mucosa may have a pH of about 6.7, about 7.1, about 6.25, about 6.78, or about 6.58. In some examples, the human mucosa may be diseased. In such examples, smokers may have a sputum mucosa pH of about 7.25 or about 6.82. In other examples, patients suffering with chronic bronchitis may have a sputum mucoid pH of about 7.59 and/or a sputum purulent pH of about 7.83. In other examples, patients suffering with rhinitis may have a nasal mucosa pH range of about 7.2 to about 8.3. In other examples still, patients suffering with the common cold may have a mucosa pH range of about 7.2 to about 8.3

In some embodiments, at nasal pH (e.g., ~6.5), the various properties (e.g., pI, net charge, and molecular weight) of polycationic peptides described herein may be calculated. In some examples, at nasal pH (e.g., ~6.5), the equivalent of a 20-mer polypeptide may be calculated. The 20-mer polypeptide will be linear, and the size of each polypeptide will be proportional to the molecular weight. The pI and molecular weight of various exemplary 20-mer polypeptides at nasal pH were calculated and are listed in Table 5. The interactions between the positively charged polypeptides and mucosal cells or mucin may primarily occur by charge.

TABLE 5

Exemplary amino acid and corresponding 20-mer polypeptides properties at nasal pH

| Amino acid or polypeptide | pI | Net charge | Molecular weight (Da) |
| --- | --- | --- | --- |
| Lysine (K) | 8.8 | +1 | 146.2 |
| Arginine (R) | 10.0 | +1 | 174.2 |
| Histidine (H) | 7.2 | +0.5 | 155.2 |
| K-20 | 11.3 | +20 | 2581.5 |
| R-20 | 13.3 | +20 | 3141.8 |
| H-20 | 8.1 | +10 | 2760.8 |

In some embodiments, the pI range of the mucoadhesive peptide fragment is at least about any one of 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.5, 12, 12.5, 13, or more. In some embodiments, the pI range of the mucoadhesive peptide fragment is about 8-14. In some embodiments, the range of pI values of the mucoadhesive peptide fragment is about 8.8-10.0. In some embodiments, the range of pI values of the mucoadhesive peptide fragment is about 11.3-13.3. In some embodiments, the range of pI values of the chimeric protein is at least about any one of 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.5, 12, 12.5, 13, or more, including, about any one of 8-8.3, 8.3-8.5, 8.5-8.7, 8.7-8.9, 8.9-9.1, 9.1-9.3, 9.3-9.4, 9.4-10, 8-10, 8-9, 9-10, 8-11, 8.5-9.5, 8.76-9.44, 8.77-9.61, and 8.32-9.33.

In some embodiments, the mucoadhesive peptide fragment is a polylysine peptide. In some embodiments, the mucoadhesive peptide fragment is a polylysine peptide having any one of 5, 6, 7, 8, 9, 10, 11, 12, 13, 14, 15, 16, 17, 18, 19, 20, 21, 22, 23, 24, 25, 26, 27, 28, 29, or 30 contiguous lysines. In some embodiments, the mucoadhesive peptide fragment is a polylysine peptide having about any one of 5-10, 10-15, 15-20, 20-25, 25-30, 30-40, 40-50, 5-15, 5-20, 5-25, 8-15, 8-20, 8-25, 10-20, 10-25, 12-20, 12-25, 15-25, 15-30, 5-30, 6-30, or 5-50 contiguous lysines.

In some embodiments, the mucoadhesive peptide fragment is a polyhistidine peptide. In some embodiments, the mucoadhesive peptide fragment is a polyhistidine peptide having any one of 5, 6, 7, 8, 9, 10, 11, 12, 13, 14, 15, 16, 17, 18, 19, 20, 21, 22, 23, 24, 25, 26, 27, 28, 29, or 30 contiguous histidines. In some embodiments, the mucoadhesive peptide fragment is a polyhistidine peptide having about any one of 5-10, 10-15, 15-20, 20-25, 25-30, 30-40, 40-50, 5-15, 5-20, 5-25, 8-15, 8-20, 8-25, 10-20, 10-25, 12-20, 12-25, 15-25, 15-30, 5-30, 6-30, or 5-50 contiguous histidines.

In some embodiments, the mucoadhesive peptide fragment is a polyarginine, polyhistidine, or polyornithine peptide. In some embodiments, the mucoadhesive peptide fragment is a polyarginine, polyhistidine, or polyornithine peptide having any one of 5, 6, 7, 8, 9, 10, 11, 12, 13, 14, 15, 16, 17, 18, 19, 20, 21, 22, 23, 24, 25, 26, 27, 28, 29, or 30 contiguous arginines, histidines, or ornithines. In some embodiments, the mucoadhesive peptide fragment is a polyarginine, polyhistidine, or polyornithine peptide having about any one of 5-10, 10-15, 15-20, 20-25, 25-30, 30-40, 40-50, 5-15, 5-20, 5-25, 8-15, 8-20, 8-25, 10-20, 10-25, 12-20, 12-25, 15-25, 15-30, 5-30, 6-30, or 5-50 contiguous arginines, histidines, or ornithines.

In some embodiments, the mucoadhesive peptide fragment comprises a continuous stretch of positively charged amino acid residues. In some embodiments, all positively charged amino acid residues are contiguous with respect to each other. In some embodiments, the positively charged amino acid residues are interspaced with non-positively charged amino acid residues. In some embodiments, the positively charged amino acid residues are present in every other position in the mucoadhesive peptide fragment. In some embodiments, the positively charged amino acid residues are present in every third position in the mucoadhesive peptide fragment. In some embodiments, the positively charged amino acid residues are randomly dispersed in the mucoadhesive peptide fragment. In some embodiments, the positive charged residues are present in one or more clusters within the mucoadhesive peptide fragment.

In some embodiments, at least about any one of 10%, 20%, 30%, 40%, 50%, 60%, 70%, 80%, 90%, 95%, 99% or more of the amino acid residues in the mucoadhesive peptide fragment are positively charged amino acid residues. In some embodiments, all amino acid residues in the mucoadhesive peptide fragment are positively charged. In some embodiments, no more than about any one of 99%, 95%, 90%, 80%, 70%, 60%, 50%, 40%, 30%, 20%, or 10% of the amino acid residues in the mucoadhesive peptide fragment are positively charged amino acid residues. In some embodiments, about any one of 10%-99%, 10%-20%, 20%-30%, 30%-40%, 40%-50%, 50%-60%, 60%-80%, 10%-100%, 10%-30%, 30%-60%, 60%-90%, 20%-50%, or 50%-100% of the amino acid residues in the mucoadhesive peptide fragment are positively charged amino acid residues. In some embodiments, at least 50% of the amino acid residues in the mucoadhesive peptide fragment are positively charged amino acid residues.

In some embodiments, the mucoadhesive peptide fragment is no more than about 15 kD. In some embodiments, the mucoadhesive peptide fragment is about 0.5 kD to about 50 kD. In some embodiments, the mucoadhesive peptide fragment is about 0.5 kD to about 15 kD. In some embodiments, the mucoadhesive peptide fragment is about 2 kD to about 12 kD. In some embodiments, the mucoadhesive peptide fragment is about 4 kD to about 10 kD. In some embodiments, the mucoadhesive peptide fragment is about 6 kD to about 14 kD. In some embodiments, the mucoadhesive peptide fragment is any one of about 0.5 kD, 1 kD, 2 kD, 3 kD, 4 kD, 5 kD, 6 kD, 7 kD, 8 kD, 9 kD, 10 kD, 11 kD, 12 kD, 13 kD, 14 kD, 15 kD, 20 kD, 25 kD, 30 kD, 35 kD, 40 kD, 45 kD, 50 kD, or more. In some embodiments, the mucoadhesive peptide fragment is any one of about 0.5-1 kD, 1-2 kD, 2-3 kD, 4-5 kD, 5-6 kD, 6-7 kD, 8-9 kD, 9-10 kD, 10-11 kD, 11-12 kD, 12-13 kD, 13-14 kD, 14-15 kD, 15-20 kD, 20-25 kD, 25-30 kD, 30-35 kD, 35-40 kD, 40-45 kD, 45-50 kD, or more. In some embodiments, the mucoadhesive peptide fragment at least about 0.5 kD, 1 kD, 2 kD, 3 kD, 4 kD, 5 kD, 6 kD, 7 kD, 8 kD, 9 kD, 10 kD, 11 kD, 12 kD, 13 kD, 14 kD, 15 kD, 20 kD, 25 kD, 30 kD, 35 kD, 40 kD, 45 kD, 50 kD, or more. In some embodiments, the mucoadhesive peptide fragment is no more than about 50 kD, 45 kD, 40 kD, 35 kD, 30 kD, 25 kD, 20 kD, 15 kD, 14 kD, 13 kD, 12 kD, 11 kD, 10 kD, 9 kD, 8 kD, 7 kD, 6 kD, 5 kD, 4 kD, 3 kD, 2 kD, 1 kD, or 0.5 kD.

In some embodiments, the mucoadhesive peptide fragment does not facilitate penetration of the chimeric protein into a cell of the mucosa. In some embodiments, the mucoadhesive peptide fragment does not comprises a motif in a cell penetrating peptide. In some embodiments, the mucoadhesive peptide is not a cell penetrating peptide.

In some embodiments, the mucoadhesive peptide fragment is not a histidine tag. In some embodiments, the mucoadhesive peptide fragment is not a peptide consisting of, or consisting essentially of, six histidines.

In some embodiments, the mucoadhesive peptide fragment does not disrupt folding of the chimeric protein within a host cell expressing the chimeric protein. In some embodiments, at least about any one of 20%, 30%, 40%, 50%, 60%, 70%, 80%, 90% or more of chimeric protein expressed in a mammalian host cell is properly folded.

In some embodiments, the mucoadhesive peptide fragment does not block secretion of the chimeric protein from a host cell expressing the chimeric protein. In some embodiments, at least about any one of 20%, 30%, 40%, 50%, 60%, 70%, 80%. 90% or more of chimeric protein expressed in a mammalian host cell is secreted. Without being bound by any theory or hypothesis, proteins with positively charged fragments tend to be trapped in the Golgi apparatus of cells expressing the proteins. The chimeric proteins described herein are readily expressed and secreted by host cells, and do not get trapped in the Golgi apparatus.

In some embodiments, the mucoadhesive peptide fragment does not interfere the specific binding between the target-binding moiety and the component of the pathogen. In some embodiments, the mucoadhesive peptide fragment reduces binding between the target-binding moiety and the component of the pathogen by no more than about any one of 50%, 40%, 30%, 20%, 10% or less.

C. Linkers

In some embodiments, the target-binding moiety is linked to the mucoadhesive peptide fragment via a linker (such as a linker peptide, also referred herein as a connecting peptide). In some embodiments, the target-binding moiety is not covalently linked to the mucoadhesive peptide fragment. In some embodiments, the mucoadhesive peptide fragment is chemically conjugated to the target-binding moiety, i.e., via a chemical linker.

In some embodiments, the mucoadhesive peptide fragment is fused to a polypeptide chain of the target-binding moiety via a peptide linker. In some embodiments, the linker is about 1 to 20 amino acid residues. In some embodiments, the linker is a glycine-serine linker. In some embodiments, the linker has the amino acid sequence of GGGGS (SEQ ID NO: 95).

The length, the degree of flexibility and/or other properties of the linker may have some influence on properties, including but not limited to the affinity, specificity or avidity for one or more targets of the fusion protein (e.g., bispecific immune cell engager or engineered receptor) described herein. For example, longer linkers may be selected to ensure that two adjacent binding moieties (e.g., the coronavirus spike protein or fragment thereof, and the effector protein or fragment thereof) do not sterically interfere with one another. In some embodiments, a linker (such as peptide linker) comprises flexible residues (such as glycine and serine) so that the adjacent binding moieties are free to move relative to each other. For example, a glycine-serine doublet can be a suitable peptide linker. In some embodiments, the linker is a non-peptide linker. In some embodiments, the linker is a peptide linker. In some embodiments, the linker is a non-cleavable linker. In some embodiments, the linker is a cleavable linker.

Other linker considerations include the effect on physical or pharmacokinetic properties of the resulting fusion protein (e.g., bispecific immune cell engager or engineered receptor), such as solubility, lipophilicity, hydrophilicity, hydrophobicity, stability (more or less stable as well as planned degradation), rigidity, flexibility, immunogenicity, modulation of antibody moiety binding, the ability to be incorporated into a micelle or liposome, and the like.

Any one or all of the linkers described herein can be accomplished by any chemical reaction that will bind the two molecules so long as the components or fragments retain their respective activities. This linkage can include many chemical mechanisms, for instance covalent binding, affinity binding, intercalation, coordinate binding and complexation. In some embodiments, the binding is covalent binding. Covalent binding can be achieved either by direct condensation of existing side chains or by the incorporation of external bridging molecules. Many bivalent or polyvalent linking agents are useful in coupling protein molecules, such as an Fc fragment. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents (see Killen and Lindstrom, Jour. Immun. 133:1335-2549 (1984); Jansen et al., Immunological Reviews 62:185-216 (1982); and Vitetta et al., Science 238:1098 (1987)).

Linkers that can be applied in the present application are described in the literature (see, for example, Ramakrishnan, S. et al., Cancer Res. 44:201-208 (1984) describing use of MBS (M-maleimidobenzoyl-N-hydroxysuccinimide ester)). In some embodiments, non-peptide linkers used herein include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat. #21651G); (iv) Sulfo-LC-SPDP (sulfosuccinimidyl 6 [3-(2-pyridyldithio)-propianamide]hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to fusion proteins with different physio-chemical properties. For example, sulfo-NHS esters of alkyl carboxylates are more stable than sulfo-NHS esters of aromatic carboxylates. NETS-ester containing linkers are less soluble than sulfo-NHS esters. Further, the linker SMPT contains a sterically hindered disulfide bond, and can form fusion protein with increased stability. Disulfide linkages, are in general, less stable than other linkages because the disulfide linkage is cleaved in vitro, resulting in less fusion protein available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Any one or all of the linkers described herein can be peptide linkers. The peptide linker may have a naturally occurring sequence, or a non-naturally occurring sequence. For example, a sequence derived from the hinge region of heavy chain only antibodies may be used as the linker. See, for example, WO1996/34103.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids (aa) long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 aa to about 10 aa, about 1 aa to about 20 aa, about 1 aa to about 30 aa, about 5 aa to about 15 aa, about 10 aa to about 25 aa, about 5 aa to about 30 aa, about 10 aa to about 30 aa, about 30 aa to about 50 aa, about 50 aa to about 100 aa, or about 1 aa to about 100 aa.

An essential technical feature of such peptide linker is that said peptide linker does not comprise any polymerization activity. The characteristics of a peptide linker, which comprise the absence of the promotion of secondary structures, are known in the art and described, e.g., in Dall'Acqua et al. (Biochem. (1998) 37, 9266-9273), Cheadle et al. (Mol Immunol (1992) 29, 21-30) and Raag and Whitlow (FASEB (1995) 9(1), 73-80). A particularly preferred amino acid in context of the "peptide linker" is Gly. Furthermore, peptide linkers that also do not promote any secondary structures are preferred. The linkage of the molecules to each other can be provided by, e.g., genetic engineering.

In some embodiments, the peptide linker is a stable linker, which is not cleavable by a protease. In some embodiments, the peptide linker is cleavable by a protease.

In some embodiments, the peptide linker tends not to adopt a rigid three-dimensional structure, but rather provide flexibility to a polypeptide. In some embodiments, the peptide linker is a flexible linker. Exemplary flexible linkers include glycine polymers $(G)_n$, glycine-serine polymers (including, for example, $(GS)_n$(SEQ ID NO: 117), $(GSGGS)_n$ (SEQ ID NO: 118), $(GGGGS)_n$ (SEQ ID NO: 119), and $(GGGS)_n$ (SEQ ID NO: 120), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine and is much less restricted than residues with longer side chains (see Scheraga, Rev. Computational Chem. 11 173-142 (1992)). The ordinarily skilled artisan will recognize that design of a fusion protein can include linkers that are all or partially flexible, such that the linker can include a flexible linker portion as well as one or more portions that confer less flexible structure to provide a desired fusion protein structure.

Natural linkers adopt various conformations in secondary structure, such as helical, β-strand, coil/bend and turns, to exert their functions. Linkers in an α-helix structure might serve as rigid spacers to effectively separate protein domains, thus reducing their unfavorable interactions. Non-helical linkers with Pro-rich sequence could increase the linker rigidity and function in reducing inter-domain interference.

III. SARS-CoV-2 Antibodies and Constructs

The present application provides isolated antibodies, antigen-binding fragments thereof, and constructs thereof that specifically bind to SARS-CoV-2 (including SARS-CoV-2 variants), e.g., an S1 subunit of a spike (S) protein (also referred herein as "S1" or "S1 protein") of SARS-CoV-2. Contemplated antibody constructs include, for example, scFv, Fab, Fc fusion protein (e.g., scFv-Fc), full-length antibodies, multi-specific molecules, chimeric proteins, and immunoconjugates.

A. Antibodies and Antigen-Binding Fragments Thereof

The present application provides isolated antibodies and antigen binding fragments thereof (also referred to as "anti-S1 antibodies") that specifically binds to a S1 protein of SARS-CoV-2 (including SARS-CoV-2 variants). The anti-S1 antibodies described herein can be of any suitable full-length antibody or antigen-binding fragment format. Any of the anti-S1 antibodies or antigen binding fragment thereof may be used as the target-binding moiety in a chimeric protein described herein, or the anti-S1 antibody moiety in an anti-S1 antibody construct described herein.

In some embodiments, the anti-S1 antibody is a full-length antibody or an immunoglobulin derivative. In some embodiments, the anti-S1 antibody is an IgG, an IgA, an IgD, an IgE, or an IgM.

In some embodiments, the anti-S1 antibody is an antigen-binding fragment, for example, an antigen-binding fragment selected from the group consisting of a Fab, a Fab', a F(ab')2, an Fv fragment, a disulfide stabilized Fv fragment (dsFv), a $(dsFv)_2$, an scFv dimer, a domain antibody, a bivalent domain antibody, a single-chain Fv (scFv), a scFv-Fc fusion protein, and a minibody (i.e., a scFv-CH3 fusion protein). In some embodiments, the anti-S1 antibody is a scFv. In some embodiments, the anti-S1 antibody is a fusion protein comprising a scFv fused to an Fc region. In some embodiments, the anti-S1 antibody is a fusion protein comprising a scFv fused to a CH3 domain.

In some embodiments, the anti-S1 antibody is chimeric, human, partially humanized, fully humanized, or semi-synthetic. In some embodiments, the anti-S1 antibody is a semi-synthetic antibody comprising fully human sequences and one or more synthetic regions. In some embodiments, the anti-S1 antibody is a semi-synthetic antibody comprising a fully human light chain variable domain and a semi-synthetic heavy chain variable domain comprising fully human FR1, HC-CDR1, FR2, HC-CDR2, FR3, and FR4 regions and a synthetic HC-CDR3. In some embodiments, the semi-synthetic heavy chain variable domain comprises a fully synthetic HC-CDR3 having a sequence from about 5 to about 25 (such as about any of 5, 6, 7, 8, 9, 10, 11, 12, 13, 14, 15, 16, 17, 18, 19, 20, 21, 22, 23, 24, or 25) amino acids in length. In some embodiments, the semi-synthetic heavy chain variable domain or the synthetic HC-CDR3 is obtained from a semi-synthetic library (such as a semi-synthetic human library) comprising fully synthetic HC-CDR3s having a sequence from about 5 to about 25 (such as about any of 5, 6, 7, 8, 9, 10, 11, 12, 13, 14, 15, 16, 17, 18, 19, 20, 21, 22, 23, 24, or 25) amino acids in length, wherein each amino acid in the sequence is randomly selected from the standard human amino acids, minus cysteine. In some embodiments, the synthetic HC-CDR3 is from about 5 to about 19 (such as about any of 5, 6, 7, 8, 9, 10, 11, 12, 13, 14, 15, 16, 17, 18 or 19) amino acids in length. In some embodiments, the anti-S1 antibody is a semi-synthetic antibody comprising human CDRs and non-human framework sequences. Non-human framework sequences include, in some embodiments, any sequence that can be used for generating synthetic heavy and/or light chain variable regions using one or more human CDR sequences as described herein, including, e.g., mammals, such as mouse, rat, rabbit, pig, bovine (e.g., cow, bull, buffalo), deer, sheep, goat, chicken, cat, dog, ferret, primate (e.g., marmoset, rhesus monkey), etc. In some embodiments, the anti-S1 antibody is generated by grafting one or more human CDR sequences as described herein onto a non-human framework sequence (e.g., a mouse or chicken framework sequence).

The anti-S1 antibodies in some embodiments comprise specific sequences or certain variants of such sequences. In some embodiments, the amino acid substitutions in the variant sequences do not substantially reduce the ability of the anti-S1 antibody to specifically recognize an S1 subunit of a Spike protein of SARS-CoV-2. For example, alterations that do not substantially reduce S1 binding affinity may be made. Alterations that substantially improve S1 binding affinity or affect some other property, such as specificity and/or cross-reactivity with related variants of the S1 protein, are also contemplated.

Exemplary antibody sequences are shown in Tables 6-8. The exemplary CDR sequences in Table 6 are predicted using the IgBLAST algorithm. See, for example, Ye J. et al. Nucleic Acids Research, 41:W34-W40 (2013), the disclosure of which is incorporated herein by reference in its entirety. Those skilled in the art will recognize that many algorithms are known for prediction of CDR positions in antibody heavy chain and light chain variable regions, and antibody agents comprising CDRs from antibodies described herein, but based on prediction algorithms other than IgBLAST, are within the scope of this invention.

The exemplary antibody heavy chain and light chain variable region sequences in Table 6 are delimited according to the INTERNATIONAL IMMUNOGENETICS INFORMATION SYSTEM® (IMGT). See, for example, Lefranc, M.-P. et al., Nucleic Acids Res., 43:D413-422 (2015), the disclosure of which is incorporated herein by reference in its entirety. Those skilled in the art will recognize that antibody agents comprising VH or VL sequences from antibodies described herein, but based on algorithms other than IMGT, are within the scope of this invention.

In some embodiments, the anti-S1 antibody or antigen binding fragment thereof comprises i) a heavy chain variable domain (VH) comprising an HC-CDR3 comprising the amino acid sequence of any one of SEQ ID NOs: 3, 9, 15, 21, 27, 33, 39, 45, 51 and 57, or a variant thereof comprising up to about 5 (such as about any of 1, 2, 3, 4, or 5) amino acid substitutions; and ii) a light chain variable domain (VL) comprising an LC-CDR3 comprising the amino acid sequence of any one of SEQ ID NOs: 6, 12, 18, 24, 30, 36, 42, 48, 54, and 60, or a variant thereof comprising up to about 5 (such as about any of 1, 2, 3, 4, or 5) amino acid substitutions.

In some embodiments, the anti-S1 antibody or antigen binding fragment thereof comprises i) a VH comprising an HC-CDR3 comprising the amino acid sequence of any one of SEQ ID NOs: 3, 9, 15, 21, 27, 33, 39, 45, 51 and 57; and ii) a VL comprising an LC-CDR3 comprising the amino acid sequence of any one of SEQ ID NOs: 6, 12, 18, 24, 30, 36, 42, 48, 54, and 60.

In some embodiments, the anti-S1 antibody or antigen binding fragment thereof comprises i) a VH comprising an HC-CDR1 comprising the amino acid sequence of any one of SEQ ID NOs: 1, 7, 13, 19, 25, 31, 37, 43, 49, and 55, or a variant thereof comprising up to about 5 (such as about any of 1, 2, 3, 4, or 5) amino acid substitutions, an HC-CDR2 comprising the amino acid sequence of any one of SEQ ID NOs: 2, 8, 14, 20, 26, 32, 38, 44, 50, and 56, or a variant thereof comprising up to about 5 (such as about any of 1, 2, 3, 4, or 5) amino acid substitutions, and an HC-CDR3 comprising the amino acid sequence of any one of SEQ ID NOs: 3, 9, 15, 21, 27, 33, 39, 45, 51 and 57, or a variant thereof comprising up to about 5 (such as about any of 1, 2, 3, 4, or 5) amino acid substitutions; and ii) a VL comprising an LC-CDR1 comprising the amino acid sequence of any one of SEQ ID NOs: 4, 10, 16, 22, 28, 34, 40, 46, 52, and 58, or a variant thereof comprising up to about 5 (such as about any of 1, 2, 3, 4, or 5) amino acid substitutions, an LC-CDR2 comprising the amino acid sequence of any one of SEQ ID NOs: 5, 11, 17, 23, 29, 35, 41, 47, 53, and 59, or a variant thereof comprising up to about 3 (such as about any of 1, 2, or 3) amino acid substitutions, and an LC-CDR3 comprising the amino acid sequence of any one of SEQ ID NOs: 6, 12, 18, 24, 30, 36, 42, 48, 54, and 60, or a variant thereof comprising up to about 5 (such as about any of 1, 2, 3, 4, or 5) amino acid substitutions.

In some embodiments, the anti-S1 antibody or antigen binding fragment thereof comprises i) a VH comprising an HC-CDR1 comprising the amino acid sequence of any one of SEQ ID NOs: 1, 7, 13, 19, 25, 31, 37, 43, 49, and 55, or a variant thereof comprising up to about 5 (such as about any of 1, 2, 3, 4, or 5) amino acid substitutions, an HC-CDR2 comprising the amino acid sequence of any one of SEQ ID NOs: 2, 8, 14, 20, 26, 32, 38, 44, 50, and 56, or a variant thereof comprising up to about 5 (such as about any of 1, 2, 3, 4, or 5) amino acid substitutions, and an HC-CDR3 comprising the amino acid sequence of any one of SEQ ID NOs: 3, 9, 15, 21, 27, 33, 39, 45, 51 and 57; and ii) a VL comprising an LC-CDR1 comprising the amino acid sequence of any one of SEQ ID NOs: 4, 10, 16, 22, 28, 34, 40, 46, 52, and 58, or a variant thereof comprising up to about 5 (such as about any of 1, 2, 3, 4, or 5) amino acid substitutions, an LC-CDR2 comprising the amino acid sequence of any one of SEQ ID NOs: 5, 11, 17, 23, 29, 35, 41, 47, 53, and 59, or a variant thereof comprising up to about 3 (such as about any of 1, 2, or 3) amino acid substitutions, and an LC-CDR3 comprising the amino acid sequence of any one of SEQ ID NOs: 6, 12, 18, 24, 30, 36, 42, 48, 54, and 60.

In some embodiments, the anti-S1 antibody or antigen binding fragment thereof comprises i) a VH comprising an HC-CDR1 comprising the amino acid sequence of any one of SEQ ID NOs: 1, 7, 13, 19, 25, 31, 37, 43, 49, and 55, an HC-CDR2 comprising the amino acid sequence of any one of SEQ ID NOs: 2, 8, 14, 20, 26, 32, 38, 44, 50, and 56, and an HC-CDR3 comprising the amino acid sequence of any one of SEQ ID NOs: 3, 9, 15, 21, 27, 33, 39, 45, 51 and 57; or a variant thereof comprising up to about 5 (such as about any of 1, 2, 3, 4, or 5) amino acid substitutions in the HC-CDR sequences; and ii) a VL comprising an LC-CDR1 comprising the amino acid sequence of any one of SEQ ID NOs: 4, 10, 16, 22, 28, 34, 40, 46, 52, and 58, an LC-CDR2 comprising the amino acid sequence of any one of SEQ ID NOs: 5, 11, 17, 23, 29, 35, 41, 47, 53, and 59, and an LC-CDR3 comprising the amino acid sequence of any one of SEQ ID NOs: 6, 12, 18, 24, 30, 36, 42, 48, 54, and 60; or a variant thereof comprising up to about 5 (such as about any of 1, 2, 3, 4, or 5) amino acid substitutions in the LC-CDR sequences.

In some embodiments, the anti-S1 antibody or antigen binding fragment thereof comprises i) a VH comprising an HC-CDR1 comprising the amino acid sequence of any one of SEQ ID NOs: 1, 7, 13, 19, 25, 31, 37, 43, 49, and 55, an HC-CDR2 comprising the amino acid sequence of any one of SEQ ID NOs: 2, 8, 14, 20, 26, 32, 38, 44, 50, and 56, and an HC-CDR3 comprising the amino acid sequence of any one of SEQ ID NOs: 3, 9, 15, 21, 27, 33, 39, 45, 51 and 57;

or a variant thereof comprising up to about 5 (such as about any of 1, 2, 3, 4, or 5) amino acid substitutions, wherein the amino acid substitutions are in HC-CDR1 or HC-CDR2; and ii) a VL comprising an LC-CDR1 comprising the amino acid sequence of any one of SEQ ID NOs: 4, 10, 16, 22, 28, 34, 40, 46, 52, and 58, an LC-CDR2 comprising the amino acid sequence of any one of SEQ ID NOs: 5, 11, 17, 23, 29, 35, 41, 47, 53, and 59, and an LC-CDR3 comprising the amino acid sequence of any one of SEQ ID NOs: 6, 12, 18, 24, 30, 36, 42, 48, 54, and 60; or a variant thereof comprising up to about 5 (such as about any of 1, 2, 3, 4, or 5) amino acid substitutions, wherein the amino acid substitutions are in LC-CDR1 or LC-CDR2.

In some embodiments, the anti-S1 antibody or antigen binding fragment thereof comprises i) a VH comprising an HC-CDR1 comprising the amino acid sequence of any one of SEQ ID NOs: 1, 7, 13, 19, 25, 31, 37, 43, 49, and 55, an HC-CDR2 comprising the amino acid sequence of any one of SEQ ID NOs: 2, 8, 14, 20, 26, 32, 38, 44, 50, and 56, and an HC-CDR3 comprising the amino acid sequence of any one of SEQ ID NOs: 3, 9, 15, 21, 27, 33, 39, 45, 51 and 57; and ii) a VL comprising an LC-CDR1 comprising the amino acid sequence of any one of SEQ ID NOs: 4, 10, 16, 22, 28, 34, 40, 46, 52, and 58, an LC-CDR2 comprising the amino acid sequence of any one of SEQ ID NOs: 5, 11, 17, 23, 29, 35, 41, 47, 53, and 59, and an LC-CDR3 comprising the amino acid sequence of any one of SEQ ID NOs: 6, 12, 18, 24, 30, 36, 42, 48, 54, and 60.

In some embodiments, the anti-S1 antibody or antigen binding fragment thereof comprises: a) VH comprising the amino acid sequence of any one of SEQ ID NOs: 1, 7, 13, 19, 25, 31, 37, 43, 49, and 55, the amino acid sequence of any one of SEQ ID NOs: 2, 8, 14, 20, 26, 32, 38, 44, 50, and 56, and the amino acid sequence of any one of SEQ ID NOs: 3, 9, 15, 21, 27, 33, 39, 45, 51 and 57; and ii) a VL comprising the amino acid sequence of any one of SEQ ID NOs: 4, 10, 16, 22, 28, 34, 40, 46, 52, and 58, the amino acid sequence of any one of SEQ ID NOs: 5, 11, 17, 23, 29, 35, 41, 47, 53, and 59, and the amino acid sequence of any one of SEQ ID NOs: 6, 12, 18, 24, 30, 36, 42, 48, 54, and 60.

In some embodiments, the anti-S1 antibody or antigen binding fragment thereof comprises: a) a VH comprising one, two or three CDRs of any one of SEQ ID NOs: 61, 63, 65, 67, 69, 71, 73, 75, 77, and 79, and b) a VL comprising one, two or three CDRs of any one of SEQ ID NOs: 62, 64, 66, 68, 70, 72, 74, 76, 78, and 80. In some embodiments, the anti-S1 antibody or antigen binding fragment thereof comprises: a) a VH comprising HC-CDR1, HC-CDR2 and HC-CDR3 of the heavy chain variable domain of any one of SEQ ID NOs: 61, 63, 65, 67, 69, 71, 73, 75, 77, and 79, and b) a VL comprising LC-CDR1, LC-CDR2 and LC-CDR3 of the light chain variable domain of CDRs of any one of SEQ ID NOs: 62, 64, 66, 68, 70, 72, 74, 76, 78, and 80.

In some embodiments, the anti-S1 antibody or antigen binding fragment thereof comprises: a) a VH comprising the amino acid sequence of any one of SEQ ID NOs: 61, 63, 65, 67, 69, 71, 73, 75, 77, and 79, or a variant thereof having at least about 80% (including for example at least about any of 80%, 85%, 90%, 95%, 96%, 97%, 98%, or 99%) sequence identity to any one of SEQ ID NOs: 61, 63, 65, 67, 69, 71, 73, 75, 77, and 79; and b) a VL comprising the amino acid sequence of any one of SEQ ID NOs: 62, 64, 66, 68, 70, 72, 74, 76, 78, and 80, or a variant thereof having at least about 80% (including for example at least about any of 80%, 85%, 90%, 95%, 96%, 97%, 98%, or 99%) sequence identity to any one of SEQ ID NOs: 62, 64, 66, 68, 70, 72, 74, 76, 78, and 80.

In some embodiments, the anti-S1 antibody or antigen binding fragment thereof comprises: a) a VH comprising the amino acid sequence of any one of SEQ ID NOs: 61, 63, 65, 67, 69, 71, 73, 75, 77, and 79; and b) a VL comprising the amino acid sequence of any one of SEQ ID NOs: 62, 64, 66, 68, 70, 72, 74, 76, 78, and 80.

In some embodiments, the anti-S1 antibody or antigen binding fragment thereof comprises the HC-CDRs of a VH comprising the amino acid sequence of any one of SEQ ID NOs: 61, 63, 65, 67, 69, 71, 73, 75, 77, and 79, and the LC-CDRs of a VL comprising the amino acid sequence of any one of SEQ ID NOs: 62, 64, 66, 68, 70, 72, 74, 76, 78, and 80.

The heavy and light chain variable domains can be combined in various pair-wise combinations to generate a number of anti-S1 antibody moieties. Exemplary anti-S1 antibodies are provided in Tables 6-8.

TABLE 6

CDR sequences of exemplary anti-S1 (SARS-CoV-2) antibodies

| Clone No. | SEQ ID NO: | HCDR1/ LCDR1 | SEQ ID NO: | HCDR2/ LCDR2 | SEQ ID NO: | HCDR3/ LCDR3 |
|---|---|---|---|---|---|---|
| 04 | 1 | GYTFTGYY | 2 | INPNSGGT | 3 | ARGYSDR |
| | 4 | SSNIGSNP | 5 | SNN | 6 | AAWDDSLSGSVL |
| 09 | 7 | GYTFTSYG | 8 | ISAYNGNT | 9 | ARTWYSYHYDI |
| | 10 | SGSIASNY | 11 | EDK | 12 | QSYDDGNVV |
| 13 | 13 | GGTFSSYA | 14 | ISGYNGNT | 15 | ARTGWSKGEKVTTWGEWFYVDY |
| | 16 | SSNIGSNY | 17 | RNN | 18 | AAWDDSLSGPNYV |
| 15 | 19 | GYTFTGYY | 20 | INPNSGGT | 21 | ARGYGDD |
| | 22 | SSNIGNNA | 23 | FND | 24 | AAWDDSLNAVL |
| 19 | 25 | GFTFSNYP | 26 | ISYDGNHK | 27 | ARGGGMGGLDS |
| | 28 | SSDVGGYNY | 29 | EVS | 30 | SSYTSGDTLV |
| 20 | 31 | GYSFPSYW | 32 | IYPGDSDT | 33 | ARGSYTYMGGSYDY |
| | 34 | SSNIGSNT | 35 | SNN | 36 | AAWDDSLDGYV |
| 26 | 37 | GYTFTSYG | 38 | ISAYNGNT | 39 | ARGYYGDLDP |
| | 40 | TSNIGRNT | 41 | VSN | 42 | GAWDDSLDGML |

TABLE 6-continued CDR sequences of exemplary anti-S1 (SARS-CoV-2) antibodies

| Clone No. | SEQ ID NO: | HCDR1/ LCDR1 | SEQ ID NO: | HCDR2/ LCDR2 | SEQ ID NO: | HCDR3/ LCDR3 |
|---|---|---|---|---|---|---|
| 30 | 43 | GFTFSSYA | 44 | ISASGNST | 45 | ARNSDV |
|  | 46 | SSDVGGYDY | 47 | EVS | 48 | SSYTSSSTFPYV |
| 49 | 49 | GYSFTSYW | 50 | IYPGDSDT | 51 | ARSSYSYGGPDA |
|  | 52 | SSNIGSNT | 53 | SNN | 54 | AAWDDSLNGYV |
| 85 | 55 | GYTFTGYY | 56 | INPNSGGT | 57 | ARGYSDY |
|  | 58 | NSNIGSNP | 59 | GND | 60 | AAWDDSLDGHVI |

TABLE 7

VH/VL sequences of exemplary anti-S1 (SARS-CoV-2) antibodies

| Clone No. | SEQ ID NO: | VH | SEQ ID NO: | VL |
|---|---|---|---|---|
| 04 | 61 | LEMAQVQLVQSGAEVKKPGASVKVS CKASGYTFTGYYIHWVRQAPGQGLE WMGRINPNSGGTNYAQKFQGRVTMT RDTSISTAYMELSRLRSDDTAVYYC ARGYSDRWGQGTLVTVSSTSGQAGQ | 62 | QSVLTQPPSASGTPGQRVTISCSGGS SNIGSNPVNWYQQLPGTAPKLLIYSN NQRPSGVPDRFSGSKSGTSASLAISG LQSEDEADYYCAAWDDSLSGSVLFGG GTKLTVLG |
| 09 | 63 | EVQLVESGAEVKKPGASVKVSCKAS GYTFTSYGISWVRQAPGQGLEWMGW ISAYNGNTNYAQKFQDRVTLTTDTS TNTAYMLLRSLRSDDTAVYYCARTW YSYHYDIWGQGTLVTVSSTSGQAGQ | 64 | NFMLTQPHSVSESPGKTVSISCTGSS GSIASNYVQWYQQRPGSAPTTVIYED KERPSGVPNRFSGSIDRSSNSASLTI SGLKTEDEADYYCQSYDDGNVVFGGG TKLTVLG |
| 13 | 65 | QVQLVQSGAEVKKPGSSVKVSCKAS GGTFSSYAISWVRQAPGQGLEWMGW ISGYNGNTNYAQKLQGRVTMTTDTS TSTAYMELRSLRSDDTAVYYCARTG WSKGEKVTTWGEWFYVDYWGQGTLV TVSSTSGQAGQ | 66 | QSVLTQPPSASGTPGQRVTISCSGSS SNIGSNYVYWYQQLPGTAPKLLIYRN NQRPSGVPDRFSGSKSGTSASLAISG LRSEDEADYYCAAWDDSLSGPNYVFG TGTKVTVLG |
| 15 | 67 | EVQLVQSGAEVKKPGASVKVSCKAS GYTFTGYYMHWVRQAPGQGLEWMGR INPNSGGTDYARKFRGRVTMTRDTS ISTAYMELSRLTSDDTAMYYCARGY GDDWGQGTLVTVSSTSGQAGQ | 68 | QSVLTQPPSVSEAPRQRVTISCSGSS SNIGNNAVNWYQQLPGKAPKLLIYFN DVQSSGVSDRFSGSKSGTSASLAISG LQSEDEADYYCAAWDDSLNAVLFGGG TKLTVLG |
| 19 | 69 | ELQLVESGGGVVQPGRSPRLSCAAS GFTFSNYPMHWVRQAPGKGLEWVAV ISYDGNHKYYADSLEGRFSISRDNS KNTLYLQMNSLTAADTAVYYCARGG GMGGLDSWGQGTLVTVSS | 70 | QSALTQPASVSGSPGQSITISCTGTS SDVGGYNYVSWYQQHPGKVPKLMIYE VSNRPSGVSNRFSGSKSGNTASLTIS GLQAEDEADYYCSSYTSGDTLVFGGG TKVTVLG |
| 20 | 71 | EVQLVQSGAEVKKPGESLKISCKGS GYSFPSYWIGWVRQMPGKGLEWMGI IYPGDSDTRYSPSFQGQVTISADKS ISTAYLQWSSLKASDTAMYYCARGS YTYMGGSYDYWGQGTLVTVSS | 72 | SYVLTQPPSASGTPGQRVTISCSGSS SNIGSNTVNWYQQLPGTAPKLLIYSN NQRPSGVPDRFSASKSGTSASLAISG FQSEDEADYYCAAWDDSLDGYVFGTG TKVTVLG |
| 26 | 73 | QVQLVQSGAEVKKPGASVKVSCKAS GYTFTSYGISWVRQAPGQGLEWMGW ISAYNGNTNYAQKLQGRVTMTTDTS TSTAYMELRSLRSDDTAVYYCARGY YGDLDPWGQGTLVTVSS | 74 | QAVLTQAPSASGTLGQQVTISCSGTT SNIGRNTVNWYQHLPGTAPKLLIFVS NQRPSGVPDRFSGSKSGTSASLVISG LQSEDEADYYCGAWDDSLDGMLFGGG TKLTVLG |
| 30 | 75 | EVQLVESGGGLEQPGGSLRLSCAAS GFTFSSYAMSWVRQAPGKGLEWVSA ISASGNSTFYADSVKGRFTISRDNS KHTLDLQMNSLRADDTAVYYCARNS DVWGQGTLVTVSS | 76 | QSALTQPPSASGSPGQSVTISCTGTS SDVGGYDYVSWYQQHPGKAPKLMIYE VSKRPSGVSNRFSGSKSGNTASLTIS GLQAEDEADYYCSSYTSSSTFPYVFG TGTKVTVLG |

TABLE 7-continued

VH/VL sequences of exemplary anti-S1 (SARS-CoV-2) antibodies

| Clone No. | SEQ ID NO: | VH | SEQ ID NO: | VL |
|---|---|---|---|---|
| 49 | 77 | EVQLVQSGAEVKKPGESLKISCKGS GYSFTSYWIGWVRQMPGKGLEWMGI IYPGDSDTRYSPSFQGQVTISADKS ISTAYLQWSSLKASDTAMYYCARSS YSYGGPDAWGQGTLVTVSS | 78 | QAVLTQPPSASGTPGQRVTISCSGSS SNIGSNTVNWYQQLPGTAPKLLIYSN NQRPSGVPDRFSGSKSGTSASLAISG LQSEDEADYYCAAWDDSLNGYVFGTG TKVTVLG |
| 85 | 79 | EVQLVQSGAEVKKPGASVKVSCKAS GYTFTGYYMHWVRQAPGQGLEWMGR INPNSGGTNYAQKFQGRVTMTRDTS ISTAYMELSRLRSDDTAVYYCARGY SDYWGQGTLVTVSS | 80 | QAVLTQPPSASGTPGQMVTISCSGSN SNIGSNPVNWYQQLPGTAPKLLIYGN DERPSGVPDRFSGSKSGTSASLAISG LQSEDEADYYCAAWDDSLDGHVIFGG GTKLTVLG |

TABLE 8 scFv sequences based on exemplary anti-S1 (SARS-CoV-2) antibodies

| Clone No. | SEQ ID NO: | scFv |
|---|---|---|
| 04 | 81 | QSVLTQPPSASGTPGQRVTISCSGGSSNIGSNPVNWYQQLPGTAPKLLIYSNNQRPSGVPD RFSGSKSGTSASLAISGLQSEDEADYYCAAWDDSLSGSVLFGGGTKLTVLGSRGGGGSGGG GSGGGGSLEMAQVQLVQSGAEVKKPGASVKVSCKASGYTFTGYYIHWVRQAPGQGLEWMGR INPNSGGTNYAQKFQGRVTMTRDTSISTAYMELSRLRSDDTAVYYCARGYSDRWGQGTLVT VSSTSGQAGQ |
| 09 | 82 | NFMLTQPHSVSESPGKTVSISCTGSSGSIASNYVQWYQQRPGSAPTTVIYEDKERPSGVPN RFSGSIDRSSNSASLTISGLKTEDEADYYCQSYDDGNVVFGGGTKLTVLGSRGGGGSGGGG SGGGGSLEMAEVQLVESGAEVKKPGASVKVSCKASGYTFTSYGISWVRQAPGQGLEWMGWI SAYNGNTNYAQKFQDRVTLTTDTSTNTAYMLLRSLRSDDTAVYYCARTWYSYHYDIWGQGT LVTVSSTSGQAGQ |
| 13 | 83 | QSVLTQPPSASGTPGQRVTISCSGSSSNIGSNYVYWYQQLPGTAPKLLIYRNNQRPSGVPD RFSGSKSGTSASLAISGLRSEDEADYYCAAWDDSLSGPNYVFGTGTKVTVLGSRGGGGSGG GGSGGGGSLEMAQVQLVQSGAEVKKPGSSVKVSCKASGGTFSSYAISWVRQAPGQGLEWMG WISGYNGNTNYAQKLQGRVTMTTDTSTSTAYMELRSLRSDDTAVYYCARTGWSKGEKVTTW GEWFYVDYWGQGTLVTVSSTSGQAGQ |
| 15 | 84 | QSVLTQPPSVSEAPRQRVTISCSGSSSNIGNNAVNWYQQLPGKAPKLLIYFNDVQSSGVSD RFSGSKSGTSASLAISGLQSEDEADYYCAAWDDSLNAVLFGGGTKLTVLGSRGGGGSGGGG SGGGGSLEMAEVQLVQSGAEVKKPGASVKVSCKASGYTFTGYYMHWVRQAPGQGLEWMGRI NPNSGGTDYARKFRGRVTMTRDTSISTAYMELSRLTSDDTAMYYCARGYGDDWGQGTLVTV SSTSGQAGQ |
| 19 | 85 | QSALTQPASVSGSPGQSITISCTGTSSDVGGYNYVSWYQQHPGKVPKLMIYEVSNRPSGVS NRFSGSKSGNTASLTISGLQAEDEADYYCSSYTSGDTLVFGGGTKVTVLGSRGGGGSGGGG SGGGGSLEMAELQLVESGGGVVQPGRSPRLSCAASGFTFSNYPMHWVRQAPGKGLEWVAVI SYDGNHKYYADSLEGRFSISRDNSKNTLYLQMNSLTAADTAVYYCARGGGMGGLDSWGQGT LVTVSSTSGQAGQ |
| 20 | 86 | SYVLTQPPSASGTPGQRVTISCSGSSSNIGSNTVNWYQQLPGTAPKLLIYSNNQRPSGVPD RFSASKSGTSASLAISGFQSEDEADYYCAAWDDSLDGYVFGTGTKVTVLGSRGGGGSGGGG SGGGGSLEMAEVQLVQSGAEVKKPGESLKISCKGSGYSFPSYWIGWVRQMPGKGLEWMGII YPGDSDTRYSPSFQGQVTISADKSISTAYLQWSSLKASDTAMYYCARGSYTYMGGSYDYWG QGTLVTVSSTSGQAGQ |
| 26 | 87 | QAVLTQAPSASGTLGQQVTISCSGTTSNIGRNTVNWYQHLPGTAPKLLIFVSNQRPSGVPD RFSGSKSGTSASLVISGLQSEDEADYYCGAWDDSLDGMLFGGGTKLTVLGSRGGGGSGGGG SGGGGSLEMAQVQLVQSGAEVKKPGASVKVSCKASGYTFTSYGISWVRQAPGQGLEWMGWI SAYNGNTNYAQKLQGRVTMTTDTSTSTAYMELRSLRSDDTAVYYCARGYYGDLDPWGQGTL VTVSSTSGQAGQ |
| 30 | 88 | QSALTQPPSASGSPGQSVTISCTGTSSDVGGYDYVSWYQQHPGKAPKLMIYEVSKRPSGVS NRFSGSKSGNTASLTISGLQAEDEADYYCSSYTSSSTFPYVFGTGTKVTVLGSRGGGGSGG GGSGGGGSLEMAEVQLVESGGGLEQPGGSLRLSCAASGFTFSSYAMSWVRQAPGKGLEWVS AISASGNSTFYADSVKGRFTISRDNSKHTLDLQMNSLRADDTAVYYCARNSDVWGQGTLVT VSSTSGQAGQ |
| 49 | 89 | QAVLTQPPSASGTPGQRVTISCSGSSSNIGSNTVNWYQQLPGTAPKLLIYSNNQRPSGVPD RFSGSKSGTSASLAISGLQSEDEADYYCAAWDDSLNGYVFGTGTKVTVLGSRGGGGSGGGG SGGGGSLEMAEVQLVQSGAEVKKPGESLKISCKGSGYSFTSYWIGWVRQMPGKGLEWMGII YPGDSDTRYSPSFQGQVTISADKSISTAYLQWSSLKASDTAMYYCARSSYSYGGPDAWGQG TLVTVSSTSGQAGQ |

TABLE 8-continued scFv sequences based on exemplary anti-S1 (SARS-CoV-2) antibodies

| Clone No. | SEQ ID NO: | scFv |
|---|---|---|
| 85 | 90 | QAVLTQPPSASGTPGQMVTISCSGSNSNIGSNPVNWYQQLPGTAPKLLIYGNDERPSGVPDRFSGSKSGTSASLAISGLQSEDEADYYCAAWDDSLDGHVIFGGGTKLTVLGSRGGGGSGGGGSGGGGSLEMAEVQLVQSGAEVKKPGASVKVSCKASGYTFTGYYMHWVRQAPGQGLEWMGRINPNSGGTNYAQKFQGRVTMTRDTSISTAYMELSRLRSDDTAVYYCARGYSDYWGQGTLVTVSSTSGQAGQ |

In some embodiments, the anti-S1 antibody or antigen binding fragment thereof comprises HC-CDR1, HC-CDR2, HC-CDR3, LC-CDR1, LC-CDR2, and LC-CDR3 of antibody clone 04, 09, 13, 15, 19, 20, 26, 30, 49 or 85 of Table 6. In some embodiments, the anti-S1 antibody or antigen binding fragment thereof comprises VH and VL of antibody clone 04, 09, 13, 15, 19, 20, 26, 30, 49 or 85 of Table 7.

In some embodiments, there is provided an anti-S1 antibody or antigen binding fragment thereof comprising: i) a VH comprising an HC-CDR1 comprising the amino acid sequence of SEQ ID NO: 1, or a variant thereof comprising up to about 5 (such as about any of 1, 2, 3, 4, or 5) amino acid substitutions, an HC-CDR2 comprising the amino acid sequence of SEQ ID NO: 2, or a variant thereof comprising up to about 5 (such as about any of 1, 2, 3, 4, or 5) amino acid substitutions, and an HC-CDR3 comprising the amino acid sequence of SEQ ID NO: 3, or a variant thereof comprising up to about 5 (such as about any of 1, 2, 3, 4, or 5) amino acid substitutions; and ii) a VL comprising an LC-CDR1 comprising the amino acid sequence of SEQ ID NO: 4, or a variant thereof comprising up to about 5 (such as about any of 1, 2, 3, 4, or 5) amino acid substitutions, an LC-CDR2 comprising the amino acid sequence of SEQ ID NO: 5, or a variant thereof comprising up to about 3 (such as about any of 1, 2, or 3) amino acid substitutions, and an LC-CDR3 comprising the amino acid sequence of SEQ ID NO: 6, or a variant thereof comprising up to about 5 (such as about any of 1, 2, 3, 4, or 5) amino acid substitutions. In some embodiments, the anti-S1 antibody or antigen binding fragment thereof comprises: (1) i) a VH comprising an HC-CDR1 comprising the amino acid sequence of SEQ ID NO: 1, an HC-CDR2 comprising the amino acid sequence of SEQ ID NO: 2, and an HC-CDR3 comprising the amino acid sequence of SEQ ID NO: 3; or a variant thereof comprising up to about 5 (such as about any of 1, 2, 3, 4, or 5) amino acid substitutions in the HC-CDR sequences; and ii) a VL comprising an LC-CDR1 comprising the amino acid sequence of SEQ ID NO: 4, an LC-CDR2 comprising the amino acid sequence of SEQ ID NO: 5, and an LC-CDR3 comprising the amino acid sequence of SEQ ID NO: 6; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-S1 antibody or antigen binding fragment thereof comprises i) a VH comprising an HC-CDR1 comprising the amino acid sequence of SEQ ID NO: 1, an HC-CDR2 comprising the amino acid sequence of SEQ ID NO: 2, and an HC-CDR3 comprising the amino acid sequence of SEQ ID NO: 3; and ii) a VL comprising an LC-CDR1 comprising the amino acid sequence of SEQ ID NO: 4, an LC-CDR2 comprising the amino acid sequence of SEQ ID NO: 5, and an LC-CDR3 comprising the amino acid sequence of SEQ ID NO: 6.

In some embodiments, the anti-S1 antibody or antigen binding fragment thereof comprises a VH comprising the amino acid sequences of SEQ ID NOs: 1, 2, and 3; and a VL comprising the amino acid sequences of SEQ ID NOs: 4, 5, and 6. In some embodiments, the anti-S1 antibody or antigen binding fragment thereof comprises a VH comprising an HC-CDR1, an HC-CDR2, and an HC-CDR3 of the amino acid sequence of SEQ ID NO: 61 and a VL comprising an LC-CDR1, an LC-CDR2, and an LC-CDR3 of the amino acid sequence of SEQ ID NO: 62.

In some embodiments, there is provided an anti-S1 antibody or antigen binding fragment thereof comprising: i) a VH comprising an HC-CDR1 comprising the amino acid sequence of SEQ ID NO: 7, or a variant thereof comprising up to about 5 (such as about any of 1, 2, 3, 4, or 5) amino acid substitutions, an HC-CDR2 comprising the amino acid sequence of SEQ ID NO: 8, or a variant thereof comprising up to about 5 (such as about any of 1, 2, 3, 4, or 5) amino acid substitutions, and an HC-CDR3 comprising the amino acid sequence of SEQ ID NO: 9, or a variant thereof comprising up to about 5 (such as about any of 1, 2, 3, 4, or 5) amino acid substitutions; and ii) a VL comprising an LC-CDR1 comprising the amino acid sequence of SEQ ID NO: 10, or a variant thereof comprising up to about 5 (such as about any of 1, 2, 3, 4, or 5) amino acid substitutions, an LC-CDR2 comprising the amino acid sequence of SEQ ID NO: 11, or a variant thereof comprising up to about 3 (such as about any of 1, 2, or 3) amino acid substitutions, and an LC-CDR3 comprising the amino acid sequence of SEQ ID NO: 12, or a variant thereof comprising up to about 5 (such as about any of 1, 2, 3, 4, or 5) amino acid substitutions. In some embodiments, the anti-S1 antibody or antigen binding fragment thereof comprises: (1) i) a VH comprising an HC-CDR1 comprising the amino acid sequence of SEQ ID NO: 7, an HC-CDR2 comprising the amino acid sequence of SEQ ID NO: 8, and an HC-CDR3 comprising the amino acid sequence of SEQ ID NO: 9; or a variant thereof comprising up to about 5 (such as about any of 1, 2, 3, 4, or 5) amino acid substitutions in the HC-CDR sequences; and ii) a VL comprising an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-S1 antibody or antigen binding fragment thereof comprises i) a VH comprising an HC-CDR1 comprising the amino acid sequence of SEQ ID NO: 7, an HC-CDR2 comprising the amino acid sequence of SEQ ID NO: 8, and an HC-CDR3 comprising the amino acid sequence of SEQ ID NO: 9; and ii) a VL comprising an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12.

In some embodiments, the anti-S1 antibody or antigen binding fragment thereof comprises a VH comprising the amino acid sequences of SEQ ID NOs: 7, 8, and 9; and a VL comprising the amino acid sequences of SEQ ID NOs: 10, 11, and 12. In some embodiments, the anti-S1 antibody or antigen binding fragment thereof comprises a VH comprising an HC-CDR1, an HC-CDR2, and an HC-CDR3 of the amino acid sequence of SEQ ID NO: 63 and a VL comprising an LC-CDR1, an LC-CDR2, and an LC-CDR3 of the amino acid sequence of SEQ ID NO: 64.

In some embodiments, there is provided an anti-S1 antibody or antigen binding fragment thereof comprising: i) a VH comprising an HC-CDR1 comprising the amino acid sequence of SEQ ID NO: 13, or a variant thereof comprising up to about 5 (such as about any of 1, 2, 3, 4, or 5) amino acid substitutions, an HC-CDR2 comprising the amino acid sequence of SEQ ID NO: 14, or a variant thereof comprising up to about 5 (such as about any of 1, 2, 3, 4, or 5) amino acid substitutions, and an HC-CDR3 comprising the amino acid sequence of SEQ ID NO: 15, or a variant thereof comprising up to about 5 (such as about any of 1, 2, 3, 4, or 5) amino acid substitutions; and ii) a VL comprising an LC-CDR1 comprising the amino acid sequence of SEQ ID NO: 16, or a variant thereof comprising up to about 5 (such as about any of 1, 2, 3, 4, or 5) amino acid substitutions, an LC-CDR2 comprising the amino acid sequence of SEQ ID NO: 17, or a variant thereof comprising up to about 3 (such as about any of 1, 2, or 3) amino acid substitutions, and an LC-CDR3 comprising the amino acid sequence of SEQ ID NO: 18, or a variant thereof comprising up to about 5 (such as about any of 1, 2, 3, 4, or 5) amino acid substitutions. In some embodiments, the anti-S1 antibody or antigen binding fragment thereof comprises: (1) i) a VH comprising an HC-CDR1 comprising the amino acid sequence of SEQ ID NO: 13, an HC-CDR2 comprising the amino acid sequence of SEQ ID NO: 14, and an HC-CDR3 comprising the amino acid sequence of SEQ ID NO: 15; or a variant thereof comprising up to about 5 (such as about any of 1, 2, 3, 4, or 5) amino acid substitutions in the HC-CDR sequences; and ii) a VL comprising an LC-CDR1 comprising the amino acid sequence of SEQ ID NO: 16, an LC-CDR2 comprising the amino acid sequence of SEQ ID NO: 17, and an LC-CDR3 comprising the amino acid sequence of SEQ ID NO: 18; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-S1 antibody or antigen binding fragment thereof comprises i) a VH comprising an HC-CDR1 comprising the amino acid sequence of SEQ ID NO: 13, an HC-CDR2 comprising the amino acid sequence of SEQ ID NO: 14, and an HC-CDR3 comprising the amino acid sequence of SEQ ID NO: 15; and ii) a VL comprising an LC-CDR1 comprising the amino acid sequence of SEQ ID NO: 16, an LC-CDR2 comprising the amino acid sequence of SEQ ID NO: 17, and an LC-CDR3 comprising the amino acid sequence of SEQ ID NO: 18.

In some embodiments, the anti-S1 antibody or antigen binding fragment thereof comprises a VH comprising the amino acid sequences of SEQ ID NOs: 13, 14, and 15; and a VL comprising the amino acid sequences of SEQ ID NOs: 16, 17, and 18. In some embodiments, the anti-S1 antibody or antigen binding fragment thereof comprises a VH comprising an HC-CDR1, an HC-CDR2, and an HC-CDR3 of the amino acid sequence of SEQ ID NO: 65 and a VL comprising an LC-CDR1, an LC-CDR2, and an LC-CDR3 of the amino acid sequence of SEQ ID NO: 66.

In some embodiments, there is provided an anti-S1 antibody or antigen binding fragment thereof comprising: i) a VH comprising an HC-CDR1 comprising the amino acid sequence of SEQ ID NO: 19, or a variant thereof comprising up to about 5 (such as about any of 1, 2, 3, 4, or 5) amino acid substitutions, an HC-CDR2 comprising the amino acid sequence of SEQ ID NO: 20, or a variant thereof comprising up to about 5 (such as about any of 1, 2, 3, 4, or 5) amino acid substitutions, and an HC-CDR3 comprising the amino acid sequence of SEQ ID NO: 21, or a variant thereof comprising up to about 5 (such as about any of 1, 2, 3, 4, or 5) amino acid substitutions; and ii) a VL comprising an LC-CDR1 comprising the amino acid sequence of SEQ ID NO: 22, or a variant thereof comprising up to about 5 (such as about any of 1, 2, 3, 4, or 5) amino acid substitutions, an LC-CDR2 comprising the amino acid sequence of SEQ ID NO: 23, or a variant thereof comprising up to about 3 (such as about any of 1, 2, or 3) amino acid substitutions, and an LC-CDR3 comprising the amino acid sequence of SEQ ID NO: 24, or a variant thereof comprising up to about 5 (such as about any of 1, 2, 3, 4, or 5) amino acid substitutions. In some embodiments, the anti-S1 antibody or antigen binding fragment thereof comprises: (1) i) a VH comprising an HC-CDR1 comprising the amino acid sequence of SEQ ID NO: 19, an HC-CDR2 comprising the amino acid sequence of SEQ ID NO: 20, and an HC-CDR3 comprising the amino acid sequence of SEQ ID NO: 21; or a variant thereof comprising up to about 5 (such as about any of 1, 2, 3, 4, or 5) amino acid substitutions in the HC-CDR sequences; and ii) a VL comprising an LC-CDR1 comprising the amino acid sequence of SEQ ID NO: 22, an LC-CDR2 comprising the amino acid sequence of SEQ ID NO: 23, and an LC-CDR3 comprising the amino acid sequence of SEQ ID NO: 24; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-S1 antibody or antigen binding fragment thereof comprises i) a VH comprising an HC-CDR1 comprising the amino acid sequence of SEQ ID NO: 19, an HC-CDR2 comprising the amino acid sequence of SEQ ID NO: 20, and an HC-CDR3 comprising the amino acid sequence of SEQ ID NO: 21; and ii) a VL comprising an LC-CDR1 comprising the amino acid sequence of SEQ ID NO: 22, an LC-CDR2 comprising the amino acid sequence of SEQ ID NO: 23, and an LC-CDR3 comprising the amino acid sequence of SEQ ID NO: 24.

In some embodiments, the anti-S1 antibody or antigen binding fragment thereof comprises a VH comprising the amino acid sequences of SEQ ID NOs: 19, 20, and 21; and a VL comprising the amino acid sequences of SEQ ID NOs: 22, 23, and 24. In some embodiments, the anti-S1 antibody or antigen binding fragment thereof comprises a VH comprising an HC-CDR1, an HC-CDR2, and an HC-CDR3 of the amino acid sequence of SEQ ID NO: 67 and a VL comprising an LC-CDR1, an LC-CDR2, and an LC-CDR3 of the amino acid sequence of SEQ ID NO: 68.

In some embodiments, there is provided an anti-S1 antibody or antigen binding fragment thereof comprising: i) a VH comprising an HC-CDR1 comprising the amino acid sequence of SEQ ID NO: 25, or a variant thereof comprising up to about 5 (such as about any of 1, 2, 3, 4, or 5) amino acid substitutions, an HC-CDR2 comprising the amino acid sequence of SEQ ID NO: 26, or a variant thereof comprising up to about 5 (such as about any of 1, 2, 3, 4, or 5) amino acid substitutions, and an HC-CDR3 comprising the amino acid sequence of SEQ ID NO: 27, or a variant thereof comprising up to about 5 (such as about any of 1, 2, 3, 4, or 5) amino acid substitutions; and ii) a VL comprising an LC-CDR1 comprising the amino acid sequence of SEQ ID NO: 28, or a variant thereof comprising up to about 5 (such as about any of 1, 2, 3, 4, or 5) amino acid substitutions, an LC-CDR2 comprising the amino acid sequence of SEQ ID NO: 29, or a variant thereof comprising up to about 3 (such as about any of 1, 2, or 3) amino acid substitutions, and an LC-CDR3 comprising the amino acid sequence of SEQ ID NO: 30, or a variant thereof comprising up to about 5 (such as about any of 1, 2, 3, 4, or 5) amino acid substitutions. In some embodiments, the anti-S1 antibody or antigen binding fragment thereof comprises: (1) i) a VH comprising an HC-CDR1 comprising the amino acid sequence of SEQ ID NO: 25, an HC-CDR2 comprising the amino acid sequence of SEQ ID NO: 26, and an HC-CDR3 comprising the amino acid sequence of SEQ ID NO: 27; or a variant thereof comprising up to about 5 (such as about any of 1, 2, 3, 4, or 5) amino acid substitutions in the HC-CDR sequences; and ii) a VL comprising an LC-CDR1 comprising the amino acid sequence of SEQ ID NO: 28, an LC-CDR2 comprising the amino acid sequence of SEQ ID NO: 29, and an LC-CDR3 comprising the amino acid sequence of SEQ ID NO: 30; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-S1 antibody or antigen binding fragment thereof comprises i) a VH comprising an HC-CDR1 comprising the amino acid sequence of SEQ ID NO: 25, an HC-CDR2 comprising the amino acid sequence of SEQ ID NO: 26, and an HC-CDR3 comprising the amino acid sequence of SEQ ID NO: 27; and ii) a VL comprising an LC-CDR1 comprising the amino acid sequence of SEQ ID NO: 28, an LC-CDR2 comprising the amino acid sequence of SEQ ID NO: 29, and an LC-CDR3 comprising the amino acid sequence of SEQ ID NO: 30.

In some embodiments, the anti-S1 antibody or antigen binding fragment thereof comprises a VH comprising the amino acid sequences of SEQ ID NOs: 25, 26, and 27; and a VL comprising the amino acid sequences of SEQ ID NOs: 28, 29, and 30. In some embodiments, the anti-S1 antibody or antigen binding fragment thereof comprises a VH comprising an HC-CDR1, an HC-CDR2, and an HC-CDR3 of the amino acid sequence of SEQ ID NO: 69 and a VL comprising an LC-CDR1, an LC-CDR2, and an LC-CDR3 of the amino acid sequence of SEQ ID NO: 70.

In some embodiments, there is provided an anti-S1 antibody or antigen binding fragment thereof comprising: i) a VH comprising an HC-CDR1 comprising the amino acid sequence of SEQ ID NO: 31, or a variant thereof comprising up to about 5 (such as about any of 1, 2, 3, 4, or 5) amino acid substitutions, an HC-CDR2 comprising the amino acid sequence of SEQ ID NO: 32, or a variant thereof comprising up to about 5 (such as about any of 1, 2, 3, 4, or 5) amino acid substitutions, and an HC-CDR3 comprising the amino acid sequence of SEQ ID NO: 33, or a variant thereof comprising up to about 5 (such as about any of 1, 2, 3, 4, or 5) amino acid substitutions; and ii) a VL comprising an LC-CDR1 comprising the amino acid sequence of SEQ ID NO: 34, or a variant thereof comprising up to about 5 (such as about any of 1, 2, 3, 4, or 5) amino acid substitutions, an LC-CDR2 comprising the amino acid sequence of SEQ ID NO: 35, or a variant thereof comprising up to about 3 (such as about any of 1, 2, or 3) amino acid substitutions, and an LC-CDR3 comprising the amino acid sequence of SEQ ID NO: 36, or a variant thereof comprising up to about 5 (such as about any of 1, 2, 3, 4, or 5) amino acid substitutions. In some embodiments, the anti-S1 antibody or antigen binding fragment thereof comprises: (1) i) a VH comprising an HC-CDR1 comprising the amino acid sequence of SEQ ID NO: 31, an HC-CDR2 comprising the amino acid sequence of SEQ ID NO: 32, and an HC-CDR3 comprising the amino acid sequence of SEQ ID NO: 33; or a variant thereof comprising up to about 5 (such as about any of 1, 2, 3, 4, or 5) amino acid substitutions in the HC-CDR sequences; and ii) a VL comprising an LC-CDR1 comprising the amino acid sequence of SEQ ID NO: 34, an LC-CDR2 comprising the amino acid sequence of SEQ ID NO: 35, and an LC-CDR3 comprising the amino acid sequence of SEQ ID NO: 36; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-S1 antibody or antigen binding fragment thereof comprises i) a VH comprising an HC-CDR1 comprising the amino acid sequence of SEQ ID NO: 31, an HC-CDR2 comprising the amino acid sequence of SEQ ID NO: 32, and an HC-CDR3 comprising the amino acid sequence of SEQ ID NO: 33; and ii) a VL comprising an LC-CDR1 comprising the amino acid sequence of SEQ ID NO: 34, an LC-CDR2 comprising the amino acid sequence of SEQ ID NO: 35, and an LC-CDR3 comprising the amino acid sequence of SEQ ID NO: 36.

In some embodiments, the anti-S1 antibody or antigen binding fragment thereof comprises a VH comprising the amino acid sequences of SEQ ID NOs: 31, 32, and 33; and a VL comprising the amino acid sequences of SEQ ID NOs: 34, 35, and 36. In some embodiments, the anti-S1 antibody or antigen binding fragment thereof comprises a VH comprising an HC-CDR1, an HC-CDR2, and an HC-CDR3 of the amino acid sequence of SEQ ID NO: 71 and a VL comprising an LC-CDR1, an LC-CDR2, and an LC-CDR3 of the amino acid sequence of SEQ ID NO: 72.

In some embodiments, there is provided an anti-S1 antibody or antigen binding fragment thereof comprising: i) a VH comprising an HC-CDR1 comprising the amino acid sequence of SEQ ID NO: 37, or a variant thereof comprising up to about 5 (such as about any of 1, 2, 3, 4, or 5) amino acid substitutions, an HC-CDR2 comprising the amino acid sequence of SEQ ID NO: 38, or a variant thereof comprising up to about 5 (such as about any of 1, 2, 3, 4, or 5) amino acid substitutions, and an HC-CDR3 comprising the amino acid sequence of SEQ ID NO: 39, or a variant thereof comprising up to about 5 (such as about any of 1, 2, 3, 4, or 5) amino acid substitutions; and ii) a VL comprising an LC-CDR1 comprising the amino acid sequence of SEQ ID NO: 40, or a variant thereof comprising up to about 5 (such as about any of 1, 2, 3, 4, or 5) amino acid substitutions, an LC-CDR2 comprising the amino acid sequence of SEQ ID NO: 41, or a variant thereof comprising up to about 3 (such as about any of 1, 2, or 3) amino acid substitutions, and an LC-CDR3 comprising the amino acid sequence of SEQ ID NO: 42, or a variant thereof comprising up to about 5 (such as about any of 1, 2, 3, 4, or 5) amino acid substitutions. In some embodiments, the anti-S1 antibody or antigen binding fragment thereof comprises: (1) i) a VH comprising an HC-CDR1 comprising the amino acid sequence of SEQ ID NO: 37, an HC-CDR2 comprising the amino acid sequence of SEQ ID NO: 38, and an HC-CDR3 comprising the amino acid sequence of SEQ ID NO: 39; or a variant thereof comprising up to about 5 (such as about any of 1, 2, 3, 4, or 5) amino acid substitutions in the HC-CDR sequences; and ii) a VL comprising an LC-CDR1 comprising the amino acid sequence of SEQ ID NO: 40, an LC-CDR2 comprising the amino acid sequence of SEQ ID NO: 41, and an LC-CDR3 comprising the amino acid sequence of SEQ ID NO: 42; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-S1 antibody or antigen binding fragment thereof comprises i) a VH comprising an HC-CDR1 comprising the amino acid sequence of SEQ ID NO: 37, an HC-CDR2 comprising the amino acid sequence of SEQ ID NO: 38, and an HC-CDR3 comprising the amino acid sequence of SEQ ID NO: 39; and ii) a VL comprising an LC-CDR1 comprising the amino acid sequence of SEQ ID NO: 40, an LC-CDR2 comprising the amino acid sequence of SEQ ID NO: 41, and an LC-CDR3 comprising the amino acid sequence of SEQ ID NO: 42.

In some embodiments, the anti-S1 antibody or antigen binding fragment thereof comprises a VH comprising the amino acid sequences of SEQ ID NOs: 37, 38, and 39; and a VL comprising the amino acid sequences of SEQ ID NOs: 40, 41, and 42. In some embodiments, the anti-S1 antibody or antigen binding fragment thereof comprises a VH comprising an HC-CDR1, an HC-CDR2, and an HC-CDR3 of the amino acid sequence of SEQ ID NO: 73 and a VL comprising an LC-CDR1, an LC-CDR2, and an LC-CDR3 of the amino acid sequence of SEQ ID NO: 74.

In some embodiments, there is provided an anti-S1 antibody or antigen binding fragment thereof comprising: i) a VH comprising an HC-CDR1 comprising the amino acid sequence of SEQ ID NO: 43, or a variant thereof comprising up to about 5 (such as about any of 1, 2, 3, 4, or 5) amino acid substitutions, an HC-CDR2 comprising the amino acid sequence of SEQ ID NO: 44, or a variant thereof comprising up to about 5 (such as about any of 1, 2, 3, 4, or 5) amino acid substitutions, and an HC-CDR3 comprising the amino acid sequence of SEQ ID NO: 45, or a variant thereof comprising up to about 5 (such as about any of 1, 2, 3, 4, or 5) amino acid substitutions; and ii) a VL comprising an LC-CDR1 comprising the amino acid sequence of SEQ ID NO: 46, or a variant thereof comprising up to about 5 (such as about any of 1, 2, 3, 4, or 5) amino acid substitutions, an LC-CDR2 comprising the amino acid sequence of SEQ ID NO: 47, or a variant thereof comprising up to about 3 (such as about any of 1, 2, or 3) amino acid substitutions, and an LC-CDR3 comprising the amino acid sequence of SEQ ID NO: 48, or a variant thereof comprising up to about 5 (such as about any of 1, 2, 3, 4, or 5) amino acid substitutions. In some embodiments, the anti-S1 antibody or antigen binding fragment thereof comprises: (1) i) a VH comprising an HC-CDR1 comprising the amino acid sequence of SEQ ID NO: 43, an HC-CDR2 comprising the amino acid sequence of SEQ ID NO: 44, and an HC-CDR3 comprising the amino acid sequence of SEQ ID NO: 45; or a variant thereof comprising up to about 5 (such as about any of 1, 2, 3, 4, or 5) amino acid substitutions in the HC-CDR sequences; and ii) a VL comprising an LC-CDR1 comprising the amino acid sequence of SEQ ID NO: 46, an LC-CDR2 comprising the amino acid sequence of SEQ ID NO: 47, and an LC-CDR3 comprising the amino acid sequence of SEQ ID NO: 48; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-S1 antibody or antigen binding fragment thereof comprises i) a VH comprising an HC-CDR1 comprising the amino acid sequence of SEQ ID NO: 43, an HC-CDR2 comprising the amino acid sequence of SEQ ID NO: 44, and an HC-CDR3 comprising the amino acid sequence of SEQ ID NO: 45; and ii) a VL comprising an LC-CDR1 comprising the amino acid sequence of SEQ ID NO: 46, an LC-CDR2 comprising the amino acid sequence of SEQ ID NO: 47, and an LC-CDR3 comprising the amino acid sequence of SEQ ID NO: 48.

In some embodiments, the anti-S1 antibody or antigen binding fragment thereof comprises a VH comprising the amino acid sequences of SEQ ID NOs: 43, 44, and 45; and a VL comprising the amino acid sequences of SEQ ID NOs: 46, 47, and 48. In some embodiments, the anti-S1 antibody or antigen binding fragment thereof comprises a VH comprising an HC-CDR1, an HC-CDR2, and an HC-CDR3 of the amino acid sequence of SEQ ID NO: 75 and a VL comprising an LC-CDR1, an LC-CDR2, and an LC-CDR3 of the amino acid sequence of SEQ ID NO: 76.

In some embodiments, there is provided an anti-S1 antibody or antigen binding fragment thereof comprising: i) a VH comprising an HC-CDR1 comprising the amino acid sequence of SEQ ID NO: 49, or a variant thereof comprising up to about 5 (such as about any of 1, 2, 3, 4, or 5) amino acid substitutions, an HC-CDR2 comprising the amino acid sequence of SEQ ID NO: 50, or a variant thereof comprising up to about 5 (such as about any of 1, 2, 3, 4, or 5) amino acid substitutions, and an HC-CDR3 comprising the amino acid sequence of SEQ ID NO: 51, or a variant thereof comprising up to about 5 (such as about any of 1, 2, 3, 4, or 5) amino acid substitutions; and ii) a VL comprising an LC-CDR1 comprising the amino acid sequence of SEQ ID NO: 52, or a variant thereof comprising up to about 5 (such as about any of 1, 2, 3, 4, or 5) amino acid substitutions, an LC-CDR2 comprising the amino acid sequence of SEQ ID NO: 53, or a variant thereof comprising up to about 3 (such as about any of 1, 2, or 3) amino acid substitutions, and an LC-CDR3 comprising the amino acid sequence of SEQ ID NO: 54, or a variant thereof comprising up to about 5 (such as about any of 1, 2, 3, 4, or 5) amino acid substitutions. In some embodiments, the anti-S1 antibody or antigen binding fragment thereof comprises: (1) i) a VH comprising an HC-CDR1 comprising the amino acid sequence of SEQ ID NO: 49, an HC-CDR2 comprising the amino acid sequence of SEQ ID NO: 50, and an HC-CDR3 comprising the amino acid sequence of SEQ ID NO: 51; or a variant thereof comprising up to about 5 (such as about any of 1, 2, 3, 4, or 5) amino acid substitutions in the HC-CDR sequences; and ii) a VL comprising an LC-CDR1 comprising the amino acid sequence of SEQ ID NO: 52, an LC-CDR2 comprising the amino acid sequence of SEQ ID NO: 53, and an LC-CDR3 comprising the amino acid sequence of SEQ ID NO: 54; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-S1 antibody or antigen binding fragment thereof comprises i) a VH comprising an HC-CDR1 comprising the amino acid sequence of SEQ ID NO: 49, an HC-CDR2 comprising the amino acid sequence of SEQ ID NO: 50, and an HC-CDR3 comprising the amino acid sequence of SEQ ID NO: 51; and ii) a VL comprising an LC-CDR1 comprising the amino acid sequence of SEQ ID NO: 52, an LC-CDR2 comprising the amino acid sequence of SEQ ID NO: 53, and an LC-CDR3 comprising the amino acid sequence of SEQ ID NO: 54.

In some embodiments, the anti-S1 antibody or antigen binding fragment thereof comprises a VH comprising the amino acid sequences of SEQ ID NOs: 49, 50, and 51; and a VL comprising the amino acid sequences of SEQ ID NOs: 52, 53, and 54. In some embodiments, the anti-S1 antibody or antigen binding fragment thereof comprises a VH comprising an HC-CDR1, an HC-CDR2, and an HC-CDR3 of the amino acid sequence of SEQ ID NO: 77 and a VL comprising an LC-CDR1, an LC-CDR2, and an LC-CDR3 of the amino acid sequence of SEQ ID NO: 78.

In some embodiments, there is provided an anti-S1 antibody or antigen binding fragment thereof comprising: i) a VH comprising an HC-CDR1 comprising the amino acid sequence of SEQ ID NO: 55, or a variant thereof comprising up to about 5 (such as about any of 1, 2, 3, 4, or 5) amino acid substitutions, an HC-CDR2 comprising the amino acid sequence of SEQ ID NO: 56, or a variant thereof comprising up to about 5 (such as about any of 1, 2, 3, 4, or 5) amino acid substitutions, and an HC-CDR3 comprising the amino acid sequence of SEQ ID NO: 57, or a variant thereof comprising up to about 5 (such as about any of 1, 2, 3, 4, or 5) amino acid substitutions; and ii) a VL comprising an LC-CDR1 comprising the amino acid sequence of SEQ ID NO: 58, or a variant thereof comprising up to about 5 (such as about any of 1, 2, 3, 4, or 5) amino acid substitutions, an LC-CDR2 comprising the amino acid sequence of SEQ ID NO: 59, or a variant thereof comprising up to about 3 (such as about any of 1, 2, or 3) amino acid substitutions, and an LC-CDR3 comprising the amino acid sequence of SEQ ID NO: 60, or a variant thereof comprising up to about 5 (such as about any of 1, 2, 3, 4, or 5) amino acid substitutions. In some embodiments, the anti-S1 antibody or antigen binding fragment thereof comprises: (1) i) a VH comprising an HC-CDR1 comprising the amino acid sequence of SEQ ID NO: 55, an HC-CDR2 comprising the amino acid sequence of SEQ ID NO: 56, and an HC-CDR3 comprising the amino acid sequence of SEQ ID NO: 57; or a variant thereof comprising up to about 5 (such as about any of 1, 2, 3, 4, or 5) amino acid substitutions in the HC-CDR sequences; and ii) a VL comprising an LC-CDR1 comprising the amino acid sequence of SEQ ID NO: 58, an LC-CDR2 comprising the amino acid sequence of SEQ ID NO: 59, and an LC-CDR3 comprising the amino acid sequence of SEQ ID NO: 60; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-S1 antibody or antigen binding fragment thereof comprises i) a VH comprising an HC-CDR1 comprising the amino acid sequence of SEQ ID NO: 55, an HC-CDR2 comprising the amino acid sequence of SEQ ID NO: 56, and an HC-CDR3 comprising the amino acid sequence of SEQ ID NO: 57; and ii) a VL comprising an LC-CDR1 comprising the amino acid sequence of SEQ ID NO: 58, an LC-CDR2 comprising the amino acid sequence of SEQ ID NO: 59, and an LC-CDR3 comprising the amino acid sequence of SEQ ID NO: 60.

In some embodiments, the anti-S1 antibody or antigen binding fragment thereof comprises a VH comprising the amino acid sequences of SEQ ID NOs: 55, 56, and 57; and a VL comprising the amino acid sequences of SEQ ID NOs: 58, 59, and 60. In some embodiments, the anti-S1 antibody or antigen binding fragment thereof comprises a VH comprising an HC-CDR1, an HC-CDR2, and an HC-CDR3 of the amino acid sequence of SEQ ID NO: 79 and a VL comprising an LC-CDR1, an LC-CDR2, and an LC-CDR3 of the amino acid sequence of SEQ ID NO: 80.

In some embodiments, there is provided an anti-S1 antibody or antigen binding fragment thereof comprises: a) a VH comprising the amino acid sequence of SEQ ID NO: 61, or a variant thereof having at least about 80% (including for example at least about any of 80%, 85%, 90%, 95%, 96%, 97%, 98%, or 99%) sequence identity to SEQ ID NO: 61; and b) a VL comprising the amino acid sequence of SEQ ID NO: 62, or a variant thereof having at least about 80% (including for example at least about any of 80%, 85%, 90%, 95%, 96%, 97%, 98%, or 99%) sequence identity to SEQ ID NO: 62. In some embodiments, the anti-S1 antibody or antigen binding fragment thereof comprises: a) a VH comprising the amino acid sequence of SEQ ID NO: 61; and b) a VL comprising the amino acid sequence of SEQ ID NO: 62. In some embodiments, the anti-S1 antibody or antigen binding fragment thereof comprises the HC-CDRs of a VH comprising the amino acid sequence of SEQ ID NO: 61, and the LC-CDRs of a VL comprising the amino acid sequence of SEQ ID NO: 62. In some embodiments, the anti-S1 antibody or antigen binding thereof comprises an scFv comprising the amino acid sequence of SEQ ID NO: 81, or a variant thereof having at least about 80% (including for example at least about any of 80%, 85%, 90%, 95%, 96%, 97%, 98%, or 99%) sequence identity to SEQ ID NO: 81.

In some embodiments, there is provided an anti-S1 antibody or antigen binding fragment thereof comprises: a) a VH comprising the amino acid sequence of SEQ ID NO: 63, or a variant thereof having at least about 80% (including for example at least about any of 80%, 85%, 90%, 95%, 96%, 97%, 98%, or 99%) sequence identity to SEQ ID NO: 63; and b) a VL comprising the amino acid sequence of SEQ ID NO: 64, or a variant thereof having at least about 80% (including for example at least about any of 80%, 85%, 90%, 95%, 96%, 97%, 98%, or 99%) sequence identity to SEQ ID NO: 64. In some embodiments, the anti-S1 antibody or antigen binding fragment thereof comprises: a) a VH comprising the amino acid sequence of SEQ ID NO: 63; and b) a VL comprising the amino acid sequence of SEQ ID NO: 64. In some embodiments, the anti-S1 antibody or antigen binding fragment thereof comprises the HC-CDRs of a VH comprising the amino acid sequence of SEQ ID NO: 63, and the LC-CDRs of a VL comprising the amino acid sequence of SEQ ID NO: 64. In some embodiments, the anti-S1 antibody or antigen binding thereof comprises an scFv comprising the amino acid sequence of SEQ ID NO: 82, or a variant thereof having at least about 80% (including for example at least about any of 80%, 85%, 90%, 95%, 96%, 97%, 98%, or 99%) sequence identity to SEQ ID NO: 82.

In some embodiments, there is provided an anti-S1 antibody or antigen binding fragment thereof comprises: a) a VH comprising the amino acid sequence of SEQ ID NO: 65, or a variant thereof having at least about 80% (including for example at least about any of 80%, 85%, 90%, 95%, 96%, 97%, 98%, or 99%) sequence identity to SEQ ID NO: 65;

and b) a VL comprising the amino acid sequence of SEQ ID NO: 66, or a variant thereof having at least about 80% (including for example at least about any of 80%, 85%, 90%, 95%, 96%, 97%, 98%, or 99%) sequence identity to SEQ ID NO: 66. In some embodiments, the anti-S1 antibody or antigen binding fragment thereof comprises: a) a VH comprising the amino acid sequence of SEQ ID NO: 65; and b) a VL comprising the amino acid sequence of SEQ ID NO: 66. In some embodiments, the anti-S1 antibody or antigen binding fragment thereof comprises the HC-CDRs of a VH comprising the amino acid sequence of SEQ ID NO: 65, and the LC-CDRs of a VL comprising the amino acid sequence of SEQ ID NO: 66. In some embodiments, the anti-S1 antibody or antigen binding thereof comprises an scFv comprising the amino acid sequence of SEQ ID NO: 83, or a variant thereof having at least about 80% (including for example at least about any of 80%, 85%, 90%, 95%, 96%, 97%, 98%, or 99%) sequence identity to SEQ ID NO: 83.

In some embodiments, there is provided an anti-S1 antibody or antigen binding fragment thereof comprises: a) a VH comprising the amino acid sequence of SEQ ID NO: 67, or a variant thereof having at least about 80% (including for example at least about any of 80%, 85%, 90%, 95%, 96%, 97%, 98%, or 99%) sequence identity to SEQ ID NO: 67; and b) a VL comprising the amino acid sequence of SEQ ID NO: 68, or a variant thereof having at least about 80% (including for example at least about any of 80%, 85%, 90%, 95%, 96%, 97%, 98%, or 99%) sequence identity to SEQ ID NO: 68. In some embodiments, the anti-S1 antibody or antigen binding fragment thereof comprises: a) a VH comprising the amino acid sequence of SEQ ID NO: 67; and b) a VL comprising the amino acid sequence of SEQ ID NO: 68. In some embodiments, the anti-S1 antibody or antigen binding fragment thereof comprises the HC-CDRs of a VH comprising the amino acid sequence of SEQ ID NO: 67, and the LC-CDRs of a VL comprising the amino acid sequence of SEQ ID NO: 68. In some embodiments, the anti-S1 antibody or antigen binding thereof comprises an scFv comprising the amino acid sequence of SEQ ID NO: 84, or a variant thereof having at least about 80% (including for example at least about any of 80%, 85%, 90%, 95%, 96%, 97%, 98%, or 99%) sequence identity to SEQ ID NO: 84.

In some embodiments, there is provided an anti-S1 antibody or antigen binding fragment thereof comprises: a) a VH comprising the amino acid sequence of SEQ ID NO: 69, or a variant thereof having at least about 80% (including for example at least about any of 80%, 85%, 90%, 95%, 96%, 97%, 98%, or 99%) sequence identity to SEQ ID NO: 69; and b) a VL comprising the amino acid sequence of SEQ ID NO: 70, or a variant thereof having at least about 80% (including for example at least about any of 80%, 85%, 90%, 95%, 96%, 97%, 98%, or 99%) sequence identity to SEQ ID NO: 70. In some embodiments, the anti-S1 antibody or antigen binding fragment thereof comprises: a) a VH comprising the amino acid sequence of SEQ ID NO: 69; and b) a VL comprising the amino acid sequence of SEQ ID NO: 70. In some embodiments, the anti-S1 antibody or antigen binding fragment thereof comprises the HC-CDRs of a VH comprising the amino acid sequence of SEQ ID NO: 69, and the LC-CDRs of a VL comprising the amino acid sequence of SEQ ID NO: 70. In some embodiments, the anti-S1 antibody or antigen binding thereof comprises an scFv comprising the amino acid sequence of SEQ ID NO: 85, or a variant thereof having at least about 80% (including for example at least about any of 80%, 85%, 90%, 95%, 96%, 97%, 98%, or 99%) sequence identity to SEQ ID NO: 85.

In some embodiments, there is provided an anti-S1 antibody or antigen binding fragment thereof comprises: a) a VH comprising the amino acid sequence of SEQ ID NO: 71, or a variant thereof having at least about 80% (including for example at least about any of 80%, 85%, 90%, 95%, 96%, 97%, 98%, or 99%) sequence identity to SEQ ID NO: 71; and b) a VL comprising the amino acid sequence of SEQ ID NO: 72, or a variant thereof having at least about 80% (including for example at least about any of 80%, 85%, 90%, 95%, 96%, 97%, 98%, or 99%) sequence identity to SEQ ID NO: 72. In some embodiments, the anti-S1 antibody or antigen binding fragment thereof comprises: a) a VH comprising the amino acid sequence of SEQ ID NO: 71; and b) a VL comprising the amino acid sequence of SEQ ID NO: 72. In some embodiments, the anti-S1 antibody or antigen binding fragment thereof comprises the HC-CDRs of a VH comprising the amino acid sequence of SEQ ID NO: 71, and the LC-CDRs of a VL comprising the amino acid sequence of SEQ ID NO: 72. In some embodiments, the anti-S1 antibody or antigen binding thereof comprises an scFv comprising the amino acid sequence of SEQ ID NO: 86, or a variant thereof having at least about 80% (including for example at least about any of 80%, 85%, 90%, 95%, 96%, 97%, 98%, or 99%) sequence identity to SEQ ID NO: 86.

In some embodiments, there is provided an anti-S1 antibody or antigen binding fragment thereof comprises: a) a VH comprising the amino acid sequence of SEQ ID NO: 73, or a variant thereof having at least about 80% (including for example at least about any of 80%, 85%, 90%, 95%, 96%, 97%, 98%, or 99%) sequence identity to SEQ ID NO: 73; and b) a VL comprising the amino acid sequence of SEQ ID NO: 74, or a variant thereof having at least about 80% (including for example at least about any of 80%, 85%, 90%, 95%, 96%, 97%, 98%, or 99%) sequence identity to SEQ ID NO: 74. In some embodiments, the anti-S1 antibody or antigen binding fragment thereof comprises: a) a VH comprising the amino acid sequence of SEQ ID NO: 73; and b) a VL comprising the amino acid sequence of SEQ ID NO: 74. In some embodiments, the anti-S1 antibody or antigen binding fragment thereof comprises the HC-CDRs of a VH comprising the amino acid sequence of SEQ ID NO: 73, and the LC-CDRs of a VL comprising the amino acid sequence of SEQ ID NO: 74. In some embodiments, the anti-S1 antibody or antigen binding thereof comprises an scFv comprising the amino acid sequence of SEQ ID NO: 87, or a variant thereof having at least about 80% (including for example at least about any of 80%, 85%, 90%, 95%, 96%, 97%, 98%, or 99%) sequence identity to SEQ ID NO: 87.

In some embodiments, there is provided an anti-S1 antibody or antigen binding fragment thereof comprises: a) a VH comprising the amino acid sequence of SEQ ID NO: 75, or a variant thereof having at least about 80% (including for example at least about any of 80%, 85%, 90%, 95%, 96%, 97%, 98%, or 99%) sequence identity to SEQ ID NO: 75; and b) a VL comprising the amino acid sequence of SEQ ID NO: 76, or a variant thereof having at least about 80% (including for example at least about any of 80%, 85%, 90%, 95%, 96%, 97%, 98%, or 99%) sequence identity to SEQ ID NO: 76. In some embodiments, the anti-S1 antibody or antigen binding fragment thereof comprises: a) a VH comprising the amino acid sequence of SEQ ID NO: 75; and b) a VL comprising the amino acid sequence of SEQ ID NO: 76. In some embodiments, the anti-S1 antibody or antigen binding fragment thereof comprises the HC-CDRs of a VH comprising the amino acid sequence of SEQ ID NO: 75, and the LC-CDRs of a VL comprising the amino acid sequence of SEQ ID NO: 76. In some embodiments, the anti-S1 antibody or antigen binding thereof comprises an scFv comprising the amino acid sequence of SEQ ID NO: 88, or a variant thereof having at least about 80% (including for example at least about any of 80%, 85%, 90%, 95%, 96%, 97%, 98%, or 99%) sequence identity to SEQ ID NO: 88.

In some embodiments, there is provided an anti-S1 antibody or antigen binding fragment thereof comprises: a) a VH comprising the amino acid sequence of SEQ ID NO: 77, or a variant thereof having at least about 80% (including for example at least about any of 80%, 85%, 90%, 95%, 96%, 97%, 98%, or 99%) sequence identity to SEQ ID NO: 77; and b) a VL comprising the amino acid sequence of SEQ ID NO: 78, or a variant thereof having at least about 80% (including for example at least about any of 80%, 85%, 90%, 95%, 96%, 97%, 98%, or 99%) sequence identity to SEQ ID NO: 78. In some embodiments, the anti-S1 antibody or antigen binding fragment thereof comprises: a) a VH comprising the amino acid sequence of SEQ ID NO: 77; and b) a VL comprising the amino acid sequence of SEQ ID NO: 78. In some embodiments, the anti-S1 antibody or antigen binding fragment thereof comprises the HC-CDRs of a VH comprising the amino acid sequence of SEQ ID NO: 77, and the LC-CDRs of a VL comprising the amino acid sequence of SEQ ID NO: 78. In some embodiments, the anti-S1 antibody or antigen binding thereof comprises an scFv comprising the amino acid sequence of SEQ ID NO: 89, or a variant thereof having at least about 80% (including for example at least about any of 80%, 85%, 90%, 95%, 96%, 97%, 98%, or 99%) sequence identity to SEQ ID NO: 89.

In some embodiments, there is provided an anti-S1 antibody or antigen binding fragment thereof comprises: a) a VH comprising the amino acid sequence of SEQ ID NO: 79, or a variant thereof having at least about 80% (including for example at least about any of 80%, 85%, 90%, 95%, 96%, 97%, 98%, or 99%) sequence identity to SEQ ID NO: 79; and b) a VL comprising the amino acid sequence of SEQ ID NO: 80, or a variant thereof having at least about 80% (including for example at least about any of 80%, 85%, 90%, 95%, 96%, 97%, 98%, or 99%) sequence identity to SEQ ID NO: 80. In some embodiments, the anti-S1 antibody or antigen binding fragment thereof comprises: a) a VH comprising the amino acid sequence of SEQ ID NO: 79; and b) a VL comprising the amino acid sequence of SEQ ID NO: 80. In some embodiments, the anti-S1 antibody or antigen binding fragment thereof comprises the HC-CDRs of a VH comprising the amino acid sequence of SEQ ID NO: 79, and the LC-CDRs of a VL comprising the amino acid sequence of SEQ ID NO: 80. In some embodiments, the anti-S1 antibody or antigen binding thereof comprises an scFv comprising the amino acid sequence of SEQ ID NO: 90, or a variant thereof having at least about 80% (including for example at least about any of 80%, 85%, 90%, 95%, 96%, 97%, 98%, or 99%) sequence identity to SEQ ID NO: 90.

In some embodiments, the anti-S1 antibody or antigen binding fragment thereof specifically binds to the S1 protein of SARS-CoV-2. In some embodiments, the anti-S1 antibody or antigen binding fragment thereof specifically binds to the non-RBD region of the S1 protein of SARS-CoV-2. In some embodiments, the anti-S1 antibody or antigen binding fragment thereof specifically binds to the RBD of the S1 protein of SARS-CoV-2. In some embodiments, the anti-S1 antibody or antigen binding fragment thereof is a neutralizing antibody. In some embodiments, the anti-S1 antibody or antigen binding fragment thereof specifically blocks binding of the RBD of the S1 protein of SARS-CoV-2 to human ACE2 (huACE2). In some embodiments, the anti-S1 antibody or antigen binding fragment thereof specifically blocks huACE2 binding of a wildtype S1 protein of SARS-CoV-2 (e.g., SEQ ID NO: 93), or a variant of the S1 protein of SARS-CoV-2, including the SARS-CoV-2 S1 spike protein variants of Table 10, such as an S1 protein comprising one or more mutations selected from the group consisting of D614G, V367F, N439K, A435S, V483A, K458R, G476S, R408I, V503F, A522V, Y508H, L452R, A520S, I472V, T478I, F490S, and/or P384L. In some embodiments, the anti-S1 antibody or antigen binding fragment thereof specifically blocks huACE2 binding of an S1 protein of SARS-CoV-2 comprising the D614G mutation. In some embodiments, the anti-S1 antibody or antigen binding fragment thereof does not specifically bind to an S1 protein of another coronavirus, such as SARS-CoV, MERS-CoV, HCoV-HKU1, HCoV-NL63, HCoV-229E, or HCoV-OC43. In some embodiments, the anti-S1 antibody or antigen binding fragment thereof does not block huACE2 binding of an S1 protein of another coronavirus, such as SARS-CoV, MERS-CoV, HCoV-HKU1, HCoV-NL63, HCoV-229E, or HCoV-OC43.

In some embodiments, the anti-S1 antibody or antigen binding fragment thereof specifically binds to the S1 protein of SARS-CoV-2 with a $K_D$ of no more than about any one of 100 nM, 50 nM, 20 nM, 10 nM, 5 nM, 4 nM, 3 nM, 2 nM, 1 nM, 0.75 nM, 0.5 nM, 0.2 nM, 0.1 nM, 0.05 nM, 0.01 nM, or less, including any values and ranges in between these values. In some embodiments, anti-S1 antibody or antigen binding fragment thereof specifically binds to the S1 protein of SARS-CoV-2 with a $K_D$ of about any one of 0.01 nM to 0.1 nM, 0.1 nM to 1 nM, 1 nM to 5 nM, 5 nM to 10 nM, 10 nM-100 nM, 0.01 nM to 1 nM, 0.5 nM to 10 nM, 0.1 nM to 1 nM, 0.1 nM to 10 nM, or 0.01 nM to 100 nM.

In some embodiments, there is provided an anti-S1 antibody competes for binding to an S1 subunit of a spike protein of SARS-CoV-2 with a second anti-S1 antibody according to any of the anti-S1 antibodies described herein. In some embodiments, the anti-S1 antibody binds to the same, or substantially the same, epitope as the second anti-S1 antibody. In some embodiments, binding of the anti-S1 antibody to an S1 subunit of a spike protein of SARS-CoV-2 inhibits the binding of a second anti-S1 antibody to the same S1 subunit of the spike protein of SARS-CoV-2 by at least about 70% (such as by at least about any of 75%, 80%, 85%, 90%, 95%, 98% or 99%), or vice versa. In some embodiments, the anti-S1 antibody and the second anti-S1 antibody cross-compete for binding to the S1 subunit of the spike protein of SARS-CoV-2, i.e., each of the anti-S1 antibody moieties competes with the other for binding to the S1 subunit of the spike protein of SARS-CoV-2.

B. Antibody Constructs

Also provided are isolated antibody constructs comprising an antibody moiety comprising any one of the anti-S1 antibodies or antigen binding fragments described herein. It is to be understood that antibody constructs described herein in some embodiments, can be the chimeric proteins comprising mucoadhesive peptide fragments as described herein. In some embodiments, the antibody constructs do not comprise a mucoadhesive peptide fragment.

In some embodiments, the antibody construct is a chimeric protein comprising any one of the anti-S1 antibodies or antigen binding fragments described herein (e.g., a full-length antibody, an scFv, an scFv-Fc fusion protein, or an scFv-CH3 fusion protein) and a mucoadhesive peptide fragment comprising about 5 to about 50 positively charged amino acid residues, wherein the mucoadhesive peptide fragment facilitates attachment of the chimeric protein to a mucosa.

In some embodiments, the antibody construct is a multi-specific antibody comprising a first antibody moiety comprising any one of the anti-S1 antibodies or antigen binding fragments described herein and a second antibody moiety. In some embodiments, the antibody construct is a bispecific antibody. In some embodiments, the antibody construct is a trispecific antibody.

In some embodiments, the antibody construct is a Fab.

In some embodiments, the antibody construct is an Fc fusion protein comprising an anti-S1 antibody described herein fused to an Fc fragment (such as IgG1 Fc fragment). In some embodiments, the anti-S1 antibody is fused to an Fc fragment via a linker (such as peptide linker). In some embodiments, the antibody construct is a full-length antibody. In some embodiments, the antibody construct is a scFv-Fc fusion protein.

In some embodiments, the antibody construct is an immunoconjugate comprising any one of the anti-S1 antibodies or antigen binding fragments described herein and an effector molecule. In some embodiments, the effector molecule is a therapeutic agent selected from the group consisting of a drug, a toxin, a radioisotope, a protein, a peptide, and a nucleic acid.

In some embodiments, the antibody construct is an immunoconjugate comprising any one of the anti-S1 antibodies or antigen binding fragments described herein and a label.

C. Fc Region

The antibodies, e.g., the antibody-comprising target-binding moiety of the chimeric proteins described herein and the anti-S1 antibody or construct thereof, in some embodiments comprise an Fc region. The term "Fc region," "Fc domain" or "Fc" refers to a C-terminal non-antigen binding region of an immunoglobulin heavy chain that contains at least a portion of the constant region. The term includes native Fc regions and variant Fc regions. In some embodiments, a human IgG heavy chain Fc region extends from Cys226 to the carboxyl-terminus of the heavy chain. However, the C-terminal lysine (Lys447) of the Fc region may or may not be present, without affecting the structure or stability of the Fc region. Unless otherwise specified herein, numbering of amino acid residues in the IgG or Fc region is according to the EU numbering system for antibodies, also called the EU index, as described in Kabat et al., Sequences of Proteins of Immunological Interest, 5th Ed. Public Health Service, National Institutes of Health, Bethesda, Md., 1991.

In some embodiments, the Fc fragment comprises an immunoglobulin IgG heavy chain constant region comprising a hinge region (starting at Cys226), an IgG CH2 domain and CH3 domain. The term "hinge region" or "hinge sequence" as used herein refers to the amino acid sequence located between the linker and the CH2 domain. In some embodiments, the fusion protein comprises an Fc fragment comprising a hinge region. In some embodiments, the fusion protein comprises an Fc fragment that does not comprise the hinge region.

In some embodiments, the anti-S1 antibody or construct thereof comprises an Fc fragment selected from the group consisting of Fc fragments from IgG, IgA, IgD, IgE, IgM, and combinations and hybrids thereof. In some embodiments, the Fc fragment is derived from a human IgG. In some embodiments, the Fc fragment comprises the Fc region of human IgG1, IgG2, IgG3, IgG4, or a combination or hybrid IgG. In some embodiments, the Fc fragment is an IgG1 Fc fragment. In some embodiments, the Fc fragment comprises the CH2 and CH3 domains of IgG1. In some embodiments, the Fc fragment is an IgG4 Fc fragment. In some embodiments, the Fc fragment comprises the CH2 and CH3 domains of IgG4. IgG4 Fc is known to exhibit less effector activity than IgG1 Fc, and thus may be desirable for some applications. In some embodiments, the Fc fragment is derived from of a mouse immunoglobulin.

In some embodiments, the IgG CH2 domain starts at Ala231. In some embodiments, the CH3 domain starts at Gly341. It is understood that the C-terminus Lys residue of human IgG can be optionally absent. It is also understood that conservative amino acid substitutions of the Fc region without affecting the desired structure and/or stability of Fc is contemplated within the scope of the invention.

Additionally, anti-S1 antibodies or constructs thereof comprising any of the Fc variants known in the art, or combinations thereof, are contemplated. In some embodiments, the Fc fragment comprises sequence that has been altered or otherwise changed so that it has enhanced antibody dependent cellular cytotoxicity (ADCC) or complement dependent cytotoxicity (CDC) effector function.

In some embodiments, each chain of the Fc fragment is fused to the same entity. In some embodiments, the anti-S1 antibody or construct thereof comprises two identical anti-S1 antibody moieties described herein, each fused with one chain of the Fc fragment. In some embodiments, the two chains of the Fc fragment are identical. In some embodiments, the anti-S1 antibody or construct thereof comprising the Fc fragment is a homodimer.

In some embodiments, each chain of the Fc fragment is fused to a different entity. In some embodiments, the anti-S1 antibody or construct thereof comprises two different anti-S1 antibody moieties, each fused to one chain of the Fc fragment. In some embodiments, the two anti-S1 antibody moieties are different but both specifically recognize an S1 protein. In some embodiments, the anti-S1 antibody or construct thereof is monovalent, i.e., only one anti-S1 antibody moiety is fused to one chain of the Fc fragment, and the second chain of the Fc fragment is not fused to an anti-S1 antibody moiety. In some embodiments, the anti-S1 antibody or construct thereof comprising the Fc fragment is a heterodimer.

Heterodimerization of non-identical polypeptides in the anti-S1 antibody or construct thereof can be facilitated by methods known in the art, including without limitation, heterodimerization by the knob-into-hole technology. The structure and assembly method of the knob-into-hole technology can be found in, e.g., U.S. Pat. Nos. 5,821,333, 7,642,228, US 2011/0287009 and PCT/US2012/059810, hereby incorporated by reference in their entireties. This technology was developed by introducing a "knob" (or a protuberance) by replacing a small amino acid residue with a large one in the CH3 domain of one Fc and introducing a "hole" (or a cavity) in the CH3 domain of the other Fc by replacing one or more large amino acid residues with smaller ones. In some embodiments, one chain of the Fc fragment in the fusion protein comprises a knob, and the second chain of the Fc fragment comprises a hole.

The preferred residues for the formation of a knob are generally naturally occurring amino acid residues and are preferably selected from arginine (R), phenylalanine (F), tyrosine (Y) and tryptophan (W). Most preferred are tryptophan and tyrosine. In one embodiment, the original residue for the formation of the knob has a small side chain volume, such as alanine, asparagine, aspartic acid, glycine, serine, threonine or valine. Exemplary amino acid substitutions in the CH3 domain for forming the knob include without limitation the T366W, T366Y or F405W substitution.

The preferred residues for the formation of a hole are usually naturally occurring amino acid residues and are preferably selected from alanine (A), serine (S), threonine (T) and valine (V). In one embodiment, the original residue for the formation of the hole has a large side chain volume, such as tyrosine, arginine, phenylalanine or tryptophan. Exemplary amino acid substitutions in the CH3 domain for generating the hole include without limitation the T366S, L368A, F405A, Y407A, Y407T and Y407V substitutions. In certain embodiments, the knob comprises T366W substitution, and the hole comprises the T366S/L368A/Y 407V substitutions. It is understood that other modifications to the Fc region known in the art that facilitate heterodimerization are also contemplated and encompassed by the instant application.

D. Variants

In some embodiments, amino acid sequence variants of the anti-S1 antibodies or constructs thereof, target-binding moieties (including antibody moieties and inhibitory polypeptides such as ACE2 receptor fragments) of the chimeric proteins, and chimeric proteins provided herein are contemplated. For example, it may be desirable to improve the binding affinity and/or other biological properties of the target-binding moieties. Amino acid sequence variants of a target-binding moiety (e.g., an anti-S1 antibody or antigen-binding fragment thereof) may be prepared by introducing appropriate modifications into the nucleotide sequence encoding the target-binding moiety, or by peptide synthesis. Such modifications include, for example, deletions from, and/or insertions into and/or substitutions of residues within the amino acid sequences of the target-binding moiety (e.g., an anti-S1 antibody or antigen-binding fragment thereof). Any combination of deletion, insertion, and substitution can be made to arrive at the final construct, provided that the final construct possesses the desired characteristics, e.g., target-binding.

In some embodiments, variants having one or more amino acid substitutions are provided. Sites of interest for substitutional mutagenesis include the HVRs and FRs of antibody moieties. Amino acid substitutions may be introduced into a target-binding moiety of interest (e.g., an anti-S1 antibody or antigen-binding fragment thereof) and the products screened for a desired activity, e.g., retained/improved target binding or decreased immunogenicity.

Conservative substitutions are shown in Table C below.

TABLE C

CONSERVATIVE SUBSTITITIONS

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped into different classes according to common side-chain properties:
 a. hydrophobic: Norleucine, Met, Ala, Val, Leu, Ile;
 b. neutral hydrophilic: Cys, Ser, Thr, Asn, Gln;
 c. acidic: Asp, Glu;
 d. basic: His, Lys, Arg;
 e. residues that influence chain orientation: Gly, Pro;
 f. aromatic: Trp, Tyr, Phe.

Non-conservative substitutions will entail exchanging a member of one of these classes for another class.

An exemplary substitutional variant is an affinity matured antibody moiety, which may be conveniently generated, e.g., using phage display-based affinity maturation techniques. Briefly, one or more CDR residues are mutated and the variant antibody moieties displayed on phage and screened for a particular biological activity (e.g., binding affinity). Alterations (e.g., substitutions) may be made in HVRs, e.g., to improve antibody moiety affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or specificity determining residues (SDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).)

In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody moiety variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody moiety to bind antigen. For example, conservative alterations (e.g., conservative substitutions as provided herein) that do not substantially reduce binding affinity may be made in HVRs. Such alterations may be outside of HVR "hotspots" or SDRs. In some embodiments of the variant VH and VL sequences provided above, each HVR either is unaltered, or contains no more than one, two or three amino acid substitutions.

A useful method for identification of residues or regions of a target-binding moiety that may be targeted for mutagenesis is called "alanine scanning mutagenesis" as described by Cunningham and Wells (1989) *Science,* 244: 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the target-binding moiety with its target is affected. Further substitutions may be introduced at the amino acid locations demonstrating functional sensitivity to the initial substitutions. Alternatively, or additionally, a crystal structure of a target-binding moiety-target complex can be determined to identify contact points between the target-binding moiety and the target. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include a target-binding moiety with an N-terminal methionyl residue. Other insertional variants of the target-binding moiety include the fusion to the N- or C-terminus of the target-binding moiety to an enzyme (e.g., for ADEPT) or a polypeptide which increases the serum half-life of the target-binding moiety.

IV. Methods of Prevention, Treatment and Diagnosis

The present application further provides methods of preventing or treating an infection caused by a pathogen that infects through a mucosa in an individual, comprising administering to the individual an effective amount of any one of the chimeric proteins described herein, or a cocktail composition of chimeric proteins, or any one of the anti-S1 antibodies or constructs described herein. In some embodiments, the method is for preventing an infection caused by a pathogen in an individual. In some embodiments, the method is for treating an infection caused by a pathogen in an individual. In some embodiments, the pathogen is coronavirus, such as SARS-CoV-2, including SARS-CoV-2 variants. Use of the chimeric proteins, anti-S1 antibodies or constructs in prevention or treatment of an infection and use of the chimeric proteins, anti-S1 antibodies or constructs in the preparation of a medicament for preventing or treating an infection are also provided. Methods of veterinary use are also contemplated herein.

In some embodiments, there is provided a method of preventing or treating an infection caused by a pathogen that infects through a mucosa in an individual, comprising administering to the individual an effective amount of a chimeric protein comprising: (a) a target-binding moiety that specifically binds to a component of the pathogen; and (b) a mucoadhesive peptide fragment comprising about 5 to about 50 positively charged amino acid residues, wherein the mucoadhesive peptide fragment facilitates attachment of the chimeric protein to the mucosa.

In some embodiments, the chimeric protein is administered to the individual before the individual is exposed to the pathogen. In some embodiments, the chimeric protein is administered to the individual within about any one of 72 hours, 48 hours, 36 hours, 24 hours, 12 hours, 6 hours, 4 hours or less from exposure of the individual to the pathogen. In some embodiments, administration of the chimeric protein to the individual protects the individual from infection by the pathogen for about any one of 1, 2, 3, 4, 5, 6, 7, 8, 9, 10, 11, 12, 13, 14 or more days. In some embodiments, the chimeric protein is administered topically to the mucosa. In some embodiments, the chimeric protein is administered via a nasal spray, an inhaler, a nebulizer, or an eye drop. In some embodiments, the chimeric protein is administered to both nostrils of the individual. In some embodiments, the chimeric protein is administered once every two days, once daily, or twice daily.

In some embodiments, the individual is a mammal (e.g., human, non-human primate, rat, mouse, cow, horse, pig, sheep, goat, dog, cat, etc.). In some embodiments, the individual is a human. In some embodiments, the individual is a clinical patient, a clinical trial volunteer, an experimental animal, etc. In some embodiments, the individual is younger than about 60 years old (including for example younger than about any of 50, 40, 30, 25, 20, 15, or 10 years old). In some embodiments, the individual is older than about 60 years old (including for example older than about any of 70, 80, 90, or 100 years old). In some embodiments, the individual has not been exposed to the pathogen. In some embodiments, the individual is diagnosed with SARS-CoV-2. In some embodiments, the individual is diagnosed with a SARS-CoV-2 variant, such as a variant selected from the group consisting of a B.1.1.7 variant, a B.1.351 variant, a B.1.526 variant, a B1.526.1 variant, a B1.617 variant, a B.1.617.1 variant, a B.1.617.2 variant, a B1.617.3 variant, a P.2 variant, a P.1 (B.1.1.28.1) variant, an A.23.1 variant, a CAL.20C variant, a B.1.427 variant, a B.1.429 variant, a B.1.525 variant, and a P.1.351 variant. In some embodiments, the individual is at a risk of developing severe symptoms of the infection (e.g., coronavirus infection). In some embodiments, the individual has an underlying medical condition, such as cardiovascular disease, diabetes, chronic respiratory disease, and/or cancer.

In some embodiments, the method is for preventing or treating infection by one or more SARS-CoV-2 variants. In some embodiments, the method prevents or treats infection by a plurality (e.g., 2, 3, 4, 5, 6, 7, 8, 9, 10, or more) of SARS-CoV-2 variants. In some embodiments, the one or more SARS-CoV-2 variants are selected from the group consisting of a B.1.1.7 variant, a B.1.351 variant, a B.1.526 variant, a B1.526.1 variant, a B1.617 variant, a B.1.617.1 variant, a B.1.617.2 variant, a B1.617.3 variant, a P.2 variant, a P.1 (B.1.1.28.1) variant, an A.23.1 variant, a CAL.20C variant, a B.1.427 variant, a B.1.429 variant, a B.1.525 variant, and a P.1.351 variant.

In some embodiments, there is provided a method of treating or preventing infection of an individual by a plurality of SARS-CoV-2 variants, comprising administering to the individual an effective amount of a pharmaceutical composition (e.g., a cocktail composition) comprising a plurality of chimeric proteins, wherein the plurality of chimeric proteins each comprises: (a) a target-binding moiety that specifically binds to a component of the pathogen; and (b) a mucoadhesive peptide fragment comprising about 5 to about 50 positively charged amino acid residues, wherein the mucoadhesive peptide fragment facilitates attachment of the chimeric protein to the mucosa of the individual. In some embodiments, the plurality of chimeric proteins each comprise a different target-binding moiety that specifically recognize different SARS-CoV-2 variants. In some embodiments, the target-binding moiety is derived from a neutralizing antibody that specifically binds to a spike protein of SARS-CoV-2, e.g., an anti-S1 antibody. For example, the pharmaceutical composition may comprise a cocktail of chimeric proteins each comprising a target-binding fragment derived from a different anti-S1 antibody described herein or known in the art. In some embodiments, the mucoadhesive peptide fragment is a polylysine peptide comprising at least 12 lysines. In some embodiments, the chimeric protein is administered via a nasal spray.

In some embodiments, there is provide a method of treating or preventing infection of an individual by a plurality of SARS-CoV-2 variants, comprising administering to the individual an effective amount of a chimeric protein comprising: (a) a target-binding moiety that specifically binds to a component of the pathogen; and (b) a mucoadhesive peptide fragment comprising about 5 to about 50 positively charged amino acid residues, wherein the mucoadhesive peptide fragment facilitates attachment of the chimeric protein to the mucosa of the individual. In some embodiments, the target-binding moiety is derived from a neutralizing antibody that specifically binds to a spike protein of SARS-CoV-2, e.g., an anti-S1 antibody. In some embodiments, the mucoadhesive peptide fragment is a polylysine peptide comprising at least 12 lysines. In some embodiments, the chimeric protein is administered via a nasal spray.

In some embodiments, the chimeric protein, anti-S1 antibody or construct of the present application is administered as a single agent, or in combination with a second, third, or fourth agent (including, e.g., anti-viral drugs, convalescent plasma, anti-inflammatory drugs etc.) to treat the infection.

Efficacy of the treatments can be evaluated, for example, by viral load (e.g., via detection of viral DNA), duration of survival, quality of life, viral protein expression and/or activity, detection of serological antibodies against the coronavirus, assessment of respiratory functions, and/or Computerized Tomography (CT) imaging.

Further provided are methods of diagnosis using any one of the anti-S1 antibodies or constructs described herein. In some embodiments, the method is carried out in vitro. In some embodiments, the method is carried out in vivo.

In some embodiments, the method comprises detecting SARS-CoV-2 in a sample obtained from a subject suspected of having a SARS-CoV-2 infection. In some embodiments, the method of detection comprises contacting the sample with an anti-S1 antibody or construct thereof described herein and determining whether the level of binding differs from that of a reference or comparison sample. The method is also useful to determine whether the anti-S1 antibodies or constructs described herein are an appropriate treatment for the subject.

Various methods known in the art for detecting specific antibody-antigen binding can be used. Exemplary immunoassays which can be conducted according to the invention include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the subject antibodies and is selected so as to meet the needs of various uses of the method which are often dictated by the availability of assay equipment and compatible immunoassay procedures. Appropriate labels include, without limitation, radionuclides (e.g. $^{125}$I, $^{131}$I, $^{35}$S, $^{3}$H, or $^{32}$P), enzymes (e.g., alkaline phosphatase, horseradish peroxidase, luciferase, or β-galactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). General techniques to be used in performing the various immunoassays noted above are known to those of ordinary skill in the art.

For purposes of diagnosis, the polypeptide including antibodies can be labeled with a detectable moiety including but not limited to radioisotopes, fluorescent labels, and various enzyme-substrate labels know in the art. Methods of conjugating labels to an antibody are known in the art.

In some embodiments, the polypeptides including anti-S1 antibodies of the present application is not labeled, and the presence thereof can be detected using a labeled antibody which binds to the anti-S1 antibody.

The anti-S1 antibodies of the present application can be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987).

The anti-S1 antibodies and constructs can also be used for in vivo diagnostic assays, such as in vivo imaging. Generally, the antibody or the polypeptide is labeled with a radionuclide (such as $^{111}$In, $^{99}$Tc, $^{14}$C, $^{131}$I, $^{125}$I, or $^{3}$H) so that the cells or tissue of interest can be localized using immunoscintiography. The antibody may also be used as staining reagent in pathology using techniques well known in the art.

V. Nucleic Acids and Methods of Preparation

Nucleic acid molecules encoding the chimeric proteins, anti-S1 antibodies or constructs thereof described herein or polypeptide components thereof are contemplated. Nucleic acid molecules may be constructed using recombinant DNA techniques conventional in the art. In some embodiments, a nucleic acid molecule is an expression vector that is suitable for expression in a selected host cell.

Vectors comprising polynucleotides that encode the chimeric proteins, anti-S1 antibodies or constructs thereof described herein or polypeptide components thereof are also provided. Such vectors include, but are not limited to, DNA vectors, phage vectors, viral vectors, retroviral vectors, etc.

In various embodiments, the chimeric proteins, anti-S1 antibodies or constructs thereof may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO—S, DG44. Lec13 CHO cells, and FUT8 CHO cells; PER.C6® cells (Crucell); and NSO cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, e.g., in Sambrook et al., Molecular Cloning, A Laboratory Manual, 3$^{rd}$ ed. Cold Spring Harbor Laboratory Press (2001). Nucleic acids may be transiently or stably transfected in the desired host cells, according to any suitable method.

The invention also provides host cells comprising any of the nucleic acids or vectors described herein. In some embodiments, the invention provides a host cell comprising a chimeric protein, an anti-S1 antibody or construct thereof described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. Suitable non-mammalian host cells include prokaryotes (such as *E. coli* or *B. subtillis*) and yeast (such as *S. cerevisae, S. pombe*; or *K. lactis*).

The chimeric proteins, anti-S1 antibodies or constructs thereof may be purified by any suitable method. Such methods include, but are not limited to, the use of affinity matrices or hydrophobic interaction chromatography. Suitable affinity ligands include ligands that bind antibody constant regions. For example, a Protein A, Protein G, Protein A/G, or an antibody affinity column may be used to bind the constant region and to purify a chimeric protein or anti-S1 antibody comprising an Fc region. Hydrophobic interactive chromatography, for example, a butyl or phenyl column, may also be suitable for purifying some polypeptides such as antibodies. Ion exchange chromatography (e.g. anion exchange chromatography and/or cation exchange chromatography) may also be suitable for purifying some polypeptides such as antibodies. Mixed-mode chromatography (e.g. reversed phase/anion exchange, reversed phase/cation exchange, hydrophilic interaction/anion exchange, hydrophilic interaction/cation exchange, etc.) may also be suitable for purifying some polypeptides such as antibodies. Many methods of purifying polypeptides are known in the art.

VI. Pharmaceutical Compositions, Kits and Articles of Manufacture

A. Formulation

One aspect of the present application provides formulations of antibodies that specifically target SARS-CoV-2 or components thereof (e.g., spike protein such as S1 protein), including any one of the chimeric proteins described herein or any one of the anti-S1 antibodies or constructs described herein. In some embodiments, the formulation is suitable for nasal administration. In some embodiments, the formulation is suitable for respiratory (e.g., upper respiratory airway) administration. In some embodiments, the formulation is suitable for administration by inhalation. In some embodiments, the formulation is a nasal spray formulation.

Also provided are compositions (e.g., formulations or pharmaceutical compositions) comprising any one of the chimeric proteins described herein or any one of the anti-S1 antibodies or constructs described herein. The terms "formulation" and "pharmaceutical composition" are used herein interchangeably. In some embodiments, the pharmaceutical composition comprises a pharmaceutically acceptable carrier. In some embodiments, the pharmaceutical composition comprises a citrate-buffered saline carrier. In some embodiments, the pharmaceutical composition comprises a stabilizing agent, a viscosity enhancing agent, a surfactant, and/or a preservative. In some embodiments, the pharmaceutical composition comprises 25 mM citrate buffer, pH 6.5, 100 mM NaCl, 0.1% methionine, 0.02% polysorbate 80, and 0.1% potassium sorbate. In some embodiments, the pharmaceutical composition comprises 25 mM citrate buffer, pH 6.5, 125 mM NaCl, 5% glycerin, 0.1% methionine, 0.02% polysorbate 80, and 0.1% potassium sorbate.

In some embodiments, the pharmaceutical composition comprises a single type of chimeric protein. In some embodiments, the pharmaceutical composition comprises at least two chimeric proteins, wherein the two chimeric proteins have different target-binding moieties. In some embodiments, the pharmaceutical composition comprises a plurality (e.g., 2, 3, 4, 5, 6, 7, 8, 9, 10, 15, 20, or more) of chimeric proteins, wherein the target-binding moieties of the chimeric proteins are different from each other. In some embodiments, the pharmaceutical composition comprises a cocktail of chimeric proteins that target different component of the same pathogen, the same component of different variants (e.g., strains) of the pathogen, and/or different pathogens. In some embodiments, the chimeric proteins in the cocktail composition each comprise the same mucoadhesive peptide fragment(s). In some embodiments, the chimeric proteins in the cocktail composition each comprise different mucoadhesive peptide fragment(s).

In some embodiments, the pharmaceutical composition is formulated for topical administration to a mucosa, such as nasal mucosa, larynx mucosa, trachea mucosa, bronchi mucosa, lung mucosa, eye mucosa, and combinations thereof. In some embodiments, the pharmaceutical composition is formulated for administration via a nasal spray, an inhaler, a nebulizer, or an eye drop.

In some embodiments, there is provided a formulation for nasal administration comprising: (a) an antibody that specifically binds to a component of SARS-CoV-2, (b) a stabilizing agent that maintains the weak reducing environment in nasal area, (c) a buffering agent, and (d) an osmolality adjusting agent, wherein the formulation has a pH of about 4.5 to about 7.5 (e.g., about 6.0 to about 7.0), and wherein the formulation has an osmolality of about 230 to about 330 Osm/kg (e.g., about 250 to about 300 Osm/kg). In some embodiments, the antibody specifically binds the S1 protein of SARS-CoV-2. In some embodiments, the antibody is any one of the SARS-CoV-2 antibodies or constructs as described in Section III. In some embodiments, the antibody is any one of the chimeric proteins described in Section II, comprising an antibody moiety that specifically binds the S1 protein of SARS-CoV-2, and a mucoadhesive peptide fragment comprising about 5 to about 50 (e.g., about 6-30 such as 12) positively charged amino acid residues (e.g., lysine or histidine). In some embodiments, the formulation further comprises a viscosity-enhancing agent. In some embodiments, the formulation further comprises a surfactant. In some embodiments, the formulation further comprises a preservative.

In some embodiments, there is provided a formulation for nasal administration comprising: (a) an antibody that specifically binds to a component of SARS-CoV-2, (b) a methionine, (c) a buffering agent, (d) an osmolality adjusting agent, (e) a viscosity enhancing agent, (f) a surfactant, and (g) a preservative, wherein the formulation has a pH of about 4.5 to about 7.5 (e.g., about 6.0 to about 7.0), and wherein the formulation has an osmolality of about 230 to about 330 Osm/kg (e.g., about 250 to about 300 Osm/kg). In some embodiments, the antibody specifically binds the S1 protein of SARS-CoV-2. In some embodiments, the antibody is any one of the SARS-CoV-2 antibodies or constructs as described in Section III. In some embodiments, the antibody is any one of the chimeric proteins described in Section II, comprising an antibody moiety that specifically binds the S1 protein of SARS-CoV-2, and a mucoadhesive peptide fragment comprising about 5 to about 50 (e.g., about 6-30 such as 12) positively charged amino acid residues (e.g., lysine or histidine).

In some embodiments, there is provided a formulation for nasal administration comprising: (a) an antibody that specifically binds to a component of SARS-CoV-2, (b) a methionine, (c) a citrate buffer, and (d) NaCl, wherein the formulation has a pH of about 4.5 to about 7.5 (e.g., about 6.0 to about 7.0), and wherein the formulation has an osmolality of about 230 to about 330 Osm/kg (e.g., about 250 to about 300 Osm/kg). In some embodiments, the antibody specifically binds the S1 protein of SARS-CoV-2. In some embodiments, the antibody is any one of the SARS-CoV-2 antibodies or constructs as described in Section III. In some embodiments, the antibody is any one of the chimeric proteins described in Section II, comprising an antibody moiety that specifically binds the S1 protein of SARS-CoV-2, and a mucoadhesive peptide fragment comprising about 5 to about 50 (e.g., about 6-30 such as 12) positively charged amino acid residues (e.g., lysine or histidine). In some embodiments, the formulation further comprises a viscosity-enhancing agent (e.g., glycerin). In some embodiments, the formulation further comprises a surfactant (e.g., polysorbate 80). In some embodiments, the formulation further comprises a preservative (e.g., potassium sorbate).

In some embodiments, there is provided a formulation for nasal administration comprising: (a) an antibody that specifically binds to a component of SARS-CoV-2 at a concentration of about 0.6 mg/mL to about 1 mg/mL (e.g., about 1 mg/mL to about 3 mg/mL), (b) a methionine at about 0.05% to 0.2% (e.g., about 0.075% to about 0.125%) (w/w), (c) a citrate buffer at about 20 mM to about 50 mM (e.g., about 20 mM to about 30 mM), (d) NaCl at about 100 mM to about 150 mM (e.g., about 110 mM to about 130 mM), (e) glycerin at about 1% to about 10% (e.g., about 2.5% to about 7.5%) (w/w), (f) polysorbate 80 at about 0.01% to about 0.1% (e.g., about 0.01% to about 0.05%) (w/w), and (g) potassium polysorbate at about 0.05% to 0.2% (e.g., about 0.075% to about 0.125%) (w/w), wherein the formulation has a pH of about 4.5 to about 7.5 (e.g., about 6.0 to about 7.0). In some embodiments, the formulation comprises about 25 mM citrate at pH 6.5, about 125 mM NaCl, about 5% glycerin, about 0.1% methionine, about 0.02% polysorbate 80, and about 0.1% potassium sorbate. In some embodiments, the antibody specifically binds the S1 protein of SARS-CoV-2. In some embodiments, the antibody is any one of the SARS-CoV-2 antibodies or constructs as described in Section III. In some embodiments, the antibody is any one of the chimeric proteins described in Section II, comprising an antibody moiety that specifically binds the S1 protein of SARS-CoV-2, and a mucoadhesive peptide fragment comprising about 5 to about 50 (e.g., about 6-30 such as 12) positively charged amino acid residues (e.g., lysine or histidine).

In some embodiments, the formulation described herein is for administration via a nasal spray. In some embodiments, the formulation is for prophylactic use. In some embodiments, the formulation maintains the stability (including physical and chemical stability) of the antibody at 37° C. for at least about any one of 1, 2, 3, 4, 5, 6, 7, 8, 9, 10, 11, 12, 13, 14 or more days, including any values and ranges in between these values. In some embodiments, the formulation promotes adhesion of the antibody to a mucosa, such as nasal mucosa. In some embodiments, the formulation prolongs the residence time of the antibody in nostrils and other upper respiratory tract areas, for example, by at least about any one of 12 hours, 24 hours, 2 days, 3 days, 4 days, 5 days, 6 days, 7 days, 8 days, 9 days, 10 days, or more, compared to the antibody in PBS. In some embodiments, the formulation is neutral and gentle to the nasal surfaces. In some embodiments, the formulation is a solution of the antibody. In some embodiments, the formulation is an aqueous solution.

Nasal spray formulation parameters and excipients have been described, for example, in V. Kulkami and C. Shaw, *Inhalation*, 2021, 10-11; S. Thorat, *Scholars Journal of Applied Medical Sciences (SJAMS)*, 2016, 4(8D):2976-2985, which are incorporated by reference in their entirety. Commonly used excipients for nasal spray formulation include, but are not limited to, tonicity agent or osmolality adjustment agent, buffering agent, purging agent, preservative, surfactant, chelating agent, suspending agent, co-solvent, antioxidant, and humectant. Antibody formulations for various route of administration, including nasal formulation, have been described, for example, in Cui Y. et al., Drug Development and Industrial Pharmacy, 2017, 11:28, which is incorporated herein by reference. Any excipients compatible with the FDA guideline for nasal spray formulation and/or antibody formulation may be used here.

In some embodiments, the formulation has a pH that is compatible with the nasal environment. The average baseline human nasal pH is about 6.3. The optimal pH of the formulation also depends on factors, including, for example, pI of the antibody (including positively charged mucoadhesive peptide), protein stability, net charge of the antibody, etc. In some embodiments, the formulation has a pH of about 4.5 to about 7.5, such as about any one of 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4 or 7.5, including any values or ranges in between the values. In some embodiments, the formulation has a pH of about any one of 4.5-5.0, 5.0-5.5, 5.5-6.0, 6.0-6.5, 4.5-5.5, 5.5-6.5, 5.0-6.5, 4.5-6.0, 6.5-7.0, 7.0-7.5, 6.0-7.5, 5.5-7, 6-7, or 6.5-7.5. In some embodiments, the formulation has a pH of about 6.5.

For adjusting and buffering pH value, physiologically acceptable acids, bases, salts, and combinations of these may be used. Suitable excipients for lowering the pH value or as acidic components of a buffer system are strong mineral acids, in particular, sulfuric acid and hydrochloric acid. Moreover, inorganic and organic acids of medium strength as well as acidic salts may be used, for example, phosphoric acid, citric acid, tartaric acid, succinic acid, fumaric acid, methionine, acidic hydrogen phosphates with sodium or potassium, lactic acid, glucuronic acid etc. Suitable for raising the pH value or as basic component for buffer system are, in particular, mineral bases such as sodium hydroxide or other alkali and alkaline earth hydroxides and oxides such as, in particular, magnesium hydroxide and calcium hydroxide, ammonium hydroxide and basic ammonium salts such as ammonium acetate, as well as basic amino acids such as lysine, carbonates such as sodium or magnesium carbonate, sodium hydrogen carbonate, citrates such as sodium citrate etc.

In some embodiments, the formulation comprises a citrate buffer. In some embodiments, the citrate buffer contains citric acid and sodium citrate. The citrate buffer has a pKa of about 6.4. In some embodiments, the citrate buffer is present a concentration of about 20 mM to about 50 mM, such as about any one of 20, 25, 30, 35, 40, 45, or 50 mM, including any values or ranges in between these values. In some embodiments, the citrate buffer is present a concentration of about any one of 20-30, 30-40, 40-50, 25-50, 25-35, or 25-40 mM. In some embodiments, the formulation comprises a citrate buffer at about 25 mM.

In some embodiments, the formulation comprises a phosphate buffer. The phosphate buffer has a pKa of about 7.2.

In some embodiments, the formulation has an osmolality that is close to the nasal environment. In some embodiments, the formulation has an osmolality that facilitates adhesion of the antibody to a mucosa (e.g., nasal mucosa). In some embodiments, the formulation minimizes penetration of the antibody into blood stream. In some embodiments, the formulation has an osmolality of about 230 Osm/kg to about 330 Osm/kg, such as about any one of 230, 240, 250, 260, 270, 280, 290, 300, 310, 320, or 330 Osm/kg, including any values or ranges in between these values. In some embodiments, the formulation has an osmolality of about any one of 230-250, 250-270, 270-290, 290-310, 310-330, 230-275, 275-300, 300-330, 230-280, 280-330, or 260-320 Osm/kg. In some embodiments, the formulation has an osmolality of about 280 Osm/kg. A skilled person in the art could readily convert these osmolality values to osmolality.

In some embodiments, the formulation comprises an osmolality adjusting agent. Exemplary osmolality adjusting agents or tonicity agents include, but are not limited to, sodium, calcium or magnesium chloride, sulfate or phosphate. In some embodiments, the osmolality adjusting agent is sodium chloride. Calcium and magnesium salts may have a positive or auxiliary influence in the inhalation of active agent solutions, possibly because they themselves counteract the local irritations caused by the administration. Alternatively, physiologically safe organic compounds may be used as the osmolality adjusting agent. Particularly suitable are water-soluble substances with a relatively low molecular weight, for example, with a molecular weight of less than 300 or, better still, less than 200 and with a correspondingly high osmotic activity. Examples for such excipients are sugars and sugar alcohols, in particular, trehalose, mannitol, sorbitol and isomalt.

In some embodiments, the formulation comprises about 100 mM to about 150 mM NaCl, such as any one of 100, 105, 110, 115, 120, 125, 130, 135, 140, 145, or 150 mM, including any values or ranges in between these values. In some embodiments, the formulation comprises about any one of 100-120, 120-140, 100-125, 125-150, 130-150, or 110-130 mM NaCl. In some embodiments, the formulation comprises about 125 mM NaCl.

In some embodiments, the formulation comprises one or more stabilizing agents. In some embodiments, the stabilizing agent maintains the weak reducing environment in nasal areas. In some embodiments, the one or more stabilizing agents comprises methionine. In some embodiments, the one or more stabilizing agents comprise glycerin. In some embodiments, the one or more stabilizing agents comprise trehalose, e.g., 10% trehalose. In some embodiments, the formulation comprises about 0.05% to about 0.2% (w/w) methionine, such as about any one of 0.05%, 0.06%, 0.07%, 0.08%, 0.09%, 0.1%, 0.11%, 0.12%, 0.13%, 0.14%, 0.15%, 0.16%, 0.17%, 0.18%, 0.19% or 0.2% (w/w), including any values or ranges in between these values. In some embodiments, the formulation comprises about any one of 0.05%-0.1%, 0.75%-1.25%, 0.1%-0.15%, 0.15%-0.2%, 0.1%-0.2%, 0.125-0.175%, 0.8%-1.6%, or 0.5%-0.15% (w/w) methionine. In some embodiments, the formulation comprises about 0.1% methionine.

In some embodiments, the formulation comprises a viscosity-enhancing agent. In some embodiments, the viscosity-enhancing agent is selected from the group consisting of glycerin, dextran and hydroxyethylcellulose. In some embodiments, the viscosity-enhancing agent is glycerin. In some embodiments, the formulation comprises about 1% to about 10% (w/w) glycerin, such as about any one of 1%, 2%, 3%, 3%, 4%, 5%, 6%, 7%, 8%, 9%, or 10% (w/w), including any values or ranges in between these values. In some embodiments, the formulation comprises about any one of 1%-4%, 2%-6%, 3%-7%, 5%-8%, 7%-10%, 2.5%-7.5%, 4%-6%, 1%-2.5%, 2.5%-5%, 5%-7.5%, or 7.5%-10% (w/w) glycerin. In some embodiments, the formulation comprises about 5% glycerin.

In some embodiments, the formulation comprises surfactant. In some embodiments, the surfactant allows the antibody to cross a mucosa (e.g., nasal mucosa) and/or allows absorption of the antibody across the mucosa. Suitable surfactants include, in particular, those that are to be considered safe for oral or nasal inhalation or oromucosal administration. Examples of surfactants with particularly good physiological compatibility include tyloxapol, polysorbates (such as polysorbate 20, polysorbate 80), PEG400, PEG3500, polyoxyl 400 stearate, vitamin E-TPGS, and macrogol hydroxystearates such as macrogol-15-hydroxystearate. In some embodiments, the surfactant is polysorbate 80. In some embodiments, the formulation comprises about 0.01% to about 0.1% (w/w) polysorbate 80, such as about any one of 0.01%, 0.02%, 0.03%, 0.04%, 0.05%, 0.06%, 0.07%, 0.08%, 0.09%, or 0.1% (w/w) polysorbate 80, including any values or ranges in between these values. In some embodiments, the formulation comprises about any one of 0.01%-0.02%, 0.02%-0.05%, 0.05%-0.1%, 0.01%-0.05%, 0.02%-0.04%, 0.04%-0.08%, 0.02%-0.08%, or 0.02%-0.1% (w/w) polysorbate 80. In some embodiments, the formulation comprises about 0.02% polysorbate.

In some embodiments, the formulation comprises a preservative. In some embodiments, the preservative maintains sterility of the formulation. Exemplary preservatives include, but are not limited to, benzyl alcohol, benzalkonium chloride, chlorobutanol, methylparaben, phenylethyl alcohol, propylparaben, and potassium sorbate. In some embodiments, the preservative is potassium sorbate. In some embodiments, the formulation comprises about 0.05% to about 0.2% (w/w) potassium polysorbate, such as about any one of 0.05%, 0.06%, 0.07%, 0.08%, 0.09%, 0.1%, 0.11%, 0.12%, 0.13%, 0.14%, 0.15%, 0.16%, 0.17%, 0.18%, 0.19% or 0.2% (w/w), including any values or ranges in between these values. In some embodiments, the formulation comprises about any one of 0.05%-0.1%, 0.75%-1.25%, 0.1%-0.15%, 0.15%-0.2%, 0.1%-0.2%, 0.125-0.175%, 0.8%-1.6%, or 0.5%-0.15% (w/w) potassium sorbate. In some embodiments, the formulation comprises about 0.1% potassium sorbate.

In some embodiments, the antibody is present in the formulation at a concentration of about 0.6 mg/mL to about 6 mg/mL, such as about any one of 0.6, 0.8, 1, 1.5, 2, 2.5, 3, 3.5, 4, 4.5, 5, 5.5 or 6 mg/mL, including about any values or ranges in between these values. In some embodiments, the antibody is present in the formulation at a concentration of about any one of 0.6-1, 1-2, 2-3, 3-4, 4-5, 5-6, 0.6-2.5, 2.5-5, 2-4, 4-6, 0.6-3, 3-6, or 2-5 mg/mL.

A nasal spray containing IgG antibodies can be used as a complement to vaccines, therapeutics and other preventive measures against the spread of COVID-19. Human IgG antibody nasal sprays have many advantages. One advantage of using antibodies or chimeric proteins comprising antibodies in a prophylaxis nasal spray is the well-established manufacturing process and scale-up capacity for antibodies. More than two dozen IgG antibodies have been approved by the U.S. Food and Drug Administration (FDA) for human use. The IgG antibody manufacturing process, from cell line development to large-scale bioreactor culture, has been optimized to produce high quality and yield for use in humans. In addition, the effectiveness of IgG antibodies against SARS-CoV-2 has already been demonstrated in patients in a therapeutic setting. Multiple clinical trials are currently testing SARS-CoV-2 blocking IgG antibodies as a therapeutic. In November 2020, the FDA granted Eli Lilly and Regeneron emergency use authorization of their IgG antibody therapeutics by intravenous administration, for the treatment of confirmed cases of COVID-19. An IgG in a nasal spray application also has the advantage of a much lower dosage requirement (approximately 10,000 times lower) than an IgG therapeutic. This will significantly lower the cost and make it affordable for wider use. Furthermore, use of a human IgG antibody significantly reduces the risk of immunogenicity, which is an important consideration for a prophylactic nasal spray formulation subject to long-term repeated use. The long-term stability of the modified IgG antibody at room temperature in the nasal spray formulation makes it easy for daily use and storage.

In some embodiments, the pharmaceutical composition (e.g., nasal spray formulation or eye drop formulation) is administered at a dosage of about 0.1 mg to about 1 mg of the antibody, e.g., per nostril or per eye. In some embodiments, about 100 μl of the pharmaceutical composition (e.g., nasal spray formulation or eye drop formulation) is administered at a time, e.g., to both nostrils of an individual (e.g., 100 μl per nostril or per eye).

Suitable formulations are obtained by mixing the chimeric protein(s), anti-S1 antibody or construct described herein having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The formulation herein may also contain one or more active compounds in addition to the compositions described herein as necessary for the infection being treated, preferably those with complementary activities that do not adversely affect each other. Such molecules are suitably present in combination in amounts that are effective for the purpose intended. The effective amount of such other agents depends on the amount of the composition described herein present in the formulation, the type and severity of infection in the treatment, and other factors discussed above. These are generally used in the same dosages and with administration routes as described herein or about from 1 to 99% of the heretofore employed dosages.

The formulations to be used for in vivo administration must be sterile. This is readily accomplished by, e.g., filtration through sterile filtration membranes.

Further provided are methods and use of the formulations and pharmaceutical compositions described herein for preventing or treating an infection, e.g., SARS-CoV-2 infection.

B. Kits and Articles of Manufacture

In some embodiments, there is provided an article of manufacture comprising materials useful for the prevention or treatment of a microbial infection (e.g., infection by SARS-CoV-2). The article of manufacture can comprise a container and a label or package insert on or associated with the container. Suitable containers include, for example, bottles, vials, syringes, etc. The containers may be formed from a variety of materials such as glass or plastic. Generally, the container holds a composition, which is effective for treating a microbial infection, described herein, and may have a sterile access port. In some embodiments, the article of manufacture is a nasal spray, an inhaler, a nebulizer, or an eye drop. Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating a microbial infection. The label or package insert may further comprise instructions for administering the composition to a patient.

Additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In some embodiments, there is provided an article of manufacture (e.g., a nasal spray) comprising a formulation comprising any one of the chimeric proteins or SARS-CoV-antibodies or constructs described herein, and a spray device for applying the formulation to a nostril of a subject. In some embodiments, the nasal spray provides a uniform plume with droplets having a diameter of 10 μm or more. In some embodiments, the device sprays a volume of about 100 μl at a time. In some embodiments, the spray device is for an adult patient. In some embodiments, the spray device is for a pediatric patient. In some embodiments, the article of manufacture comprises a single dose of the active agent. In some embodiments, the article of manufacture comprises at least any one of 2, 5, 10, 20, 30, 40, 50 or more doses of the active agent.

Kits are also provided that are useful for various purposes, e.g., for prevention or treatment of a microbial infection described herein, optionally in combination with the articles of manufacture. Kits of the invention include one or more containers comprising any one of the compositions described herein (or unit dosage form and/or article of manufacture). In some embodiments, the kit further comprises other agents and/or instructions for use in accordance with any of the methods described herein. The kit may further comprise a description of selection of individuals suitable for prevention or treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a chimeric protein comprising: (a) a target-binding moiety that specifically binds to a component of a pathogen that infects through a mucosa; and (b) a mucoadhesive peptide fragment comprising about 5 to about 50 positively charged amino acid residues (e.g., lysines), wherein the mucoadhesive peptide fragment facilitates attachment of the chimeric protein to the mucosa. In some embodiments, the pathogen is SARS-CoV-2.

The kits of the invention are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The containers may be unit doses, bulk packages (e.g., multi-dose packages) or sub-unit doses. Kits may also include multiple unit doses of the pharmaceutical compositions and instructions for use and packaged in quantities sufficient for storage and use in pharmacies, for example, hospital pharmacies and compounding pharmacies.

Exemplary Embodiments

The following exemplary embodiments are provided herein:

Embodiment 1. A chimeric protein comprising: (a) a target-binding moiety that specifically binds to a component of a pathogen that infects through a mucosa; and (b) a mucoadhesive peptide fragment comprising about 5 to about 50 positively charged amino acid residues, wherein the mucoadhesive peptide fragment facilitates attachment of the chimeric protein to the mucosa.

Embodiment 2. The chimeric protein of embodiment 1, comprising a single polypeptide chain.

Embodiment 3. The chimeric protein of embodiment 1, comprising two or more polypeptide chains.

Embodiment 4. The chimeric protein of embodiment 3, comprising two or more mucoadhesive peptide fragments.

Embodiment 5. The chimeric protein of embodiment 4, wherein each of the two or more mucoadhesive peptide fragments comprises about 5 to about 50 positively charged amino acid residues.

Embodiment 6a. The chimeric protein of any one of embodiments 1-5, wherein the mucoadhesive peptide fragment or each of the two or more mucoadhesive peptide fragments comprises about 6 to about 30 positively charged amino acid residues.

Embodiment 6b. The chimeric protein of embodiment 6a, wherein the chimeric protein comprises two or more mucoadhesive peptide fragments, and wherein each of the two or more mucoadhesive peptide fragments comprises about 11 to about 15 positively charged amino acid residues.

Embodiment 7. The chimeric protein of any one of embodiments 1-6b, wherein the positively charged amino acid residues are selected from the group consisting of lysine, arginine, histidine, ornithine, and combinations thereof.

Embodiment 8. The chimeric protein of embodiment 7, wherein the positively charged amino acid residues are lysines.

Embodiment 9. The chimeric protein of embodiment 8, wherein the mucoadhesive peptide fragment comprises about 6 or about 30 lysines.

Embodiment 10. The chimeric protein of embodiment 7, wherein the positively charged amino acid residues are arginines.

Embodiment 11. The chimeric protein of embodiment 10, wherein the mucoadhesive peptide fragment comprises about 6 or about 30 arginines.

Embodiment 12. The chimeric protein of embodiment 7, wherein the positively charged amino acid residues are histidines.

Embodiment 13. The chimeric protein of embodiment 12, wherein the mucoadhesive peptide fragment comprises about 6 or about 30 histidines.

Embodiment 14. The chimeric protein of any one of embodiments 1-13, the positively charged amino acid residues are contiguous with each other.

Embodiment 15. The chimeric protein of any one of embodiments 1-13, the positively charged amino acid residues are interspersed with non-positively charged amino acid residues.

Embodiment 16. The chimeric protein of embodiment 15, wherein at least 50% of the amino acid residues in the mucoadhesive peptide fragment are positively charged amino acid residues.

Embodiment 17. The chimeric protein of any one of embodiments 1-16, wherein the mucoadhesive peptide fragment is no more than about 15 kD.

Embodiment 18. The chimeric protein of any one of embodiments 1-17, wherein the mucoadhesive peptide fragment has an isoelectric point (pI) higher than the pH of the mucosa.

Embodiment 19. The chimeric protein of any one of embodiments 1-18, wherein the half-life of the chimeric protein on the mucosa is at least 12 hours.

Embodiment 20. The chimeric protein of any one of embodiments 1-19, wherein the mucoadhesive peptide fragment does not facilitate penetration of the chimeric protein into a cell of the mucosa.

Embodiment 21. The chimeric protein of any one of embodiments 1-20, wherein the mucoadhesive peptide fragment does not disrupt folding of the chimeric protein within a host cell expressing the chimeric protein.

Embodiment 22. The chimeric protein of any one of embodiments 1-21, wherein the mucoadhesive peptide fragment does not block secretion of the chimeric protein from a host cell expressing the chimeric protein.

Embodiment 23. The chimeric protein of any one of embodiments 1-22, wherein the mucoadhesive peptide fragment does not interfere the specific binding between the target-binding moiety and the component of the pathogen.

Embodiment 24. The chimeric protein of any one of embodiments 1-23, wherein the mucoadhesive peptide fragment is covalently fused to the target-binding moiety.

Embodiment 25. The chimeric protein of any one of embodiments 1-24, wherein the mucoadhesive peptide fragment is fused to the target-binding moiety via a bond or a peptide linker.

Embodiment 26. The chimeric protein of any one of embodiments 1-25, wherein the component of the pathogen is a surface molecule.

Embodiment 27. The chimeric protein of any one of embodiments 1-25, wherein the component of the pathogen is a secreted molecule.

Embodiment 28. The chimeric protein of any one of embodiments 1-27, wherein the target-binding moiety comprises an inhibitory polypeptide that inhibits binding of the component of the pathogen to a receptor on a cell of the mucosa.

Embodiment 29. The chimeric protein of embodiment 28, wherein the target-binding moiety comprises a natural receptor of the component of the pathogen or a fragment derived from the natural receptor.

Embodiment 30. The chimeric protein of embodiment 29, wherein the target-binding moiety comprises an extracellular binding domain (EBD) of the natural receptor.

Embodiment 31. The chimeric protein of embodiment 30, wherein the target-binding moiety comprises an extracellular binding domain (EBD) of ACE2.

Embodiment 32. The chimeric protein of any one of embodiments 1-27, wherein the target-binding moiety comprises an antibody moiety.

Embodiment 33. The chimeric protein of embodiment 32, wherein the antibody moiety is a full-length antibody.

Embodiment 34. The chimeric protein of embodiment 33, wherein the antibody moiety is selected from the group consisting of an IgG, an IgA, an IgM, and an IgD.

Embodiment 35. The chimeric protein of embodiment 32, wherein the antibody moiety is an antigen-binding fragment selected from the group consisting of a Fab, a Fab', a $(Fab')_2$, an Fv, a single chain Fv (scFv), an scFv-Fc, a disulfide stabilized Fv fragment (dsFv), a $(dsFv)_2$, an scFv dimer, a domain antibody, a camelized single domain antibody, a bivalent domain antibody, a minibody, and a VHH.

Embodiment 36. The chimeric protein of any one of embodiments 32-35, wherein the antibody moiety is a human, humanized, camelid, or chimeric antibody or an antigen-binding fragment thereof.

Embodiment 37. The chimeric protein of any one of embodiments 32-36, wherein the mucoadhesive peptide fragment is fused to the C-terminus of a heavy chain of the antibody moiety.

Embodiment 38. The chimeric protein of embodiment 37, comprising: (1) two polypeptide chains each comprising from the N-terminus to the C-terminus: an antibody heavy chain of the antibody moiety, optionally a peptide linker, and the mucoadhesive peptide fragment; and (2) two polypeptide chains each comprising an antibody light chain of the antibody moiety.

Embodiment 39. The chimeric protein of any one of embodiments 32-36, wherein the mucoadhesive peptide fragment is fused to the C-terminus of a light chain of the antibody moiety.

Embodiment 40. The chimeric protein of any one of embodiments 1-30 or 32-39, wherein the pathogen is a bacterium that causes a respiratory infection.

Embodiment 41. The chimeric protein of embodiment 40, wherein the bacterium is selected from the group consisting of *Streptococcus pyogenes, Haemophilus influenzae, Streptococcus pneumoniae, Mycoplasma pneumoniae, Moraxella catarrhalis, Pseudomonas aeruginosa*, and *Mycobacterium tuberculosis.*

Embodiment 42. The chimeric protein of any one of embodiments 1-39, wherein the pathogen is a virus that causes a respiratory infection.

Embodiment 43. The chimeric protein of embodiment 42, wherein the virus is selected from the group consisting of coronaviruses, respiratory syncytial viruses, influenza viruses, and adenoviruses.

Embodiment 44. The chimeric protein of embodiment 43, wherein the virus is a coronavirus.

Embodiment 45. The chimeric protein of embodiment 44, wherein the virus is selected from the group consisting of SARS-CoV, SARS-CoV-2, and MERS-CoV.

Embodiment 46. The chimeric protein of embodiment 45, wherein the virus is SARS-CoV-2.

Embodiment 47. The chimeric protein of embodiment 46, wherein the SARS-CoV-2 is WIV4.

Embodiment 48. The chimeric protein of embodiment 46, wherein the SARS-CoV-2 is a variant selected from the group consisting of a B.1.1.7 variant, a B.1.351 variant, a B.1.526 variant, a B1.526.1 variant, a B1.617 variant, a B.1.617.1 variant, a B.1.617.2 variant, a B1.617.3 variant, a P.2 variant, a P.1 variant, an A.23.1 variant, a CAL.20C variant, a B.1.427 variant, a B.1.429 variant, a B.1.525 variant, and a P.1.351 variant.

Embodiment 49. The chimeric protein of embodiment 46, wherein the SARS-CoV-2 is a B.1.1.7 variant.

Embodiment 50. The chimeric protein of embodiment 46, wherein the SARS-CoV-2 is a B.1.351 variant.

Embodiment 51. The chimeric protein of embodiment 46, wherein the SARS-CoV-2 is a B.1.617.2 variant.

Embodiment 52. The chimeric protein of any one of embodiments 44-51, wherein the component of the pathogen is a spike (S) protein.

Embodiment 53a. The chimeric protein of embodiment 52, wherein the target-binding moiety comprises:

(1) an antibody heavy chain variable region (VH) comprising a heavy chain complementarity determining region (HC-CDR)1 comprising the amino acid sequence of SEQ ID NO: 37, an HC-CDR2 comprising the amino acid sequence of SEQ ID NO: 38, and an HC-CDR3 comprising the amino acid sequence of SEQ ID NO: 39; and a light chain variable region comprising a light chain complementarity determining region (LC-CDR)1 comprising the amino acid sequence of SEQ ID NO: 40, an HC-CDR2 comprising the amino acid sequence of SEQ ID NO: 41, and an HC-CDR3 comprising the amino acid sequence of SEQ ID NO: 42;

(2) a VH comprising an HC-CDR1 comprising the amino acid sequence of SEQ ID NO: 1, an HC-CDR2 comprising the amino acid sequence of SEQ ID NO: 2, and an HC-CDR3 comprising the amino acid sequence of SEQ ID NO: 3; a VL comprising an LC-CDR1 comprises the amino acid sequence of SEQ ID NO: 4, an LC-CDR2 comprising the amino acid sequence of SEQ ID NO: 5, and an LC-CDR3 comprising the amino acid sequence of SEQ ID NO: 6;

(3) a VH comprising an HC-CDR1 comprising the amino acid sequence of SEQ ID NO: 7, an HC-CDR2 comprising the amino acid sequence of SEQ ID NO: 8, and an HC-CDR3 comprising the amino acid sequence of SEQ ID NO: 9; a VL comprising an LC-CDR1 comprises the amino acid sequence of SEQ ID NO: 10, an LC-CDR2 comprising the amino acid sequence of SEQ ID NO: 11, and an LC-CDR3 comprising the amino acid sequence of SEQ ID NO: 12;

(4) a VH comprising an HC-CDR1 comprising the amino acid sequence of SEQ ID NO: 13, an HC-CDR2 comprising the amino acid sequence of SEQ ID NO: 14, and an HC-CDR3 comprising the amino acid sequence of SEQ ID NO: 15; a VL comprising an LC-CDR1 comprises the amino acid sequence of SEQ ID NO: 16, the HC-LDR2 comprises the amino acid sequence of SEQ ID NO: 17, and an LC-CDR3 comprising the amino acid sequence of SEQ ID NO: 18;

(5) a VH comprising an HC-CDR1 comprising the amino acid sequence of SEQ ID NO: 19, an HC-CDR2 comprising the amino acid sequence of SEQ ID NO: 20, and an HC-CDR3 comprising the amino acid sequence of SEQ ID NO: 21; a VL comprising an LC-CDR1 comprises the amino acid sequence of SEQ ID NO: 22, an LC-CDR2 comprising the amino acid sequence of SEQ ID NO: 23, and an LC-CDR3 comprising the amino acid sequence of SEQ ID NO: 24;

(6) a VH comprising an HC-CDR1 comprising the amino acid sequence of SEQ ID NO: 25, an HC-CDR2 comprising the amino acid sequence of SEQ ID NO: 26, and an HC-CDR3 comprising the amino acid sequence of SEQ ID NO: 27; a VL comprising LC-CDR1 comprises the amino acid sequence of SEQ ID NO: 28, an LC-CDR2 comprising the amino acid sequence of SEQ ID NO: 29, and an LC-CDR3 comprising the amino acid sequence of SEQ ID NO: 30;

(7) a VH comprising an HC-CDR1 comprising the amino acid sequence of SEQ ID NO: 31, an HC-CDR2 comprising the amino acid sequence of SEQ ID NO: 32, and an HC-CDR3 comprising the amino acid sequence of SEQ ID NO: 33; a VL comprising LC-CDR1 comprises the amino acid sequence of SEQ ID NO: 34, an LC-CDR2 comprising the amino acid sequence of SEQ ID NO: 35, and an LC-CDR3 comprising the amino acid sequence of SEQ ID NO: 36;

(8) a VH comprising an HC-CDR1 comprising the amino acid sequence of SEQ ID NO: 43, an HC-CDR2 comprising the amino acid sequence of SEQ ID NO: 44, and an HC-CDR3 comprising the amino acid sequence of SEQ ID NO: 45; a VL comprising LC-CDR1 comprises the amino acid sequence of SEQ ID NO: 46, an LC-CDR2 comprising the amino acid sequence of SEQ ID NO: 47, and an LC-CDR3 comprising the amino acid sequence of SEQ ID NO: 48;

(9) a VH comprising an HC-CDR1 comprising the amino acid sequence of SEQ ID NO: 49, an HC-CDR2 comprising the amino acid sequence of SEQ ID NO: 50, and an HC-CDR3 comprising the amino acid sequence of SEQ ID NO: 51; a VL comprising LC-CDR1 comprises the amino acid sequence of SEQ ID NO: 52, an LC-CDR2 comprising the amino acid sequence of SEQ ID NO: 53, and an LC-CDR3 comprising the amino acid sequence of SEQ ID NO: 54; or

(10) a VH comprising an HC-CDR1 comprising the amino acid sequence of SEQ ID NO: 55, an HC-CDR2 comprising the amino acid sequence of SEQ ID NO: 56, and an HC-CDR3 comprising the amino acid sequence of SEQ ID NO: 57; a VL comprising LC-CDR1 comprises the amino acid sequence of SEQ ID NO: 58, an LC-CDR2 comprising the amino acid sequence of SEQ ID NO: 59, and an LC-CDR3 comprising the amino acid sequence of SEQ ID NO: 60

Embodiment 53b. The chimeric protein of embodiment 53a, wherein the target-binding moiety comprises: a VH comprising a HC-CDR1 comprising the amino acid sequence of SEQ ID NO: 37, an HC-CDR2 comprising the amino acid sequence of SEQ ID NO: 38, and an HC-CDR3 comprising the amino acid sequence of SEQ ID NO: 39; and a VL comprising a LC-CDR1 comprising the amino acid sequence of SEQ ID NO: 40, an HC-CDR2 comprising the amino acid sequence of SEQ ID NO: 41, and an HC-CDR3 comprising the amino acid sequence of SEQ ID NO: 42.

Embodiment 54a. The chimeric protein of embodiment 53a, wherein the target-binding moiety comprises:

(1) a VH comprising an amino acid sequence having at least about 90% sequence identity to the amino acid sequence of SEQ ID NO: 75, and a VL comprising an amino acid sequence having at least about 90% sequence identity to the amino acid sequence of SEQ ID NO: 76;

(2) a VH comprising an amino acid sequence having at least about 90% sequence identity to the amino acid sequence of SEQ ID NO: 61, and a VL comprising an amino acid sequence having at least about 90% sequence identity to the amino acid sequence of SEQ ID NO: 62;

(3) a VH comprising an amino acid sequence having at least about 90% sequence identity to the amino acid sequence of SEQ ID NO: 63, and a VL comprising an amino acid sequence having at least about 90% sequence identity to the amino acid sequence of SEQ ID NO: 64;

(4) a VH comprising an amino acid sequence having at least about 90% sequence identity to the amino acid sequence of SEQ ID NO: 65, and a VL comprising an amino acid sequence having at least about 90% sequence identity to the amino acid sequence of SEQ ID NO: 66;

(5) a VH comprising an amino acid sequence having at least about 90% sequence identity to the amino acid sequence of SEQ ID NO: 67, and a VL comprising an amino acid sequence having at least about 90% sequence identity to the amino acid sequence of SEQ ID NO: 68;

(6) a VH comprising an amino acid sequence having at least about 90% sequence identity to the amino acid sequence of SEQ ID NO: 69 and a VL comprising an amino acid sequence having at least about 90% sequence identity to the amino acid sequence of SEQ ID NO: 70;

(7) a VH comprising an amino acid sequence having at least about 90% sequence identity to the amino acid sequence of SEQ ID NO: 71, and a VL comprising an amino acid sequence having at least about 90% sequence identity to the amino acid sequence of SEQ ID NO: 72;

(8) a VH comprising an amino acid sequence having at least about 90% sequence identity to the amino acid sequence of SEQ ID NO: 73, and a VL comprising an amino acid sequence having at least about 90% sequence identity to the amino acid sequence of SEQ ID NO: 74;

(9) a VH comprising an amino acid sequence having at least about 90% sequence identity to the amino acid sequence of SEQ ID NO: 77, and a VL comprising an amino acid sequence having at least about 90% sequence identity to the amino acid sequence of SEQ ID NO: 78; or

(10) a VH comprising an amino acid sequence having at least about 90% sequence identity to the amino acid sequence of SEQ ID NO: 79, and a VL comprising an amino acid sequence having at least about 90% sequence identity to the amino acid sequence of SEQ ID NO: 80.

Embodiment 54b. The chimeric protein of embodiment 54a, wherein the target-binding moiety comprises: a VH comprising an amino acid sequence having at least about 90% sequence identity to the amino acid sequence of SEQ ID NO: 75, and a VL comprising an amino acid sequence having at least about 90% sequence identity to the amino acid sequence of SEQ ID NO: 76.

Embodiment 55. The chimeric protein of embodiment 51, wherein the target-binding moiety comprises a scFv comprising an amino acid sequence having at least about 90% sequence identity to the amino acid sequence of SEQ ID NO: 87.

Embodiment 56. The chimeric protein of any one of embodiments 1-55, wherein the mucosa is selected from the group consisting of nasal mucosa, larynx mucosa, trachea mucosa, bronchi mucosa, lung mucosa, eye mucosa, and combinations thereof.

Embodiment 57. A pharmaceutical composition comprising the chimeric protein of any one of embodiments 1-56, and a pharmaceutically acceptable carrier.

Embodiment 58. The pharmaceutical composition of embodiment 57, comprising a plurality of chimeric proteins, wherein the target-binding moieties of the chimeric proteins are different from each other.

Embodiment 59. A pharmaceutical composition comprising at least two chimeric proteins of any one of embodiments 1-56, wherein the two chimeric proteins have different target-binding moieties.

Embodiment 60. The pharmaceutical composition of any one of embodiments 57-59, wherein the chimeric protein is present at a concentration of about 0.6 mg/mL to about 6 mg/mL.

Embodiment 61. The pharmaceutical composition of any one of embodiments 57-60, wherein the pharmaceutically acceptable carrier comprises about 0.05% to about 0.2% (w/w) methionine.

Embodiment 62. The pharmaceutical composition of any one of embodiments 57-61, wherein the pharmaceutical composition has a pH of about 4.5 to about 7.5.

Embodiment 63. The pharmaceutical composition of embodiment 62, wherein the pharmaceutical composition has a pH of about 6.5.

Embodiment 64. The pharmaceutical composition of embodiment 62 or 63, wherein the pharmaceutically acceptable carrier comprises about 20 mM to about 50 mM citrate.

Embodiment 65. The pharmaceutical composition of any one of embodiments 57-64, wherein the pharmaceutical composition has an osmolality of about 230 to about 330 Osm/kg.

Embodiment 66. The pharmaceutical composition of embodiment 65, wherein the pharmaceutically acceptable carrier comprises about 100 mM to about 150 mM NaCl.

Embodiment 67. The pharmaceutical composition of any one of embodiments 57-66, wherein the pharmaceutically acceptable carrier further comprises a surfactant.

Embodiment 68. The pharmaceutical composition of embodiment 67, wherein the surfactant is polysorbate 80.

Embodiment 69. The pharmaceutical composition of embodiment 68, wherein the pharmaceutically acceptable carrier comprises about 0.01% to about 0.1% (w/w) polysorbate 80.

Embodiment 70. The pharmaceutical composition of any one of embodiments 57-69, wherein the pharmaceutically acceptable carrier further comprises a viscosity-enhancing agent.

Embodiment 71. The pharmaceutical composition of embodiment 70, wherein the viscosity-enhancing agent is glycerin.

Embodiment 72. The pharmaceutical composition of embodiment 71, wherein the pharmaceutically acceptable carrier comprises about 1% to about 10% (w/w) glycerin.

Embodiment 73. The pharmaceutical composition of any one of embodiments 57-72, wherein the pharmaceutically acceptable carrier further comprises a preservative.

Embodiment 74. The pharmaceutical composition of embodiment 73, wherein the preservative is potassium sorbate.

Embodiment 75. The pharmaceutical composition of embodiment 74, wherein the pharmaceutically acceptable carrier comprises about 0.05% to about 0.2% (w/w) potassium sorbate.

Embodiment 76. The pharmaceutical composition of any one of embodiments 57-75, wherein the pharmaceutically acceptable carrier comprises about 25 mM citrate at pH 6.5, about 125 mM NaCl, about 5% glycerin, about 0.1% methionine, about 0.02% polysorbate 80, and about 0.1% potassium sorbate.

Embodiment 77. The pharmaceutical composition of any one of embodiments 57-76, wherein the pharmaceutical composition is for nasal administration.

Embodiment 78. An isolated nucleic acid or a set of isolated nucleic acids encoding the chimeric protein of any one of embodiments 1-56.

Embodiment 79. A vector comprising the nucleic acid of embodiment 78.

Embodiment 80. A set of vectors comprising the set of nucleic acids of embodiment 78.

Embodiment 81. A host cell comprising the chimeric protein of any one of embodiments 1-56, the nucleic acid or set of nucleic acids of embodiment 78, the vector of embodiment 79, or the set of vectors of embodiment 80.

Embodiment 82. A method of preparing a chimeric protein, comprising: (a) culturing a host cell of embodiment 81 under conditions effective to express the chimeric protein; and (b) obtaining the expressed chimeric protein from the host cell.

Embodiment 83. A method of preventing or treating an infection caused by a pathogen that infects through a mucosa in an individual, comprising administering to the individual an effective amount of the chimeric protein of any one of embodiments 1-56, or the pharmaceutical composition of any one of embodiments 57-77.

Embodiment 84. The method of embodiment 83, wherein the pharmaceutical composition is administered to the individual before the individual is exposed to the pathogen.

Embodiment 85. The method of embodiment 83, wherein the pharmaceutical composition is administered to the individual within about 72 hours after the individual is exposed to the pathogen.

Embodiment 86. The method of any one of embodiments 83-85, wherein the chimeric protein or the pharmaceutical composition is administered topically onto the mucosa.

Embodiment 87. The method of embodiment 86, wherein the chimeric protein or the pharmaceutical composition is administered via a nasal spray, an inhaler, a nebulizer, or an eye drop.

Embodiment 88. The method of any one of embodiments 83-87, wherein the chimeric protein or the pharmaceutical composition is administered once or twice daily.

Embodiment 89. The method of any one of embodiments 83-88, wherein the chimeric protein is administered at a dose of about 0.1 mg to about 1 mg.

Embodiment 90. An isolated antibody or antigen binding fragment thereof, comprising:
(1) a VH comprising a HC-CDR1 sequence, a HC-CDR2 sequence, and a HC-CDR3 sequence of the VH sequence of SEQ ID NO: 73 and a VL comprising a LC-CDR1 sequence, a LC-CDR2 sequence, and a LC-CDR3 sequence of the VL sequence SEQ ID NO: 74;
(2) a VH comprising a HC-CDR1 sequence, a HC-CDR2 sequence, and a HC-CDR3 sequence of the VH sequence of SEQ ID NO: 61 and a VL comprising a LC-CDR1 sequence, a LC-CDR2 sequence, and a LC-CDR3 sequence of the VL sequence SEQ ID NO: 62;
(3) a VH comprising a HC-CDR1 sequence, a HC-CDR2 sequence, and a HC-CDR3 sequence of the VH sequence of SEQ ID NO: 63 and a VL comprising a LC-CDR1 sequence, a LC-CDR2 sequence, and a LC-CDR3 sequence of the VL sequence SEQ ID NO: 64;
(4) a VH comprising a HC-CDR1 sequence, a HC-CDR2 sequence, and a HC-CDR3 sequence of the VH sequence of SEQ ID NO: 65 and a VL comprising a LC-CDR1 sequence, a LC-CDR2 sequence, and a LC-CDR3 sequence of the VL sequence SEQ ID NO: 66;
(5) a VH comprising a HC-CDR1 sequence, a HC-CDR2 sequence, and a HC-CDR3 sequence of the VH sequence of SEQ ID NO: 67 and a VL comprising a LC-CDR1 sequence, a LC-CDR2 sequence, and a LC-CDR3 sequence of the VL sequence SEQ ID NO: 68;
(6) a VH comprising a HC-CDR1 sequence, a HC-CDR2 sequence, and a HC-CDR3 sequence of the VH sequence of SEQ ID NO: 69 and a VL comprising a LC-CDR1 sequence, a LC-CDR2 sequence, and a LC-CDR3 sequence of the VL sequence SEQ ID NO: 70;

(7) a VH comprising a HC-CDR1 sequence, a HC-CDR2 sequence, and a HC-CDR3 sequence of the VH sequence of SEQ ID NO: 71 and a VL comprising a LC-CDR1 sequence, a LC-CDR2 sequence, and a LC-CDR3 sequence of the VL sequence SEQ ID NO: 72;

(8) a VH comprising a HC-CDR1 sequence, a HC-CDR2 sequence, and a HC-CDR3 sequence of the VH sequence of SEQ ID NO: 75 and a VL comprising a LC-CDR1 sequence, a LC-CDR2 sequence, and a LC-CDR3 sequence of the VL sequence SEQ ID NO: 76;

(9) a VH comprising a HC-CDR1 sequence, a HC-CDR2 sequence, and a HC-CDR3 sequence of the VH sequence of SEQ ID NO: 77 and a VL comprising a LC-CDR1 sequence, a LC-CDR2 sequence, and a LC-CDR3 sequence of the VL sequence SEQ ID NO: 78; or

(10) a VH comprising a HC-CDR1 sequence, a HC-CDR2 sequence, and a HC-CDR3 sequence of the VH sequence of SEQ ID NO: 79 and a VL comprising a LC-CDR1 sequence, a LC-CDR2 sequence, and a LC-CDR3 sequence of the VL sequence SEQ ID NO: 80;

Embodiment 91. The isolated antibody or antigen binding fragment of embodiment 90, comprising:

(1) a VH comprising an HC-CDR1 comprising the amino acid sequence of SEQ ID NO: 37, an HC-CDR2 comprising the amino acid sequence of SEQ ID NO: 38, and an HC-CDR3 comprising the amino acid sequence of SEQ ID NO: 39; a VL comprising LC-CDR1 comprises the amino acid sequence of SEQ ID NO: 40, an LC-CDR2 comprising the amino acid sequence of SEQ ID NO: 41, and an LC-CDR3 comprising the amino acid sequence of SEQ ID NO: 42;

(2) a VH comprising an HC-CDR1 comprising the amino acid sequence of SEQ ID NO: 1, an HC-CDR2 comprising the amino acid sequence of SEQ ID NO: 2, and an HC-CDR3 comprising the amino acid sequence of SEQ ID NO: 3; a VL comprising an LC-CDR1 comprises the amino acid sequence of SEQ ID NO: 4, an LC-CDR2 comprising the amino acid sequence of SEQ ID NO: 5, and an LC-CDR3 comprising the amino acid sequence of SEQ ID NO: 6;

(3) a VH comprising an HC-CDR1 comprising the amino acid sequence of SEQ ID NO: 7, an HC-CDR2 comprising the amino acid sequence of SEQ ID NO: 8, and an HC-CDR3 comprising the amino acid sequence of SEQ ID NO: 9; a VL comprising an LC-CDR1 comprises the amino acid sequence of SEQ ID NO: 10, an LC-CDR2 comprising the amino acid sequence of SEQ ID NO: 11, and an LC-CDR3 comprising the amino acid sequence of SEQ ID NO: 12;

(4) a VH comprising an HC-CDR1 comprising the amino acid sequence of SEQ ID NO: 13, an HC-CDR2 comprising the amino acid sequence of SEQ ID NO: 14, and an HC-CDR3 comprising the amino acid sequence of SEQ ID NO: 15; a VL comprising an LC-CDR1 comprises the amino acid sequence of SEQ ID NO: 16, the HC-LDR2 comprises the amino acid sequence of SEQ ID NO: 17, and an LC-CDR3 comprising the amino acid sequence of SEQ ID NO: 18;

(5) a VH comprising an HC-CDR1 comprising the amino acid sequence of SEQ ID NO: 19, an HC-CDR2 comprising the amino acid sequence of SEQ ID NO: 20, and an HC-CDR3 comprising the amino acid sequence of SEQ ID NO: 21; a VL comprising an LC-CDR1 comprises the amino acid sequence of SEQ ID NO: 22, an LC-CDR2 comprising the amino acid sequence of SEQ ID NO: 23, and an LC-CDR3 comprising the amino acid sequence of SEQ ID NO: 24;

(6) a VH comprising an HC-CDR1 comprising the amino acid sequence of SEQ ID NO: 25, an HC-CDR2 comprising the amino acid sequence of SEQ ID NO: 26, and an HC-CDR3 comprising the amino acid sequence of SEQ ID NO: 27; a VL comprising LC-CDR1 comprises the amino acid sequence of SEQ ID NO: 28, an LC-CDR2 comprising the amino acid sequence of SEQ ID NO: 29, and an LC-CDR3 comprising the amino acid sequence of SEQ ID NO: 30;

(7) a VH comprising an HC-CDR1 comprising the amino acid sequence of SEQ ID NO: 31, an HC-CDR2 comprising the amino acid sequence of SEQ ID NO: 32, and an HC-CDR3 comprising the amino acid sequence of SEQ ID NO: 33; a VL comprising LC-CDR1 comprises the amino acid sequence of SEQ ID NO: 34, an LC-CDR2 comprising the amino acid sequence of SEQ ID NO: 35, and an LC-CDR3 comprising the amino acid sequence of SEQ ID NO: 36;

(8) a VH comprising an HC-CDR1 comprising the amino acid sequence of SEQ ID NO: 43, an HC-CDR2 comprising the amino acid sequence of SEQ ID NO: 44, and an HC-CDR3 comprising the amino acid sequence of SEQ ID NO: 45; a VL comprising LC-CDR1 comprises the amino acid sequence of SEQ ID NO: 46, an LC-CDR2 comprising the amino acid sequence of SEQ ID NO: 47, and an LC-CDR3 comprising the amino acid sequence of SEQ ID NO: 48;

(9) a VH comprising an HC-CDR1 comprising the amino acid sequence of SEQ ID NO: 49, an HC-CDR2 comprising the amino acid sequence of SEQ ID NO: 50, and an HC-CDR3 comprising the amino acid sequence of SEQ ID NO: 51; a VL comprising LC-CDR1 comprises the amino acid sequence of SEQ ID NO: 52, an LC-CDR2 comprising the amino acid sequence of SEQ ID NO: 53, and an LC-CDR3 comprising the amino acid sequence of SEQ ID NO: 54; or

(10) a VH comprising an HC-CDR1 comprising the amino acid sequence of SEQ ID NO: 55, an HC-CDR2 comprising the amino acid sequence of SEQ ID NO: 56, and an HC-CDR3 comprising the amino acid sequence of SEQ ID NO: 57; a VL comprising LC-CDR1 comprises the amino acid sequence of SEQ ID NO: 58, an LC-CDR2 comprising the amino acid sequence of SEQ ID NO: 59, and an LC-CDR3 comprising the amino acid sequence of SEQ ID NO: 60.

Embodiment 92. The isolated antibody or antigen binding fragment thereof of embodiment 90 or 91, comprising:

(1) a VH comprising an amino acid sequence having at least about 90% sequence identity to the amino acid sequence of SEQ ID NO: 61, and a VL comprising an amino acid sequence having at least about 90% sequence identity to the amino acid sequence of SEQ ID NO: 62;

(2) a VH comprising an amino acid sequence having at least about 90% sequence identity to the amino acid sequence of SEQ ID NO: 63, and a VL comprising an amino acid sequence having at least about 90% sequence identity to the amino acid sequence of SEQ ID NO: 64;

(3) a VH comprising an amino acid sequence having at least about 90% sequence identity to the amino acid sequence of SEQ ID NO: 65, and a VL comprising an amino acid sequence having at least about 90% sequence identity to the amino acid sequence of SEQ ID NO: 66;

(4) a VH comprising an amino acid sequence having at least about 90% sequence identity to the amino acid sequence of SEQ ID NO: 67, and a VL comprising an amino acid sequence having at least about 90% sequence identity to the amino acid sequence of SEQ ID NO: 68;

(5) a VH comprising an amino acid sequence having at least about 90% sequence identity to the amino acid sequence of SEQ ID NO: 69 and a VL comprising an amino acid sequence having at least about 90% sequence identity to the amino acid sequence of SEQ ID NO: 70;

(6) a VH comprising an amino acid sequence having at least about 90% sequence identity to the amino acid sequence of SEQ ID NO: 71, and a VL comprising an amino acid sequence having at least about 90% sequence identity to the amino acid sequence of SEQ ID NO: 72;

(7) a VH comprising an amino acid sequence having at least about 90% sequence identity to the amino acid sequence of SEQ ID NO: 73, and a VL comprising an amino acid sequence having at least about 90% sequence identity to the amino acid sequence of SEQ ID NO: 74;

(8) a VH comprising an amino acid sequence having at least about 90% sequence identity to the amino acid sequence of SEQ ID NO: 75, and a VL comprising an amino acid sequence having at least about 90% sequence identity to the amino acid sequence of SEQ ID NO: 76;

(9) a VH comprising an amino acid sequence having at least about 90% sequence identity to the amino acid sequence of SEQ ID NO: 77, and a VL comprising an amino acid sequence having at least about 90% sequence identity to the amino acid sequence of SEQ ID NO: 78; or

(10) a VH comprising an amino acid sequence having at least about 90% sequence identity to the amino acid sequence of SEQ ID NO: 79, and a VL comprising an amino acid sequence having at least about 90% sequence identity to the amino acid sequence of SEQ ID NO: 80.

Embodiment 93. The isolated antibody or antigen binding fragment thereof of any one of embodiments 90-92, wherein the antibody or antigen binding fragment thereof specifically binds an S1 subunit of a spike (S) protein of SARS-CoV-2.

Embodiment 94. The isolated antibody or antigen binding fragment thereof of any one of embodiments 90-93, wherein the antibody or antigen binding fragment thereof is selected from the group consisting of a full-length antibody, a Fab, a Fab', a (Fab')$_2$, an Fv, a single chain Fv (scFv), an scFv-Fc, a disulfide stabilized Fv fragment (dsFv), a (dsFv)$_2$, an scFv dimer, a domain antibody, a bivalent domain antibody, and a minibody.

Embodiment 95. An isolated antibody or antigen binding fragment thereof that specifically binds to the same or substantially the same epitope competitively with the isolated antibody or antigen binding fragment of any one of embodiments 90-94.

Embodiment 96. An isolated antibody construct comprising an antibody moiety comprising the antibody or antigen binding fragment of any one of embodiments 90-95.

Embodiment 97. The isolated antibody construct of embodiment 96, wherein the construct is a chimeric protein further comprising a mucoadhesive peptide fragment comprising about 5 to about 50 positively charged amino acid residues, wherein the mucoadhesive peptide fragment facilitates attachment of the chimeric protein to a mucosa.

Embodiment 98. The isolated antibody construct of embodiment 96, wherein the construct is a multispecific antibody.

Embodiment 99. The isolated antibody construct of embodiment 96, wherein the construct is an immunoconjugate comprising the antibody moiety and an effector molecule.

Embodiment 100. The isolated antibody construct of embodiment 99, wherein the effector molecule is a therapeutic agent selected from the group consisting of a drug, a toxin, a radioisotope, a protein, a peptide, and a nucleic acid.

Embodiment 101. The isolated antibody construct of embodiment 100, wherein the effector molecule is a label.

Embodiment 102. An isolated nucleic acid or a set of isolated nucleic acids encoding the antibody or antigen binding fragment thereof of any one of embodiments 90-995, or one or more polypeptides of the antibody construct of any one of embodiments 96-101.

Embodiment 103. A vector comprising the nucleic acid of embodiment 102.

Embodiment 104. A set of vectors comprising the set of nucleic acids of embodiment 102.

Embodiment 105. A host cell comprising the antibody or antigen binding fragment thereof of any one of embodiments 90-95, the antibody construct of any one of embodiments 96-101, the nucleic acid or set of nucleic acids of embodiment 102, the vector of embodiment 103, or the set of vectors of embodiment 104.

Embodiment 106. A pharmaceutical composition comprising the antibody or antigen binding fragment thereof of any one of embodiments 90-95, or the antibody construct of any one of embodiments 93-97, and a pharmaceutically acceptable carrier.

Embodiment 107. A formulation for nasal administration comprising: (a) an antibody that specifically binds to a component of SARS-CoV-2, (b) a methionine, (c) a buffering agent, and (d) an osmolality adjusting agent, wherein the formulation has a pH of about 4.5 to about 7.5, and wherein the formulation has an osmolality of about 230 to about 330 Osm/kg.

Embodiment 108. The formulation of embodiment 107, wherein the antibody is present at a concentration of about 0.6 mg/mL to about 6 mg/mL.

Embodiment 109. The formulation of embodiment 107 or 108, wherein the methionine is present at a concentration of about 0.05% to about 0.2% (w/w).

Embodiment 110. The formulation of any one of embodiments 107-109, wherein the formulation has a pH of about 6.5.

Embodiment 111. The formulation of any one of embodiments 107-110, wherein the buffering agent is a citrate or a phosphate.

Embodiment 112. The formulation of embodiment 111, wherein the buffering agent is a citrate at a concentration of about 20 mM to about 50 mM.

Embodiment 113. The formulation of any one of embodiments 107-112, wherein the osmolality adjusting agent is NaCl at a concentration of about 100 mM to about 150 mM.

Embodiment 114. The formulation of any one of embodiments 107-113, further comprising a surfactant.

Embodiment 115. The formulation of embodiment 114, the surfactant is polysorbate 80 at a concentration of about 0.01% to about 0.1% (w/w).

Embodiment 116. The formulation of any one of embodiments 107-115, further comprising a viscosity-enhancing agent.

Embodiment 117. The formulation of embodiment 116, wherein the viscosity-enhancing agent is selected from the group consisting of glycerin, dextran and hydroxyethylcellulose.

Embodiment 118. The formulation of embodiment 116 or 117, wherein the viscosity enhancing agent is glycerin at a concentration of about 1% to about 10% (w/w).

Embodiment 119. The formulation of any one of embodiments 107-118, further comprising a preservative.

Embodiment 120. The formulation of embodiment 119, wherein the preservative is potassium sorbate at a concentration of about 0.05% to about 0.2% (w/w).

Embodiment 121. The formulation of any one of embodiments 107-120, comprising about 25 mM citrate at pH 6.5, about 125 mM NaCl, about 5% glycerin, about 0.1% methionine, about 0.02% polysorbate 80, and about 0.1% potassium sorbate.

Embodiment 122. A method of preventing or treating a SARS-CoV-2 infection in an individual, comprising administering to the individual an effective amount of the antibody or antigen binding fragment thereof of any one of embodiments 90-95, the antibody construct of any one of embodiments 96-101, or the formulation of any one of embodiments 107-121.

Embodiment 123. The method of embodiment 122, wherein the SARS-CoV-2 is WIV4.

Embodiment 124. The method of embodiment 122, wherein the SARS-CoV-2 is a variant selected from the group consisting of a B.1.1.7 variant, a B.1.351 variant, a B.1.526 variant, a B1.526.1 variant, a B1.617 variant, a B.1.617.1 variant, a B.1.617.2 variant, a B1.617.3 variant, a P.2 variant, a P.1 variant, an A.23.1 variant, a CAL.20C variant, a B.1.427 variant, a B.1.429 variant, a B.1.525 variant, and a P.1.351 variant.

Embodiment 125. The method of embodiment 124, wherein the SARS-CoV-2 is a B.1.1.7 variant.

Embodiment 126. The method of embodiment 124, wherein the SARS-CoV-2 is a B.1.351 variant.

Embodiment 127. The method of embodiment 124, wherein the SARS-CoV-2 is a B.1.617.2 variant.

Embodiment 128. The method of any one of embodiments 122-127, wherein the method prevents infection of the individual by a plurality of SARS-CoV-2 variants.

Embodiment 129. A method of detecting SARS-CoV-2 in a sample, comprising contacting the sample with the antibody or antigen binding fragment thereof of any one of embodiments 90-95, or the antibody construct of any one of embodiments 96 and 99-101.

Embodiment 130. A method of diagnosing whether an individual has a SARS-CoV-2 infection, comprising: a) administering an effective amount of the antibody construct of embodiment 101 to the individual; and b) determining the level of the label in the individual.

Embodiment 131. The method of embodiment 130, wherein a level of the label above a threshold level indicates that the individual has SARS-CoV-2 infection.

Embodiment 132. A method of diagnosing whether an individual has a SARS-CoV-2 infection, comprising: a) contacting a sample derived from the individual with the antibody or antigen binding fragment thereof of any one of embodiments 90-95, or the antibody construct of any one of embodiments 96 and 99-101; and b) determining the amount of SARS-CoV-2 S1 in the sample bound with the antibody, antigen binding fragment thereof, or the antibody construct.

Embodiment 133. The method of embodiment 132, wherein a value for the amount of SARS-CoV-2 S1 bound above a threshold level indicates that the individual has SARS-CoV-2 infection.

Embodiment 134. A method of diagnosing whether an individual has a SARS-CoV-2 infection, comprising: a) contacting a sample derived from the individual with any one of the antibodies or antigen binding fragments thereof of described above, or any one of the antibody constructs described above; and b) determining the amount of the antibody, antigen binding fragment thereof, or the antibody construct bound with materials in the sample.

Embodiment 135. The method of embodiment 134, wherein a value for the amount of the antibody, antigen binding fragment thereof, or the antibody construct bound above a threshold level indicates that the individual has SARS-CoV-2 infection.

Embodiment 136. Use of the chimeric protein of any one of embodiments 1-56, or the pharmaceutical composition of any one of embodiments 57-77, in the preparation of a medicament for preventing or treating an infection caused by a pathogen that infects through a mucosa in an individual.

Embodiment 137. Use of the chimeric protein of any one of embodiments 1-56, or the pharmaceutical composition of any one of embodiments 57-77, in a method for preventing or treating an infection caused by a pathogen that infects through a mucosa in an individual.

Embodiment 138. Use of the antibody or antigen binding fragment thereof of any one of embodiments 90-95, the antibody construct of any one of embodiments 96-101, or the formulation of any one of embodiments 107-121 in the preparation of a medicament for preventing or treating a SARS-CoV-2 infection in an individual.

Embodiment 139. Use of the antibody or antigen binding fragment thereof of any one of embodiments 90-95, the antibody construct of any one of embodiments 96-101, or the formulation of any one of embodiments 107-121, in a method for preventing or treating a SARS-CoV-2 infection in an individual.

Embodiment 140. Use of the antibody construct of embodiment 101 in the preparation of a diagnostic agent for diagnosing whether an individual has a SARS-CoV-2 infection, comprising: a) administering an effective amount of the antibody construct to the individual; and b) determining the level of the label in the individual.

Embodiment 141. Use of the antibody construct of embodiment 101 in a method for diagnosing whether an individual has a SARS-CoV-2 infection, comprising: a) administering an effective amount of the antibody construct to the individual; and b) determining the level of the label in the individual.

Embodiment 142. Use of the antibody or antigen binding fragment thereof of any one of embodiments 90-95, or the antibody construct of any one of embodiments 96 and 99-101 in the preparation of a diagnostic agent for diagnosing whether an individual has a SARS-CoV-2 infection, comprising: a) contacting a sample derived from the individual with the antibody or antigen binding fragment thereof or the antibody construct; and b) determining the amount of SARS-CoV-2 S1 in the sample bound with the antibody, antigen binding fragment thereof, or the antibody construct.

Embodiment 143. Use of the antibody or antigen binding fragment thereof of any one of embodiments 90-95, or the antibody construct of any one of embodiments 96 and 99-101 in a method for diagnosing whether an individual has a SARS-CoV-2 infection, comprising: a) contacting a sample derived from the individual with the antibody or antigen binding fragment thereof or the antibody construct; and b) determining the amount of SARS-CoV-2 S1 in the sample bound with the antibody, antigen binding fragment thereof, or the antibody construct.

Embodiment 144. Use of the antibody or antigen binding fragment thereof of any one of embodiments 90-95, or the antibody construct of any one of embodiments 96 and 99-101 in the preparation of a diagnostic agent for diagnosing whether an individual has a SARS-CoV-2 infection, comprising: a) contacting a sample derived from the individual with the antibodies or antigen binding fragments thereof or the antibody construct; and b) determining the amount of the antibody, antigen binding fragment thereof, or the antibody construct bound with materials in the individual.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1. Generation and Selection of Human Anti-SARS-CoV-2 Spike Protein Antibody Constructs This example demonstrates the generation of novel human antibody constructs specific for the S1 subunit of the spike protein of SARS-CoV-2. In particular, this example demonstrates the generation of novel human single chain variable fragments (scFvs) that specifically bind to SARS-CoV-2 spike protein. Human antibody constructs described herein were developed using naïve or semi-synthetic human phage libraries developed from normal donors and/or diseased donors and were selected based on high specificity for SARS-CoV-2 spike protein via panning. Such human antibody constructs may serve as a valuable source for construction of, among other things, full-length IgG, multispecific antibodies, caTCRs, and chimeric antigen receptors.

Briefly, an exemplary outline for the development of anti-SARS-CoV-2 spike protein antibody constructs is set forth in Table 9. The process was initiated with the identification of antibodies against SARS-CoV-2 from Eureka Therapeutics's proprietary E-ALPHA® phage library, a collection of human scFv antibody phage display libraries with a diversity of $10 \times 10^{10}$ unique clones constructed by Eureka Therapeutics, Inc. This phage library includes naive libraries consisting of fully naïve human heavy and light chain repertoires derived from PBMCs and spleens of healthy donors or from PBMCs of disease donors, and from semi-synthetic libraries having completely randomized heavy chain CDR3 regions. The scFv libraries were used in panning against the S1 subunit polypeptide of SARS-CoV-2 spike protein (SEQ ID NO: 93; Sino biological, 40591-V08H, which is the Val16-Arg685 fragment of NCBI Ref. No. YP 009724390.1) of the isolate 2019-nCoV, also known as WIV4 (hCoV-19/WIV04/2019 or BetaCoV/WIV04/2019). For protein panning, the SARS-CoV-2 spike protein (5 µg/mL) was coated on to high binding 96 well assay plates (Corning, Cat #3361). Human scFv phage libraries were pre-incubated with a coronavirus protein mixture which includes spike proteins from SARS (Sino biological, 40150-V08B1), MERS (Sino biological, 40069-V08H), HCoV-HKU1 (Sino biological, 40021-V08H), HCoV-NL63 (Sino biological, 40600-V08H), HCoV-229E (Sino biological, 40601-V08H) and HCoV-OC43 (Sino biological, 40607-V08B), before being added to the SARS2-CoV-2 spike protein coated plate. After extended washing with PBS, the bound clones were then eluted and used to infect E. coli XL1-Blue cells. The phage clones were expressed in bacteria and purified. The panning was performed for three to four rounds to enrich for scFv phage clones that specifically bound the SARS-CoV-2 spike protein.

TABLE 9

Methodologies for antibody characterization

| Stage | Methodology |
| --- | --- |
| Primary panning with phage library | Protein panning |
| | ELISA screening of phage clones |
| Clone characterization | Binding specificity |
| | Blocking assay |

Figure 2:
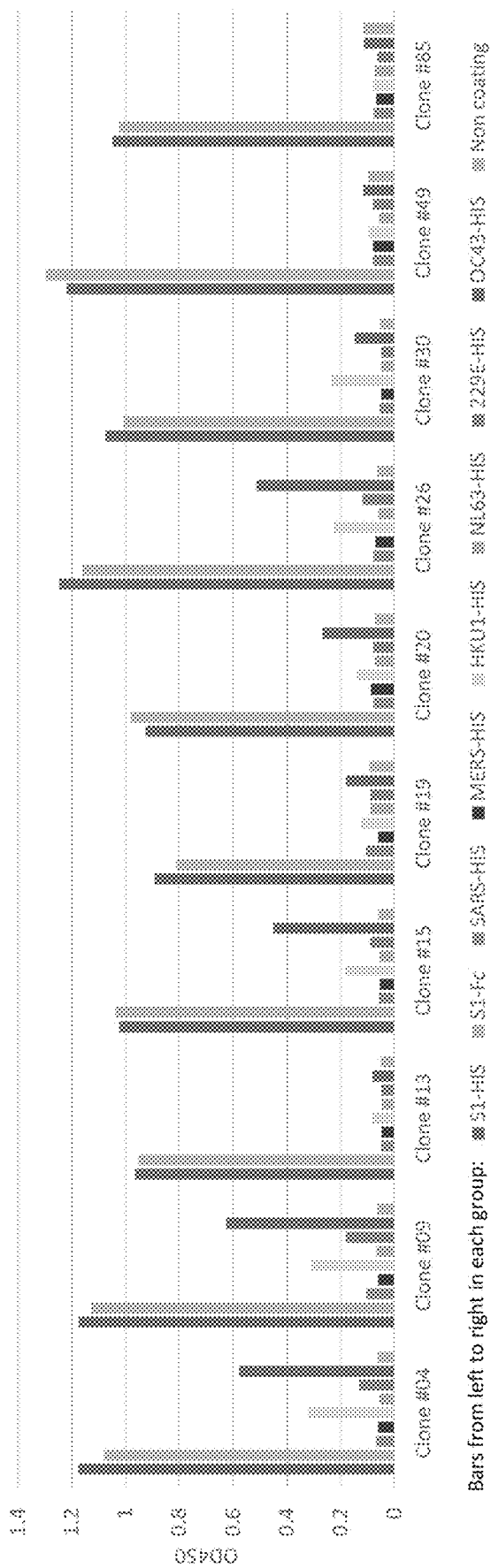
FIG. 2 shows binding specificity of exemplary phage clones to SARS-CoV-2 spike protein S1 compared to other coronavirus S1 proteins as confirmed by ELISA.

Phage clones selected by protein panning were tested for binding to SARS-CoV-2 spike protein by ELISA against SARS-CoV-2 spike protein. Out of the 960 clones screened by phage display, 10 clones were SARS-CoV-2 binders as confirmed by ELISA. As shown in FIG. 1, all 10 clones can bind to SARS-CoV-2 spike protein compared to control proteins. FIG. 2 further shows that clones #13, 19, 20, 30, 49 and 85 bind to SARS-CoV-2 spike protein with high specificity, but do not bind to the spike proteins of other coronaviruses, such as SARS, MERS, HCoV-HKU1, HCoV-NL63, HCoV-229E, HCoV-OC43. Clone #19 and clone #30 bind to the conserved non-receptor binding domain (non-RBD) region of the spike protein and thus do not possess blocking activity. The sequences of the anti-S1 antibodies encoded by the phage clones are shown in Tables 6-8.

Example 2. Characterization of scFv Clones and Exemplary scFv Clone #26 by Binding Activity Example 2A. Characterization of Neutralizing Antibodies A blocking assay was carried out by ELISA to determine if the selected antibodies can block the SARS-CoV-2 spike protein from binding to human ACE2. In this assay, His-tagged scFvs were produced using TOP10F' TM competent E. coli (Life Technologies, C303003) infected by different phage clones. After purification, the concentrations of the scFvs were determined.

High binding plates (Cat #9018, Corning) were coated with 2 µg/mL SARS-CoV-2 spike proteins or variants (from Sino Biological) for at least 2 hours at room temperature (RT).

Figure 3:
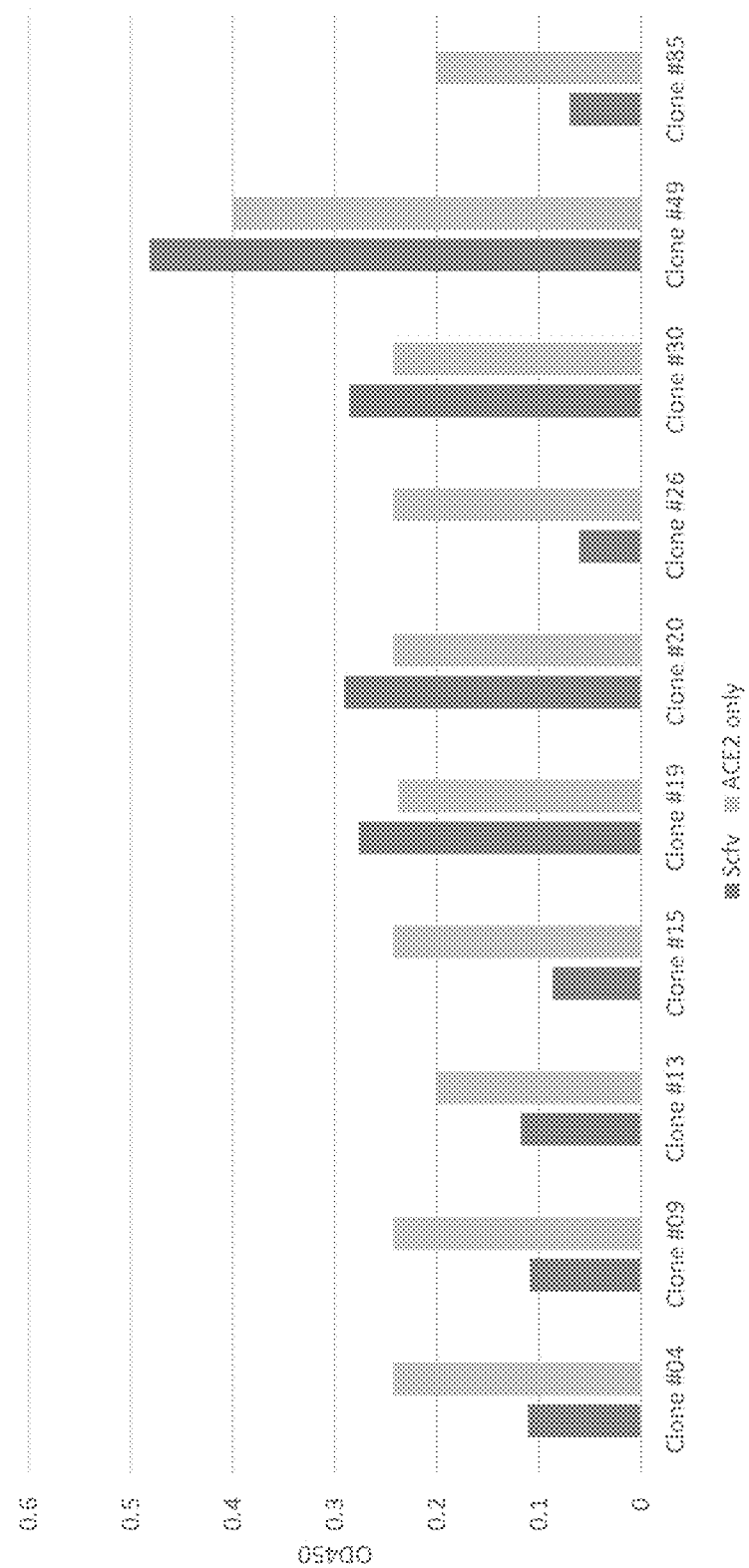
FIG. 3 represents an ELISA-based blocking assay of various scFv clones' effect on the binding between ACE2 and SARS-CoV-2 spike protein S1, showing that several exemplary scFv clones blocked ACE2's binding to SARS-CoV-2 spike protein S1.

10 µg/mL of scFv and 10 µg/mL ACE2-hFc (Sino biological, 10108-H02H) were added to the SARS-CoV-2 spike-coated plate to a total volume of 100 µL and incubated for 1 h at room temperature. After washing with PBS, ACE2 binding was detected using horseradish peroxidase (HRP)-conjugated anti-human Fc, which binds to ACE2-hFc. HRP activity was assayed using TMB (3,3',5,5"-tetramethylbenzidine) and hydrogen peroxide, and the reaction quenched with 100 µL of 1-2 M H2504. In FIG. 3, binding of the ACE2-hFc to SARS-CoV-2 spike protein was measured at 450 nm on a BioTek Epoch 2 Microplate Spectrophotometer.

The scFv bar (left) represents the relative blocking ability of the individual phage clones to the spike-coated plates. In the ACE2 only control (right), ACE protein alone was added to the SARS-CoV-2 spike-coated plates. As FIG. 3 shows, scFv clones #04, 09, 13, 15, 26 and 85 could block ACE2 binding to SARS-CoV-2 coated plates, whereas scFv clones #19, 20 and 30 could not block ACE2 binding. This indicates that antibody clones #04, 09, 13, 15, 26 and 85 are potential neutralizing antibodies for SARS-CoV-2.

Example 2B. Binding of scFv Clone #26 to S1 and Inhibition of Binding of S1 to hACE2 by scFv Clone #26

In this example, scFv clone #26 was shown to block the binding of huACE2 to various mutated forms of the S1 spike protein identified from COVID-19 patients, including that of the most infectious strain SARS-CoV-2 (D614G).

To assess the binding of scFv clone #26 to a panel of Coronavirus spike proteins, an ELISA assay was employed; high binding plates (Cat #9018, Corning) were coated with 2 µg/mL SARS-CoV-2 spike proteins or variants (from Sino Biological) for at least 2 hours at room temperature (RT). Plates were washed with PBS containing 0.05% Tween-20 and blocked with 3% bovine serum albumin in PBS at 4° C. overnight. ScFvs were added to the plates and incubated for 1 hour at RT. Plates were washed three times and incubated with horseradish peroxidase (HRP)-conjugated anti-His antibody at a 1:2000 dilution. After five final washes with PBS containing 0.05% Tween-20, color was developed using TMB (3,3',5,5'-tetramethylbenzidine) substrate. Absorbance at an optical density at 450 nm (OD450) was measured on a BioTek Epoch 2 Microplate Spectrophotometer. Binding by scFv clone #26 to spike proteins/variants is defined as positive when the ELISA detection signal is at least 10-fold higher than that of background. The results are shown in Table 10.

To assess the ability of scFv clone #26 to inhibit the binding of S1 proteins to the hACE2 receptor, another ELISA assay was employed. High binding plates were coated with 2 µg/mL hACE2-hFc protein for 2 hours at RT. The plates were blocked with 3% BSA in PBS overnight at 4° C. 2 µg/mL of antibodies were incubated with His-tagged S1 protein (2 µg/mL) for 1 hour. The mixture was added to the plates and incubated for 1 hour at RT. After 3 washes with PBS containing 0.05% Tween-20, HRP-Anti-His (1:2000) was added and incubated for another hour. The assay was developed using the method described for binding, above. Binding is defined as inhibited when 2 µg/ml of scFv clone #26 leads to at least 50% signal reduction of S1 binding to hACE2. For $IC_{50}$ determination, serial dilutions of the antibodies from 0.04-10 µg/mL of antibodies were used in this assay. The data was analyzed and $IC_{50}$ values were generated by GraphPad Prism 9. The results are shown in Table 10.

TABLE 10

Binding of phage clone #26 to Coronavirus S1 proteins and inhibition of S1 binding to hACE2.

| SARS-Cov-2 spike variants and other coronavirus spike proteins | Binding to S1* | Inhibition of S1 binding to hACE2** | $IC_{50}$, nM*** |
|---|---|---|---|
| SARS-CoV-2 S1 (WIV4) | + | + | 1.33 |
| SARS-CoV-2 S1 (D614G) | + | + | 1.40 |
| SARS-CoV-2 S1 Alpha Variant (HV69-70 deletion, Y144 deletion, N501Y, A570D, D614G, P681H) | + | + | 4.0 |
| SARS-CoV-2 S1 Beta Variant (K417N, E484K, N501Y, D614G) | + | + | 2.27 |
| SARS-CoV-2 S1 Delta Variant (T19R, G142D, E156G, 157-158 deletion, L452R, T478K, D614G, P681R) | + | + | 1.19 |
| SARS-CoV-2 RBD | + | + | N/D |
| nnnSARS-CoV-2 RBD (V367F) | + | + | N/D |
| SARS-CoV-2 RBD (N439K) | + | + | N/D |
| SARS-CoV-2 RBD (A435S) | + | + | N/D |
| SARS-CoV-2 RBD (V483A) | + | + | N/D |
| SARS-CoV-2 RBD (K458R) | + | + | N/D |
| SARS-CoV-2 RBD (G476S) | + | + | N/D |
| SARS-CoV-2 RBD (R408I) | + | + | N/D |
| SARS-CoV-2 RBD (V503F) | + | + | N/D |
| SARS-CoV-2 RBD (A522V) | + | + | N/D |
| SARS-CoV-2 RBD (Y508H) | + | + | N/D |
| SARS-CoV-2 RBD (L452R) | + | + | N/D |
| SARS-CoV-2 RBD (A520S) | + | + | N/D |
| SARS-CoV-2 RBD (I472V) | + | + | N/D |
| SARS-CoV-2 RBD (T478I) | + | + | N/D |
| SARS-CoV-2 RBD (V341I) | + | + | N/D |
| SARS-CoV-2 RBD (F490S) | + | + | N/D |
| SARS-CoV-2 RBD (P384L) | + | + | N/D |
| SARS-CoV Spike/S1 Protein | − | | |
| MERS-CoV Spike/S1 Protein | − | | |
| HCoV-HKU1 Spike/S1 Protein | − | | |
| HCoV-NL63 Spike/S1 Protein | − | | |
| HCoV-229E Spike/S1 Protein | − | | |
| HCoV-OC43 Spike Protein | − | | |

*+: Binding; −: No Binding
**+: Inhibition. −: No inhibition
***N/D: Not Determined.

Example 3. Binding Specificity of Phage Clone #26 and αSARS-CoV-2 #26 IgG1 Antibody This example demonstrates the binding capability of phage clone #26 and an αSARS-CoV-2 IgG1 antibody based on clone #26 (i.e., clone #26 IgG1 antibody) to the S1 subunit of SARS-CoV-2 spike protein. In particular, this example establishes that antibodies derived from phage clone #26 selectively target and tightly bind the S1 subunit of SARS-CoV-2 spike protein S1.

Figure 4:
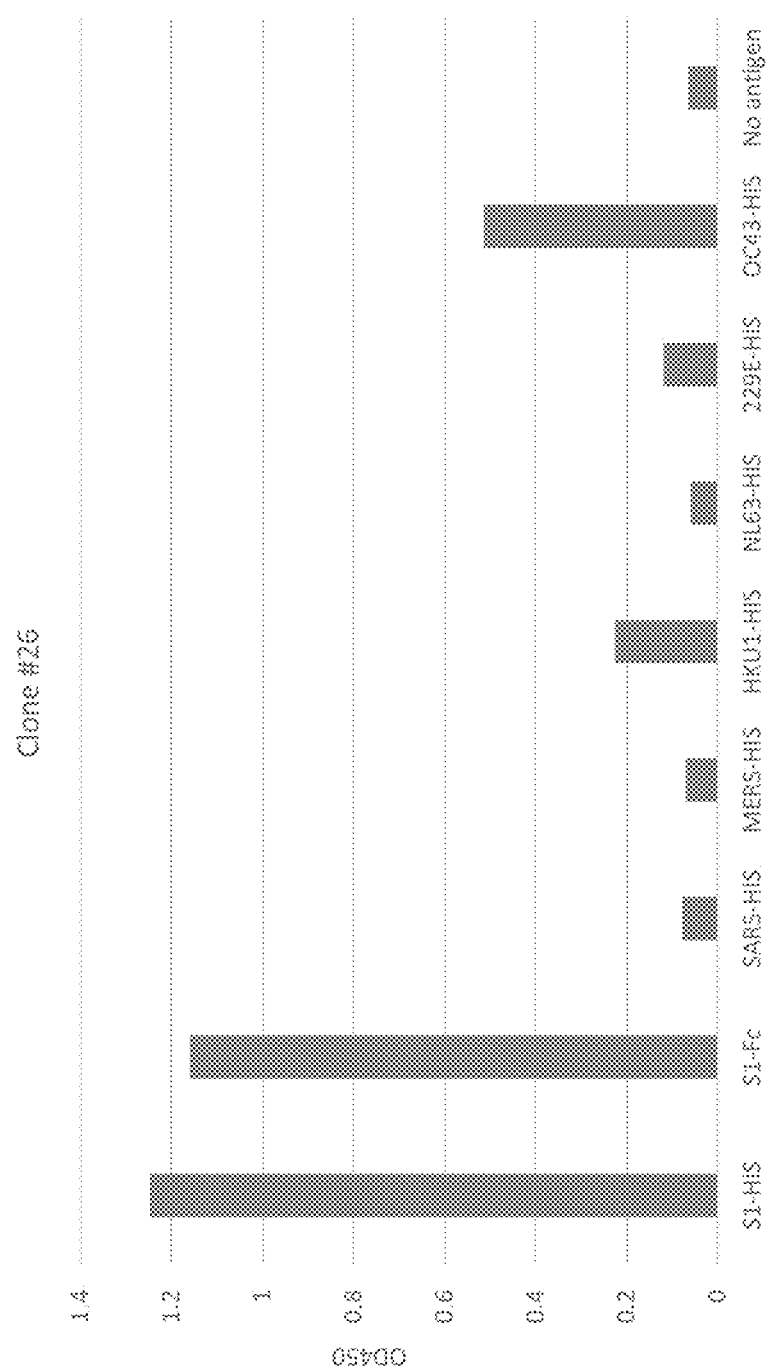
FIG. 4 shows binding of phage clone #26 to SARS-CoV-2 spike protein S1 compared to binding of other coronavirus spike proteins as measured by ELISA.

The binding ability of the phage clone #26 to various S1 proteins was determined by ELISA. A collection of S1 proteins (2 µg/mL) from different viruses were plated on a 96 well plate and incubated with phage clone #26 ($10^9$ phages were added per well in a volume of 50 µL) for 1 h at room temperature and washed in PBST. Binding of the phages was detected by staining with a mouse anti-M13 monoclonal antibody conjugated to HRP. An HRP substrate was used to detect binding of phage clone #26 to each S1 protein, and absorbance was read at 450 nm. As shown in FIG. 4, phage clone #26 binds both His-tagged (S1-HIS) and Fc-tagged SARS-CoV-2 (S1-Fc) S1 to a greater extent than the S1 proteins of other viruses, e.g., SARS-HIS, MERS-HIS, HKU1-HIS, NL63-HIS, 229E-HIS, OC43-HIS, and the no-antigen control.

Figure 5:
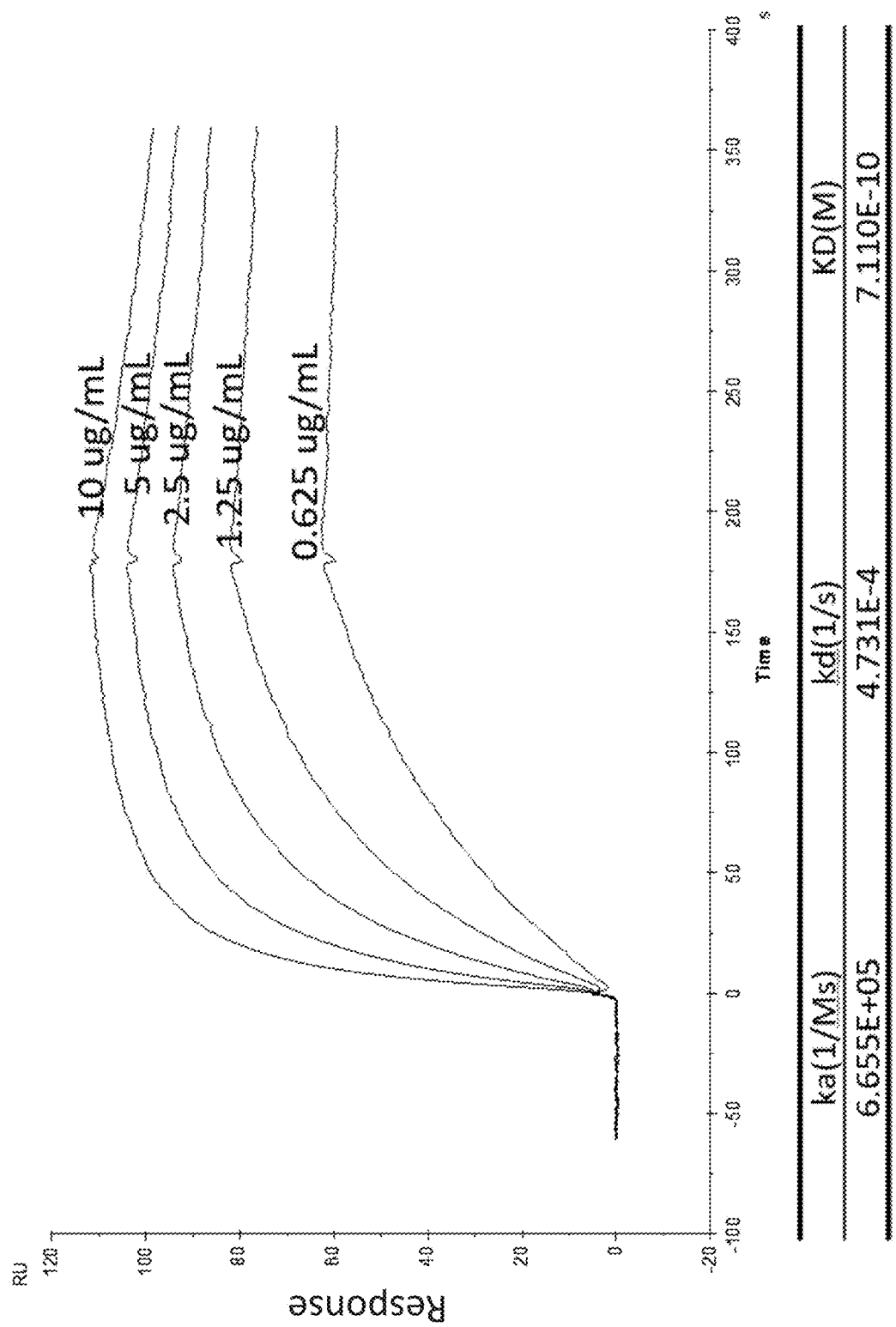
FIG. 5 shows binding kinetics of biotinylated αSARS-CoV-2-S1 #26 IgG1 antibody to SARS-CoV-2 spike protein S1 measured by surface plasmon resonance.

The binding kinetics of clone #26 IgG1 antibody were then measured by surface plasmon resonance (SPR) on a BIACORE X100 with a Sensor Chip CAP, as illustrated in FIG. 5. Biotinylated SARS-CoV-2 spike protein S1 was first loaded onto the surface of the Sensor Chip CAP. Following the loading step, clone #26 IgG1 antibody was injected onto the Sensor Chip at concentrations of 10, 5, 2.5, 1.25, and 0.625 μg/mL. The S1 protein was allowed to associate with clone #26 IgG1 antibody for 180 s and was subsequently dissociated for 180 s. FIG. 5 shows the on rate between the antibody and the spike protein S1 (i.e., ka, e.g., $k_{on}$), the off rate between the antibody and the spike protein S1 (i.e., kd, e.g., $k_{off}$), and the dissociation constant (i.e., binding affinity) between the antibody and the spike protein S1 (i.e., $K_D$=0.71 nM). This data indicates that clone #26 IgG1 antibody selectively and strongly binds SARS-CoV-2 spike protein S1 and is a potential therapeutic antibody for SARS-CoV-2.

Figure 6:
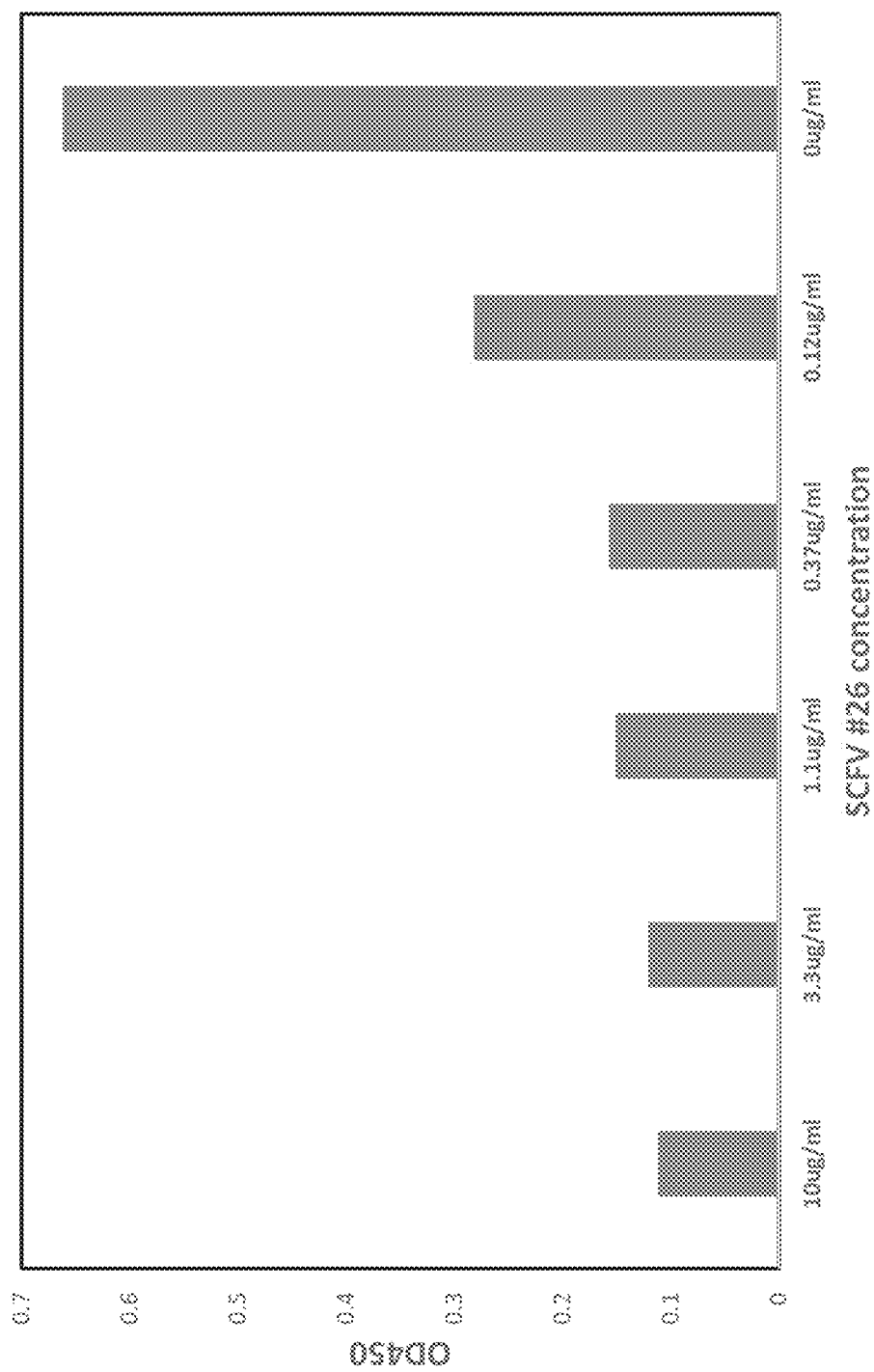
FIG. 6 shows the result of an ELISA assay using varying concentrations of clone #26 scFv to block binding of huACE2 to SARS-CoV-2 spike protein attached to plates. The result indicates that clone #26 scFv blocked the binding of huACE2 to SARS-CoV-2 spike protein S1.

High binding plates were coated with SARS-CoV-2 spike protein S1. Clone #26 scFvs were then added to the plates in various concentrations (e.g., 0 μg/mL, 0.12 m/mL, 0.37 m/mL, 1.1 m/mL, 3.3 μg/mL, and 10 μg/mL). After a 1 h incubation, huACE2-Fc was added and incubated for an additional hour. Binding of huACE2-Fc to SARS-CoV-2 spike protein S1 substrate in the presence of varying concentrations of clone #26 scFvs was detected by HRP-conjugated anti-human Fc antibodies and developed using an HRP substrate. The absorbance was measured at 450 nm and is shown in FIG. 6. As illustrated in FIG. 6, huACE2-Fc binding to SARS-CoV-2 spike protein S1 was blocked by clone #26 scFv in a dose dependent manner.

Example 4. αSARS-CoV-2-S1 #26 Murine IgG Antibody Blocked Pseudovirus Infection

Figure 7A:
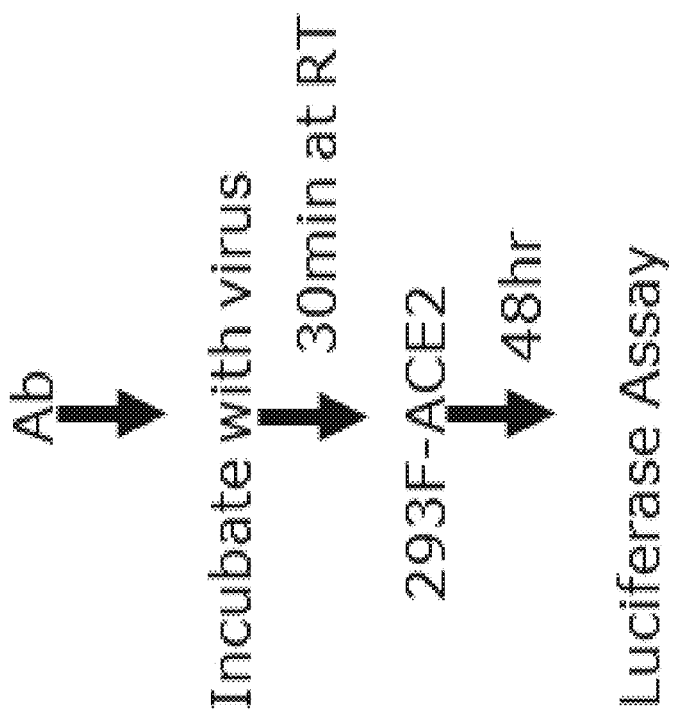
FIG. 7A shows an exemplary workflow of the assay performed in FIG. 7B.
Figure 7B:
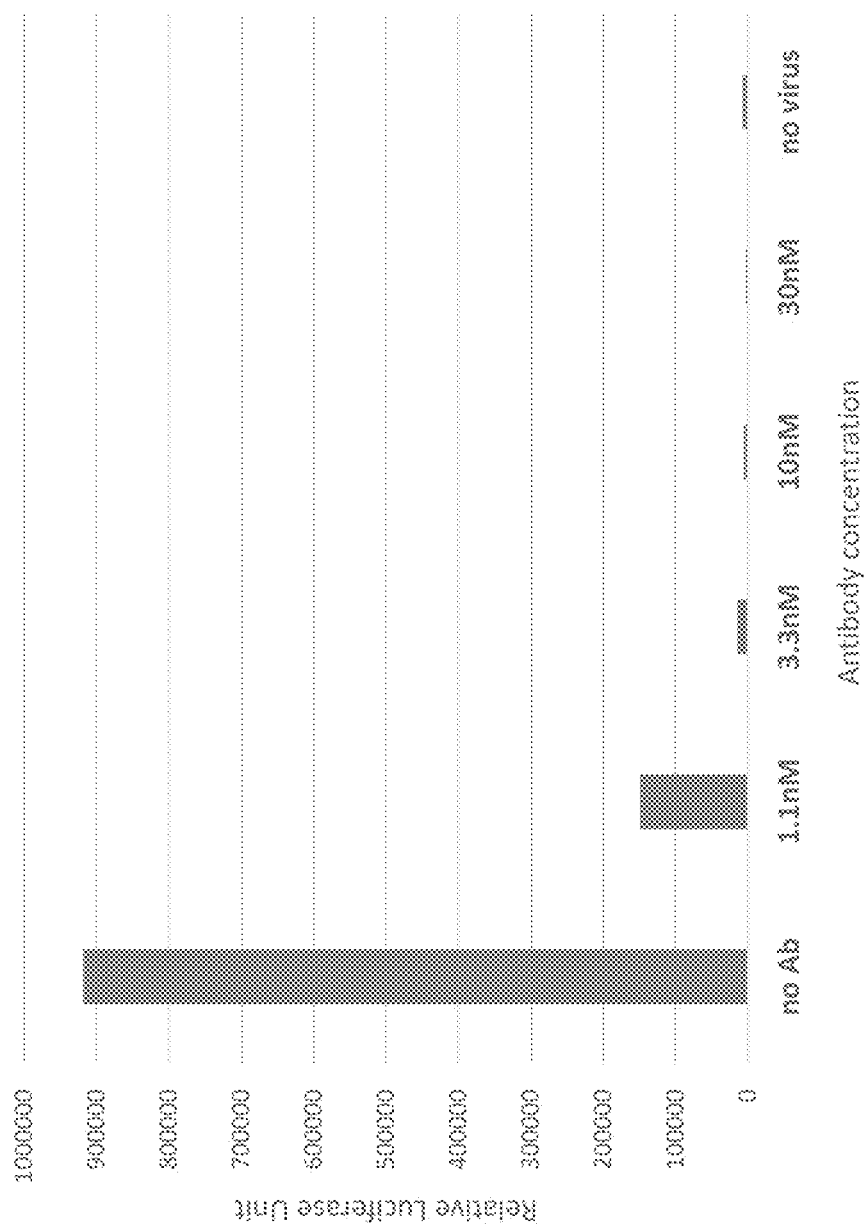
FIG. 7B shows an exemplary αSARS-CoV-2-S1 #26 murine IgG antibody blocking SARS-CoV-2 pseudovirus infection of 293F cells expressing huACE2 using a luciferase assay. The pseudotyped virus contains the CMV-driven luciferase (and GFP) reporter genes for detection of infected cells using a multiwell plate luminometer.
Figure 7C:
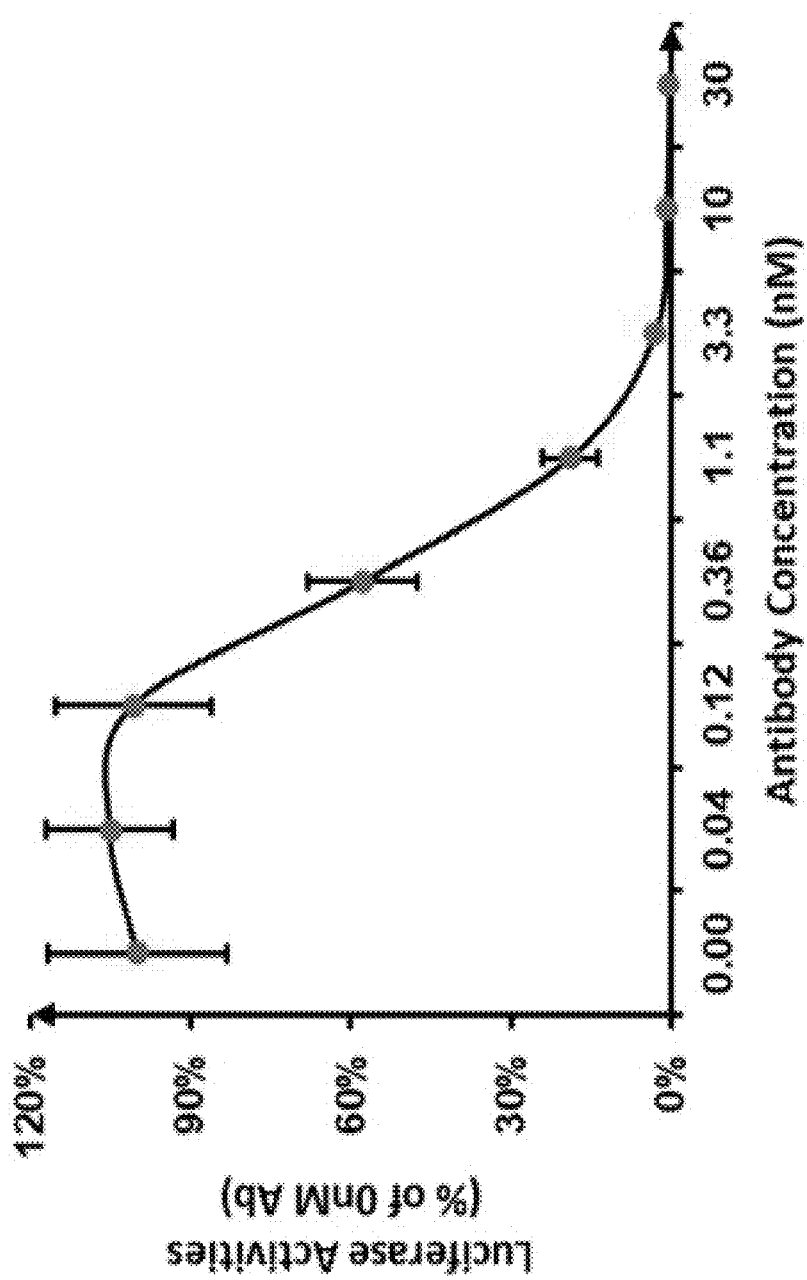
FIG. 7C shows antibody-mediated neutralization of infection by luciferase-encoding lentiviral particles pseudotyped with spike proteins of SARS-CoV-2 as in FIG. 7B. Pseudotyped virus pre-incubated with antibodies at indicated concentrations were used to infect 293F cells overexpressing human ACE2.
Figure 7D:
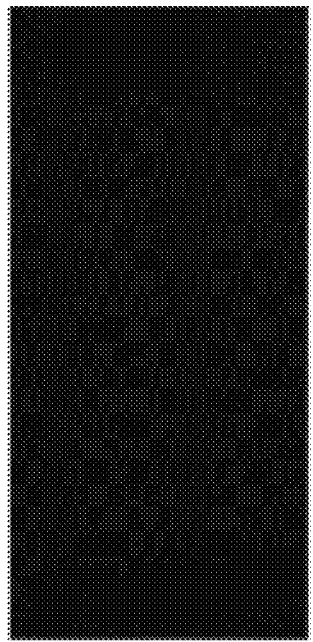
FIG. 7D shows exemplary GFP fluorescent images (upper panels) and light microscopy images (lower panels) of αSARS-CoV-2-S1 #26 murine IgG antibody blocking SARS-CoV-2 pseudovirus infection using fluorescence microscopy and a luciferase assay. Pseudotyped virus pre-incubated with no antibody or 10 nM of antibody were used to infect 293F cells overexpressing human ACE2. The upper panels show GFP fluorescent images of the transfected cells; the same cells using light microscopy shown below.
Figure 7D:
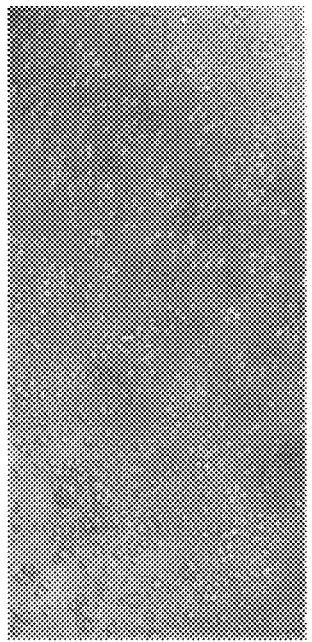
Figure 7D:
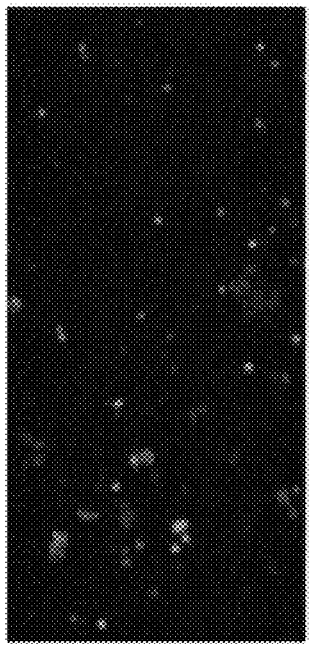
Figure 7D:
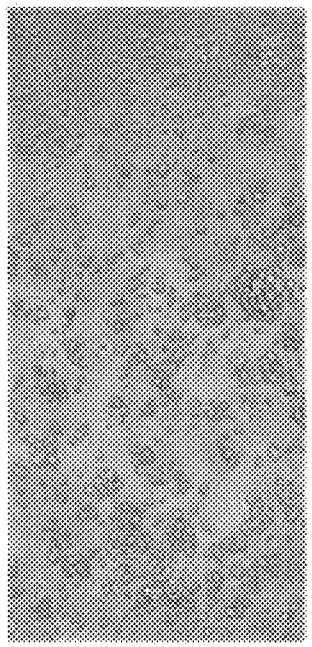

This example demonstrates clone #26 murine IgG antibody blocking of SARS-CoV-2 pseudovirus infection in HEK293F cells expressing human ACE2. FIG. 7A provides an outline of the assay performed herein.

Full-length mouse anti-human spike protein monospecific IgG antibodies were constructed using heavy chain and light chain variable region sequences of clone #26 for VH and VL to fuse to mouse IgG1 constant region and Fc region sequences using a cloning plasmid expressing the Fc region of murine IgG1 heavy chain (SEQ ID NO: 133) and a plasmid expressing the IgG light chain (SEQ ID NO: 134).

Briefly, clone #26 murine IgG antibody was incubated with SARS-CoV-2 spike-pseudotyped lentivirus. The pseudotyped virus contained the CMV-driven luciferase and GFP reporter genes separated by a P2A self-cleaving peptide. Following a 30 min incubation of clone #26 mIgG antibody with SARS-CoV-2 spike-pseudotyped lentivirus, the lentivirus was added to HEK293F cells expressing human ACE2. Cells were cultured in 5% $CO_2$ at 37° C. for 48 h. The degree of cellular infection with the pseudotyped virus was determined by detecting the luciferase level of the infected cells (Promega Luciferase Assay) or by detecting GFP-positive cells using fluorescence microscopy. As demonstrated in FIGS. 7B-7D, 10 nM of clone #26 murine IgG antibody is a sufficient antibody concentration to completely block the SARS-CoV-2 pseudovirus infection.

Example 5. Characterization of αSARS-CoV-2-S1 #26 Murine IgG Antibody in a Transgenic Mouse Model of SARS-CoV-2 Infection This example demonstrates clone #26 murine IgG antibody blocking of SARS-CoV-2 pseudovirus infection in a transgenic mouse model. Female transgenic mice (K18-ACE2, full-length huACE2 under the control of the keratin-18 promoter) aged 4-6 weeks were used for this assay. Clone #26 mIgG antibody was delivered to the transgenic mice through nasal administration, applying 100 μg of antibody in 40 μL of PBS buffer, 20 μL in each nostril. SARS-CoV-2 (isolate 2019-nCoV, i.e., WIV4) spike pseudotyped lentivirus was delivered to mice through nasal administration, 30 mins following administration of clone #26 mIgG antibody. Bioluminescence imaging was used to measure the degree of infection on Day 3, 5, and 7, after nasal administration.

Figure 8:
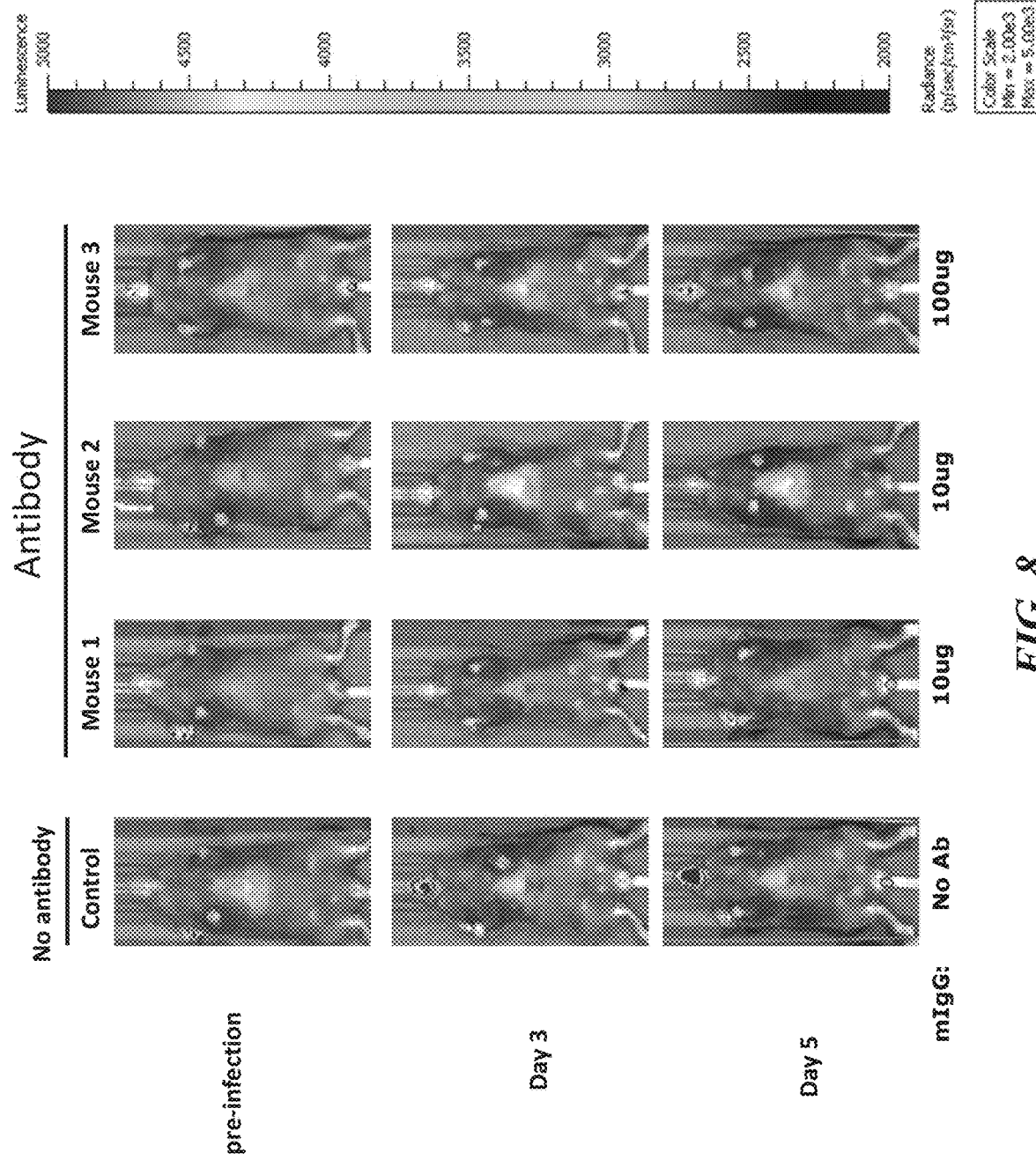
FIG. 8 shows bioluminescent imaging of huACE2 transgenic mice infected with luciferase-expressing SARS-CoV-2 pseudovirus, with or without prior treatment of an exemplary αSARS-CoV-2-S1 #26 murine IgG antibody. The result indicates that the αSARS-CoV-2-S1 #26 murine IgG antibody blocked SARS-CoV-2 pseudovirus infection.

FIG. 8 shows lower bioluminescence in mice treated with varying concentrations of clone #26 mIgG antibody compared to corresponding control mice not treated with an antibody, demonstrating blocking of viral infection by clone #26 mIgG antibody. Lower bioluminescence in mice treated with clone #26 mIgG antibody compared to control mice was observed on both Day 3 and Day 5 following nasal administration of the pseudoviruses. Therefore, mice treated with clone #26 mIgG antibody have lower rates of SARS-CoV-2 pseudovirus infection over the evaluated time interval compared to untreated control mice.

Example 6. Design and Expression of Chimeric Proteins Comprising Mucoadhesive Peptide Fragments This example demonstrates the design and expression of exemplary chimeric proteins comprising mucoadhesive peptides. In particular, this example demonstrates the design and expression of chimeric proteins each comprising an αSARS-CoV-2 antibody (e.g., clone #26) moiety (e.g., full length human IgG or scFv) and a polylysine peptide of varying lengths.

In some examples, the full-length clone #26 human IgG antibody was fused to a polylysine peptide having 6-30 contiguous lysine polypeptides. In some examples, the full-length clone #26 human IgG antibody was fused to a polylysine peptide having 6-30 contiguous lysine polypeptides. The polylysine peptide was fused to the C-terminus of the heavy chain of the IgG1 antibody via a flexible peptide linker (GGGGS; SEQ ID NO: 95). The polylysine peptide is a mucoadhesive peptide that facilitates attachment of the exemplary chimeric protein to mucosa. For example, #26-hIgG-6 Lys (i.e., #26-hIgG-6K) has a polylysine peptide with 6 lysines. Each #26-hIgG-6K molecule has four polypeptide chains, including two copies of SEQ ID NO: 96 and two copies of SEQ ID NO: 97. Exemplary chimeric protein sequences comprising mucoadhesive peptides are listed in Table 11.

TABLE 11

Exemplary anti-S1 antibody and chimeric proteins

| Protein | Number of lysines | Molecular Weight (KDa) |
|---|---|---|
| #26-hIgG | 0 | ~150 |
| #26-hIgG-6 Lys (#26-hIgG-6K; #26-M1) | 6 | ~151 |
| #26-hIgG-12 Lys (#26-hIgG-12K; #26-M2) | 12 | ~153 |
| #26-hIgG-18 Lys (#26-hIgG-18K; #26-M3) | 18 | ~154.6 |
| #26-hIgG-24 Lys (#26-hIgG-24K; #26-M4) | 24 | ~156 |
| #26-hIgG-30 Lys (#26-hIgG-30K; #26-M5) | 30 | ~157.2 |

26-hIgG-6K heavy chain (heavy chain of Clone #26 hIgG antibody fused to 6 lysines)

SEQ ID NO: 96

QVQLVQSGAEVKKPGASVKVSCKASGYTFTSYGISWVRQAPGQGLEWMGW

ISAYNGNTNYAQKLQGRVTMTTDTSTSTAYMELRSLRSDDTAVYYCARGY

-continued

YGDLDPWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGKGGG

GSKKKKKK

26-hIgG-6K (light chain of Clone #26 hIgG antibody)
SEQ ID NO: 97
QAVLTQAPSASGTLGQQVTISCSGTTSNIGRNTVNWYQHLPGTAPKLLIF

VSNQRPSGVPDRFSGSKSGTSASLVISGLQSEDEADYYCGAWDDSLDGML

FGGGTKLTVLGQPKANPTVTLFPPSSEELQANKATLVCLISDFYPGAVTV

AWKADGSPVKAGVETTKPSKQSNNKYAASSYLSLTPEQWKSHRSYSCQVT

HEGSTVEKTVAPTECS

Similarly, scFv-polylysine fusion proteins based on clone #26 hIgG antibody and a polylysine peptide are designed. As an example, an scFv-polylysine fusion protein comprises a clone #26 scFv fused to a polylysine peptide with 6 lysine residues at the C-terminus of the scFv (SEQ ID NO: 98). In additional examples, scFv-polylysine fusion proteins comprise a clone #26 scFv comprise a polylysine peptide having 12, 18, 24 or 30 lysine residues, respectively.

scFv based on Clone #26 with 6 lysines
SEQ ID NO: 98
QAVLTQAPSASGTLGQQVTISCSGTTSNIGRNTVNWYQHLPGTAPKLLIF

VSNQRPSGVPDRFSGSKSGTSASLVISGLQSEDEADYYCGAWDDSLDGML

FGGGTKLTVLGSRGGGSGGGGSGGGGSLEMAQVQLVQSGAEVKKPGASV

KVSCKASGYTFTSYGISWVRQAPGQGLEWMGWISAYNGNTNYAQKLQGRV

TMTTDTSTSTAYMELRSLRSDDTAVYYCARGYYGDLDPWGQGTLVTVSST

SGGGGSKKKKKK

Chimeric proteins based on clone #26 hIgG1 antibody and a polylysine peptide (e.g., #26-hIgG1-6K and #26-hIgG1-30K) were expressed and DNA constructs that encode human antibody heavy chain and light chain were transfected into host 293F cells. After 7 days of culture at 37° C., culture medium was harvested, and the antibodies were isolated or purified from the culture using a protein A column (HITRAP® Protein A HP column). The purification production yield varied based on the length of the polylysine peptide, as shown in Table 12.

TABLE 12

Expression of exemplary anti-S1 antibody and chimeric proteins

| Protein | Purification volume (mL) | Final yield (mg) |
|---|---|---|
| #26-hIgG1 | 60 | 7.2 |
| #26-hIgG1-6 Lys (#26-hIgG1-6K) | 60 | 5.87 |
| #26-26H-hIgG1-30 Lys (#26-hIgG1-30K) | 60 | 0.39 |

Exemplary chimeric proteins comprising an αSARS-CoV-2 antibody (e.g., clone #26) moiety (e.g., full length human IgG or scFv) and a polyhistidine peptide of varying lengths (e.g., 6, 12, 18, 24 or 30 histidines) are designed and expressed using the same methods as described in this example.

Example 7. Non-Specific Cell Surface Binding by Exemplary Chimeric Proteins

This example demonstrates that an exemplary chimeric protein based on clone #26 hIgG1 antibody fused to polylysine peptides as described in Example 6 (i.e., #26-hIgG1-30K), is able to nonspecifically bind to the 293F cell surface. In particular, this example demonstrates that #26-hIgG1-30K is able to block SARS-CoV-2 spike protein S1 binding to huACE2 on the cell surface.

Figure 9:
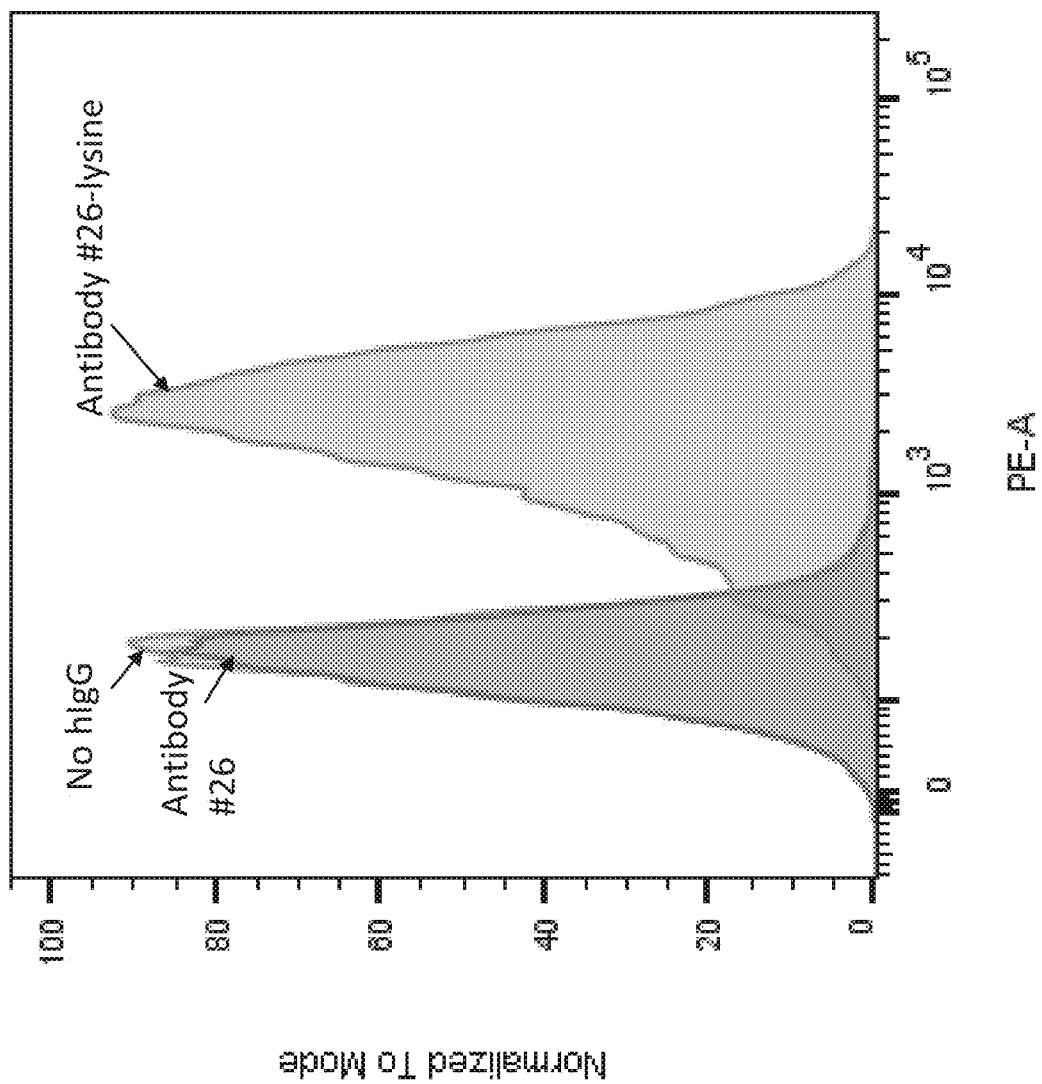
FIG. 9 shows nonspecific binding of an exemplary chimeric protein αSARS-CoV-2-S1 #26-hIgG1-6K to the surface of a 293F-ACE2 cell by flow cytometry using human IgG and PE-conjugated goat anti-human Fc for detection.

Human IgG (30 nM) was incubated with $2 \times 10^5$ 293 F-ACE2 cells for 1 h at room temperature (RT). Goat anti-human IgG Fc conjugated with PE were added and incubated for another 30 min at RT. Cells were washed once with FACS buffer (2% FBS, 2 mM EDTA in 1×DPBS), and binding of #26-hIgG1-30K or antibodies was assessed by flow cytometry. As seen in FIG. 9, clone #26 hIgG1 antibody (i.e., antibody #26) and no hIgG control (i.e., no hIgG) were unable to bind 293F-ACE2 cell. In contrast, #26-hIgG1-30K (i.e., antibody #26-lysine) was able to nonspecifically bind to the cell surface.

Nonspecific binding to the 293F cell surface by exemplary chimeric proteins based on clone #26 hIgG1 antibody fused to polyhistidine peptides of varying lengths (e.g., 12 or 30 histidines) is tested using the same method as described in this example. #26-hIgG1-12H and #26-hIgG1-30H are able to nonspecifically bind to the 293F cell surface. In addition, #26-hIgG1-12H and #26-hIgG1-30H are able to block SARS-CoV-2 spike protein S1 binding to huACE2 on the cell surface.

Example 8. Exemplary Chimeric Proteins Blocked SARS-CoV-2 Binding to huACE2

Figure 10:
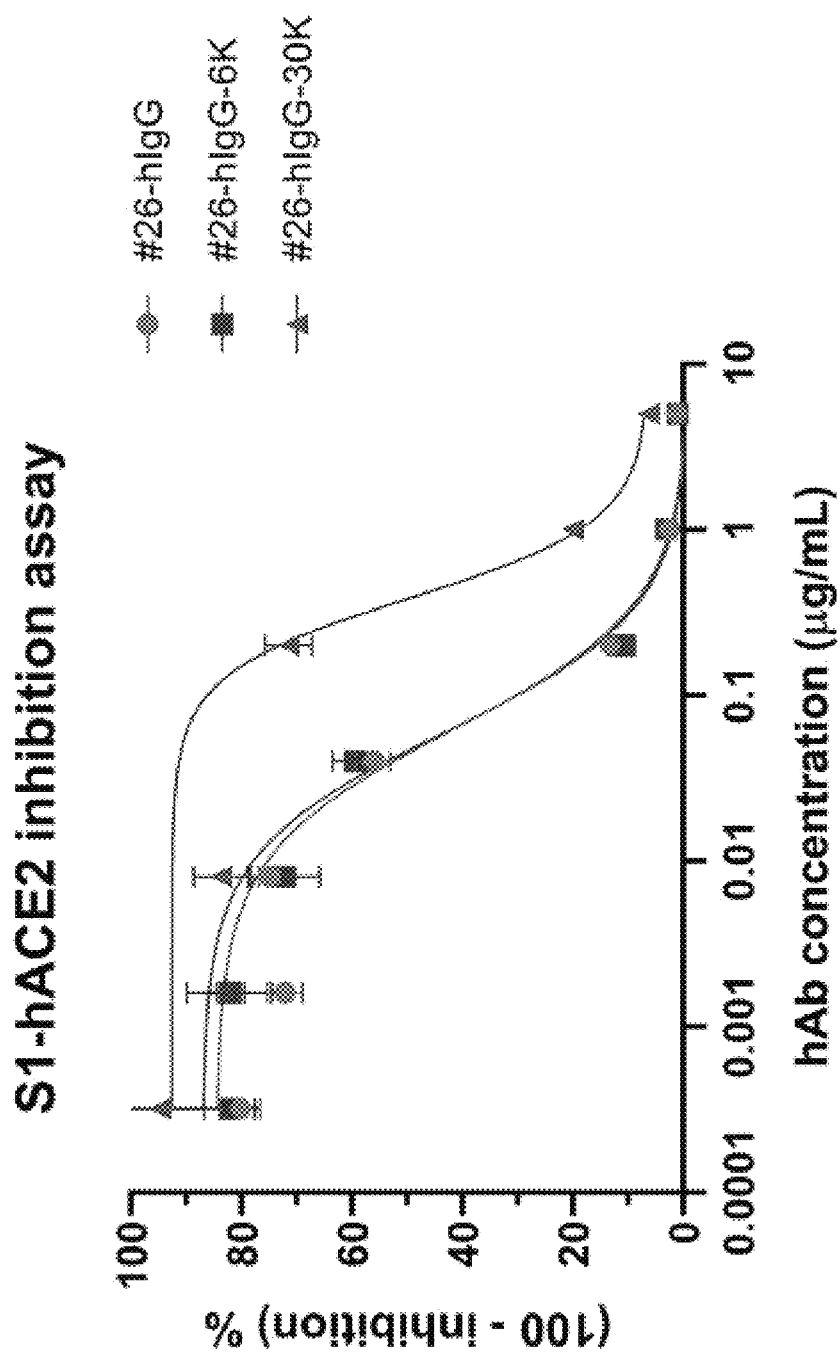
FIG. 10 shows that an exemplary chimeric protein αSARS-CoV-2-S1 #26-hIgG1-6K blocked His-tagged SARS-CoV-2 S1's binding to huACE2 attached to plates, measured by ELISA using HRP-conjugated anti-His tag antibodies.

ELISA plates were coated with 2 µg/mL huACE2-hFc protein in 100 µL PBS, at 4° C. overnight. The plates were then blocked with 3% blocking buffer at 4° C. overnight. Serial dilutions of #26-hIgG1-6K and #26-hIgG1-30K (i.e., #26-hIgG-6K and #26-hIgG-30K), or antibody #26 without a polylysine tail (i.e., #26-hIgG), were incubated with SARS-CoV-2-His (2 µg/mL) for 1 h at RT. The incubated mixtures were subsequently added to an ELISA plate, developed for 1 h, and the plates were washed with PBST three times. HRP-Anti-HIS was added, incubated for 1 h at RT, and then washed with PBST three times. TMB substrate (100 µL) was added and the reaction was quenched with 100 µL of 1-2 M H2SO4. The absorbance was measured at 450 nm and is shown in FIG. 10. As illustrated in FIG. 10, #26-hIgG, #26-hIgG-6K, and #26-hIgG-30K all blocked SARS-CoV-2 S1 binding to huACE2 in a dose dependent manner.

The ability to block SARS-CoV-2 binding to huACE2-hFc protein by exemplary chimeric proteins based on clone #26 hIgG1 antibody fused to polyhistidine peptides of varying lengths (e.g., 6, 12, or 30 histidines) is tested using the same method as described in this example. #26-hIgG-6H, #26-hIgG-12H, and #26-hIgG-30K all block SARS-CoV-2 S1 binding to huACE2.

Example 9. Exemplary Chimeric Proteins Based on αSARS-CoV-2 #26 hIgG1 Antibody Blocked SARS-CoV-2 Pseudovirus Infection This example demonstrates #26-hIgG1-6K and #26-hIgG1-30K blocking SARS-CoV-2 infection. In particular, this example demonstrates that #26-hIgG1-6K and #26-hIgG-30K are able to block SARS-CoV-2 pseudovirus infection in 293F-ACE2 cells (HEK-293F cells expressing human ACE2). An outline of the experiment described herein is shown in FIG. 7A.

Figure 11:
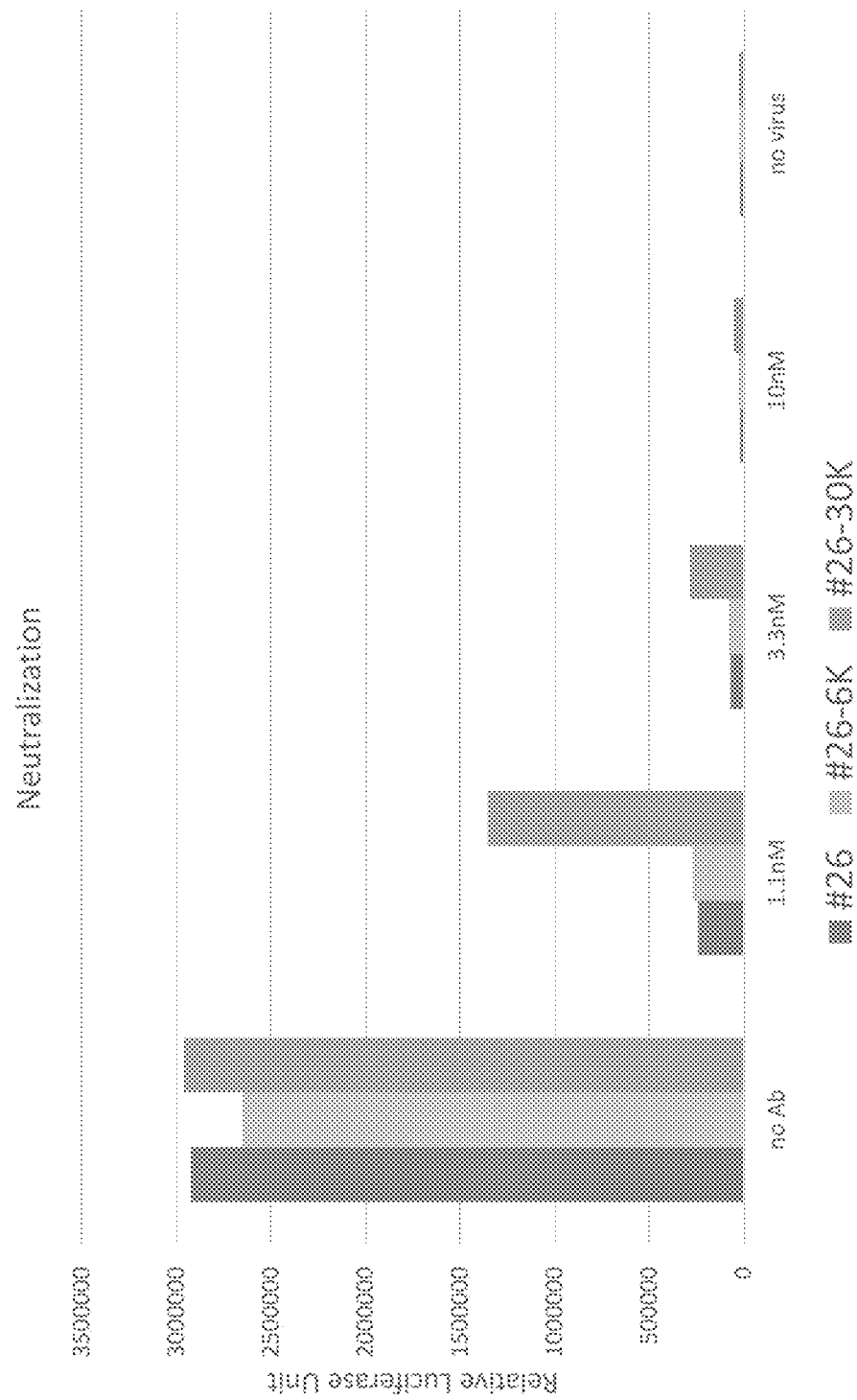
FIG. 11 shows that an exemplary chimeric protein αSARS-CoV-2-S1 #26-hIgG1-6K blocked SARS-CoV-2 pseudovirus infection in vitro in an assay measuring the level of pseudovirus expressing a CMV-driven luciferase gene in 293F cells.

Briefly, #26-hIgG1-6K and #26-hIgG1-30K were purified as described. Varying concentrations of #26-hIgG1-6K and #26-hIgG1-30K (i.e., #26-6K and #26-30K, respectively), or clone #26 hIgG1 antibody without a polylysine peptide tail (i.e., #26), were incubated with SARS-CoV-2 spike-pseudotyped lentivirus containing the CMV-driven luciferase and GFP reporter genes separated by a P2A self-cleaving peptide. Following a 30 min incubation, the SARS-CoV-2 pseudovirus was added to HEK-293F cells expressing human ACE2. Cells were cultured in 5% $CO_2$ at 37° C. for 48 h. The degree of cellular infection with the pseudotyped virus was determined by detecting the luciferase level of the infected cells (Promega Luciferase Assay). As demonstrated in FIG. 11, the SARS CoV-2 pseudovirus infection was effectively blocked by all three constructs of clone #26 hIgG1 antibody chimeric protein with or without a polylysine peptide tail in a dose dependent manner.

Blocking of SARS-CoV-2 pseudovirus infection by exemplary chimeric proteins based on clone #26 hIgG1 antibody fused to polyhistidine peptides of varying lengths (e.g., 6, 12, or 30 histidines) is tested using the same method as described in this example. #26-hIgG-6H, #26-hIgG-12H, and #26-hIgG-30K all block SARS-CoV-2 pseudovirus infection.

Example 10. Exemplary Chimeric Proteins Based on αSARS-CoV-2 #26 hIgG1 Antibody Blocked SARS-CoV-2 Pseudovirus Infection in a Transgenic Mouse Model This example demonstrates how an exemplary chimeric protein based on clone #26 hIgG1 antibody and a mucoadhesive polylysine peptide of varying length may prevent SARS-CoV-2 pseudovirus infection in a transgenic mouse model. In particular, this example demonstrates #26-hIgG1-6K and #26-hIgG1-30K blocking SARS-CoV-2 infection in a transgenic mouse model.

Female transgenic mice (K18-ACE2, full-length huACE2 under the control of the keratin-18 promoter) aged 4-6 weeks were used for this assay. An exemplary chimeric protein based on clone #26 hIgG1 antibody and a mucoadhesive polylysine peptide was expressed and purified as described. In some examples, the positively charged mucoadhesive polylysine peptide may be 6-30 lysines in length. In some examples, the exemplary chimeric protein is #26-hIgG1-6K or #26-hIgG1-30K. In some examples, the exemplary chimeric protein is #26-hIgG1-6K, #26-hIgG1-12K, #26-hIgG1-18K, #26-hIgG1-24K, or #26-hIgG1-30K, as described in Example 6. In some examples, the exemplary chimeric protein is a scFv chimeric protein. In some examples, the chimeric protein comprises, from the N-terminus to the C-terminus: a scFv (e.g., clone #26 scFv), an optional peptide linker, a mucoadhesive peptide fragment, another optional peptide linker, and a 6×His tag. In some examples, the chimeric protein comprises, from the N-terminus to the C-terminus: a scFv (e.g., clone #26 scFv), an optional peptide linker, and a mucoadhesive peptide fragment. In some examples, the mucoadhesive peptide fragment may be of any composition and length described herein.

Briefly, #26-hIgG1-6K or #26-hIgG1-30K were delivered to the transgenic mice through nasal administration, at a concentration of 20 μL/nostril. The chimeric protein was provided in a citrate buffered saline formulation, with a stabilizing agent, viscosity enhancing agent, surfactant and preservative (e.g., 5 mM citrate buffer, pH 6.5, 100 mM NaCl, 0.1% methionine, 0.02% polysorbate 80, 0.1% potassium sorbate). SARS-CoV-2 (isolate 2019-nCoV, i.e., WIV4) spike pseudotyped lentivirus was delivered to mice through nasal administration, 2-24 h following administration of #26-hIgG-6K or #26-hIgG-30K (e.g., the virus was delivered 2 h, 4 h, 6 h, and 24 h following #26-hIgG-6K or #26-hIgG-30 administration).

Figure 12:
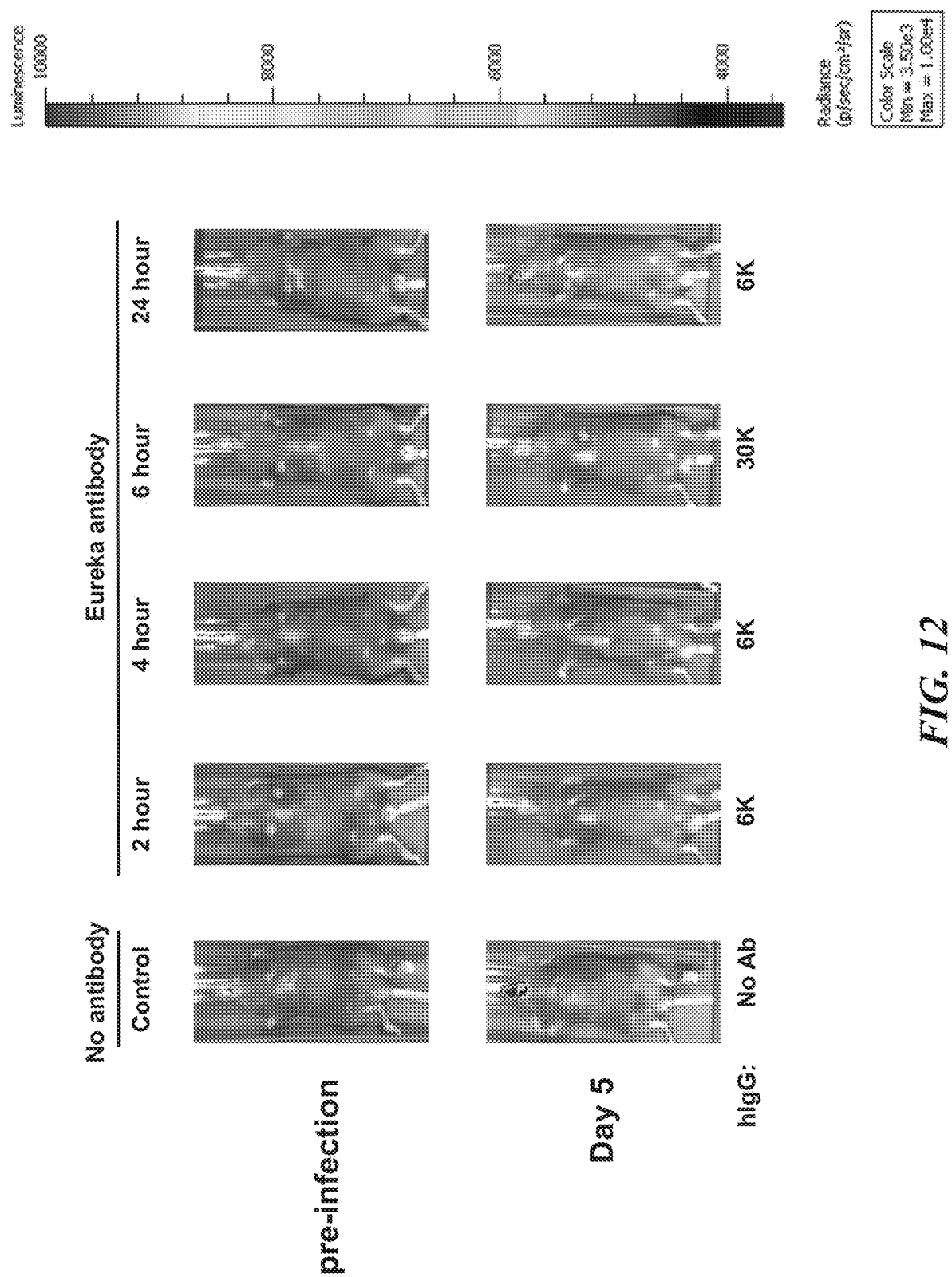
FIG. 12 shows that exemplary chimeric proteins αSARS-CoV-2-S1 #26-hIgG1-6K and SARS-CoV-2-S1 #26-hIgG1-30K blocked SARS-CoV-2 pseudovirus infection in a transgenic mouse model.

As shown in FIG. 12, bioluminescence imaging was used to measure the degree of infection on Day 5 after nasal administration of the virus. Mice administered with #26-hIgG1-6K or #26-hIgG1-30 have decreased bioluminescence, and a lower degree of SARS-CoV-2 pseudovirus infection, compared to untreated control mice. Exemplary chimeric proteins #26-hIgG1-6K or #26-hIgG1-30 may therefore be effective in preventing SARS-CoV-2 viral infection through the nasal mucosa in mice. It will be appreciated that exemplary chimeric proteins #26-hIgG1-6K, #26-hIgG1-12K, #26-hIgG1-18K, #26-hIgG-24K, or #26-hIgG1-30K, will demonstrate similar blocking of SARS-CoV-2 viral infection through the nasal mucosa in mice.

The ability to block SARS-CoV-2 pseudovirus infection in a transgenic mouse model by exemplary chimeric proteins based on clone #26 hIgG1 antibody fused to polyhistidine peptides of varying lengths (e.g., 6, 12, or 30 histidines) is tested using the same method as described in this example. #26-hIgG-6H, #26-hIgG-12H, and #26-hIgG-30K all block SARS-CoV-2 pseudovirus infection in the transgenic mouse model.

Example 11. Characterization of Lysine-Modified αSARS-CoV-2 #26 hIgG1 Antibodies This example demonstrates that αSARS-CoV-2 #26 hIgG1 antibodies modified with different numbers of lysine residues in the Fc region (e.g., lysine tail moiety), have increased binding to mucin compared to unmodified αSARS-CoV-2 #26 hIgG1 antibody, without disrupting binding to SARS-CoV-2 pseudovirus.

Various lysine-modified forms of αSARS-CoV-2 #26 hIgG antibody as described in Example 6 were tested for their ability to bind mucin. 96-well plates were coated with 50 μg/mL mucin (Sigma, M3895) for 2 hr at room temperature. The plates were blocked with 3% BSA overnight at 4° C. 5 μg/mL antibodies in 25 mM HEPES (pH6.5) were added to the plates and incubated for 1 h at room temperature. After a wash with washing buffer (25 mM HEPES, 50 nM NaCl, pH6.5), plates were stained with HRP-conjugated goat anti human IgG and developed using 3,3',5,5'-Tetramethylbenzidine (TMB). Absorbance at an optical density at 450 nm (OD450) was measured.

Figure 13:
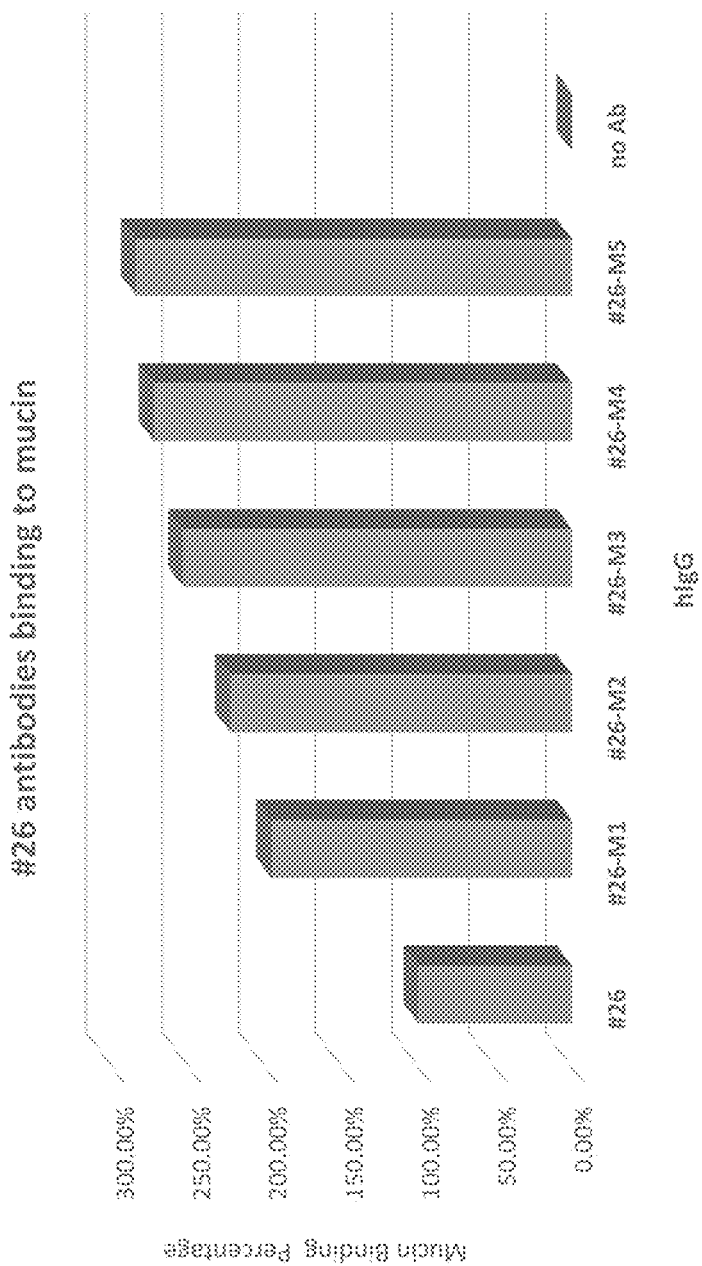
FIG. 13 shows that modification of αSARS-CoV-2-S1 #26-hIgG1 antibodies with polylysine peptides increased binding to mucin attached to plates and detected with HRP-conjugated goat anti-human IgG.

As shown in FIG. 13, the modifications significantly increased binding to mucin in vitro compared to unmodified αSARS-CoV-2 #26 hIgG1. Mucin glycoproteins produced by mucus-producing cells in the epithelium or submucosal glands are the major macromolecular constituent of mucus.

Binding to mucin can potentially extend the retention time of an antibody in the mucus of the respiratory tract.

The lysine-modified αSARS-CoV-2 #26 hIgG antibodies were also tested for their ability to neutralize SARS-CoV-2 pseudovirus infection. Virus neutralization assays are usually performed with antibodies present in solution. However, such assays are not suitable for effectively evaluating the antibody binding to mucin-bearing cells in blocking viral infection. An assay was developed to evaluate the effect of direct antibody binding to the cell surface on SARS-CoV-2 pseudovirus infection. Briefly, pseudovirus was generated employing an pCDH lentivirial vector that encodes luciferase and GFP genes, and pseudotyped with SARS-CoV-2 spike protein. To assess αSARS-CoV-2-S1 #26 hIgG1 neutralization, pseudovirus was pre-incubated with varying concentrations of αSARS-CoV-2-S1 #26 hIgG1 antibody for 1 hour at room temperature before adding to 293F cells expressing human ACE2. To assess modified αSARS-CoV-2-S1 #26 hIgG1 antibodies, 293F cells expressing human ACE2 were pre-incubated with modified antibodies for 30 min at room temperature followed by removing the supernatant, and pseudovirus was then added to the cells. 48 hours after transduction, infection was determined by detecting luciferase levels in infected cells using a Promega Luciferase Assay. The infected 293F cells were also imaged for GFP using fluorescence microscopy.

Figure 14:
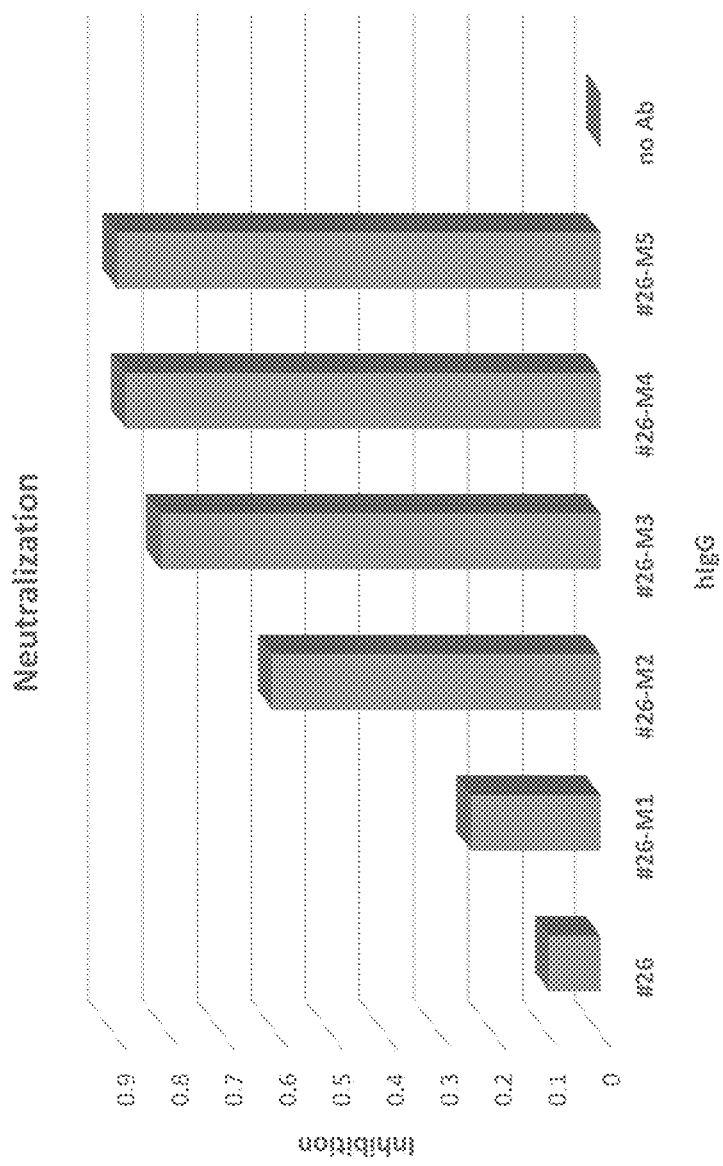
FIG. 14 shows that modification of αSARS-CoV-2-S1 #26-hIgG1 antibodies with polylysine peptides enhanced neutralization of SARS-CoV-2 pseudovirus infection of 293F cells, measured by the antibodies' effect on pseudoviral luciferase activity.

As shown in FIG. 14, all lysine-modified αSARS-CoV-2 #26 hIgG1 antibodies, with enhanced mucin binding affinity, showed an increased ability to neutralize SARS-CoV-2 pseudovirus infection, which correlated well with the increased binding affinity to mucin.

Figure 15:
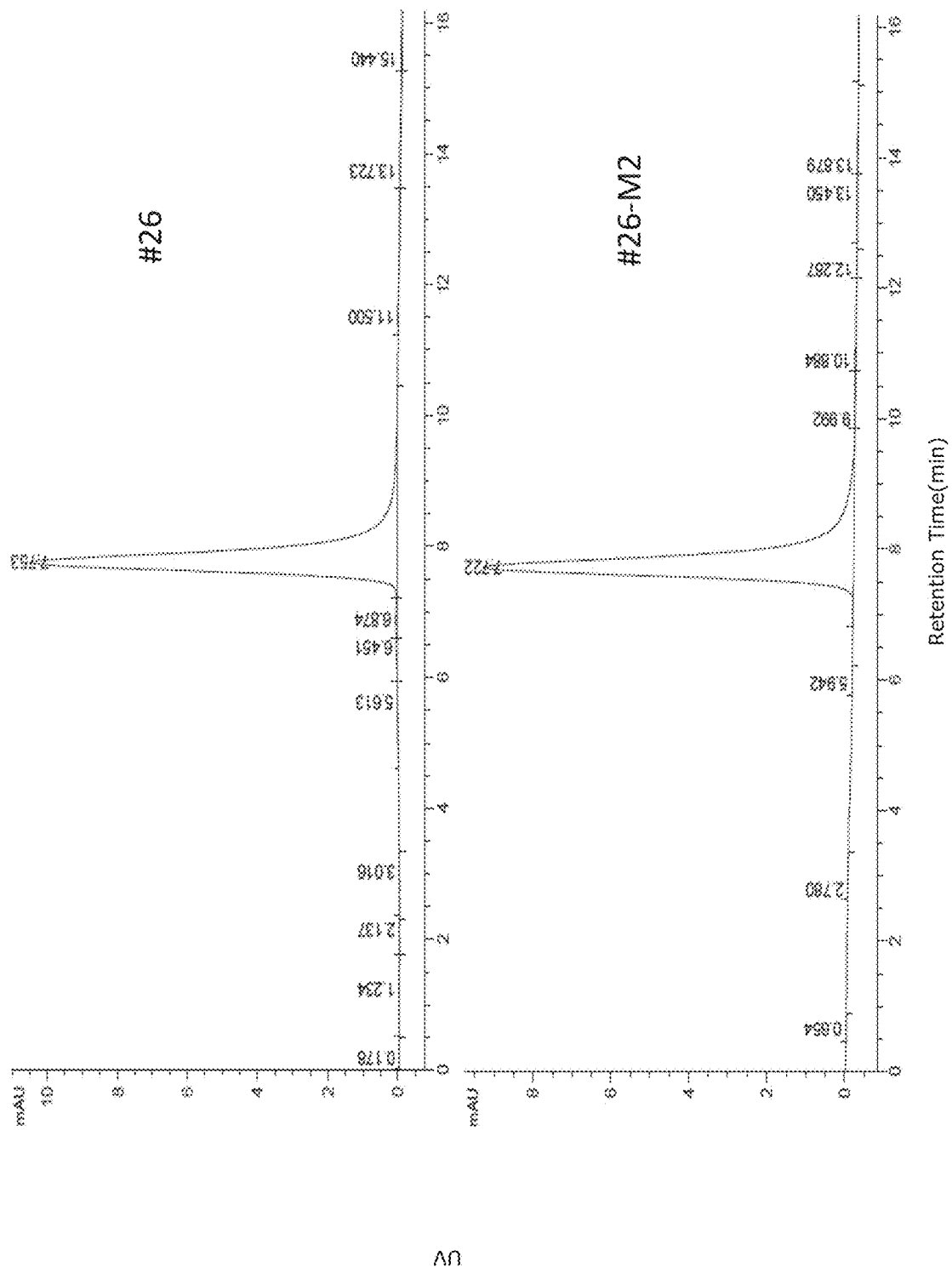
FIG. 15 shows that αSARS-CoV-2-S1 #26-M2 hIgG1 (#26-12K) maintained the same monomeric configuration as compared to αSARS-CoV-2-S1 #26-hIgG1, indicated by the same elution profile using HPLC size exclusion chromatography.

It is important to note that the modified αSARS-CoV-2 #26-M2 (i.e., #26-12K) hIgG1 antibody maintained the same monomeric form as the unmodified αSARS-CoV-2 #26 hIgG1 antibody (FIG. 15), as determined by HPLC size exclusion chromatography. Briefly, 5 µL of 1 µg/µL antibody in PBS was loaded onto a Waters)(Bridge protein BEH 200A SEC column, 3.5 µm 7.2×300 mm on an Agilent 1260 Infinity HPLC system. The antibody was eluted using D-PBS buffer, pH 7.0 at a flow rate of 0.5 mL/min. A UV reading of the elution flow was monitored.

Figure 16:
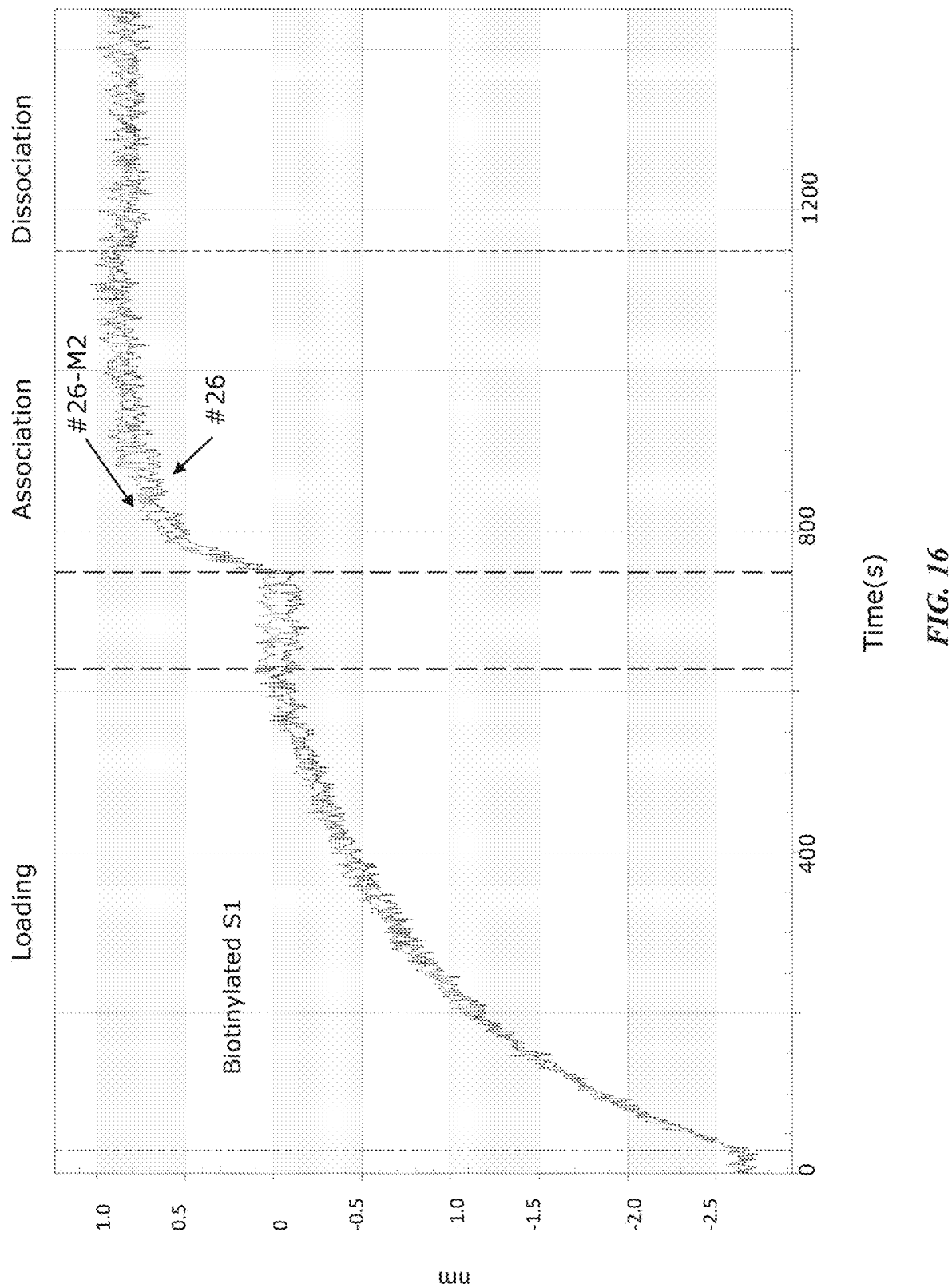
FIG. 16 shows that αSARS-CoV-2-S1 #26-M2 hIgG1 had the same binding affinity to the S1 spike protein of SARS-CoV-2 as compared to αSARS-CoV-2-S1 #26-hIgG1. A ForteBio Octet system was used to measure binding kinetics.
Figure 17:
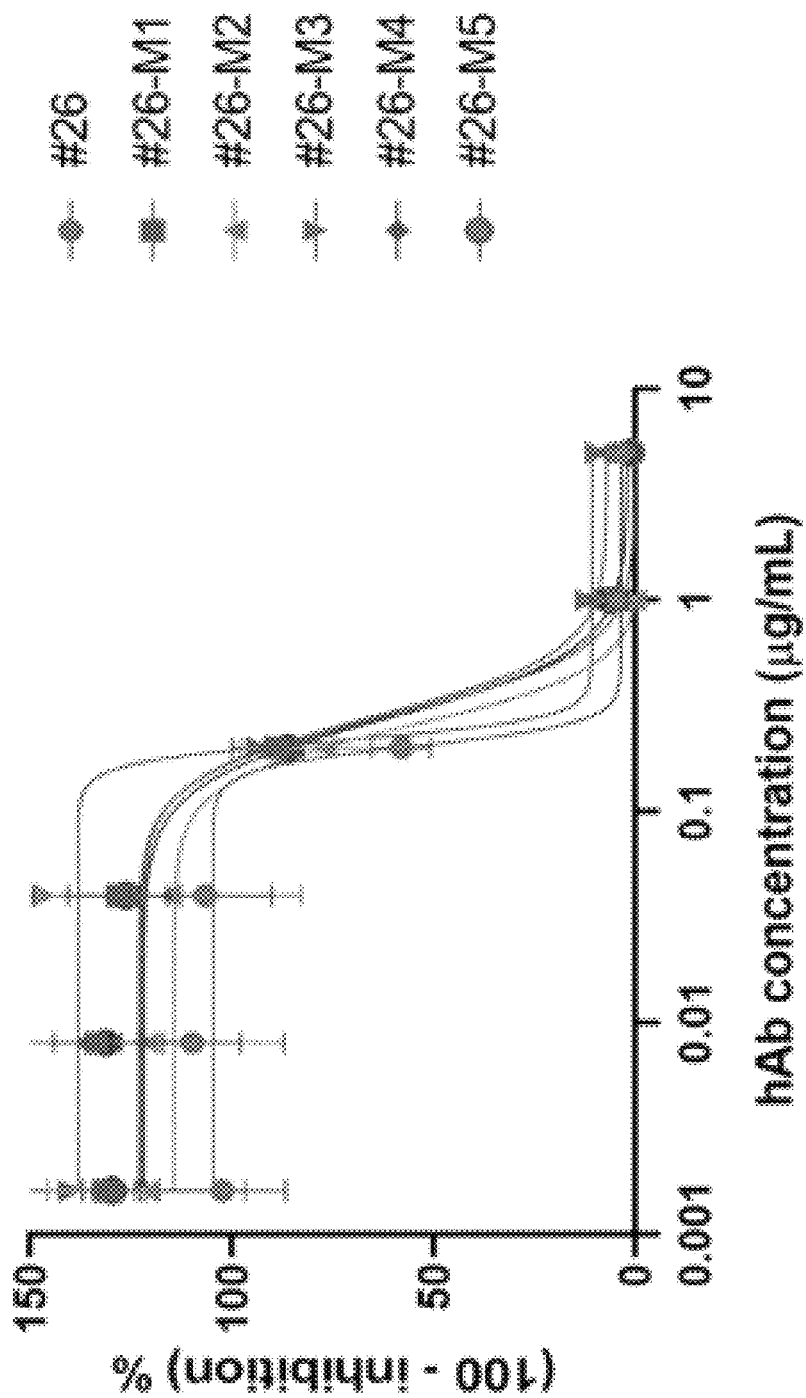
FIG. 17 shows that various modified αSARS-CoV-2-S1 #26 hIgG1 antibody constructs blocked His-tagged SARS-CoV-2 S1 binding to hACE2 as measured by ELISA using HRP-conjugated anti-His tag antibodies. The modified αSARS-CoV-2-S1 #26 hIgG1 antibodies have a similar $IC_{50}$ of S1-hACE2 as unmodified αSARS-CoV-2-S1 #26 hIgG1 antibody.

To confirm that the lysine modification does not affect the binding ability of the αSARS-CoV-2 #26 hIgG1 antibody to the SARS CoV-2 spike (S1) protein, the binding capacity of each antibody was determined using a ForteBio Octet instrument with SA sensor tips using Octet Data Acquisition and Analysis software 9.0. Binding of the αSARS-CoV-2 #26 hIgG antibody (#26) to the S1 spike protein was compared to binding by the lysine-modified #26-12K hIgG antibody (#26-M2) to spike protein. In this assay, biotinylated S1 protein was immobilized onto SA sensor tips and exposed to antibody, and association of antibody to S1 spike was measured over a period of several minutes. Following the association step, the sensor tips were moved into PBS-B (binding buffer) and the dissociation of the antibody from the sensor also measured over time. FIG. 16 shows comparable binding (association and dissociation) to the S1 spike by the αSARS-CoV-2 #26 antibody with or without the lysine modification. The ability of the lysine-modified αSARS-CoV-2-S1 #26 hIgG1 antibodies to block SARS-CoV-2 S1 binding to hACE2 was assessed using the method of Example 8. As illustrated in FIG. 17, the various modified αSARS-CoV-2 #26 hIgG1 antibody constructs all blocked SARS-CoV-2 S1 binding to hACE2 in a dose dependent manner. The modified αSARS-CoV-2-S1 #26 hIgG1 antibodies have a similar $IC_{50}$ for blocking S1-hACE2 as unmodified αSARS-CoV-2-S1 #26 hIgG1 antibody.

The ability of lysine-modified #26-12K hIgG antibody (#26-M2) to neutralize live SARS-CoV-2 virus is determined. Live SARS-CoV-2 virus is pre-incubated with varying concentrations of lysine-modified #26-12K hIgG antibody (#26-M2) and unmodified #26 hIgG antibody (#26) for 1 h at room temperature, prior to the addition of Vero E6 cells. Viral cytopathic effect (CPE) is determined by detecting the ATP levels of infected cells with Promega Viral ToxGlo™. #26-12K hIgG neutralizes live SARS-CoV-2 viruses.

Exemplary chimeric proteins based on clone #26 hIgG1 antibody fused to polyhistidine peptides of varying lengths (e.g., 6, 12, or 30 histidines) are also characterized using the same methods as described in this example. #26-hIgG-6H, #26-hIgG-12H, and #26-hIgG-30K all have increased binding to mucin compared to unmodified αSARS-CoV-2 #26 hIgG1 antibody, without disrupting binding to SARS-CoV-2 pseudovirus. They also neutralize live SARS-CoV-2 viruses.

Example 12. Ionization States of αSARS-CoV-2 #26-12K hIgG1 Antibody at Different pH Values Determined by Chromatography To determine the net charge on the αSARS-CoV-2 #26-12K hIgG1antibody (pI 6-9.5) in solutions with different pH values, 1 mL of the antibody was loaded onto a HITRAP™ SP HP cation exchange column (GE Healthcare) in a total volume of 4 mL in 25 mM HEPES buffer, pH 6.5. The column was washed with a low ionic strength Buffer A (25 mM HEPES, pH 6.0 or 8.0) at a flow rate of 1 mL/min. After 8 min, the sample was eluted from the column using a step gradient of 5%-25% Buffer B (25 mM HEPES, 0.5 M NaCl, pH 6.0 or pH 8.0). The αSARS-CoV-2 #26-12K hIgG1 antibody was eluted off the SP cation exchange column by 5% Buffer B at pH 8.0, or by 20% Buffer B at pH 6.0, confirming the expected behavior contributed by the lysine tail moiety at different pH values.

The net charge on exemplary chimeric proteins based on clone #26 hIgG1 antibody fused to polyhistidine peptides of varying lengths (e.g., 6, 12, or 30 histidines) is determined using the same methods as described in this example.

Example 13. αSARS-CoV-2 #26-12K hIgG1 Antibody in a Nasal Spray Formulation

Figure 18:
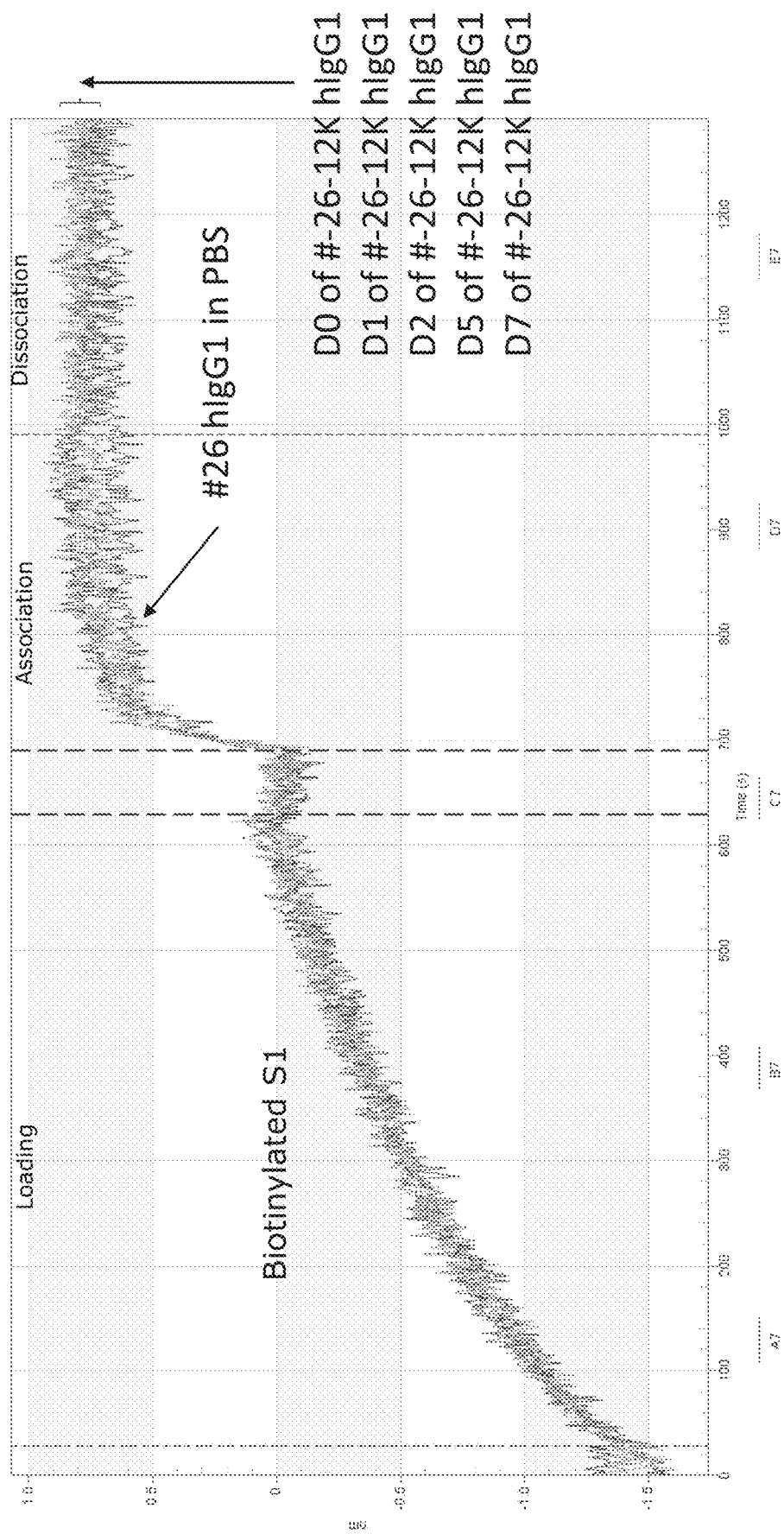
FIG. 18 shows S1 binding curves of the αSARS-CoV-2-S1 #26-12K hIgG1 antibody after storage in a nasal spray formulation buffer ("NS buffer") for 0-7 days. A ForteBio Octet system was used to measure binding kinetics.

The αSARS-CoV-2 #26-12K hIgG1 antibody was formulated in a nasal spray formulation comprising the following formulation buffer ("nasal spray buffer" or "NS buffer"): 25 mM citrate buffer, pH 6.5, 125 mM NaCl, 5% glycerin, 0.1% methionine, 0.02% polysorbate 80, and 0.1% potassium sorbate. Stability and activities of the αSARS-CoV-2 #26-12K hIgG1 antibody in the NS buffer were assessed.
αSARS-CoV-2 #26-12K hIgG1 Antibody Stored in NS Buffer Maintains Binding Affinity to S1 Protein To confirm that the formulation buffer does not affect the binding ability of the αSARS-CoV-2 #26-12K hIgG1 antibody to the SARS CoV-2 spike (S1) protein, an accelerated antibody stability assay was performed. Briefly, binding of the antibody was determined by employing a ForteBio Octet instrument with SA sensor tips using Octet Data Acquisition software 9.0. The binding curves of various samples of the antibody in NS buffer, maintained at 37° C. over a maximum period of 7 days, were compared to the binding curve of a sample of the unmodified #26 hIgG1 antibody stored in phosphate buffered saline (PBS) at 4° C. The graph in FIG. 18 shows highly comparable binding (association and dissociation) of the αSARS-CoV-2 #26-12K hIgG1 to biotinylated S1 spike protein after storage in the nasal spray formulation for 0, 1, 3, 5 or 7 days.

During the 7 day period, no aggregation of the αSARS-CoV-2 #26-12K hIgG1 antibody in the NS buffer was detected, as assayed using size exclusion chromatography (SEC). The antibody stored in PBS at 4° C. showed a comparable lack of aggregation (data not shown).

The accelerated antibody stability test at 37° C. showed that the antibody is stable in the formulation for at least 2 weeks, which is equivalent to >1.5 years at 4° C.

αSARS-CoV-2 #26-12K hIgG1 Antibody Stored in NS Buffer Maintains Ability to Block huACE2 Binding An ELISA blocking assay was performed as described in Example 8 to test the blocking ability of the αSARS-CoV-2 #26-12K antibody stored in NS buffer at 37° C. over a period of 7 days. Antibody blocking ability was tested at varying concentrations, see FIG. 19.

Figure 19:
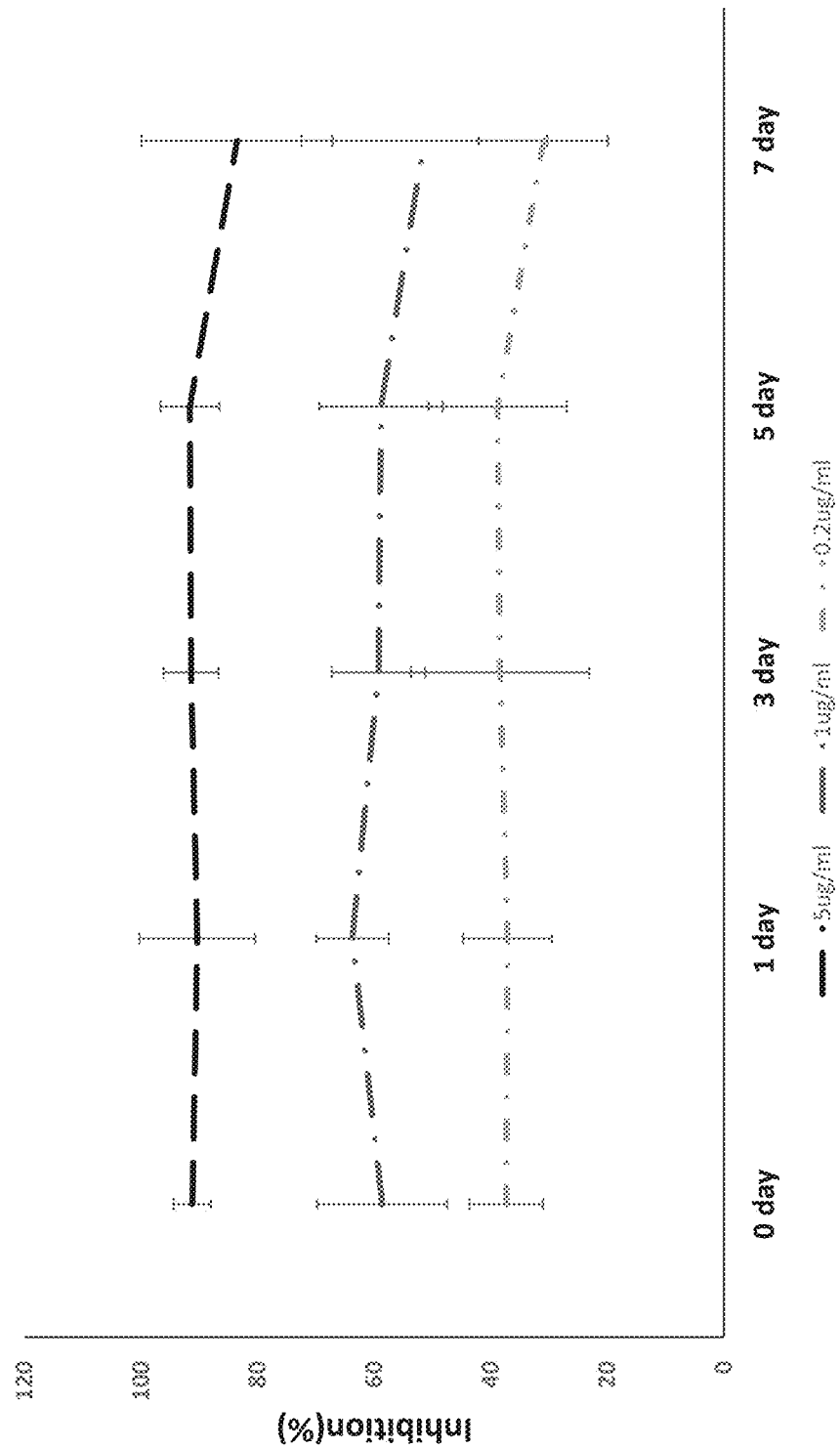
FIG. 19 shows the ability of αSARS-CoV-2-S1 #26-12K hIgG1 antibody to inhibit/block the binding of His-tagged SARS-CoV-2 S1 to hACE-2 after storage in NS buffer for 0-7 days, as measured by ELISA. The percent inhibition (compared to no antibody) was calculated.

As shown in FIG. 19, the αSARS-CoV-2 #26-12K antibody stored in NS buffer retained the ability to block the SARS CoV-2 S1 spike protein binding to the huACE2 receptor in vitro.

αSARS-CoV-2 #26-12K hIgG1 Antibody Stored in NS Buffer Maintains Ability to Block SARS CoV-2 Pseudovirus Infection of 293F-ACE2 Cells A luciferase Assay (Promega) was performed as described in Example 9, using a SARS-CoV-2 spike-pseudotyped lentivirus and αSARS-CoV-2 #26-12K hIgG1 antibody in NS buffer. The assay was performed using 3.3 nM, 10 nM or 30 nM #26-hIgG1-12K antibody stored in NS buffer at 37° C. over a period of 7 days.

Figure 20:
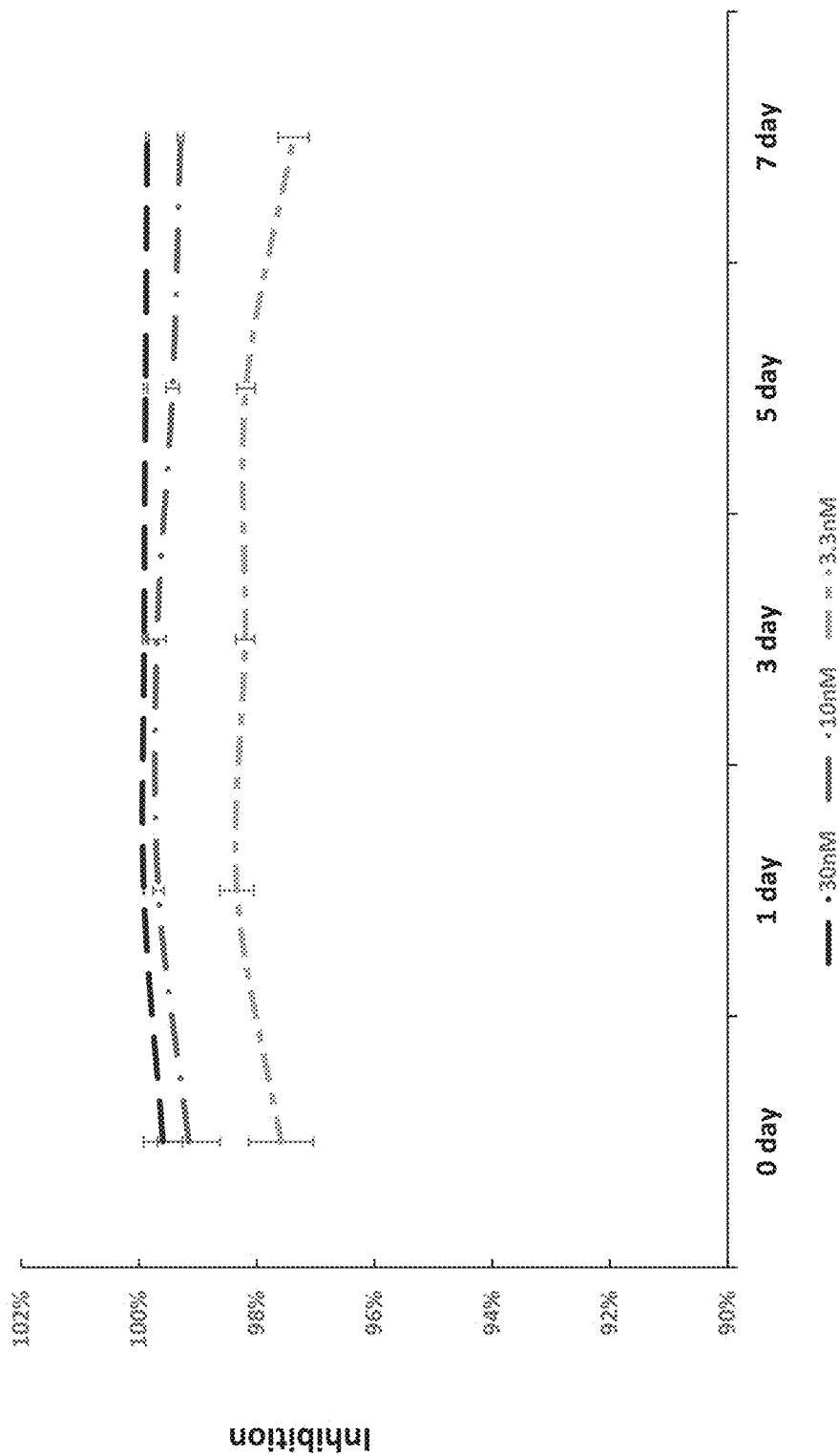
FIG. 20 shows inhibition of SARS-CoV-2 pseudovirus infection of 293F-ACE2 cells by the αSARS-CoV-2-S1 #26-12K hIgG1 antibody after storage in NS buffer for 0-7 days, measured by luciferase activity of the pseudovirus. The percent inhibition (compared to no antibody) was calculated.

As demonstrated in FIG. 20, the αSARS-CoV-2 #26-12K hIgG1 antibody stored in NS buffer effectively blocked pseudovirus infection.

αSARS-CoV-2 #26-12K hIgG1 Antibody Stored in NS Buffer Prevents SARS CoV-2 Pseudovirus Infection in a Mouse Model Female transgenic mice aged 4-6 weeks expressing full-length huACE2 were administered #26-hIgG1-12K antibody nasally (20 μL instilled per nostril) at various concentrations (25 μg to 200 μg). 10 hours after antibody administration, SARS-CoV-2 (isolate 2019-nCoV, i.e., WIV4), YP 009724390.1) spike pseudotyped lentivirus was administered to mice intranasally (20 μL instilled per nostril). Bioluminescence imaging was used to assess the degree of infection on day 7 after the mice were treated with the αSARS-CoV-2 #26-12K hIgG1 antibody in NS buffer. After measurement, the lungs were dissected and imaged.

Figure 21:
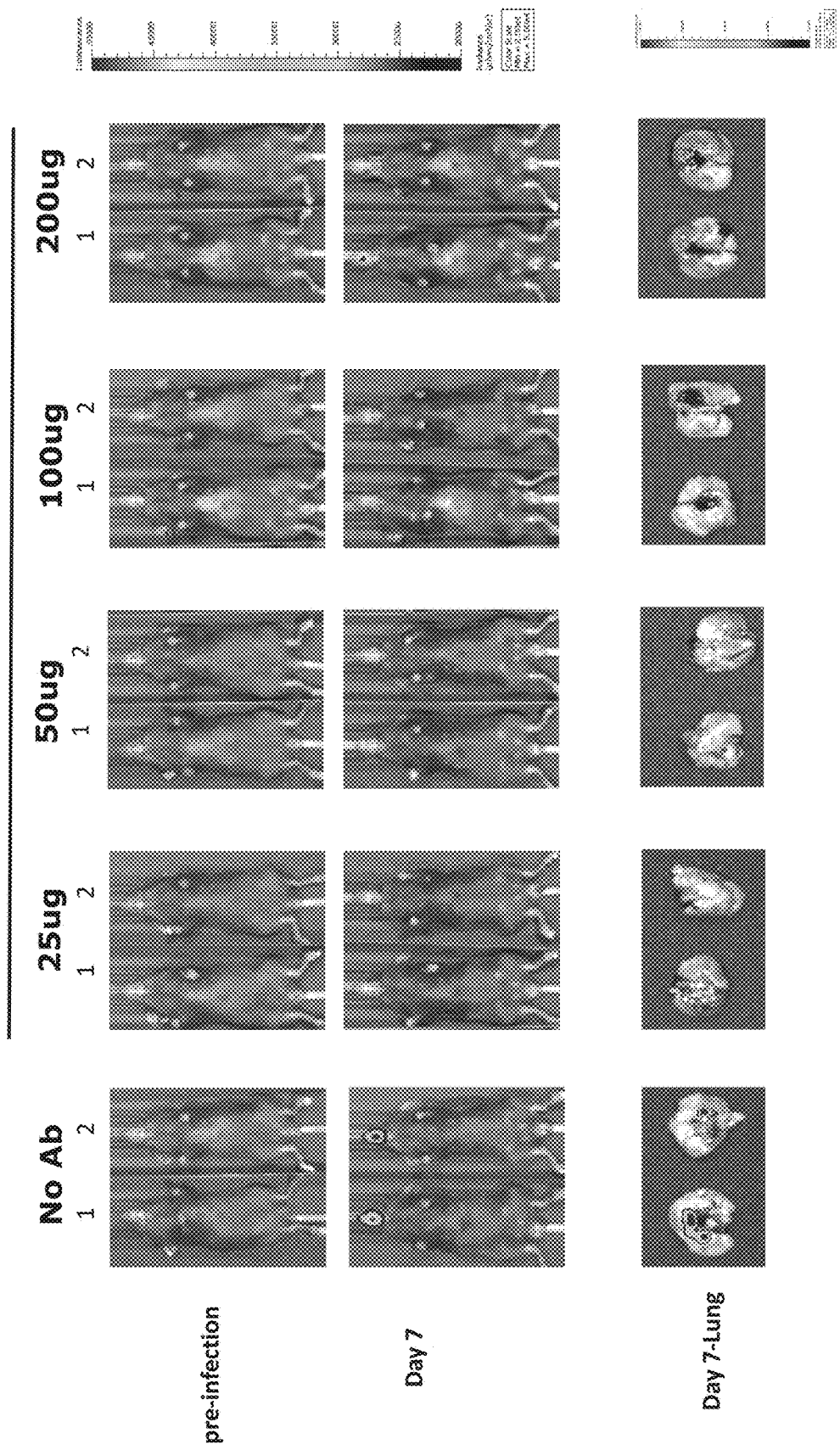
FIG. 21 shows that the αSARS-CoV-2-S1 #26-12K hIgG1 antibody blocked SARS CoV-2 pseudovirus infection in a mouse model shown by bioluminescent imaging.

As demonstrated in FIG. 21, the αSARS-CoV-2 #26-12K hIgG1 antibody in NS buffer prevented SARS CoV-2 pseudovirus infection in huACE2-expressing mice. The infected mice showed a strong luciferase signal in the nasal areas 3 days after the viral dosage, and in both nose and lung areas 7 days after the viral dosage. The duration of protection was tested and showed that αSARS-CoV-2 #26-12K hIgG1 provided at least 10 hours of protection against pseudoviral infection. Neither the nasal cavity nor lung areas showed signs of infection in αSARS-CoV-2 #26-12K hIgG1 antibody-treated mice 7 days after the viral dosage.

It has been estimated that the concentration of virus in droplets in a room with an individual who is coughing frequently can be as high as 7.44 million copies/m$^3$ from an individual who is a high emitter of virus. Regular breathing from an individual who is a high emitter was modeled to result in lower room concentrations of up to 1,248 copies/m$^3$. See, Riediker M. and Tsai D., *JAMA Netw Open.*, 2020, 3(7): e2013807. In the experiments described here, we challenged the mice with SARS-CoV-2 pseudovirus infection by directly dropping $10^7$ pseudovirus particles into the nostrils of mice. Inhibition of viral infection by pre-administration of αSARS-CoV-2 #26-12K hIgG1 antibody against this high viral titer, as demonstrated in FIG. 21, shows the promise of a nasal spray protection even in a worst-case scenario, and could provide a large cushion of protection in most common situations of a healthy person encountering an infected individual.

Role of Polylysine Tail in αSARS-CoV-2 #26-12K hIgG1 Antibody in Protection Against Pseudovirus Infection in a Mouse Model To confirm the role of the polycationic tail in blocking infectious virus, the αSARS-CoV-2 #26-12K hIgG antibody is compared to the αSARS-CoV-2 #26 hIgG unmodified antibody in an in vivo protection assay. Seven groups of female transgenic mice expressing the huACE2 receptor are pretreated with anti-SARS-CoV-2 antibody #26 with the 12 lysine C-terminal modification (αSARS-CoV-2 #26 12K) or anti-SARS-CoV-2 antibody #26 lacking the C-terminal lysine modification (αSARS-CoV-2 #26). Doses of 25 μg (A2 and A3), 75 μg (A4 and A5) or 200 μg (A6 and A7) of anti-SARS antibody with or without modification are each delivered to 3 groups of mice. A control group (A1) receives no pretreatment with any antibody.

At day 0, all groups are dosed with SARS-CoV-2 spike pseudotyped lentivirus as in Example 5. Animals are closely monitored after nasal administration of the pseudovirus on day 3, day 5 and day 7 following pseudoviral application. Bioluminescence and body weight are measured for each mouse. After the Day 7 measurement, the lungs are dissected and imaged.

If the mice pretreated with anti-SARS-CoV-2 antibody containing the 12-lysine tail, mice are free of signs of infection as measured by bioluminescent imaging, whereas the mice receiving the anti-SARS-CoV-2 antibody lacking the polylysine tail show increasing signs of infection. These mice also show signs of pseudoviral infection in their lung tissues, whereas the mice pretreated with the anti-SARS CoV-2 with the 12K modification are free of signs of lung involvement after Day 7, as measured by bioluminescence.

Comparison of αSARS-CoV-2 #26-12K hIgG1 Antibody and αSARS-CoV-2 #26 hIgG1 Antibody in Protection Against Pseudovirus Infection in a Mouse Model To confirm the role of the polycationic tail in blocking infectious virus, the αSARS-CoV-2 #26-12K hIgG antibody was compared to the αSARS-CoV-2 #26 hIgG unmodified antibody in an in vivo protection assay. Four groups of female transgenic mice expressing the huACE2 receptor were pretreated with anti-SARS-CoV-2 antibody #26 with the 12 lysine C-terminal modification (αSARS-CoV-2 #26 12K) or anti-SARS-CoV-2 antibody #26 lacking the C-terminal lysine modification (αSARS-CoV-2 #26). Doses of 100 μg (A2 and A3) or 300 μg (A4 and A5) of anti-SARS antibody with or without modification were each delivered to the corresponding groups of mice. A control group (A1) received no pretreatment with any antibody.

At day 0, all groups were dosed with SARS-CoV-2 spike pseudotyped lentivirus as in Example 5. Animals were closely monitored after nasal administration of the pseudovirus on day 3, day 5 and day 7 following pseudoviral application. Bioluminescence and body weight were measured for each mouse. After the Day 7 measurement, the lungs were dissected and imaged. Of the mice pretreated with anti-SARS-CoV-2 antibody containing the 12-lysine tail, mice were free of signs of infection as measured by bioluminescent imaging, whereas the mice receiving the anti-SARS-CoV-2 antibody lacking the polylysine tail showed increasing signs of infection. These mice also showed signs of pseudoviral infection in their lung tissues, whereas the mice pretreated with the anti-SARS CoV-2 with the 12K modification were free of signs of lung involvement after Day 7, as measured by bioluminescence.

Figure 22:
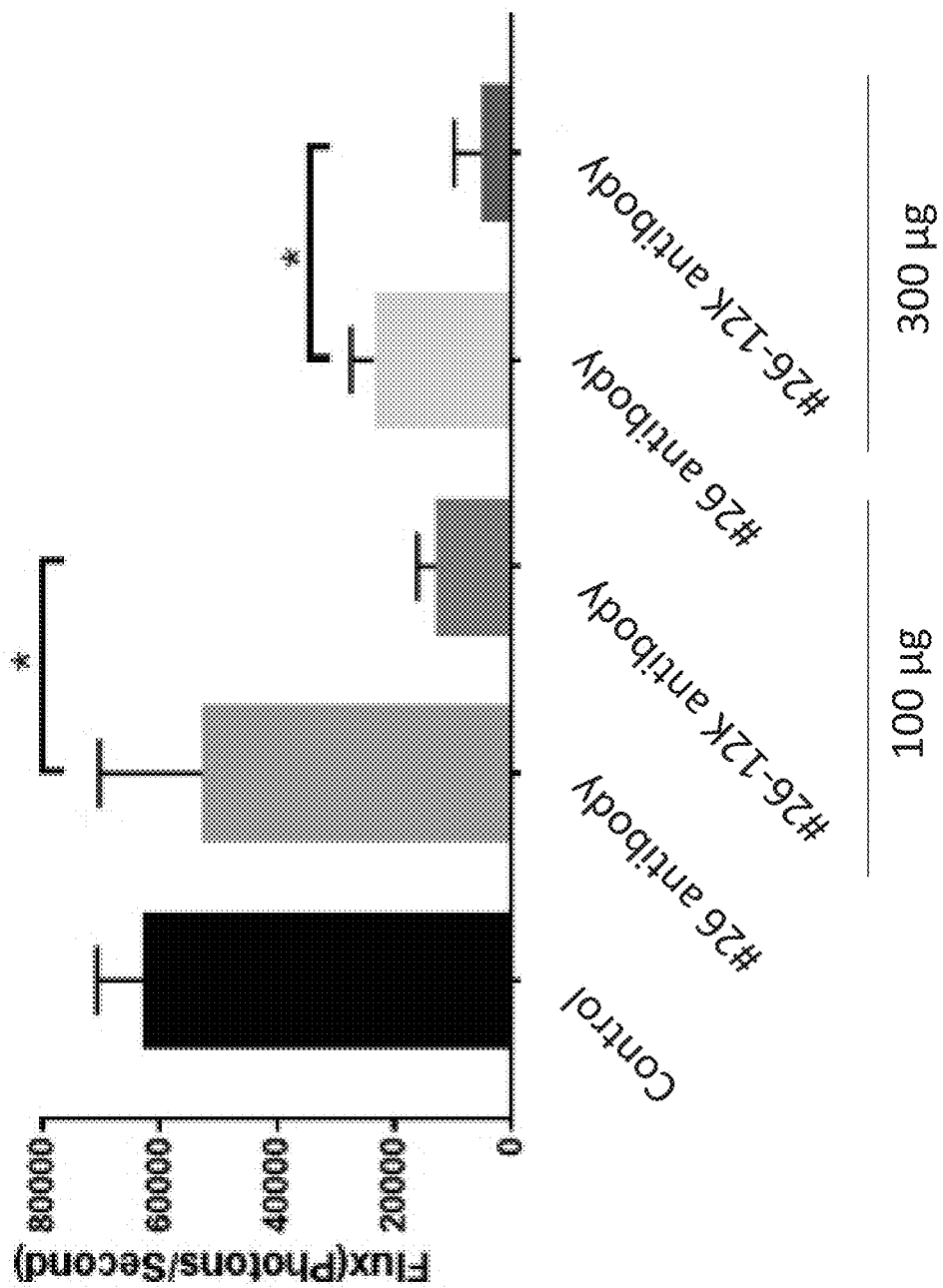
FIG. 22 shows the quantification of the bioluminescence of SARS-CoV-2 pseudovirus infected mice on Day 7.

FIG. 22 shows quantification of the bioluminescence of SARS-CoV-2 pseudovirus infected mice at Day 7. Consistent with the in vitro results, αSARS-CoV-2 #26 12K was superior to the parental αSARS-CoV-2 #26 antibody in protecting mice from virus infection when antibodies were administrated 24 hours prior to virus dosing. Thus, the mucin-binding modification in αSARS-CoV-2 #26-12K increased the antibody's protective effects significantly in vivo, compared to unmodified αSARS-CoV-2 #26 antibody.

Example 14. αSARS-CoV-2 #26-12K hIgG1 Antibody in NS Buffer Prevents SARS CoV-2 Variant Pseudovirus Infection in a Mouse Model New SARS-CoV-2 variants pose a challenge to the efforts to contain this pandemic, despite the availability of effective vaccines against the wildtype virus. There are reports of many new variants around the world, which are driving the rise of new COVID-19 cases in many counties. There are troubling signs that B.1.1.7, B.1.351, and B.1.617.2 variants may evade protection from the vaccines. While efforts of getting as many people vaccinated as possible and developing next-generation vaccines against the variants are under way, there is an urgent need to explore additional approaches to slow down the spread of the variants.

Here, we administered the same #26-12K hIgG1 antibody directly into nostrils of mice infected by pseudotyped virions expressing the B1.1.7, B1.351, and B.1.617.2 variants, three of the most prevalent SARS-CoV-2 variants. We demonstrated that the antibody was effective in protecting mice from infection by the three SARS-CoV-2 variants. These findings suggest an affordable and effective prophylactic product to protect people from exposure to SARS-CoV-2 virus in the air, in particular, against the new variants where vaccine induced antibody responses are less effective.

Methods

Female transgenic mice aged 4-6 weeks expressing full-length huACE2 were administered #26-hIgG1-12K antibody nasally (20 μL instilled per nostril). 10 hours after antibody administration, SARS-CoV-2 B.1.1.7 variant spike pseudotyped lentivirus (FIG. 23), SARS-CoV-2 B.1.351 variant spike pseudotyped lentivirus (FIG. 24), or SARS-CoV-2 Delta variant (e.g., B.1.617.2 variant) spike pseudotyped lentivirus (FIG. 25) were administered to mice intranasally (20 μL instilled per nostril). The B.1.1.7 variant is derived from the SARSCoV-2 20B/GR clade (lineage B.1.1.7) and contains multiple mutations, including a combination of the N501Y (i.e., an asparagine to tyrosine amino acid substitution at position 501 in the viral S gene) and the 69-70del (i.e., a deletion of 6 bases coding for histidine and valine at positions 69 and 70, respectively, in the viral S gene) causing a conformation change in the spike protein. See, Tang J. et al., *Journal of Infection*, 2021, 82: e27-e28. The B.1.351 variant, also known as the 20H/501Y.V2 variant, has 12 mutations and one deletion. Approximately 77% of these mutations are located in the spike protein [L18F, D80A, D215G, LAL 242-244 del, R246I, K417N, E484K, N501Y, D614G, and A701V] while the remaining ones are located in ORF1a [K1655N], envelope (E) [P71L], and N [T2051] viral proteins. The B.1.617.2 variant is characterized by the spike protein mutations T19R, 4157-158, L452R, T478K, D614G, P681R, and D950N. Several of these mutations may affect immune responses directed toward the key antigenic regions of receptor-binding protein (452 and 478) and deletion of part of the N-terminal domain. P681R is at the S1-S2 cleavage site, and it appears that strains with mutations at that site may have increased replication, which leads to higher viral loads and increased transmission.

Bioluminescence imaging was used to assess the degree of infection on day 7 after the mice were treated with the αSARS-CoV-2 #26-12K hIgG1 antibody in NS buffer. After measurement, the lungs were dissected and imaged.

Results

Figure 23:
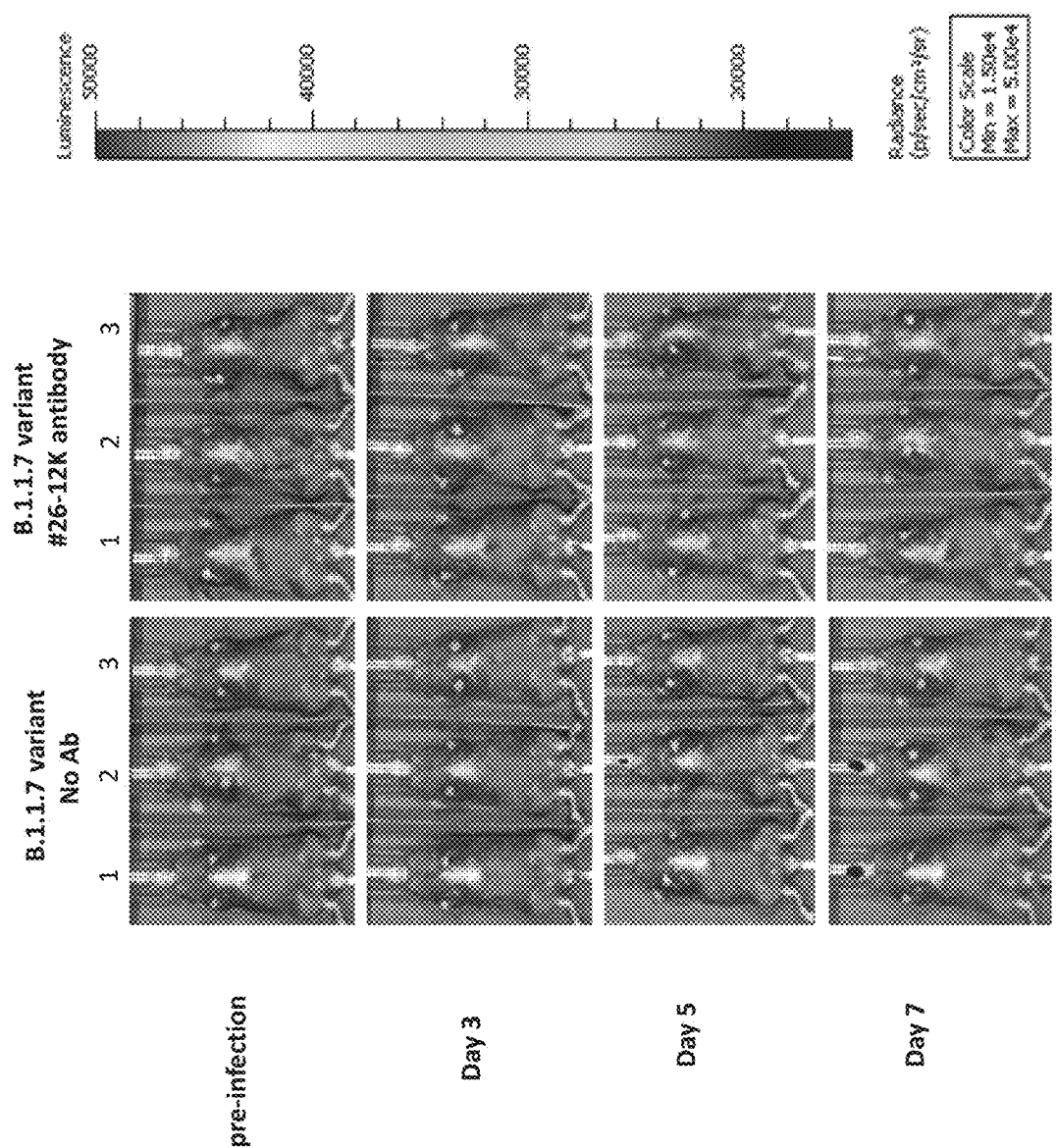
FIG. 23 shows that the αSARS-CoV-2-S1 #26-12K hIgG1 antibody blocked SARS CoV-2 B.1.1.7 variant pseudovirus infection in a mouse model shown by bioluminescent imaging.
Figure 24:
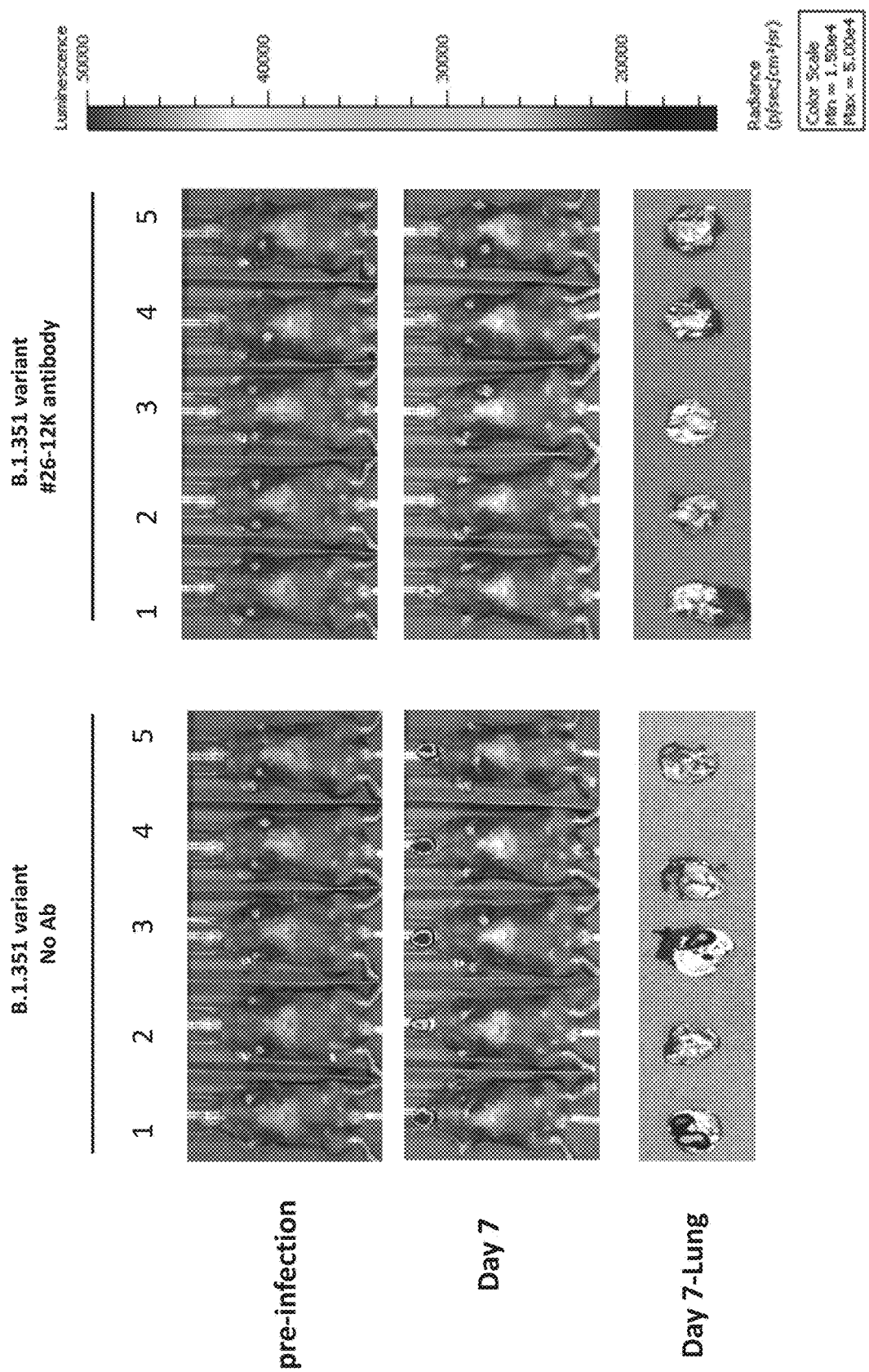
FIG. 24 shows that the αSARS-CoV-2-S1 #26-12K hIgG1 antibody blocked SARS CoV-2 B.1.351 variant pseudovirus infection in a mouse model shown by bioluminescent imaging.
Figure 25:
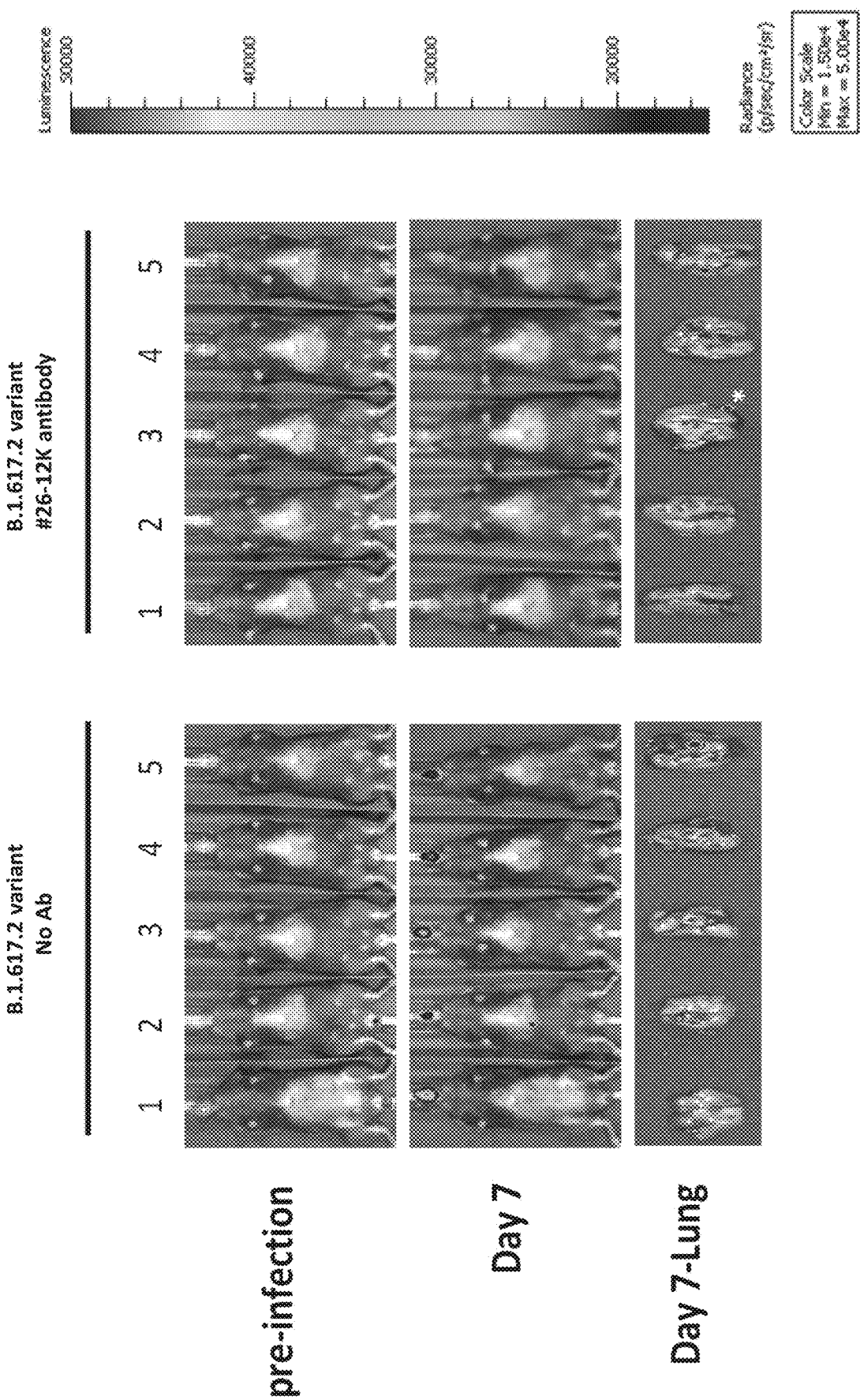
FIG. 25 shows that the αSARS-CoV-2-S1 #26-12K hIgG1 antibody blocked SARS CoV-2 B.1.617.2 variant pseudovirus infection in a mouse model shown by bioluminescent imaging.

As demonstrated in FIGS. 23-25, the αSARS-CoV-2 #26-12K hIgG1 antibody in NS buffer prevented both SARS CoV-2 B.1.1.7 variant, B.1.351 variant, and B.1.617.2 variant pseudovirus infections in huACE2-expressing mice. The infected mice showed a strong luciferase signal in the nasal and lung areas 7 days after the viral dosage. Neither the nasal cavity nor lung areas showed signs of infection in αSARS-CoV-2 #26-12K hIgG1 antibody-treated mice 7 days after the viral dosage.

Inhibition of viral infection by pre-administration of αSARS-CoV-2 #26-12K hIgG1 antibody against this high viral titer of the SARS-CoV-2 B.1.1.7 variant, SARS-CoV-2 B.1.351 variant, and SARS-CoV-2 B.1.617.2 variant spike pseudotyped lentivirus, as demonstrated in FIGS. 23-25, shows the promise of a nasal spray protection for a plurality of SARS-CoV-2 viral variants. For example, these SARS-CoV-2 variants may be inhibited by pre-administration of αSARS-CoV-2 #26-12K hIgG1 and/or a combination of αSARS-CoV-2 #26-12K hIgG1 in an antibody cocktail, such as but not limited to, an antibody cocktail comprising the anti-S1 antibodies encoded by the phage clones described in Example 1, new anti-S1 antibodies identified by additional panning experiments, and/or other commercially available anti-S1 antibodies.

The ability to block pseudovirus infection by SARS-CoV-2 variants by exemplary chimeric proteins based on clone #26 hIgG1 antibody fused to polyhistidine peptides of varying lengths (e.g., 6, 12, or 30 histidines) is assessed using the same methods as described in this example. #26-hIgG-6H, #26-hIgG-12H, and #26-hIgG-30K all block pseudovirus infection by the SARS-CoV-2 variants tested.

Example 15. αSARS-CoV-2 #26-12K hIgG1 or αSARS-CoV-2 #26-1211 hIgG1 Antibody in NS Buffer Prevents SARS CoV-2 Infection in Humans The safety and efficacy of daily nasal spray administration of αSARS-CoV-2 #26-12K hIgG1 or αSARS-CoV-2 #26-hIgG1-12H antibody are tested in human subjects, as compared with placebo.

The αSARS-CoV-2 #26-12K hIgG1 or αSARS-CoV-2 #26-hIgG1-12H antibody is formulated in NS buffer as described in Example 13. The antibody formulation is administered directly into nostrils of the human subjects at between 25 and 300 μg per dose. The antibody concentration in a Nasal Spray bottle is 0.125 mg/mL (e.g., 2.5 mg total αSARS-CoV-2 #26-hIgG1-12K or αSARS-CoV-2 #26-hIgG1-12H antibody in a 20 mL bottle volume). Each spray is about 0.1 mL. Each human subject receives one dose per day, or about 4 sprays per day. In the placebo group, each human subject receives an equivalent amount of NS buffer that does not contain αSARS-CoV-2 #26-12K hIgG1 or αSARS-CoV-2 #26-hIgG1-12H antibody. The duration of the study is 1 month or more.

Human subjects 5 years of age or older who are healthy or have stable chronic medical conditions are eligible for participation in the trial. Exclusion criteria include a medical history of COVID-19, treatment with immunosuppressive therapy, or diagnosis with an immunocompromising condition.

The safety endpoints include solicited, specific local or systemic adverse events, as prompted by and recorded in an electronic diary in a subset of participants, and unsolicited adverse events (those reported by the participants without prompts from the electronic diary).

The primary endpoints for efficacy include rate of confirmed COVID-19 with onset during the testing period and at least 7 days after the last dose. Confirmed COVID-19 is defined as the presence of at least one of the following symptoms: fever, new or increased cough, new or increased shortness of breath, chills, new or increased muscle pain, new loss of taste or smell, sore throat, diarrhea, or vomiting, combined with a respiratory specimen obtained during the symptomatic period or within 4 days before or after it that was positive for SARS-CoV-2 by nucleic acid amplification-based testing, either at the central laboratory or at a local testing facility. Secondary endpoints include efficacy of the αSARS-CoV-2 #26-12K hIgG1 or αSARS-CoV-2 #26-hIgG1-12H antibody against severe COVID-19. Severe COVID-19 is defined as confirmed COVID-19 with one of the following additional features: clinical signs at rest that are indicative of severe systemic illness; respiratory failure; evidence of shock; significant acute renal, hepatic, or neurologic dysfunction; admission to an intensive care unit; or death. Details are provided in the protocol. Additionally, efficacy of the αSARS-CoV-2 #26-12K hIgG1 or αSARS-CoV-2 #26-hIgG1-12H antibody against infection by SARS-CoV-2 variants, such as the Delta variant, is assessed.

Example 16. Characterization of Histidine- and Arginine-Modified αSARS-CoV-2 #26 hIgG1 Antibodies This example demonstrates that αSARS-CoV-2 #26 hIgG1 antibodies modified with twelve histidine or twelve arginine residues in the Fc region (e.g., histidine or arginine tail moieties) have comparable properties to the lysine modified αSARS-CoV-2 #26 hIgG1 antibodies.

Design of Chimeric Proteins Comprising Polyhistidine and Polyarginine Mucoadhesive Peptide Fragments The full-length clone #26 human IgG antibody was fused to a polyhistidine or polyarginine peptide having 12 contiguous histidine or arginine polypeptides. The polyhistidine or polyarginine peptide was fused to the C-terminus of the heavy chain of the IgG1 antibody via a flexible peptide linker (GGGGS; SEQ ID NO: 95). The polyhistidine and polyarginine peptides are mucoadhesive peptides that facilitate attachment of the exemplary chimeric protein to mucosa. Each #26-hIG1-12H has four polypeptide chains, including two copies of SEQ ID NO: 131 and two copies of SEQ ID NO: 97. While each #26-hIG1-12R has four polypeptide chains, including two copies of SEQ ID NO: 132 and two copies of SEQ ID NO: 97.

26-hIgG-12H heavy chain (heavy chain of Clone
26 hIgG antibody fused to 6 histidines)
SEQ ID NO: 131
QVQLVQSGAEVKKPGASVKVSCKASGYTFTSYGISWVRQAPGQGLEWMGW

ISAYNGNTNYAQKLQGRVTMTTDTSTSTAYMELRSLRSDDTAVYYCARGY

YGDLDPWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGKGGG

GSHHHHHHHHHHHH

26-hIgG-12R heavy chain (heavy chain of Clone
26 hIgG antibody fused to 6 arginines)
SEQ ID NO: 132
QVQLVQSGAEVKKPGASVKVSCKASGYTFTSYGISWVRQAPGQGLEWMGW

ISAYNGNTNYAQKLQGRVTMTTDTSTSTAYMELRSLRSDDTAVYYCARGY

YGDLDPWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGKGGG

GSRRRRRRRRRRRR

26-hIgG-12R (light chain of Clone #26 hIgG
antibody)
SEQ ID NO: 97
QAVLTQAPSASGTLGQQVTISCSGTTSNIGRNTVNWYQHLPGTAPKLLIF

VSNQRPSGVPDRFSGSKSGTSASLVISGLQSEDEADYYCGAWDDSLDGML

FGGGTKLTVLGQPKANPTVTLFPPSSEELQANKATLVCLISDFYPGAVTV

AWKADGSPVKAGVETTKPSKQSNNKYAASSYLSLTPEQWKSHRSYSCQVT

Figure 26:
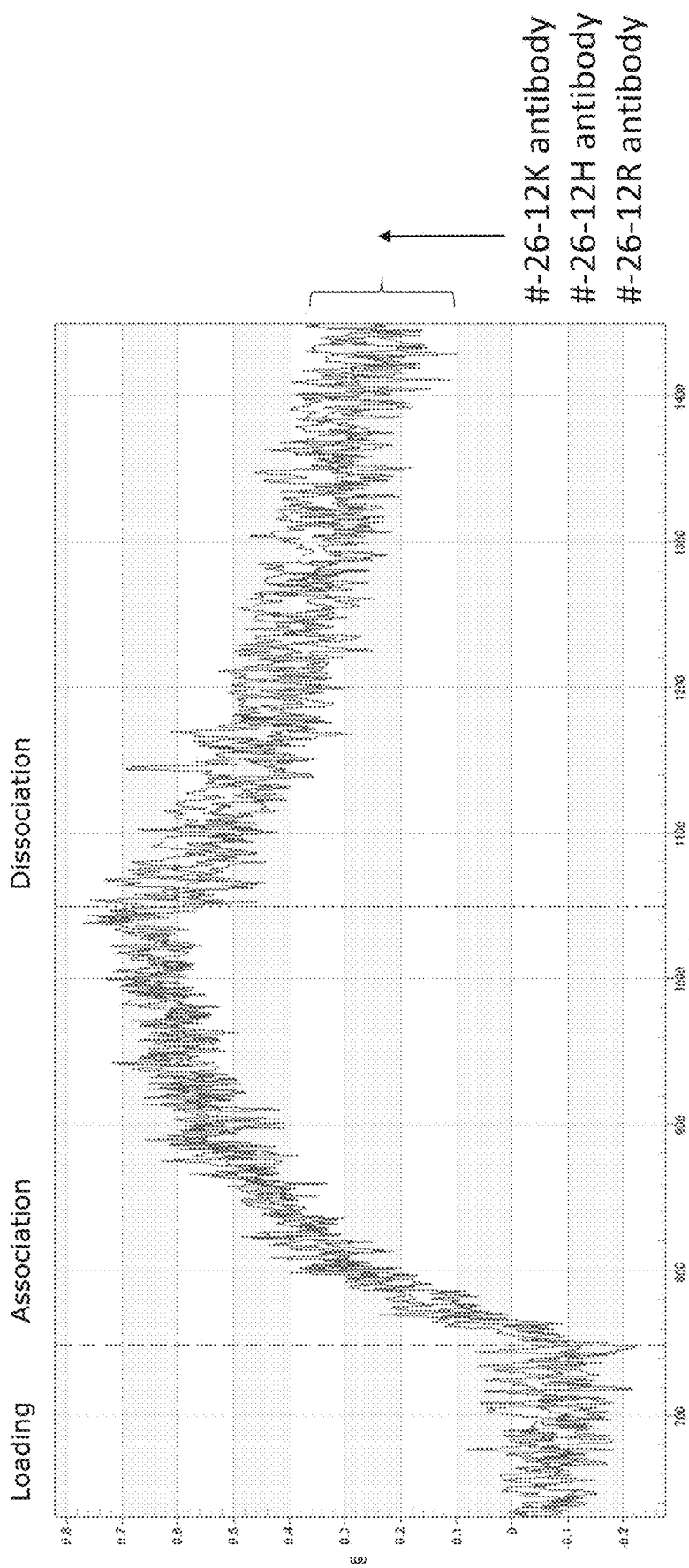
FIG. 26 shows that αSARS-CoV-2-S1 #26-12H hIgG1 and #26-12R hIgG1 had the same binding affinity to the S1 spike protein of SARS-CoV-2 as compared to αSARS-CoV-2-S1 #26-12K hIgG1. A ForteBio Octet system was used to measure binding kinetics.

HEGSTVEKTVAPTECS

αSARS-CoV-2 #26-12H hIgG1 Antibody and αSARS-CoV-2 #26-12R hIgG1 Antibody Maintain the Ability to Bind SARS CoV-2 S1 Protein To confirm that the histidine and arginine modifications do not affect the binding ability of the αSARS-CoV-2 #26 hIgG1 antibody to the SARS CoV-2 spike (S1) protein, the binding capacity of each antibody was determined using a ForteBio Octet instrument with SA sensor tips using Octet Data Acquisition and Analysis software 9.0. Binding of the αSARS-CoV-lysine-modified #26-12K hIgG antibody to the S1 spike protein was compared to binding by the histidine-modified #26-12H hIgG antibody and the arginine-modified #26-12R hIgG to spike protein. In this assay, the modified #26 hIgG antibodies were immobilized on anti-hIgG FC sensor tips and exposed to S1 spike protein, and association of antibody to S1 spike was measured over a period of several minutes. Following the association step, the sensor tips were moved into PBS-B (binding buffer) and the dissociation of the antibody from the sensor also measured over time. FIG. 26 shows comparable binding (association and dissociation) to the S1 spike by the αSARS-CoV-2 #26-12H, αSARS-CoV-2 #26-12R, and αSARS-CoV-2 #26-12K antibodies.

αSARS-CoV-2 #26-12H hIgG1 Antibody and αSARS-CoV-2 #26-12R hIgG1 Antibody Effectively Bind Mucin Histidine- and arginine-modified forms of αSARS-CoV-2 #26 hIgG antibody were then tested for their ability to bind mucin. 96-well plates were coated with 50 µg/mL mucin (Sigma, M3895) for 2 hr at room temperature. The plates were blocked with 3% BSA overnight at 4° C. 5 µg/mL antibodies in 25 mM HEPES (pH6.5) were added to the plates and incubated for 1 h at room temperature. After a wash with washing buffer (25 mM HEPES, 50 nM NaCl, pH6.5), plates were stained with HRP-conjugated goat anti human IgG and developed using 3,3',5,5'-Tetramethylbenzidine (TMB). Absorbance at an optical density at 450 nm (OD450) was measured.

Figure 27:
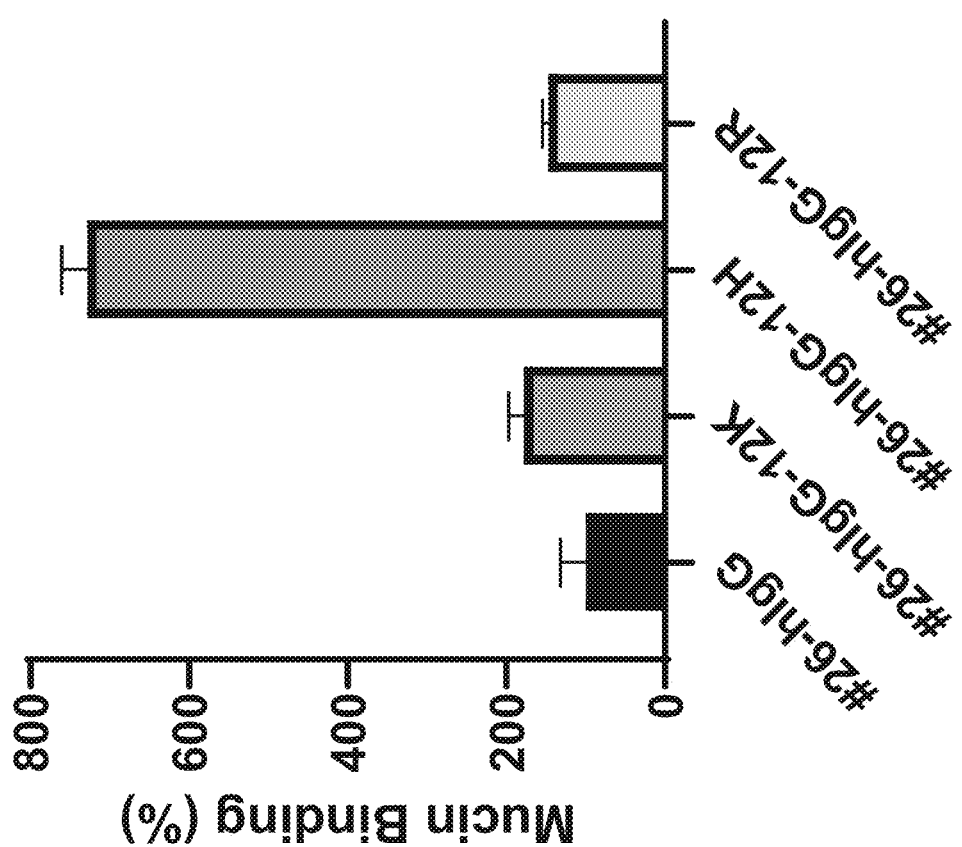
FIG. 27 shows that modification of αSARS-CoV-2-S1 #26-hIgG1 antibodies with polylysine, polyhistidine, and polyarginine peptides increased binding to mucin attached to plates and detected with HRP-conjugated anti-human Fc antibodies.

As shown in FIG. 27, the modifications significantly increased binding to mucin in vitro compared to unmodified αSARS-CoV-2 #26 hIgG1. Mucin glycoproteins produced by mucus-producing cells in the epithelium or submucosal glands are the major macromolecular constituent of mucus. Binding to mucin can potentially extend the retention time of an antibody in the mucus of the respiratory tract.

αSARS-CoV-2 #26-12H hIgG1 Antibody and αSARS-CoV-2 #26-12R hIgG1 Antibody Protect Against Pseudovirus Infection in a Mouse Model Female transgenic mice aged 4-6 weeks expressing full-length huACE2 were administered #26-hIgG1-12H or 26-hIgG1-12HR antibody nasally (20 µL instilled per nostril) at various concentrations (25 µg to 200 m). 10 hours after antibody administration, SARS-CoV-2 (isolate 2019-nCoV, i.e., WIV4), YP 009724390.1) spike pseudotyped lentivirus were administered to mice intranasally (20 µL instilled per nostril). Bioluminescence imaging was used to assess the degree of infection on day 7 after the mice were treated with the αSARS-CoV-2 #26-12H hIgG1 or #26-12R hIgG1 antibody in NS buffer. After measurement, the lungs were dissected and imaged.

Figure 28:
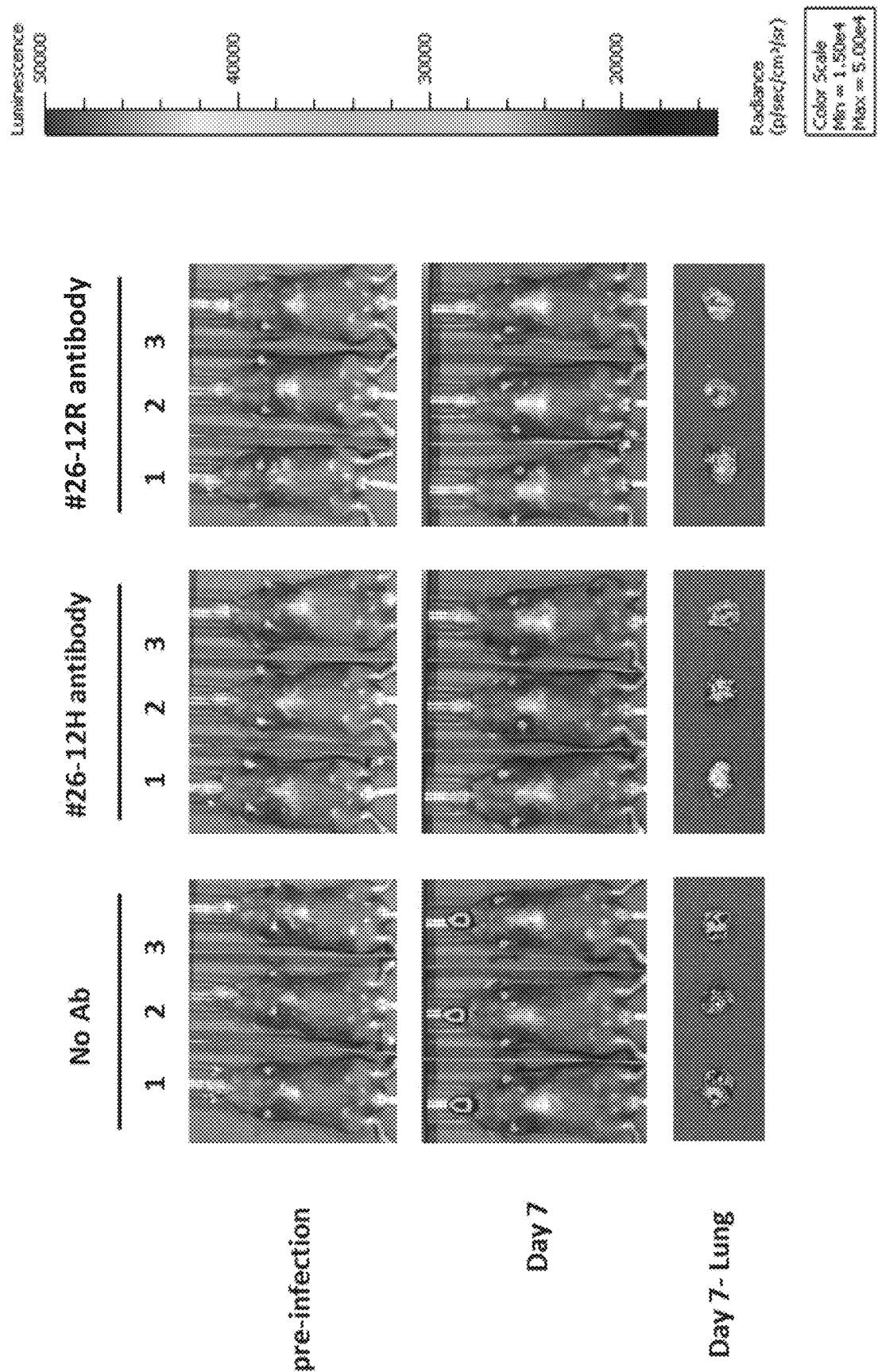
FIG. 28 shows that the αSARS-CoV-2-S1 #26-12H hIgG1 and #26-12R hIgG1 antibodies blocked SARS CoV-2 pseudovirus infection in a mouse model shown by bioluminescent imaging.

As demonstrated in FIG. 28, the αSARS-CoV-2 #26-12H hIgG1 and #26-12R hIgG1 antibodies in NS buffer prevented SARS CoV-2 pseudovirus infection in huACE2-expressing mice. The infected mice showed a strong luciferase signal in the nasal areas 3 days after the viral dosage, and in both nose and lung areas 7 days after the viral dosage. We tested the duration of protection and found that αSARS-CoV-2 #26-12K hIgG1 provided at least 10 hours of protection against pseudoviral infection. Neither the nasal cavity nor lung areas showed signs of infection in αSARS-CoV-2 #26-12H hIgG1 or αSARS-CoV-2 #26-12R hIgG1 antibody-treated mice 7 days after the viral dosage.

The invention claimed is:

1. A chimeric protein comprising:
   (a) an antibody or antigen binding fragment thereof that specifically binds to a SARS-CoV-2 spike (S) protein; and
   (b) a mucoadhesive peptide fragment comprising about 5 to about 50 contiguous positively charged amino acid residues, wherein the mucoadhesive peptide fragment facilitates attachment of the chimeric protein to a mucosa.

2. The chimeric protein of claim 1, wherein the mucoadhesive peptide fragment comprises at least about 6 contiguous positively charged amino acid residues.

3. The chimeric protein of claim 1, wherein the chimeric protein comprises two or more mucoadhesive peptide fragments.

4. The chimeric protein of claim 3, wherein each of the two or more mucoadhesive peptide fragments comprises about 11 to about 15 positively charged amino acid residues.

5. The chimeric protein of claim 1, wherein the positively charged amino acid residues are selected from the group consisting of lysine, arginine, histidine, ornithine, and combinations thereof.

6. The chimeric protein of claim 5, wherein the positively charged amino acid residues are lysines.

7. The chimeric protein of claim 5, wherein the positively charged amino acid residues are histidines.

8. The chimeric protein of claim 1, wherein the antibody or antigen binding fragment thereof inhibits binding of the SARS-CoV-2 S protein to a receptor of the SARS-CoV-2 S protein on a cell of the mucosa.

9. The chimeric protein of claim 1, wherein the SARS-CoV-2 S protein is from SARS-CoV-2 or a variant thereof.

10. The chimeric protein of claim 9, wherein the SARS-CoV-2 or variant thereof is selected from the group consisting of WIV4, a B.1.1.7 variant, a B.1.351 variant, a B.1.526 variant, a B1.526.1 variant, a B1.617 variant, a B.1.617.1 variant, a B.1.617.2 variant, a B1.617.3 variant, a P.2 variant, a P.1 variant, an A.23.1 variant, a CAL.20C variant, a B.1.427 variant, a B.1.429 variant, a B.1.525 variant, and a P.1.351 variant.

11. The chimeric protein of claim 1, wherein the antibody or antigen binding fragment thereof comprises a heavy chain complementarity determining region (HC-CDR)1 comprising the amino acid sequence of SEQ ID NO: 37, an HC-CDR2 comprising the amino acid sequence of SEQ ID NO: 38, an HC-CDR3 comprising the amino acid sequence of SEQ ID NO: 39, a light chain complementarity determining region (LC-CDR)1 comprising the amino acid sequence of SEQ ID NO: 40, an LC-CDR2 comprising the amino acid sequence of SEQ ID NO: 41, and an LC CDR3 comprising the amino acid sequence of SEQ ID NO: 42.

12. The chimeric protein of claim 1, wherein the antibody or antigen binding fragment thereof comprises a heavy chain variable region (VH) comprising the amino acid sequence of SEQ ID NO: 75, and a light chain variable region (VL) comprising the amino acid sequence of SEQ ID NO: 76.

13. The chimeric protein of claim 1, wherein the antibody or antigen binding fragment thereof comprises:

(1) an HC-CDR1 comprising the amino acid sequence of SEQ ID NO: 1, an HC-CDR2 comprising the amino acid sequence of SEQ ID NO: 2, an HC-CDR3 comprising the amino acid sequence of SEQ ID NO: 3, an LC-CDR1 comprising the amino acid sequence of SEQ ID NO: 4, an LC-CDR2 comprising the amino acid sequence of SEQ ID NO: 5, and an LC-CDR3 comprising the amino acid sequence of SEQ ID NO: 6;

(2) an HC-CDR1 comprising the amino acid sequence of SEQ ID NO: 7, an HC-CDR2 comprising the amino acid sequence of SEQ ID NO: 8, an HC-CDR3 comprising the amino acid sequence of SEQ ID NO: 9, an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12;

(3) an HC-CDR1 comprising the amino acid sequence of SEQ ID NO: 13, an HC-CDR2 comprising the amino acid sequence of SEQ ID NO: 14, an HC-CDR3 comprising the amino acid sequence of SEQ ID NO: 15, an LC-CDR1 comprising the amino acid sequence of SEQ ID NO: 16, the HC-LDR2 comprises the amino acid sequence of SEQ ID NO: 17, and an LC-CDR3 comprising the amino acid sequence of SEQ ID NO: 18;

(4) an HC-CDR1 comprising the amino acid sequence of SEQ ID NO: 19, an HC-CDR2 comprising the amino acid sequence of SEQ ID NO: 20, an HC-CDR3 comprising the amino acid sequence of SEQ ID NO: 21, an LC-CDR1 comprising the amino acid sequence of SEQ ID NO: 22, an LC-CDR2 comprising the amino acid sequence of SEQ ID NO: 23, and an LC-CDR3 comprising the amino acid sequence of SEQ ID NO: 24;

(5) an HC-CDR1 comprising the amino acid sequence of SEQ ID NO: 25, an HC-CDR2 comprising the amino acid sequence of SEQ ID NO: 26, and HC-CDR3 comprising the amino acid sequence of SEQ ID NO: 27, an LC-CDR1 comprising the amino acid sequence of SEQ ID NO: 28, an LC-CDR2 comprising the amino acid sequence of SEQ ID NO: 29, and an LC-CDR3 comprising the amino acid sequence of SEQ ID NO: 30;

(6) an HC-CDR1 comprising the amino acid sequence of SEQ ID NO: 31, an HC-CDR2 comprising the amino acid sequence of SEQ ID NO: 32, an HC-CDR3 comprising the amino acid sequence of SEQ ID NO: 33, an LC-CDR1 comprising the amino acid sequence of SEQ ID NO: 34, an LC-CDR2 comprising the amino acid sequence of SEQ ID NO: 35, and an LC-CDR3 comprising the amino acid sequence of SEQ ID NO: 36;

(7) an HC-CDR1 comprising the amino acid sequence of SEQ ID NO: 43, an HC-CDR2 comprising the amino acid sequence of SEQ ID NO: 44, an HC-CDR3 comprising the amino acid sequence of SEQ ID NO: 45, an LC-CDR1 comprising the amino acid sequence of SEQ ID NO: 46, an LC-CDR2 comprising the amino acid sequence of SEQ ID NO: 47, and an LC-CDR3 comprising the amino acid sequence of SEQ ID NO: 48;

(8) an HC-CDR1 comprising the amino acid sequence of SEQ ID NO: 49, an HC-CDR2 comprising the amino acid sequence of SEQ ID NO: 50, an HC-CDR3 comprising the amino acid sequence of SEQ ID NO: 51, an LC-CDR1 comprising the amino acid sequence of SEQ ID NO: 52, an LC-CDR2 comprising the amino acid sequence of SEQ ID NO: 53, and an LC-CDR3 comprising the amino acid sequence of SEQ ID NO: 54; or (9) an HC-CDR1 comprising the amino acid sequence of SEQ ID NO: 55, an HC-CDR2 comprising the amino acid sequence of SEQ ID NO: 56, an HC-CDR3 comprising the amino acid sequence of SEQ ID NO: 57, an LC-CDR1 comprising the amino acid sequence of SEQ ID NO: 58, an LC-CDR2 comprising the amino acid sequence of SEQ ID NO: 59, and an LC-CDR3 comprising the amino acid sequence of SEQ ID NO: 60.

14. A pharmaceutical composition comprising the chimeric protein of claim 1 and a pharmaceutically acceptable carrier.

15. The pharmaceutical composition of claim 14, comprising a plurality of chimeric proteins, wherein the antibodies or antigen binding fragments thereof of the chimeric proteins are different from each other.

16. The pharmaceutical composition of claim 14, wherein the pharmaceutical composition is for nasal administration.

17. An isolated nucleic acid or a set of isolated nucleic acids encoding the chimeric protein of claim 1.

18. The chimeric protein of claim 1, wherein the antibody or antigen binding fragment thereof specifically binds an S1 subunit of the S protein of SARS-CoV-2.

19. The chimeric protein of claim 1, wherein the antibody or antigen binding fragment thereof is a human antibody or antigen binding fragment thereof.

20. The chimeric protein of claim 1, wherein the antibody is a full-length antibody.

21. The chimeric protein of claim 20, wherein the full-length antibody is selected from the group consisting of an IgG, an IgA, an IgM, and an IgD.

22. The chimeric protein of claim 1, wherein the antibody or antigen binding fragment thereof comprises an scFv comprising the amino acid sequence of SEQ ID NO: 87.

* * * * *

SEQUENCE LISTING

```
<160> NUMBER OF SEQ ID NOS: 134

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Gly Tyr Thr Phe Thr Gly Tyr Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Ile Asn Pro Asn Ser Gly Gly Thr
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic Construct

<400> SEQUENCE: 3

Ala Arg Gly Tyr Ser Asp Arg
1               5

<210> SEQ ID NO 4
<211> LENGTH: 8
<212> TYPE: PRT
```

```
<213> ORGANISM: Artificial Sequence
<220> FEATURE:
<223> OTHER INFORMATION: Synthetic Construct

<400> SEQUENCE: 4

Ser Ser Asn Ile Gly Ser Asn Pro
1               5

<210> SEQ ID NO 5
<211> LENGTH: 3
<212> TYPE: PRT
<213> ORGANISM: Artificial Sequence
<220> FEATURE:
<223> OTHER INFORMATION: Synthetic Construct

<400> SEQUENCE: 5

Ser Asn Asn
1

<210> SEQ ID NO 6
<211> LENGTH: 12
<212> TYPE: PRT
<213> ORGANISM: Artificial Sequence
<220> FEATURE:
<223> OTHER INFORMATION: Synthetic Construct

<400> SEQUENCE: 6

Ala Ala Trp Asp Asp Ser Leu Ser Gly Ser Val Leu
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Synthetic Construct

<400> SEQUENCE: 7

Gly Tyr Thr Phe Thr Ser Tyr Gly
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Construct

<400> SEQUENCE: 8

Ile Ser Ala Tyr Asn Gly Asn Thr
1               5

<210> SEQ ID NO 9
<211> LENGTH: 11
<212> TYPE: PRT
<213> ORGANISM: Artificial Sequence
<220> FEATURE:
<223> OTHER INFORMATION: Synthetic Construct

<400> SEQUENCE: 9

Ala Arg Thr Trp Tyr Ser Tyr His Tyr Asp Ile
1               5                   10

<210> SEQ ID NO 10
<211> LENGTH: 8
<212> TYPE: PRT
<213> ORGANISM: Artificial Sequence
```

```
<220> FEATURE:
<223> OTHER INFORMATION: Synthetic Construct

<400> SEQUENCE: 10

Ser Gly Ser Ile Ala Ser Asn Tyr
1               5

<210> SEQ ID NO 11
<211> LENGTH: 3
<212> TYPE: PRT
<213> ORGANISM: Artificial Sequence
<220> FEATURE:
<223> OTHER INFORMATION: Synthetic Construct

<400> SEQUENCE: 11

Glu Asp Lys
1

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Gln Ser Tyr Asp Asp Gly Asn Val Val
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Construct

<400> SEQUENCE: 13

Gly Gly Thr Phe Ser Ser Tyr Ala
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Construct

<400> SEQUENCE: 14

Ile Ser Gly Tyr Asn Gly Asn Thr
1               5

<210> SEQ ID NO 15
<211> LENGTH: 22
<212> TYPE: PRT
<213> ORGANISM: Artificial Sequence
<220> FEATURE:
<223> OTHER INFORMATION: Synthetic Construct

<400> SEQUENCE: 15

Ala Arg Thr Gly Trp Ser Lys Gly Glu Lys Val Thr Thr Trp Gly Glu
1               5                   10                  15

Trp Phe Tyr Val Asp Tyr
            20

<210> SEQ ID NO 16
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 16

Ser Ser Asn Ile Gly Ser Asn Tyr
1               5

<210> SEQ ID NO 17
<211> LENGTH: 3
<212> TYPE: PRT
<213> ORGANISM: Artificial Sequence
<220> FEATURE:
<223> OTHER INFORMATION: Synthetic Construct

<400> SEQUENCE: 17

Arg Asn Asn
1

<210> SEQ ID NO 18
<211> LENGTH: 13
<212> TYPE: PRT
<213> ORGANISM: Artificial Sequence
<220> FEATURE:
<223> OTHER INFORMATION: Synthetic Construct

<400> SEQUENCE: 18

Ala Ala Trp Asp Asp Ser Leu Ser Gly Pro Asn Tyr Val
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Synthetic Construct

<400> SEQUENCE: 19

Gly Tyr Thr Phe Thr Gly Tyr Tyr
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic Construct

<400> SEQUENCE: 20

Ile Asn Pro Asn Ser Gly Gly Thr
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic Construct

<400> SEQUENCE: 21

Ala Arg Gly Tyr Gly Asp Asp
1               5

<210> SEQ ID NO 22
<211> LENGTH: 8
<212> TYPE: PRT
```

<213> ORGANISM: Artificial Sequence
<220> FEATURE:
<223> OTHER INFORMATION: Synthetic Construct

<400> SEQUENCE: 22

Ser Ser Asn Ile Gly Asn Asn Ala
1               5

<210> SEQ ID NO 23
<211> LENGTH: 3
<212> TYPE: PRT
<213> ORGANISM: Artificial Sequence
<220> FEATURE:
<223> OTHER INFORMATION: Synthetic Construct

<400> SEQUENCE: 23

Phe Asn Asp
1

<210> SEQ ID NO 24
<211> LENGTH: 11
<212> TYPE: PRT
<213> ORGANISM: Artificial Sequence
<220> FEATURE:
<223> OTHER INFORMATION: Synthetic Construct

<400> SEQUENCE: 24

Ala Ala Trp Asp Asp Ser Leu Asn Ala Val Leu
1               5                   10

<210> SEQ ID NO 25
<211> LENGTH: 8
<212> TYPE: PRT
<213> ORGANISM: Artificial Sequence
<220> FEATURE:
<223> OTHER INFORMATION: Synthetic Construct

<400> SEQUENCE: 25

Gly Phe Thr Phe Ser Asn Tyr Pro
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic Construct

<400> SEQUENCE: 26

Ile Ser Tyr Asp Gly Asn His Lys
1               5

<210> SEQ ID NO 27
<211> LENGTH: 11
<212> TYPE: PRT
<213> ORGANISM: Artificial Sequence
<220> FEATURE:
<223> OTHER INFORMATION: Synthetic Construct

<400> SEQUENCE: 27

Ala Arg Gly Gly Gly Met Gly Gly Leu Asp Ser
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

Ser Ser Asp Val Gly Gly Tyr Asn Tyr
1               5

<210> SEQ ID NO 29
<211> LENGTH: 3
<212> TYPE: PRT
<213> ORGANISM: Artificial Sequence
<220> FEATURE:
<223> OTHER INFORMATION: Synthetic Construct

<400> SEQUENCE: 29

Glu Val Ser
1

<210> SEQ ID NO 30
<211> LENGTH: 10
<212> TYPE: PRT
<213> ORGANISM: Artificial Sequence
<220> FEATURE:
<223> OTHER INFORMATION: Synthetic Construct

<400> SEQUENCE: 30

Ser Ser Tyr Thr Ser Gly Asp Thr Leu Val
1               5                   10

<210> SEQ ID NO 31
<211> LENGTH: 8
<212> TYPE: PRT
<213> ORGANISM: Artificial Sequence
<220> FEATURE:
<223> OTHER INFORMATION: Synthetic Construct

<400> SEQUENCE: 31

Gly Tyr Ser Phe Pro Ser Tyr Trp
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic Construct

<400> SEQUENCE: 32

Ile Tyr Pro Gly Asp Ser Asp Thr
1               5

<210> SEQ ID NO 33
<211> LENGTH: 14
<212> TYPE: PRT
<213> ORGANISM: Artificial Sequence
<220> FEATURE:
<223> OTHER INFORMATION: Synthetic Construct

<400> SEQUENCE: 33

Ala Arg Gly Ser Tyr Thr Tyr Met Gly Gly Ser Tyr Asp Tyr
1               5                   10

<210> SEQ ID NO 34
<211> LENGTH: 8
<212> TYPE: PRT
<213> ORGANISM: Artificial Sequence
<220> FEATURE:

<223> OTHER INFORMATION: Synthetic Construct

<400> SEQUENCE: 34

Ser Ser Asn Ile Gly Ser Asn Thr
1               5

<210> SEQ ID NO 35
<211> LENGTH: 3
<212> TYPE: PRT
<213> ORGANISM: Artificial Sequence
<220> FEATURE:
<223> OTHER INFORMATION: Synthetic Construct

<400> SEQUENCE: 35

Ser Asn Asn
1

<210> SEQ ID NO 36
<211> LENGTH: 11
<212> TYPE: PRT
<213> ORGANISM: Artificial Sequence
<220> FEATURE:
<223> OTHER INFORMATION: Synthetic Construct

<400> SEQUENCE: 36

Ala Ala Trp Asp Asp Ser Leu Asp Gly Tyr Val
1               5                   10

<210> SEQ ID NO 37
<211> LENGTH: 8
<212> TYPE: PRT
<213> ORGANISM: Artificial Sequence
<220> FEATURE:
<223> OTHER INFORMATION: Synthetic Construct

<400> SEQUENCE: 37

Gly Tyr Thr Phe Thr Ser Tyr Gly
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic Construct

<400> SEQUENCE: 38

Ile Ser Ala Tyr Asn Gly Asn Thr
1               5

<210> SEQ ID NO 39
<211> LENGTH: 10
<212> TYPE: PRT
<213> ORGANISM: Artificial Sequence
<220> FEATURE:
<223> OTHER INFORMATION: Synthetic Construct

<400> SEQUENCE: 39

Ala Arg Gly Tyr Tyr Gly Asp Leu Asp Pro
1               5                   10

<210> SEQ ID NO 40
<211> LENGTH: 8
<212> TYPE: PRT
<213> ORGANISM: Artificial Sequence
<220> FEATURE:
<223> OTHER INFORMATION: Synthetic Construct

```
<400> SEQUENCE: 40

Thr Ser Asn Ile Gly Arg Asn Thr
1               5

<210> SEQ ID NO 41
<211> LENGTH: 3
<212> TYPE: PRT
<213> ORGANISM: Artificial Sequence
<220> FEATURE:
<223> OTHER INFORMATION: Synthetic Construct

<400> SEQUENCE: 41

Val Ser Asn
1

<210> SEQ ID NO 42
<211> LENGTH: 11
<212> TYPE: PRT
<213> ORGANISM: Artificial Sequence
<220> FEATURE:
<223> OTHER INFORMATION: Synthetic Construct

<400> SEQUENCE: 42

Gly Ala Trp Asp Asp Ser Leu Asp Gly Met Leu
1               5                   10

<210> SEQ ID NO 43
<211> LENGTH: 8
<212> TYPE: PRT
<213> ORGANISM: Artificial Sequence
<220> FEATURE:
<223> OTHER INFORMATION: Synthetic Construct

<400> SEQUENCE: 43

Gly Phe Thr Phe Ser Ser Tyr Ala
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic Construct

<400> SEQUENCE: 44

Ile Ser Ala Ser Gly Asn Ser Thr
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic Construct

<400> SEQUENCE: 45

Ala Arg Asn Ser Asp Val
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic Construct
```

```
<400> SEQUENCE: 46

Ser Ser Asp Val Gly Gly Tyr Asp Tyr
1               5

<210> SEQ ID NO 47
<211> LENGTH: 3
<212> TYPE: PRT
<213> ORGANISM: Artificial Sequence
<220> FEATURE:
<223> OTHER INFORMATION: Synthetic Construct

<400> SEQUENCE: 47

Glu Val Ser
1

<210> SEQ ID NO 48
<211> LENGTH: 12
<212> TYPE: PRT
<213> ORGANISM: Artificial Sequence
<220> FEATURE:
<223> OTHER INFORMATION: Synthetic Construct

<400> SEQUENCE: 48

Ser Ser Tyr Thr Ser Ser Ser Thr Phe Pro Tyr Val
1               5                   10

<210> SEQ ID NO 49
<211> LENGTH: 8
<212> TYPE: PRT
<213> ORGANISM: Artificial Sequence
<220> FEATURE:
<223> OTHER INFORMATION: Synthetic Construct

<400> SEQUENCE: 49

Gly Tyr Ser Phe Thr Ser Tyr Trp
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic Construct

<400> SEQUENCE: 50

Ile Tyr Pro Gly Asp Ser Asp Thr
1               5

<210> SEQ ID NO 51
<211> LENGTH: 12
<212> TYPE: PRT
<213> ORGANISM: Artificial Sequence
<220> FEATURE:
<223> OTHER INFORMATION: Synthetic Construct

<400> SEQUENCE: 51

Ala Arg Ser Ser Tyr Ser Tyr Gly Gly Pro Asp Ala
1               5                   10

<210> SEQ ID NO 52
<211> LENGTH: 8
<212> TYPE: PRT
<213> ORGANISM: Artificial Sequence
<220> FEATURE:
<223> OTHER INFORMATION: Synthetic Construct

<400> SEQUENCE: 52
```

```
Ser Ser Asn Ile Gly Ser Asn Thr
1               5

<210> SEQ ID NO 53
<211> LENGTH: 3
<212> TYPE: PRT
<213> ORGANISM: Artificial Sequence
<220> FEATURE:
<223> OTHER INFORMATION: Synthetic Construct

<400> SEQUENCE: 53

Ser Asn Asn
1

<210> SEQ ID NO 54
<211> LENGTH: 11
<212> TYPE: PRT
<213> ORGANISM: Artificial Sequence
<220> FEATURE:
<223> OTHER INFORMATION: Synthetic Construct

<400> SEQUENCE: 54

Ala Ala Trp Asp Asp Ser Leu Asn Gly Tyr Val
1               5                   10

<210> SEQ ID NO 55
<211> LENGTH: 8
<212> TYPE: PRT
<213> ORGANISM: Artificial Sequence
<220> FEATURE:
<223> OTHER INFORMATION: Synthetic Construct

<400> SEQUENCE: 55

Gly Tyr Thr Phe Thr Gly Tyr Tyr
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic Construct

<400> SEQUENCE: 56

Ile Asn Pro Asn Ser Gly Gly Thr
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic Construct

<400> SEQUENCE: 57

Ala Arg Gly Tyr Ser Asp Tyr
1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic Construct

<400> SEQUENCE: 58
```

Asn Ser Asn Ile Gly Ser Asn Pro
1               5

<210> SEQ ID NO 59
<211> LENGTH: 3
<212> TYPE: PRT
<213> ORGANISM: Artificial Sequence
<220> FEATURE:
<223> OTHER INFORMATION: Synthetic Construct

<400> SEQUENCE: 59

Gly Asn Asp
1

<210> SEQ ID NO 60
<211> LENGTH: 12
<212> TYPE: PRT
<213> ORGANISM: Artificial Sequence
<220> FEATURE:
<223> OTHER INFORMATION: Synthetic Construct

<400> SEQUENCE: 60

Ala Ala Trp Asp Asp Ser Leu Asp Gly His Val Ile
1               5                   10

<210> SEQ ID NO 61
<211> LENGTH: 125
<212> TYPE: PRT
<213> ORGANISM: Artificial Sequence
<220> FEATURE:
<223> OTHER INFORMATION: Synthetic Construct

<400> SEQUENCE: 61

Leu Glu Met Ala Gln Val Gln Leu Val Gln Ser Gly Ala Glu Val Lys
1               5                   10                  15

Lys Pro Gly Ala Ser Val Lys Val Ser Cys Lys Ala Ser Gly Tyr Thr
            20                  25                  30

Phe Thr Gly Tyr Tyr Ile His Trp Val Arg Gln Ala Pro Gly Gln Gly
        35                  40                  45

Leu Glu Trp Met Gly Arg Ile Asn Pro Asn Ser Gly Gly Thr Asn Tyr
    50                  55                  60

Ala Gln Lys Phe Gln Gly Arg Val Thr Met Thr Arg Asp Thr Ser Ile
65                  70                  75                  80

Ser Thr Ala Tyr Met Glu Leu Ser Arg Leu Arg Ser Asp Asp Thr Ala
                85                  90                  95

Val Tyr Tyr Cys Ala Arg Gly Tyr Ser Asp Arg Trp Gly Gln Gly Thr
            100                 105                 110

Leu Val Thr Val Ser Ser Thr Ser Gly Gln Ala Gly Gln
        115                 120                 125

<210> SEQ ID NO 62
<211> LENGTH: 112
<212> TYPE: PRT
<213> ORGANISM: Artificial Sequence
<220> FEATURE:
<223> OTHER INFORMATION: Synthetic Construct

<400> SEQUENCE: 62

Gln Ser Val Leu Thr Gln Pro Pro Ser Ala Ser Gly Thr Pro Gly Gln
1               5                   10                  15

Arg Val Thr Ile Ser Cys Ser Gly Gly Ser Ser Asn Ile Gly Ser Asn
            20                  25                  30

Pro Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Ser Gly Ser Val Leu Phe Gly Gly Gly Thr Lys Leu Thr Val Leu Gly
                100                 105                 110

<210> SEQ ID NO 63
<211> LENGTH: 125
<212> TYPE: PRT
<213> ORGANISM: Artificial Sequence
<220> FEATURE:
<223> OTHER INFORMATION: Synthetic Construct

<400> SEQUENCE: 63

Glu Val Gln Leu Val Glu Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Phe
 50                  55                  60

Gln Asp Arg Val Thr Leu Thr Thr Asp Thr Ser Thr Asn Thr Ala Tyr
 65                  70                  75                  80

Met Leu Leu Arg Ser Leu Arg Ser Asp Asp Thr Ala Val Tyr Tyr Cys
                 85                  90                  95

Ala Arg Thr Trp Tyr Ser Tyr His Tyr Asp Ile Trp Gly Gln Gly Thr
                100                 105                 110

Leu Val Thr Val Ser Ser Thr Ser Gly Gln Ala Gly Gln
            115                 120                 125

<210> SEQ ID NO 64
<211> LENGTH: 111
<212> TYPE: PRT
<213> ORGANISM: Artificial Sequence
<220> FEATURE:
<223> OTHER INFORMATION: Synthetic Construct

<400> SEQUENCE: 64

Asn Phe Met Leu Thr Gln Pro His Ser Val Ser Glu Ser Pro Gly Lys
 1               5                  10                  15

Thr Val Ser Ile Ser Cys Thr Gly Ser Ser Gly Ser Ile Ala Ser Asn
                20                  25                  30

Tyr Val Gln Trp Tyr Gln Gln Arg Pro Gly Ser Ala Pro Thr Thr Val
            35                  40                  45

Ile Tyr Glu Asp Lys Glu Arg Pro Ser Gly Val Pro Asn Arg Phe Ser
 50                  55                  60

Gly Ser Ile Asp Arg Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Asp
                 85                  90                  95

Gly Asn Val Val Phe Gly Gly Gly Thr Lys Leu Thr Val Leu Gly
                100                 105                 110

<210> SEQ ID NO 65
<211> LENGTH: 136
<212> TYPE: PRT
<213> ORGANISM: Artificial Sequence
<220> FEATURE:
<223> OTHER INFORMATION: Synthetic Construct

<400> SEQUENCE: 65

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Trp Ile Ser Gly Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Thr Gly Trp Ser Lys Gly Glu Lys Val Thr Thr Trp Gly Glu
            100                 105                 110

Trp Phe Tyr Val Asp Tyr Trp Gly Gln Gly Thr Leu Val Thr Val Ser
        115                 120                 125

Ser Thr Ser Gly Gln Ala Gly Gln
            130                 135
```

<210> SEQ ID NO 66
<211> LENGTH: 113
<212> TYPE: PRT
<213> ORGANISM: Artificial Sequence
<220> FEATURE:
<223> OTHER INFORMATION: Synthetic Construct

<400> SEQUENCE: 66

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Pro Asn Tyr Val Phe Gly Thr Gly Thr Lys Val Thr Val Leu
            100                 105                 110

Gly
```

<210> SEQ ID NO 67
<211> LENGTH: 121
<212> TYPE: PRT
<213> ORGANISM: Artificial Sequence
<220> FEATURE:
<223> OTHER INFORMATION: Synthetic Construct

<400> SEQUENCE: 67

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Thr Asp Tyr Ala Arg Lys Phe
50                  55                  60

Arg Gly Arg Val Thr Met Thr Arg Asp Thr Ser Ile Ser Thr Ala Tyr
65                  70                  75                  80

Met Glu Leu Ser Arg Leu Thr Ser Asp Asp Thr Ala Met Tyr Tyr Cys
                85                  90                  95

Ala Arg Gly Tyr Gly Asp Asp Trp Gly Gln Gly Thr Leu Val Thr Val
            100                 105                 110

Ser Ser Thr Ser Gly Gln Ala Gly Gln
            115                 120

<210> SEQ ID NO 68
<211> LENGTH: 111
<212> TYPE: PRT
<213> ORGANISM: Artificial Sequence
<220> FEATURE:
<223> OTHER INFORMATION: Synthetic Construct

<400> SEQUENCE: 68

Gln Ser Val Leu Thr Gln Pro Pro Ser Val Ser Glu Ala Pro Arg Gln
1               5                   10                  15

Arg Val Thr Ile Ser Cys Ser Gly Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Phe Asn Asp Val Gln Ser Ser Gly Val Ser Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Ala Val Leu Phe Gly Gly Gly Thr Lys Leu Thr Val Leu Gly
            100                 105                 110

<210> SEQ ID NO 69
<211> LENGTH: 118
<212> TYPE: PRT
<213> ORGANISM: Artificial Sequence
<220> FEATURE:
<223> OTHER INFORMATION: Synthetic Construct

<400> SEQUENCE: 69

Glu Leu Gln Leu Val Glu Ser Gly Gly Val Val Gln Pro Gly Arg
1               5                   10                  15

Ser Pro Arg Leu Ser Cys Ala Ala Ser Gly Phe Thr Phe Ser Asn Tyr
            20                  25                  30

Pro Met His Trp Val Arg Gln Ala Pro Gly Lys Gly Leu Glu Trp Val
        35                  40                  45

Ala Val Ile Ser Tyr Asp Gly Asn His Lys Tyr Tyr Ala Asp Ser Leu
50                  55                  60

```
Glu Gly Arg Phe Ser Ile Ser Arg Asp Asn Ser Lys Asn Thr Leu Tyr
 65                  70                  75                  80

Leu Gln Met Asn Ser Leu Thr Ala Ala Asp Thr Ala Val Tyr Tyr Cys
                 85                  90                  95

Ala Arg Gly Gly Gly Met Gly Gly Leu Asp Ser Trp Gly Gln Gly Thr
            100                 105                 110

Leu Val Thr Val Ser Ser
        115

<210> SEQ ID NO 70
<211> LENGTH: 111
<212> TYPE: PRT
<213> ORGANISM: Artificial Sequence
<220> FEATURE:
<223> OTHER INFORMATION: Synthetic Construct

<400> SEQUENCE: 70

Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
                 20                  25                  30

Asn Tyr Val Ser Trp Tyr Gln Gln His Pro Gly Lys Val Pro Lys Leu
             35                  40                  45

Met Ile Tyr Glu Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Gly
                 85                  90                  95

Asp Thr Leu Val Phe Gly Gly Gly Thr Lys Val Thr Val Leu Gly
            100                 105                 110

<210> SEQ ID NO 71
<211> LENGTH: 121
<212> TYPE: PRT
<213> ORGANISM: Artificial Sequence
<220> FEATURE:
<223> OTHER INFORMATION: Synthetic Construct

<400> SEQUENCE: 71

Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Pro Ser Tyr
                 20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Ser Tyr Thr Tyr Met Gly Gly Ser Tyr Asp Tyr Trp Gly
            100                 105                 110

Gln Gly Thr Leu Val Thr Val Ser Ser
        115                 120

<210> SEQ ID NO 72
```

<211> LENGTH: 111
<212> TYPE: PRT
<213> ORGANISM: Artificial Sequence
<220> FEATURE:
<223> OTHER INFORMATION: Synthetic Construct

<400> SEQUENCE: 72

```
Ser Tyr Val Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Ser Asn
            20                  25                  30
Thr Val Asn Trp Tyr Gln Gln Leu Pro Gly Thr Ala Pro Lys Leu Leu
        35                  40                  45
Ile Tyr Ser Asn Asn Gln Arg Pro Ser Gly Val Pro Asp Arg Phe Ser
    50                  55                  60
Ala Ser Lys Ser Gly Thr Ser Ala Ser Leu Ala Ile Ser Gly Phe Gln
65                  70                  75                  80
Ser Glu Asp Glu Ala Asp Tyr Tyr Cys Ala Ala Trp Asp Asp Ser Leu
                85                  90                  95
Asp Gly Tyr Val Phe Gly Thr Gly Thr Lys Val Thr Val Leu Gly
            100                 105                 110
```

<210> SEQ ID NO 73
<211> LENGTH: 117
<212> TYPE: PRT
<213> ORGANISM: Artificial Sequence
<220> FEATURE:
<223> OTHER INFORMATION: Synthetic Construct

<400> SEQUENCE: 73

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Asn Gly Asn Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Gly Tyr Tyr Gly Asp Leu Asp Pro Trp Gly Gln Gly Thr Leu
            100                 105                 110
Val Thr Val Ser Ser
        115
```

<210> SEQ ID NO 74
<211> LENGTH: 111
<212> TYPE: PRT
<213> ORGANISM: Artificial Sequence
<220> FEATURE:
<223> OTHER INFORMATION: Synthetic Construct

<400> SEQUENCE: 74

```
Gln Ala Val Leu Thr Gln Ala Pro Ser Ala Ser Gly Thr Leu Gly Gln
1               5                   10                  15
Gln Val Thr Ile Ser Cys Ser Gly Thr Thr Ser Asn Ile Gly Arg Asn
            20                  25                  30
```

Thr Val Asn Trp Tyr Gln His Leu Pro Gly Thr Ala Pro Lys Leu Leu
            35                  40                  45

Ile Phe Val Ser Asn Gln Arg Pro Ser Gly Val Pro Asp Arg Phe Ser
    50                  55                  60

Gly Ser Lys Ser Gly Thr Ser Ala Ser Leu Val Ile Ser Gly Leu Gln
65                  70                  75                  80

Ser Glu Asp Glu Ala Asp Tyr Tyr Cys Gly Ala Trp Asp Asp Ser Leu
                85                  90                  95

Asp Gly Met Leu Phe Gly Gly Gly Thr Lys Leu Thr Val Leu Gly
            100                 105                 110

<210> SEQ ID NO 75
<211> LENGTH: 113
<212> TYPE: PRT
<213> ORGANISM: Artificial Sequence
<220> FEATURE:
<223> OTHER INFORMATION: Synthetic Construct

<400> SEQUENCE: 75

Glu Val Gln Leu Val Glu Ser Gly Gly Gly Leu Glu Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Ala Ser Gly Asn Ser Thr Phe Tyr Ala Asp Ser Val
    50                  55                  60

Lys Gly Arg Phe Thr Ile Ser Arg Asp Asn Ser Lys His Thr Leu Asp
65                  70                  75                  80

Leu Gln Met Asn Ser Leu Arg Ala Asp Asp Thr Ala Val Tyr Tyr Cys
                85                  90                  95

Ala Arg Asn Ser Asp Val Trp Gly Gln Gly Thr Leu Val Thr Val Ser
            100                 105                 110

Ser

<210> SEQ ID NO 76
<211> LENGTH: 113
<212> TYPE: PRT
<213> ORGANISM: Artificial Sequence
<220> FEATURE:
<223> OTHER INFORMATION: Synthetic Construct

<400> SEQUENCE: 76

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asp Tyr Val Ser Trp Tyr Gln Gln His Pro Gly Lys Ala Pro Lys Leu
            35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Phe Pro Tyr Val Phe Gly Thr Gly Thr Lys Val Thr Val Leu
            100                 105                 110

Gly

<210> SEQ ID NO 77
<211> LENGTH: 119
<212> TYPE: PRT
<213> ORGANISM: Artificial Sequence
<220> FEATURE:
<223> OTHER INFORMATION: Synthetic Construct

<400> SEQUENCE: 77

```
Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Thr Ser Tyr
            20                  25                  30
Trp Ile Gly Trp Val Arg Gln Met Pro Gly Lys Gly Leu Glu Trp Met
        35                  40                  45
Gly Ile Ile Tyr Pro Gly Asp Ser Asp Thr Arg Tyr Ser Pro Ser Phe
    50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Ser Ser Tyr Ser Tyr Gly Gly Pro Asp Ala Trp Gly Gln Gly
            100                 105                 110
Thr Leu Val Thr Val Ser Ser
        115
```

<210> SEQ ID NO 78
<211> LENGTH: 111
<212> TYPE: PRT
<213> ORGANISM: Artificial Sequence
<220> FEATURE:
<223> OTHER INFORMATION: Synthetic Construct

<400> SEQUENCE: 78

```
Gln Ala Val Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Ser Asn
            20                  25                  30
Thr Val Asn Trp Tyr Gln Gln Leu Pro Gly Thr Ala Pro Lys Leu Leu
        35                  40                  45
Ile Tyr Ser Asn Asn Gln Arg Pro Ser Gly Val Pro Asp Arg Phe Ser
    50                  55                  60
Gly Ser Lys Ser Gly Thr Ser Ala Ser Leu Ala Ile Ser Gly Leu Gln
65                  70                  75                  80
Ser Glu Asp Glu Ala Asp Tyr Tyr Cys Ala Ala Trp Asp Asp Ser Leu
                85                  90                  95
Asn Gly Tyr Val Phe Gly Thr Gly Thr Lys Val Thr Val Leu Gly
            100                 105                 110
```

<210> SEQ ID NO 79
<211> LENGTH: 114
<212> TYPE: PRT
<213> ORGANISM: Artificial Sequence
<220> FEATURE:
<223> OTHER INFORMATION: Synthetic Construct

<400> SEQUENCE: 79

```
Glu Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Tyr Ser Asp Tyr Trp Gly Gln Gly Thr Leu Val Thr Val
            100                 105                 110

Ser Ser

<210> SEQ ID NO 80
<211> LENGTH: 112
<212> TYPE: PRT
<213> ORGANISM: Artificial Sequence
<220> FEATURE:
<223> OTHER INFORMATION: Synthetic Construct

<400> SEQUENCE: 80

Gln Ala Val Leu Thr Gln Pro Pro Ser Ala Ser Gly Thr Pro Gly Gln
1               5                   10                  15

Met Val Thr Ile Ser Cys Ser Gly Ser Asn Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Gly Asn Asp Glu Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asp Gly His Val Ile Phe Gly Gly Gly Thr Lys Leu Thr Val Leu Gly
            100                 105                 110

<210> SEQ ID NO 81
<211> LENGTH: 254
<212> TYPE: PRT
<213> ORGANISM: Artificial Sequence
<220> FEATURE:
<223> OTHER INFORMATION: Synthetic Construct

<400> SEQUENCE: 81

Gln Ser Val Leu Thr Gln Pro Pro Ser Ala Ser Gly Thr Pro Gly Gln
1               5                   10                  15

Arg Val Thr Ile Ser Cys Ser Gly Gly Ser Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95
```

Ser Gly Ser Val Leu Phe Gly Gly Gly Thr Lys Leu Thr Val Leu Gly
                100                 105                 110

Ser Arg Gly Gly Gly Gly Ser Gly Gly Gly Ser Gly Gly Gly Gly
            115                 120                 125

Ser Leu Glu Met Ala Gln Val Gln Leu Val Gln Ser Gly Ala Glu Val
        130                 135                 140

Lys Lys Pro Gly Ala Ser Val Lys Val Ser Cys Lys Ala Ser Gly Tyr
145                 150                 155                 160

Thr Phe Thr Gly Tyr Tyr Ile His Trp Val Arg Gln Ala Pro Gly Gln
                165                 170                 175

Gly Leu Glu Trp Met Gly Arg Ile Asn Pro Asn Ser Gly Gly Thr Asn
            180                 185                 190

Tyr Ala Gln Lys Phe Gln Gly Arg Val Thr Met Thr Arg Asp Thr Ser
        195                 200                 205

Ile Ser Thr Ala Tyr Met Glu Leu Ser Arg Leu Arg Ser Asp Asp Thr
    210                 215                 220

Ala Val Tyr Tyr Cys Ala Arg Gly Tyr Ser Asp Arg Trp Gly Gln Gly
225                 230                 235                 240

Thr Leu Val Thr Val Ser Ser Thr Ser Gly Gln Ala Gly Gln
                245                 250

<210> SEQ ID NO 82
<211> LENGTH: 257
<212> TYPE: PRT
<213> ORGANISM: Artificial Sequence
<220> FEATURE:
<223> OTHER INFORMATION: Synthetic Construct

<400> SEQUENCE: 82

Asn Phe Met Leu Thr Gln Pro His Ser Val Ser Glu Ser Pro Gly Lys
1               5                   10                  15

Thr Val Ser Ile Ser Cys Thr Gly Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Lys Glu Arg Pro Ser Gly Val Pro Asn Arg Phe Ser
    50                  55                  60

Gly Ser Ile Asp Arg Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Asp
                85                  90                  95

Gly Asn Val Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Glu Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Thr Ser Tyr Gly Ile Ser Trp Val Arg Gln Ala Pro Gly Gln Gly
                165                 170                 175

Leu Glu Trp Met Gly Trp Ile Ser Ala Tyr Asn Gly Asn Thr Asn Tyr
            180                 185                 190

Ala Gln Lys Phe Gln Asp Arg Val Thr Leu Thr Thr Asp Thr Ser Thr
        195                 200                 205

Asn Thr Ala Tyr Met Leu Leu Arg Ser Leu Arg Ser Asp Thr Ala
            210                 215                 220

Val Tyr Tyr Cys Ala Arg Thr Trp Tyr Ser Tyr His Tyr Asp Ile Trp
225                 230                 235                 240

Gly Gln Gly Thr Leu Val Thr Val Ser Ser Thr Ser Gly Gln Ala Gly
                245                 250                 255

Gln

<210> SEQ ID NO 83
<211> LENGTH: 270
<212> TYPE: PRT
<213> ORGANISM: Artificial Sequence
<220> FEATURE:
<223> OTHER INFORMATION: Synthetic Construct

<400> SEQUENCE: 83

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ser Leu
                85                  90                  95

Ser Gly Pro Asn Tyr Val Phe Gly Thr Gly Thr Lys Val Thr Val Leu
            100                 105                 110

Gly Ser Arg Gly Gly Gly Gly Ser Gly Gly Gly Ser Gly Gly Gly
            115                 120                 125

Gly Ser Leu Glu Met Ala Gln Val Gln Leu Val Gln Ser Gly Ala Glu
            130                 135                 140

Val Lys Lys Pro Gly Ser Ser Val Lys Val Ser Cys Lys Ala Ser Gly
145                 150                 155                 160

Gly Thr Phe Ser Ser Tyr Ala Ile Ser Trp Val Arg Gln Ala Pro Gly
                165                 170                 175

Gln Gly Leu Glu Trp Met Gly Trp Ile Ser Gly Tyr Asn Gly Asn Thr
            180                 185                 190

Asn Tyr Ala Gln Lys Leu Gln Gly Arg Val Thr Met Thr Thr Asp Thr
            195                 200                 205

Ser Thr Ser Thr Ala Tyr Met Glu Leu Arg Ser Leu Arg Ser Asp Asp
            210                 215                 220

Thr Ala Val Tyr Tyr Cys Ala Arg Thr Gly Trp Ser Lys Gly Glu Lys
225                 230                 235                 240

Val Thr Thr Trp Gly Glu Trp Phe Tyr Val Asp Tyr Trp Gly Gln Gly
                245                 250                 255

Thr Leu Val Thr Val Ser Ser Thr Ser Gly Gln Ala Gly Gln
            260                 265                 270

<210> SEQ ID NO 84
<211> LENGTH: 253
<212> TYPE: PRT
<213> ORGANISM: Artificial Sequence
<220> FEATURE:

<223> OTHER INFORMATION: Synthetic Construct

<400> SEQUENCE: 84

```
Gln Ser Val Leu Thr Gln Pro Pro Ser Val Ser Glu Ala Pro Arg Gln
 1               5                  10                  15

Arg Val Thr Ile Ser Cys Ser Gly Ser Ser Asn Ile Gly Asn Asn
             20                  25                  30

Ala Val Asn Trp Tyr Gln Gln Leu Pro Gly Lys Ala Pro Lys Leu Leu
         35                  40                  45

Ile Tyr Phe Asn Asp Val Gln Ser Ser Gly Val Ser Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Ala Val Leu Phe Gly Gly Gly Thr Lys Leu Thr Val Leu Gly Ser
             100                 105                 110

Arg Gly Gly Gly Gly Ser Gly Gly Gly Gly Ser Gly Gly Gly Gly Ser
         115                 120                 125

Leu Glu Met Ala Glu Val Gln Leu Val Gln Ser Gly Ala Glu Val Lys
     130                 135                 140

Lys Pro Gly Ala Ser Val Lys Val Ser Cys Lys Ala Ser Gly Tyr Thr
145                 150                 155                 160

Phe Thr Gly Tyr Tyr Met His Trp Val Arg Gln Ala Pro Gly Gln Gly
                165                 170                 175

Leu Glu Trp Met Gly Arg Ile Asn Pro Asn Ser Gly Gly Thr Asp Tyr
            180                 185                 190

Ala Arg Lys Phe Arg Gly Arg Val Thr Met Thr Arg Asp Thr Ser Ile
        195                 200                 205

Ser Thr Ala Tyr Met Glu Leu Ser Arg Leu Thr Ser Asp Asp Thr Ala
    210                 215                 220

Met Tyr Tyr Cys Ala Arg Gly Tyr Gly Asp Asp Trp Gly Gln Gly Thr
225                 230                 235                 240

Leu Val Thr Val Ser Ser Thr Gly Gln Ala Gly Gln
                245                 250
```

<210> SEQ ID NO 85
<211> LENGTH: 257
<212> TYPE: PRT
<213> ORGANISM: Artificial Sequence
<220> FEATURE:
<223> OTHER INFORMATION: Synthetic Construct

<400> SEQUENCE: 85

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Val Pro Lys Leu
         35                  40                  45

Met Ile Tyr Glu Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Gly
                 85                  90                  95
```

Asp Thr Leu Val Phe Gly Gly Thr Lys Val Thr Val Leu Gly Ser
            100                 105                 110

Arg Gly Gly Gly Gly Ser Gly Gly Gly Ser Gly Gly Gly Ser
            115                 120                 125

Leu Glu Met Ala Glu Leu Gln Leu Val Glu Ser Gly Gly Val Val
            130                 135                 140

Gln Pro Gly Arg Ser Pro Arg Leu Ser Cys Ala Ala Ser Gly Phe Thr
145                 150                 155                 160

Phe Ser Asn Tyr Pro Met His Trp Val Arg Gln Ala Pro Gly Lys Gly
                165                 170                 175

Leu Glu Trp Val Ala Val Ile Ser Tyr Asp Gly Asn His Lys Tyr Tyr
            180                 185                 190

Ala Asp Ser Leu Glu Gly Arg Phe Ser Ile Ser Arg Asp Asn Ser Lys
            195                 200                 205

Asn Thr Leu Tyr Leu Gln Met Asn Ser Leu Thr Ala Ala Asp Thr Ala
210                 215                 220

Val Tyr Tyr Cys Ala Arg Gly Gly Gly Met Gly Gly Leu Asp Ser Trp
225                 230                 235                 240

Gly Gln Gly Thr Leu Val Thr Val Ser Ser Thr Ser Gly Gln Ala Gly
            245                 250                 255

Gln

<210> SEQ ID NO 86
<211> LENGTH: 260
<212> TYPE: PRT
<213> ORGANISM: Artificial Sequence
<220> FEATURE:
<223> OTHER INFORMATION: Synthetic Construct

<400> SEQUENCE: 86

Ser Tyr Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
50                  55                  60

Ala Ser Lys Ser Gly Thr Ser Ala Ser Leu Ala Ile Ser Gly Phe Gln
65                  70                  75                  80

Ser Glu Asp Glu Ala Asp Tyr Tyr Cys Ala Ala Trp Asp Asp Ser Leu
                85                  90                  95

Asp Gly Tyr Val Phe Gly Thr Gly Thr Lys Val Thr Val Leu Gly Ser
            100                 105                 110

Arg Gly Gly Gly Gly Ser Gly Gly Gly Ser Gly Gly Gly Ser
            115                 120                 125

Leu Glu Met Ala Glu Val Gln Leu Val Gln Ser Gly Ala Glu Val Lys
            130                 135                 140

Lys Pro Gly Glu Ser Leu Lys Ile Ser Cys Lys Gly Ser Gly Tyr Ser
145                 150                 155                 160

Phe Pro Ser Tyr Trp Ile Gly Trp Val Arg Gln Met Pro Gly Lys Gly
                165                 170                 175

Leu Glu Trp Met Gly Ile Ile Tyr Pro Gly Asp Ser Asp Thr Arg Tyr
            180                 185                 190

```
Ser Pro Ser Phe Gln Gly Gln Val Thr Ile Ser Ala Asp Lys Ser Ile
            195                 200                 205

Ser Thr Ala Tyr Leu Gln Trp Ser Ser Leu Lys Ala Ser Asp Thr Ala
    210                 215                 220

Met Tyr Tyr Cys Ala Arg Gly Ser Tyr Thr Tyr Met Gly Gly Ser Tyr
225                 230                 235                 240

Asp Tyr Trp Gly Gln Gly Thr Leu Val Thr Val Ser Ser Thr Ser Gly
            245                 250                 255

Gln Ala Gly Gln
            260

<210> SEQ ID NO 87
<211> LENGTH: 256
<212> TYPE: PRT
<213> ORGANISM: Artificial Sequence
<220> FEATURE:
<223> OTHER INFORMATION: Synthetic Construct

<400> SEQUENCE: 87

Gln Ala Val Leu Thr Gln Ala Pro Ser Ala Ser Gly Thr Leu Gly Gln
1               5                   10                  15

Gln Val Thr Ile Ser Cys Ser Gly Thr Thr Ser Asn Ile Gly Arg Asn
            20                  25                  30

Thr Val Asn Trp Tyr Gln His Leu Pro Gly Thr Ala Pro Lys Leu Leu
        35                  40                  45

Ile Phe Val Ser Asn Gln Arg Pro Ser Gly Val Pro Asp Arg Phe Ser
    50                  55                  60

Gly Ser Lys Ser Gly Thr Ser Ala Ser Leu Val Ile Ser Gly Leu Gln
65                  70                  75                  80

Ser Glu Asp Glu Ala Asp Tyr Tyr Cys Gly Ala Trp Asp Asp Ser Leu
                85                  90                  95

Asp Gly Met Leu Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Gln Val Gln Leu Val Gln Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Thr Ser Tyr Gly Ile Ser Trp Val Arg Gln Ala Pro Gly Gln Gly
                165                 170                 175

Leu Glu Trp Met Gly Trp Ile Ser Ala Tyr Asn Gly Asn Thr Asn Tyr
            180                 185                 190

Ala Gln Lys Leu Gln Gly Arg Val Thr Met Thr Thr Asp Thr Ser Thr
        195                 200                 205

Ser Thr Ala Tyr Met Glu Leu Arg Ser Leu Arg Ser Asp Asp Thr Ala
    210                 215                 220

Val Tyr Tyr Cys Ala Arg Gly Tyr Tyr Gly Asp Leu Asp Pro Trp Gly
225                 230                 235                 240

Gln Gly Thr Leu Val Thr Val Ser Ser Thr Ser Gly Gln Ala Gly Gln
                245                 250                 255

<210> SEQ ID NO 88
<211> LENGTH: 254
<212> TYPE: PRT
<213> ORGANISM: Artificial Sequence
<220> FEATURE:
```

<223> OTHER INFORMATION: Synthetic Construct

<400> SEQUENCE: 88

```
Gln Ser Ala Leu Thr Gln Pro Pro Ser Ala Ser Gly Ser Pro Gly Gln
1               5                   10                  15
Ser Val Thr Ile Ser Cys Thr Gly Thr Ser Ser Asp Val Gly Gly Tyr
            20                  25                  30
Asp Tyr Val Ser Trp Tyr Gln Gln His Pro Gly Lys Ala Pro Lys Leu
        35                  40                  45
Met Ile Tyr Glu Val Ser Lys Arg Pro Ser Gly Val Ser Asn Arg Phe
    50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Ser Ser Tyr Thr Ser Ser
                85                  90                  95
Ser Thr Phe Pro Tyr Val Phe Gly Thr Gly Thr Lys Val Thr Val Leu
            100                 105                 110
Gly Ser Arg Gly Gly Gly Gly Ser Gly Gly Gly Ser Gly Gly Gly
        115                 120                 125
Gly Ser Leu Glu Met Ala Glu Val Gln Leu Val Glu Ser Gly Gly Gly
    130                 135                 140
Leu Glu Gln Pro Gly Gly Ser Leu Arg Leu Ser Cys Ala Ala Ser Gly
145                 150                 155                 160
Phe Thr Phe Ser Ser Tyr Ala Met Ser Trp Val Arg Gln Ala Pro Gly
                165                 170                 175
Lys Gly Leu Glu Trp Val Ser Ala Ile Ser Ala Ser Gly Asn Ser Thr
            180                 185                 190
Phe Tyr Ala Asp Ser Val Lys Gly Arg Phe Thr Ile Ser Arg Asp Asn
        195                 200                 205
Ser Lys His Thr Leu Asp Leu Gln Met Asn Ser Leu Arg Ala Asp Asp
    210                 215                 220
Thr Ala Val Tyr Tyr Cys Ala Arg Asn Ser Asp Val Trp Gly Gln Gly
225                 230                 235                 240
Thr Leu Val Thr Val Ser Ser Thr Ser Gly Ala Gly Gln
                245                 250
```

<210> SEQ ID NO 89
<211> LENGTH: 258
<212> TYPE: PRT
<213> ORGANISM: Artificial Sequence
<220> FEATURE:
<223> OTHER INFORMATION: Synthetic Construct

<400> SEQUENCE: 89

```
Gln Ala Val Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Ser Asn
            20                  25                  30
Thr Val Asn Trp Tyr Gln Gln Leu Pro Gly Thr Ala Pro Lys Leu Leu
        35                  40                  45
Ile Tyr Ser Asn Asn Gln Arg Pro Ser Gly Val Pro Asp Arg Phe Ser
    50                  55                  60
Gly Ser Lys Ser Gly Thr Ser Ala Ser Leu Ala Ile Ser Gly Leu Gln
65                  70                  75                  80
Ser Glu Asp Glu Ala Asp Tyr Tyr Cys Ala Ala Trp Asp Asp Ser Leu
                85                  90                  95
```

```
Asn Gly Tyr Val Phe Gly Thr Gly Thr Lys Val Thr Val Leu Gly Ser
                100                 105                 110

Arg Gly Gly Gly Gly Ser Gly Gly Gly Ser Gly Gly Gly Ser
            115                 120                 125

Leu Glu Met Ala Glu Val Gln Leu Val Gln Ser Gly Ala Glu Val Lys
130                 135                 140

Lys Pro Gly Glu Ser Leu Lys Ile Ser Cys Lys Gly Ser Gly Tyr Ser
145                 150                 155                 160

Phe Thr Ser Tyr Trp Ile Gly Trp Val Arg Gln Met Pro Gly Lys Gly
                165                 170                 175

Leu Glu Trp Met Gly Ile Ile Tyr Pro Gly Asp Ser Asp Thr Arg Tyr
            180                 185                 190

Ser Pro Ser Phe Gln Gly Gln Val Thr Ile Ser Ala Asp Lys Ser Ile
        195                 200                 205

Ser Thr Ala Tyr Leu Gln Trp Ser Ser Leu Lys Ala Ser Asp Thr Ala
    210                 215                 220

Met Tyr Tyr Cys Ala Arg Ser Ser Tyr Ser Tyr Gly Pro Asp Ala
225                 230                 235                 240

Trp Gly Gln Gly Thr Leu Val Thr Val Ser Ser Thr Ser Gly Gln Ala
                245                 250                 255

Gly Gln

<210> SEQ ID NO 90
<211> LENGTH: 254
<212> TYPE: PRT
<213> ORGANISM: Artificial Sequence
<220> FEATURE:
<223> OTHER INFORMATION: Synthetic Construct

<400> SEQUENCE: 90

Gln Ala Val Leu Thr Gln Pro Pro Ser Ala Ser Gly Thr Pro Gly Gln
1               5                   10                  15

Met Val Thr Ile Ser Cys Ser Gly Ser Asn Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Gly Asn Asp Glu Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asp Gly His Val Ile Phe Gly Gly Gly Thr Lys Leu Thr Val Leu Gly
            100                 105                 110

Ser Arg Gly Gly Gly Gly Ser Gly Gly Gly Gly Ser Gly Gly Gly Gly
        115                 120                 125

Ser Leu Glu Met Ala Glu Val Gln Leu Val Gln Ser Gly Ala Glu Val
    130                 135                 140

Lys Lys Pro Gly Ala Ser Val Lys Val Ser Cys Lys Ala Ser Gly Tyr
145                 150                 155                 160

Thr Phe Thr Gly Tyr Tyr Met His Trp Val Arg Gln Ala Pro Gly Gln
                165                 170                 175

Gly Leu Glu Trp Met Gly Arg Ile Asn Pro Asn Ser Gly Gly Thr Asn
            180                 185                 190
```

Tyr Ala Gln Lys Phe Gln Gly Arg Val Thr Met Thr Arg Asp Thr Ser
            195                 200                 205

Ile Ser Thr Ala Tyr Met Glu Leu Ser Arg Leu Arg Ser Asp Asp Thr
        210                 215                 220

Ala Val Tyr Tyr Cys Ala Arg Gly Tyr Ser Asp Tyr Trp Gly Gln Gly
225                 230                 235                 240

Thr Leu Val Thr Val Ser Ser Thr Ser Gly Gln Ala Gly Gln
                245                 250

<210> SEQ ID NO 91
<211> LENGTH: 21
<212> TYPE: PRT
<213> ORGANISM: Artificial Sequence
<220> FEATURE:
<223> OTHER INFORMATION: Synthetic Construct

<400> SEQUENCE: 91

Ser Arg Gly Gly Gly Gly Ser Gly Gly Gly Gly Ser Gly Gly Gly Gly
1               5                   10                  15

Ser Leu Glu Met Ala
            20

<210> SEQ ID NO 92
<211> LENGTH: 18
<212> TYPE: PRT
<213> ORGANISM: Artificial Sequence
<220> FEATURE:
<223> OTHER INFORMATION: Synthetic Construct

<400> SEQUENCE: 92

His His His His His His Gly Ala Tyr Pro Tyr Asp Val Pro Asp Tyr
1               5                   10                  15

Ala Ser

<210> SEQ ID NO 93
<211> LENGTH: 670
<212> TYPE: PRT
<213> ORGANISM: Artificial Sequence
<220> FEATURE:
<223> OTHER INFORMATION: Synthetic Construct

<400> SEQUENCE: 93

Val Asn Leu Thr Thr Arg Thr Gln Leu Pro Pro Ala Tyr Thr Asn Ser
1               5                   10                  15

Phe Thr Arg Gly Val Tyr Tyr Pro Asp Lys Val Phe Arg Ser Ser Val
            20                  25                  30

Leu His Ser Thr Gln Asp Leu Phe Leu Pro Phe Phe Ser Asn Val Thr
        35                  40                  45

Trp Phe His Ala Ile His Val Ser Gly Thr Asn Gly Thr Lys Arg Phe
    50                  55                  60

Asp Asn Pro Val Leu Pro Phe Asn Asp Gly Val Tyr Phe Ala Ser Thr
65                  70                  75                  80

Glu Lys Ser Asn Ile Ile Arg Gly Trp Ile Phe Gly Thr Thr Leu Asp
                85                  90                  95

Ser Lys Thr Gln Ser Leu Leu Ile Val Asn Asn Ala Thr Asn Val Val
            100                 105                 110

Ile Lys Val Cys Glu Phe Gln Phe Cys Asn Asp Pro Phe Leu Gly Val
        115                 120                 125

Tyr Tyr His Lys Asn Asn Lys Ser Trp Met Glu Ser Glu Phe Arg Val
    130                 135                 140

```
Tyr Ser Ser Ala Asn Asn Cys Thr Phe Glu Tyr Val Ser Gln Pro Phe
145                 150                 155                 160

Leu Met Asp Leu Glu Gly Lys Gln Gly Asn Phe Lys Asn Leu Arg Glu
            165                 170                 175

Phe Val Phe Lys Asn Ile Asp Gly Tyr Phe Lys Ile Tyr Ser Lys His
            180                 185                 190

Thr Pro Ile Asn Leu Val Arg Asp Leu Pro Gln Gly Phe Ser Ala Leu
            195                 200                 205

Glu Pro Leu Val Asp Leu Pro Ile Gly Ile Asn Ile Thr Arg Phe Gln
            210                 215                 220

Thr Leu Leu Ala Leu His Arg Ser Tyr Leu Thr Pro Gly Asp Ser Ser
225                 230                 235                 240

Ser Gly Trp Thr Ala Gly Ala Ala Tyr Tyr Val Gly Tyr Leu Gln
            245                 250                 255

Pro Arg Thr Phe Leu Leu Lys Tyr Asn Glu Asn Gly Thr Ile Thr Asp
            260                 265                 270

Ala Val Asp Cys Ala Leu Asp Pro Leu Ser Glu Thr Lys Cys Thr Leu
            275                 280                 285

Lys Ser Phe Thr Val Glu Lys Gly Ile Tyr Gln Thr Ser Asn Phe Arg
            290                 295                 300

Val Gln Pro Thr Glu Ser Ile Val Arg Phe Pro Asn Ile Thr Asn Leu
305                 310                 315                 320

Cys Pro Phe Gly Glu Val Phe Asn Ala Thr Arg Phe Ala Ser Val Tyr
            325                 330                 335

Ala Trp Asn Arg Lys Arg Ile Ser Asn Cys Val Ala Asp Tyr Ser Val
            340                 345                 350

Leu Tyr Asn Ser Ala Ser Phe Ser Thr Phe Lys Cys Tyr Gly Val Ser
            355                 360                 365

Pro Thr Lys Leu Asn Asp Leu Cys Phe Thr Asn Val Tyr Ala Asp Ser
            370                 375                 380

Phe Val Ile Arg Gly Asp Glu Val Arg Gln Ile Ala Pro Gly Gln Thr
385                 390                 395                 400

Gly Lys Ile Ala Asp Tyr Asn Tyr Lys Leu Pro Asp Asp Phe Thr Gly
            405                 410                 415

Cys Val Ile Ala Trp Asn Ser Asn Asn Leu Asp Ser Lys Val Gly Gly
            420                 425                 430

Asn Tyr Asn Tyr Leu Tyr Arg Leu Phe Arg Lys Ser Asn Leu Lys Pro
            435                 440                 445

Phe Glu Arg Asp Ile Ser Thr Glu Ile Tyr Gln Ala Gly Ser Thr Pro
            450                 455                 460

Cys Asn Gly Val Glu Gly Phe Asn Cys Tyr Phe Pro Leu Gln Ser Tyr
465                 470                 475                 480

Gly Phe Gln Pro Thr Asn Gly Val Gly Tyr Gln Pro Tyr Arg Val Val
            485                 490                 495

Val Leu Ser Phe Glu Leu Leu His Ala Pro Ala Thr Val Cys Gly Pro
            500                 505                 510

Lys Lys Ser Thr Asn Leu Val Lys Asn Lys Cys Val Asn Phe Asn Phe
            515                 520                 525

Asn Gly Leu Thr Gly Thr Gly Val Leu Thr Glu Ser Asn Lys Lys Phe
            530                 535                 540

Leu Pro Phe Gln Gln Phe Gly Arg Asp Ile Ala Asp Thr Thr Asp Ala
545                 550                 555                 560
```

Val Arg Asp Pro Gln Thr Leu Glu Ile Leu Asp Ile Thr Pro Cys Ser
            565                 570                 575

Phe Gly Gly Val Ser Val Ile Thr Pro Gly Thr Asn Thr Ser Asn Gln
        580                 585                 590

Val Ala Val Leu Tyr Gln Asp Val Asn Cys Thr Glu Val Pro Val Ala
            595                 600                 605

Ile His Ala Asp Gln Leu Thr Pro Thr Trp Arg Val Tyr Ser Thr Gly
610                 615                 620

Ser Asn Val Phe Gln Thr Arg Ala Gly Cys Leu Ile Gly Ala Glu His
625                 630                 635                 640

Val Asn Asn Ser Tyr Glu Cys Asp Ile Pro Ile Gly Ala Gly Ile Cys
                645                 650                 655

Ala Ser Tyr Gln Thr Gln Thr Asn Ser Pro Arg Arg Ala Arg
            660                 665                 670

<210> SEQ ID NO 94
<211> LENGTH: 1255
<212> TYPE: PRT
<213> ORGANISM: Artificial Sequence
<220> FEATURE:
<223> OTHER INFORMATION: Synthetic Construct

<400> SEQUENCE: 94

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
                20                  25                  30

His Thr Ser Ser Met Arg Gly Val Tyr Tyr Pro Asp Glu Ile Phe Arg
            35                  40                  45

Ser Asp Thr Leu Tyr Leu Thr Gln Asp Leu Phe Leu Pro Phe Tyr Ser
        50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

```
Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
```

```
            675                 680                 685
Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile Arg Ala Ser Ala Asn Leu Ala Ala
        995                1000                1005

Thr Lys Met Ser Glu Cys Val Leu Gly Gln Ser Lys Arg Val Asp Phe
    1010                1015                1020

Cys Gly Lys Gly Tyr His Leu Met Ser Phe Pro Gln Ala Ala Pro His
1025                1030                1035                1040

Gly Val Val Phe Leu His Val Thr Tyr Val Pro Ser Gln Glu Arg Asn
                1045                1050                1055

Phe Thr Thr Ala Pro Ala Ile Cys His Glu Gly Lys Ala Tyr Phe Pro
            1060                1065                1070

Arg Glu Gly Val Phe Val Phe Asn Gly Thr Ser Trp Phe Ile Thr Gln
        1075                1080                1085

Arg Asn Phe Phe Ser Pro Gln Ile Ile Thr Thr Asp Asn Thr Phe Val
    1090                1095                1100
```

Ser Gly Asn Cys Asp Val Val Ile Gly Ile Ile Asn Thr Val Tyr
1105                1110                1115                1120

Asp Pro Leu Gln Pro Glu Leu Asp Ser Phe Lys Glu Leu Asp Lys
           1125                1130                1135

Tyr Phe Lys Asn His Thr Ser Pro Asp Val Asp Leu Gly Asp Ile Ser
        1140                1145                1150

Gly Ile Asn Ala Ser Val Val Asn Ile Gln Lys Glu Ile Asp Arg Leu
        1155                1160                1165

Asn Glu Val Ala Lys Asn Leu Asn Glu Ser Leu Ile Asp Leu Gln Glu
    1170                1175                1180

Leu Gly Lys Tyr Glu Gln Tyr Ile Lys Trp Pro Trp Tyr Val Trp Leu
1185                1190                1195                1200

Gly Phe Ile Ala Gly Leu Ile Ala Ile Val Met Val Thr Ile Leu Leu
            1205                1210                1215

Cys Cys Met Thr Ser Cys Cys Ser Cys Leu Lys Gly Ala Cys Ser Cys
            1220                1225                1230

Gly Ser Cys Cys Lys Phe Asp Glu Asp Asp Ser Glu Pro Val Leu Lys
            1235                1240                1245

Gly Val Lys Leu His Tyr Thr
    1250                1255

<210> SEQ ID NO 95
<211> LENGTH: 5
<212> TYPE: PRT
<213> ORGANISM: Artificial Sequence
<220> FEATURE:
<223> OTHER INFORMATION: Synthetic Construct

<400> SEQUENCE: 95

Gly Gly Gly Gly Ser
1               5

<210> SEQ ID NO 96
<211> LENGTH: 458
<212> TYPE: PRT
<213> ORGANISM: Artificial Sequence
<220> FEATURE:
<223> OTHER INFORMATION: Synthetic Construct

<400> SEQUENCE: 96

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Tyr Gly Asp Leu Asp Pro Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys

```
                    130                 135                 140
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Lys Lys Lys Lys Lys
    450                 455

<210> SEQ ID NO 97
<211> LENGTH: 216
<212> TYPE: PRT
<213> ORGANISM: Artificial Sequence
<220> FEATURE:
<223> OTHER INFORMATION: Synthetic Construct

<400> SEQUENCE: 97

Gln Ala Val Leu Thr Gln Ala Pro Ser Ala Ser Gly Thr Leu Gly Gln
1               5                   10                  15

Gln Val Thr Ile Ser Cys Ser Gly Thr Thr Ser Asn Ile Gly Arg Asn
            20                  25                  30

Thr Val Asn Trp Tyr Gln His Leu Pro Gly Thr Ala Pro Lys Leu Leu
```

```
            35                  40                  45
Ile Phe Val Ser Asn Gln Arg Pro Ser Gly Val Pro Asp Arg Phe Ser
 50                  55                  60
Gly Ser Lys Ser Gly Thr Ser Ala Ser Leu Val Ile Ser Gly Leu Gln
 65                  70                  75                  80
Ser Glu Asp Glu Ala Asp Tyr Tyr Cys Gly Ala Trp Asp Asp Ser Leu
                 85                  90                  95
Asp Gly Met Leu Phe Gly Gly Gly Thr Lys Leu Thr Val Leu Gly Gln
                100                 105                 110
Pro Lys Ala Asn Pro Thr Val Thr Leu Phe Pro Pro Ser Ser Glu Glu
            115                 120                 125
Leu Gln Ala Asn Lys Ala Thr Leu Val Cys Leu Ile Ser Asp Phe Tyr
        130                 135                 140
Pro Gly Ala Val Thr Val Ala Trp Lys Ala Asp Gly Ser Pro Val Lys
145                 150                 155                 160
Ala Gly Val Glu Thr Thr Lys Pro Ser Lys Gln Ser Asn Asn Lys Tyr
                165                 170                 175
Ala Ala Ser Ser Tyr Leu Ser Leu Thr Pro Glu Gln Trp Lys Ser His
                180                 185                 190
Arg Ser Tyr Ser Cys Gln Val Thr His Glu Gly Ser Thr Val Glu Lys
            195                 200                 205
Thr Val Ala Pro Thr Glu Cys Ser
        210                 215

<210> SEQ ID NO 98
<211> LENGTH: 262
<212> TYPE: PRT
<213> ORGANISM: Artificial Sequence
<220> FEATURE:
<223> OTHER INFORMATION: Synthetic Construct

<400> SEQUENCE: 98

Gln Ala Val Leu Thr Gln Ala Pro Ser Ala Ser Gly Thr Leu Gly Gln
  1               5                  10                  15
Gln Val Thr Ile Ser Cys Ser Gly Thr Thr Ser Asn Ile Gly Arg Asn
                 20                  25                  30
Thr Val Asn Trp Tyr Gln His Leu Pro Gly Thr Ala Pro Lys Leu Leu
            35                  40                  45
Ile Phe Val Ser Asn Gln Arg Pro Ser Gly Val Pro Asp Arg Phe Ser
 50                  55                  60
Gly Ser Lys Ser Gly Thr Ser Ala Ser Leu Val Ile Ser Gly Leu Gln
 65                  70                  75                  80
Ser Glu Asp Glu Ala Asp Tyr Tyr Cys Gly Ala Trp Asp Asp Ser Leu
                 85                  90                  95
Asp Gly Met Leu Phe Gly Gly Gly Thr Lys Leu Thr Val Leu Gly Ser
                100                 105                 110
Arg Gly Gly Gly Gly Ser Gly Gly Gly Ser Gly Gly Gly Gly Ser
            115                 120                 125
Leu Glu Met Ala Gln Val Gln Leu Val Gln Ser Gly Ala Glu Val Lys
        130                 135                 140
Lys Pro Gly Ala Ser Val Lys Val Ser Cys Lys Ala Ser Gly Tyr Thr
145                 150                 155                 160
Phe Thr Ser Tyr Gly Ile Ser Trp Val Arg Gln Ala Pro Gly Gln Gly
                165                 170                 175
Leu Glu Trp Met Gly Trp Ile Ser Ala Tyr Asn Gly Asn Thr Asn Tyr
```

```
                180             185             190
Ala Gln Lys Leu Gln Gly Arg Val Thr Met Thr Thr Asp Thr Ser Thr
            195                 200                 205

Ser Thr Ala Tyr Met Glu Leu Arg Ser Leu Arg Ser Asp Asp Thr Ala
            210                 215                 220

Val Tyr Tyr Cys Ala Arg Gly Tyr Gly Asp Leu Asp Pro Trp Gly
225                 230                 235                 240

Gln Gly Thr Leu Val Thr Val Ser Ser Thr Ser Gly Gly Gly Gly Ser
                245                 250                 255

Lys Lys Lys Lys Lys Lys
            260

<210> SEQ ID NO 99
<211> LENGTH: 5
<212> TYPE: PRT
<213> ORGANISM: Artificial Sequence
<220> FEATURE:
<223> OTHER INFORMATION: Synthetic Construct

<400> SEQUENCE: 99

Asp His Tyr Met Asp
1               5

<210> SEQ ID NO 100
<211> LENGTH: 19
<212> TYPE: PRT
<213> ORGANISM: Artificial Sequence
<220> FEATURE:
<223> OTHER INFORMATION: Synthetic Construct

<400> SEQUENCE: 100

Arg Thr Arg Asn Lys Ala Asn Ser Tyr Thr Thr Glu Tyr Ala Ala Ser
1               5                   10                  15

Val Lys Gly

<210> SEQ ID NO 101
<211> LENGTH: 9
<212> TYPE: PRT
<213> ORGANISM: Artificial Sequence
<220> FEATURE:
<223> OTHER INFORMATION: Synthetic Construct

<400> SEQUENCE: 101

Gly Ile Ser Pro Phe Tyr Phe Asp Tyr
1               5

<210> SEQ ID NO 102
<211> LENGTH: 11
<212> TYPE: PRT
<213> ORGANISM: Artificial Sequence
<220> FEATURE:
<223> OTHER INFORMATION: Synthetic Construct

<400> SEQUENCE: 102

Arg Ala Ser Gln Ser Ile Ser Ser Tyr Leu Asn
1               5                   10

<210> SEQ ID NO 103
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 103

Ala Ala Ser Ser Leu Gln Ser
1               5

<210> SEQ ID NO 104
<211> LENGTH: 9
<212> TYPE: PRT
<213> ORGANISM: Artificial Sequence
<220> FEATURE:
<223> OTHER INFORMATION: Synthetic Construct

<400> SEQUENCE: 104

Gln Gln Ser Tyr Ser Thr Pro Pro Thr
1               5

<210> SEQ ID NO 105
<211> LENGTH: 118
<212> TYPE: PRT
<213> ORGANISM: Artificial Sequence
<220> FEATURE:
<223> OTHER INFORMATION: Synthetic Construct

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Gly Ile Ser Pro Phe Tyr Phe Asp Tyr Trp Gly Gln
            100                 105                 110

Gly Thr Leu Val Thr Val
        115

<210> SEQ ID NO 106
<211> LENGTH: 105
<212> TYPE: PRT
<213> ORGANISM: Artificial Sequence
<220> FEATURE:
<223> OTHER INFORMATION: Synthetic Construct

<400> SEQUENCE: 106

Glu Leu Thr Gln Ser Pro Ser Ser Leu Ser Ala Ser Val Gly Asp Arg
1               5                   10                  15

Val Thr Ile Thr Cys Arg Ala Ser Gln Ser Ile Ser Ser Tyr Leu Asn
            20                  25                  30

Trp Tyr Gln Gln Lys Pro Gly Lys Ala Pro Lys Leu Leu Ile Tyr Ala
        35                  40                  45

Ala Ser Ser Leu Gln Ser Gly Val Pro Ser Arg Phe Ser Gly Ser Gly
    50                  55                  60

Ser Gly Thr Asp Phe Thr Leu Thr Ile Ser Ser Leu Gln Pro Glu Asp
65                  70                  75                  80

Phe Ala Thr Tyr Tyr Cys Gln Gln Ser Tyr Ser Thr Pro Pro Thr Phe
                85                  90                  95
```

Gly Gln Gly Thr Lys Val Glu Ile Lys
            100             105

<210> SEQ ID NO 107
<211> LENGTH: 5
<212> TYPE: PRT
<213> ORGANISM: Artificial Sequence
<220> FEATURE:
<223> OTHER INFORMATION: Synthetic Construct

<400> SEQUENCE: 107

Ser Tyr Ala Met His
1               5

<210> SEQ ID NO 108
<211> LENGTH: 17
<212> TYPE: PRT
<213> ORGANISM: Artificial Sequence
<220> FEATURE:
<223> OTHER INFORMATION: Synthetic Construct

<400> SEQUENCE: 108

Val Ile Ser Tyr Asp Gly Ser Asn Lys Tyr Tyr Ala Asp Ser Val Lys
1               5                   10                  15

Gly

<210> SEQ ID NO 109
<211> LENGTH: 8
<212> TYPE: PRT
<213> ORGANISM: Artificial Sequence
<220> FEATURE:
<223> OTHER INFORMATION: Synthetic Construct

<400> SEQUENCE: 109

Asp Arg Ser Tyr Tyr Leu Asp Tyr
1               5

<210> SEQ ID NO 110
<211> LENGTH: 11
<212> TYPE: PRT
<213> ORGANISM: Artificial Sequence
<220> FEATURE:
<223> OTHER INFORMATION: Synthetic Construct

<400> SEQUENCE: 110

Arg Ala Ser Gln Ser Val Arg Ser Asn Leu Ala
1               5                   10

<210> SEQ ID NO 111
<211> LENGTH: 7
<212> TYPE: PRT
<213> ORGANISM: Artificial Sequence
<220> FEATURE:
<223> OTHER INFORMATION: Synthetic Construct

<400> SEQUENCE: 111

Asp Ala Ser Thr Arg Ala Thr
1               5

<210> SEQ ID NO 112
<211> LENGTH: 9
<212> TYPE: PRT
<213> ORGANISM: Artificial Sequence
<220> FEATURE:
<223> OTHER INFORMATION: Synthetic Construct

<400> SEQUENCE: 112

Gln Gln Arg Ser Asn Trp Pro Pro Thr
1               5

<210> SEQ ID NO 113
<211> LENGTH: 117
<212> TYPE: PRT
<213> ORGANISM: Artificial Sequence
<220> FEATURE:
<223> OTHER INFORMATION: Synthetic Construct

<400> SEQUENCE: 113

Glu Val Gln Leu Val Gln Ser Gly Gly Gly Val Val Gln Pro Gly Lys
1               5                   10                  15

Ser Leu Arg Leu Ser Cys Ala Ala Ser Gly Phe Ala Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ser Tyr Tyr Leu Asp Tyr Trp Gly Gln Gly Thr Leu
            100                 105                 110

Val Thr Val Ser Ser
        115

<210> SEQ ID NO 114
<211> LENGTH: 106
<212> TYPE: PRT
<213> ORGANISM: Artificial Sequence
<220> FEATURE:
<223> OTHER INFORMATION: Synthetic Construct

<400> SEQUENCE: 114

Thr Thr Leu Thr Gln Ser Pro Ala Thr Leu Ser Leu Ser Pro Gly Glu
1               5                   10                  15

Arg Ala Thr Leu Ser Cys Arg Ala Ser Gln Ser Val Arg Ser Asn Leu
            20                  25                  30

Ala Trp Tyr Gln Gln Lys Pro Gly Gln Ala Pro Arg Pro Leu Ile Tyr
        35                  40                  45

Asp Ala Ser Thr Arg Ala Thr Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Arg Ser Asn Trp Pro Pro Thr
                85                  90                  95

Phe Gly Gln Gly Thr Lys Val Glu Val Lys
            100                 105

<210> SEQ ID NO 115
<211> LENGTH: 728
<212> TYPE: PRT
<213> ORGANISM: Homo sapiens

<400> SEQUENCE: 115

Gln Ser Thr Ile Glu Glu Gln Ala Lys Thr Phe Leu Asp Lys Phe Asn

```
1               5                   10                  15
His Glu Ala Glu Asp Leu Phe Tyr Gln Ser Ser Leu Ala Ser Trp Asn
            20                  25                  30
Tyr Asn Thr Asn Ile Thr Glu Glu Asn Val Gln Asn Met Asn Asn Ala
            35                  40                  45
Gly Asp Lys Trp Ser Ala Phe Leu Lys Glu Gln Ser Thr Leu Ala Gln
            50                  55                  60
Met Tyr Pro Leu Gln Glu Ile Gln Asn Leu Thr Val Lys Leu Gln Leu
65                  70                  75                  80
Gln Ala Leu Gln Gln Asn Gly Ser Ser Val Leu Ser Glu Asp Lys Ser
            85                  90                  95
Lys Arg Leu Asn Thr Ile Leu Asn Thr Met Ser Thr Ile Tyr Ser Thr
            100                 105                 110
Gly Lys Val Cys Asn Pro Asp Asn Pro Gln Glu Cys Leu Leu Leu Glu
            115                 120                 125
Pro Gly Leu Asn Glu Ile Met Ala Asn Ser Leu Asp Tyr Asn Glu Arg
            130                 135                 140
Leu Trp Ala Trp Glu Ser Trp Arg Ser Glu Val Gly Lys Gln Leu Arg
145                 150                 155                 160
Pro Leu Tyr Glu Glu Tyr Val Val Leu Lys Asn Glu Met Ala Arg Ala
            165                 170                 175
Asn His Tyr Glu Asp Tyr Gly Asp Tyr Trp Arg Gly Asp Tyr Glu Val
            180                 185                 190
Asn Gly Val Asp Gly Tyr Asp Tyr Ser Arg Gly Gln Leu Ile Glu Asp
            195                 200                 205
Val Glu His Thr Phe Glu Glu Ile Lys Pro Leu Tyr Glu His Leu His
            210                 215                 220
Ala Tyr Val Arg Ala Lys Leu Met Asn Ala Tyr Pro Ser Tyr Ile Ser
225                 230                 235                 240
Pro Ile Gly Cys Leu Pro Ala His Leu Leu Gly Asp Met Trp Gly Arg
            245                 250                 255
Phe Trp Thr Asn Leu Tyr Ser Leu Thr Val Pro Phe Gly Gln Lys Pro
            260                 265                 270
Asn Ile Asp Val Thr Asp Ala Met Val Asp Gln Ala Trp Asp Ala Gln
            275                 280                 285
Arg Ile Phe Lys Glu Ala Glu Lys Phe Phe Val Ser Val Gly Leu Pro
            290                 295                 300
Asn Met Thr Gln Gly Phe Trp Glu Asn Ser Met Leu Thr Asp Pro Gly
305                 310                 315                 320
Asn Val Gln Lys Ala Val Cys His Pro Thr Ala Trp Asp Leu Gly Lys
            325                 330                 335
Gly Asp Phe Arg Ile Leu Met Cys Thr Lys Val Thr Met Asp Asp Phe
            340                 345                 350
Leu Thr Ala His His Glu Met Gly His Ile Gln Tyr Asp Met Ala Tyr
            355                 360                 365
Ala Ala Gln Pro Phe Leu Leu Arg Asn Gly Ala Asn Glu Gly Phe His
            370                 375                 380
Glu Ala Val Gly Glu Ile Met Ser Leu Ser Ala Ala Thr Pro Lys His
385                 390                 395                 400
Leu Lys Ser Ile Gly Leu Leu Ser Pro Asp Phe Gln Glu Asp Asn Glu
            405                 410                 415
Thr Glu Ile Asn Phe Leu Leu Lys Gln Ala Leu Thr Ile Val Gly Thr
            420                 425                 430
```

Leu Pro Phe Thr Tyr Met Leu Glu Lys Trp Arg Trp Met Val Phe Lys
            435                 440                 445

Gly Glu Ile Pro Lys Asp Gln Trp Met Lys Lys Trp Trp Glu Met Lys
450                 455                 460

Arg Glu Ile Val Gly Val Val Glu Pro Val Pro His Asp Glu Thr Tyr
465                 470                 475                 480

Cys Asp Pro Ala Ser Leu Phe His Val Ser Asn Asp Tyr Ser Phe Ile
                485                 490                 495

Arg Tyr Tyr Thr Arg Thr Leu Tyr Gln Phe Gln Phe Gln Glu Ala Leu
            500                 505                 510

Cys Gln Ala Ala Lys His Glu Gly Pro Leu His Lys Cys Asp Ile Ser
            515                 520                 525

Asn Ser Thr Glu Ala Gly Gln Lys Leu Phe Asn Met Leu Arg Leu Gly
        530                 535                 540

Lys Ser Glu Pro Trp Thr Leu Ala Leu Glu Asn Val Val Gly Ala Lys
545                 550                 555                 560

Asn Met Asn Val Arg Pro Leu Leu Asn Tyr Phe Glu Pro Leu Phe Thr
                565                 570                 575

Trp Leu Lys Asp Gln Asn Lys Asn Ser Phe Val Gly Trp Ser Thr Asp
            580                 585                 590

Trp Ser Pro Tyr Ala Asp Gln Ser Ile Lys Val Arg Ile Ser Leu Lys
            595                 600                 605

Ser Ala Leu Gly Asp Lys Ala Tyr Glu Trp Asn Asp Asn Glu Met Tyr
        610                 615                 620

Leu Phe Arg Ser Ser Val Ala Tyr Ala Met Arg Gln Tyr Phe Leu Lys
625                 630                 635                 640

Val Lys Asn Gln Met Ile Leu Phe Gly Glu Glu Asp Val Arg Val Ala
                645                 650                 655

Asn Leu Lys Pro Arg Ile Ser Phe Asn Phe Phe Val Thr Ala Pro Lys
            660                 665                 670

Asn Val Ser Asp Ile Ile Pro Arg Thr Glu Val Glu Lys Ala Ile Arg
        675                 680                 685

Met Ser Arg Ser Arg Ile Asn Asp Ala Phe Arg Leu Asn Asp Asn Ser
690                 695                 700

Leu Glu Phe Leu Gly Ile Gln Pro Thr Leu Gly Pro Pro Asn Gln Pro
705                 710                 715                 720

Pro Val Ser Gly Gly Gly Gly Ser
                725

<210> SEQ ID NO 116
<211> LENGTH: 734
<212> TYPE: PRT
<213> ORGANISM: Homo sapiens

<400> SEQUENCE: 116

Gln Ser Thr Ile Glu Glu Gln Ala Lys Thr Phe Leu Asp Lys Phe Asn
1               5                   10                  15

His Glu Ala Glu Asp Leu Phe Tyr Gln Ser Ser Leu Ala Ser Trp Asn
            20                  25                  30

Tyr Asn Thr Asn Ile Thr Glu Asn Val Gln Asn Met Asn Asn Ala
        35                  40                  45

Gly Asp Lys Trp Ser Ala Phe Leu Lys Glu Gln Ser Thr Leu Ala Gln
    50                  55                  60

Met Tyr Pro Leu Gln Glu Ile Gln Asn Leu Thr Val Lys Leu Gln Leu

```
              65                  70                  75                  80
        Gln Ala Leu Gln Gln Asn Gly Ser Ser Val Leu Ser Glu Asp Lys Ser
                        85                  90                  95

Lys Arg Leu Asn Thr Ile Leu Asn Thr Met Ser Thr Ile Tyr Ser Thr
                       100                 105                 110

Gly Lys Val Cys Asn Pro Asp Asn Pro Gln Glu Cys Leu Leu Leu Glu
                       115                 120                 125

Pro Gly Leu Asn Glu Ile Met Ala Asn Ser Leu Asp Tyr Asn Glu Arg
                130                 135                 140

Leu Trp Ala Trp Glu Ser Trp Arg Ser Glu Val Gly Lys Gln Leu Arg
        145                 150                 155                 160

Pro Leu Tyr Glu Glu Tyr Val Val Leu Lys Asn Glu Met Ala Arg Ala
                        165                 170                 175

Asn His Tyr Glu Asp Tyr Gly Asp Tyr Trp Arg Gly Asp Tyr Glu Val
                        180                 185                 190

Asn Gly Val Asp Gly Tyr Asp Tyr Ser Arg Gly Gln Leu Ile Glu Asp
                        195                 200                 205

Val Glu His Thr Phe Glu Glu Ile Lys Pro Leu Tyr Glu His Leu His
                210                 215                 220

Ala Tyr Val Arg Ala Lys Leu Met Asn Ala Tyr Pro Ser Tyr Ile Ser
        225                 230                 235                 240

Pro Ile Gly Cys Leu Pro Ala His Leu Leu Gly Asp Met Trp Gly Arg
                        245                 250                 255

Phe Trp Thr Asn Leu Tyr Ser Leu Thr Val Pro Phe Gly Gln Lys Pro
                        260                 265                 270

Asn Ile Asp Val Thr Asp Ala Met Val Asp Gln Ala Trp Asp Ala Gln
                        275                 280                 285

Arg Ile Phe Lys Glu Ala Glu Lys Phe Phe Val Ser Val Gly Leu Pro
                290                 295                 300

Asn Met Thr Gln Gly Phe Trp Glu Asn Ser Met Leu Thr Asp Pro Gly
        305                 310                 315                 320

Asn Val Gln Lys Ala Val Cys His Pro Thr Ala Trp Asp Leu Gly Lys
                        325                 330                 335

Gly Asp Phe Arg Ile Leu Met Cys Thr Lys Val Thr Met Asp Asp Phe
                        340                 345                 350

Leu Thr Ala His His Glu Met Gly His Ile Gln Tyr Asp Met Ala Tyr
                        355                 360                 365

Ala Ala Gln Pro Phe Leu Leu Arg Asn Gly Ala Asn Glu Gly Phe His
                370                 375                 380

Glu Ala Val Gly Glu Ile Met Ser Leu Ser Ala Ala Thr Pro Lys His
        385                 390                 395                 400

Leu Lys Ser Ile Gly Leu Leu Ser Pro Asp Phe Gln Glu Asp Asn Glu
                        405                 410                 415

Thr Glu Ile Asn Phe Leu Leu Lys Gln Ala Leu Thr Ile Val Gly Thr
                        420                 425                 430

Leu Pro Phe Thr Tyr Met Leu Glu Lys Trp Arg Trp Met Val Phe Lys
                        435                 440                 445

Gly Glu Ile Pro Lys Asp Gln Trp Met Lys Lys Trp Trp Glu Met Lys
                450                 455                 460

Arg Glu Ile Val Gly Val Val Glu Pro Val Pro His Asp Glu Thr Tyr
        465                 470                 475                 480

Cys Asp Pro Ala Ser Leu Phe His Val Ser Asn Asp Tyr Ser Phe Ile
                        485                 490                 495
```

```
Arg Tyr Tyr Thr Arg Thr Leu Tyr Gln Phe Gln Phe Gln Glu Ala Leu
                500                 505                 510

Cys Gln Ala Ala Lys His Glu Gly Pro Leu His Lys Cys Asp Ile Ser
            515                 520                 525

Asn Ser Thr Glu Ala Gly Gln Lys Leu Phe Asn Met Leu Arg Leu Gly
        530                 535                 540

Lys Ser Glu Pro Trp Thr Leu Ala Leu Glu Asn Val Val Gly Ala Lys
545                 550                 555                 560

Asn Met Asn Val Arg Pro Leu Leu Asn Tyr Phe Glu Pro Leu Phe Thr
                565                 570                 575

Trp Leu Lys Asp Gln Asn Lys Asn Ser Phe Val Gly Trp Ser Thr Asp
            580                 585                 590

Trp Ser Pro Tyr Ala Asp Gln Ser Ile Lys Val Arg Ile Ser Leu Lys
        595                 600                 605

Ser Ala Leu Gly Asp Lys Ala Tyr Glu Trp Asn Asp Asn Glu Met Tyr
610                 615                 620

Leu Phe Arg Ser Ser Val Ala Tyr Ala Met Arg Gln Tyr Phe Leu Lys
625                 630                 635                 640

Val Lys Asn Gln Met Ile Leu Phe Gly Glu Glu Asp Val Arg Val Ala
                645                 650                 655

Asn Leu Lys Pro Arg Ile Ser Phe Asn Phe Val Thr Ala Pro Lys
            660                 665                 670

Asn Val Ser Asp Ile Ile Pro Arg Thr Glu Val Glu Lys Ala Ile Arg
        675                 680                 685

Met Ser Arg Ser Arg Ile Asn Asp Ala Phe Arg Leu Asn Asp Asn Ser
690                 695                 700

Leu Glu Phe Leu Gly Ile Gln Pro Thr Leu Gly Pro Pro Asn Gln Pro
705                 710                 715                 720

Pro Val Ser Gly Gly Gly Gly Ser Lys Lys Lys Lys Lys Lys
                725                 730

<210> SEQ ID NO 117
<211> LENGTH: 2
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(2)
<223> OTHER INFORMATION: Can be present in repeats of any integer

<400> SEQUENCE: 117

Gly Ser
1

<210> SEQ ID NO 118
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(5)
<223> OTHER INFORMATION: Can be present in repeats of any integer

<400> SEQUENCE: 118

Gly Ser Gly Gly Ser
1               5
```

<210> SEQ ID NO 119
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(5)
<223> OTHER INFORMATION: Can be present in repeats of any integer

<400> SEQUENCE: 119

Gly Gly Gly Gly Ser
1               5

<210> SEQ ID NO 120
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(4)
<223> OTHER INFORMATION: Can be present in repeats of any integer

<400> SEQUENCE: 120

Gly Gly Gly Ser
1

<210> SEQ ID NO 121
<211> LENGTH: 450
<212> TYPE: PRT
<213> ORGANISM: Artificial Sequence
<220> FEATURE:
<223> OTHER INFORMATION: Synthetic Construct

<400> SEQUENCE: 121

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Thr Tyr Ser Gly Ser Thr Ile Tyr Tyr Ala Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Thr Thr Met Val Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro 180                 185                 190
Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 122
<211> LENGTH: 214
<212> TYPE: PRT
<213> ORGANISM: Artificial Sequence
<220> FEATURE:
<223> OTHER INFORMATION: Synthetic Construct

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Glu Thr Gly Val Pro Ser Arg Phe Ser Gly
    50                  55                  60

Ser Gly Ser Gly Thr Asp Phe Thr Phe Thr Ile Ser Gly Leu Gln Pro
65                  70                  75                  80

Glu Asp Ile Ala Thr Tyr Tyr Cys Gln Gln Tyr Asp Asn Leu Pro Leu

```
                85                  90                  95
Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 123
<211> LENGTH: 450
<212> TYPE: PRT
<213> ORGANISM: Artificial Sequence
<220> FEATURE:
<223> OTHER INFORMATION: Synthetic Construct

<400> SEQUENCE: 123

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met Tyr Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Ser Gly Ser Asp Tyr Gly Asp Tyr Leu Leu Val Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
```

```
            225                 230                 235                 240
Pro Ser Val Phe Leu Phe Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 124
<211> LENGTH: 216
<212> TYPE: PRT
<213> ORGANISM: Artificial Sequence
<220> FEATURE:
<223> OTHER INFORMATION: Synthetic Construct

<400> SEQUENCE: 124

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Asn Ser Leu Thr Ser Ile
                85                  90                  95

Ser Thr Trp Val Phe Gly Gly Gly Thr Lys Leu Thr Val Leu Gly Gln
                100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
```

```
            130                 135                 140
Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 125
<211> LENGTH: 457
<212> TYPE: PRT
<213> ORGANISM: Artificial Sequence
<220> FEATURE:
<223> OTHER INFORMATION: Synthetic Construct

<400> SEQUENCE: 125

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Gln Gly Asn Thr Asn Tyr Ala Gln Lys Phe
    50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Trp Phe Gly Glu Ser Leu Ile Gly
            100                 105                 110

Gly Phe Asp Asn Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
```

275                 280                 285
Val Asp Gly Val Glu Val His Asn Ala Lys Thr Lys Pro Arg Glu Glu
            290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Leu His Glu Ala Leu His Ser His Tyr Thr Gln
        435                 440                 445

Lys Ser Leu Ser Leu Ser Pro Gly Lys
    450                 455

<210> SEQ ID NO 126
<211> LENGTH: 214
<212> TYPE: PRT
<213> ORGANISM: Artificial Sequence
<220> FEATURE:
<223> OTHER INFORMATION: Synthetic Construct

<400> SEQUENCE: 126

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Ser Thr
            20                  25                  30

Ser Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Asp Thr Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr

```
                    180                 185                 190
Ala Cys Glu Val Thr His Gln Gly Leu Ser Ser Pro Val Thr Lys Ser
            195                 200                 205

Phe Asn Arg Gly Glu Cys
        210

<210> SEQ ID NO 127
<211> LENGTH: 455
<212> TYPE: PRT
<213> ORGANISM: Artificial Sequence
<220> FEATURE:
<223> OTHER INFORMATION: Synthetic Construct

<400> SEQUENCE: 127

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Glu Ala Arg His Tyr Tyr Tyr Tyr Ala Met
            100                 105                 110

Asp Val Trp Gly Gln Gly Thr Ala Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
```

```
                        325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Glu Glu Met Thr Lys
            355                 360                 365
Asn Gln Val Ser Leu Thr Cys Leu Val Lys Gly Phe Tyr Pro Ser Asp
            370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
                420                 425                 430
Cys Ser Val Met His Glu Ala Leu His Asn His Tyr Thr Gln Lys Ser
                435                 440                 445
Leu Ser Leu Ser Pro Gly Lys
            450                 455

<210> SEQ ID NO 128
<211> LENGTH: 214
<212> TYPE: PRT
<213> ORGANISM: Artificial Sequence
<220> FEATURE:
<223> OTHER INFORMATION: Synthetic Construct

<400> SEQUENCE: 128

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Ser Trp Tyr Gln Gln Lys Pro Gly Lys Ala Pro Lys Leu Leu Ile
            35                  40                  45
Tyr Ala Ala Ser Ser Leu Gln Ser Gly Val Pro Ser Arg Phe Ser Gly
        50                  55                  60
Ser Gly Ser Gly Thr Asp Phe Thr Leu Thr Ile Thr Ser Leu Gln Pro
65                  70                  75                  80
Glu Asp Phe Ala Thr Tyr Tyr Cys Gln Gln Ser Tyr Ser Thr Pro Arg
            85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
                195                 200                 205
Phe Asn Arg Gly Glu Cys
        210
```

<210> SEQ ID NO 129
<211> LENGTH: 449
<212> TYPE: PRT
<213> ORGANISM: Artificial Sequence
<220> FEATURE:
<223> OTHER INFORMATION: Synthetic Construct

<400> SEQUENCE: 129

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Phe Tyr Ala Asp Ser Val Lys
    50                  55                  60

Gly Arg Phe Thr Ile Ser Arg Asp Asn Ser Met Asn Thr Leu Phe Leu
65                  70                  75                  80

Gln Met Asn Ser Leu Arg Ala Glu Asp Thr Ala Val Tyr Tyr Cys Ala
                85                  90                  95

Arg Val Leu Pro Met Tyr Gly Asp Tyr Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
```

```
                  370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 130
<211> LENGTH: 216
<212> TYPE: PRT
<213> ORGANISM: Artificial Sequence
<220> FEATURE:
<223> OTHER INFORMATION: Synthetic Construct

<400> SEQUENCE: 130

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Glu Tyr Thr Phe Gly Gln Gly Thr Lys Leu Glu Ile Lys Arg Thr Val
                100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 131
<211> LENGTH: 464
<212> TYPE: PRT
<213> ORGANISM: Artificial Sequence
<220> FEATURE:
<223> OTHER INFORMATION: Synthetic Construct

<400> SEQUENCE: 131

Gln Val Gln Leu Val Gln Ser Gly Ala Glu Val Lys Lys Pro Gly Ala
```

```
1               5                   10                  15
Ser Val Lys Val Ser Cys Lys Ala Ser Gly Tyr Thr Phe Thr Ser Tyr
                20                  25                  30
Gly Ile Ser Trp Val Arg Gln Ala Pro Gly Gln Gly Leu Glu Trp Met
                35                  40                  45
Gly Trp Ile Ser Ala Tyr Asn Gly Asn Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Gly Tyr Tyr Gly Asp Leu Asp Pro Trp Gly Gln Gly Thr Leu
                100                 105                 110
Val Thr Val Ser Ser Ala Ser Thr Lys Gly Pro Ser Val Phe Pro Leu
                115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
                180                 185                 190
Leu Gly Thr Gln Thr Tyr Ile Cys Asn Val Asn His Lys Pro Ser Asn
                195                 200                 205
Thr Lys Val Asp Lys Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
                260                 265                 270
Val Lys Phe Asn Trp Tyr Val Asp Gly Val Glu Val His Asn Ala Lys
                275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Arg Glu Glu Met Thr Lys Asn Gln Val Ser Leu Thr Cys Leu
                355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
                420                 425                 430
```

His Asn His Tyr Thr Gln Lys Ser Leu Ser Leu Ser Pro Gly Lys Gly
                435                 440                 445

Gly Gly Gly Ser His His His His His His His His
            450             455                 460

<210> SEQ ID NO 132
<211> LENGTH: 464
<212> TYPE: PRT
<213> ORGANISM: Artificial Sequence
<220> FEATURE:
<223> OTHER INFORMATION: Synthetic Construct

<400> SEQUENCE: 132

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Tyr Gly Asp Leu Asp Pro Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

-continued

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
                435                 440                 445

Gly Gly Gly Ser Arg Arg Arg Arg Arg Arg Arg Arg Arg
    450                 455                 460

<210> SEQ ID NO 133
<211> LENGTH: 105
<212> TYPE: PRT
<213> ORGANISM: Mus musculus

<400> SEQUENCE: 133

Gln Pro Lys Ser Ser Pro Ser Val Thr Leu Phe Pro Pro Ser Ser Glu
1               5                   10                  15

Glu Leu Glu Thr Asn Lys Ala Thr Leu Val Cys Thr Ile Thr Asp Phe
            20                  25                  30

Tyr Pro Gly Val Val Thr Val Asp Trp Lys Val Asp Gly Thr Pro Val
        35                  40                  45

Thr Gln Gly Met Glu Thr Thr Gln Pro Ser Lys Gln Ser Asn Asn Lys
    50                  55                  60

Tyr Met Ala Ser Ser Tyr Leu Thr Leu Thr Ala Arg Ala Trp Glu Arg
65                  70                  75                  80

His Ser Ser Tyr Ser Cys Gln Val Thr His Glu Gly His Thr Val Glu
                85                  90                  95

Lys Ser Leu Ser Arg Ala Asp Cys Ser
            100                 105

<210> SEQ ID NO 134
<211> LENGTH: 324
<212> TYPE: PRT
<213> ORGANISM: Mus musculus

<400> SEQUENCE: 134

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

```
Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
            115                 120                 125

Thr Ile Thr Leu Thr Pro Lys Val Thr Cys Val Val Val Ala Ile Ser
130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
                180                 185                 190

Gly Lys Glu Phe Lys Cys Arg Val Asn Ser Ala Ala Phe Pro Ala Pro
                195                 200                 205

Ile Glu Lys Thr Ile Ser Lys Thr Lys Gly Arg Pro Lys Ala Pro Gln
            210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
                260                 265                 270

Pro Ile Met Asp Thr Asp Gly Ser Tyr Phe Val Tyr Ser Lys Leu Asn
                275                 280                 285

Val Gln Lys Ser Asn Trp Glu Ala Gly Asn Thr Phe Thr Cys Ser Val
            290                 295                 300

Leu His Glu Gly Leu His Asn His His Thr Glu Lys Ser Leu Ser His
305                 310                 315                 320

Ser Pro Gly Lys
```